US007872115B2

(12) United States Patent
Hosted et al.

(10) Patent No.: US 7,872,115 B2
(45) Date of Patent: Jan. 18, 2011

(54) **REPORTER ASSAY SCREENS FOR PROTEIN TARGETS IN *SACCHAROMYCES CEREVISIAE***

(75) Inventors: Thomas J. Hosted, Summit, NJ (US); Scott Walker, Basking Ridge, NJ (US); Marvin Bayne, Westfield, NJ (US)

(73) Assignee: Schering Corporation, Kenilworth, NJ (US)

( * ) Notice: Subject to any disclaimer, the term of this patent is extended or adjusted under 35 U.S.C. 154(b) by 946 days.

(21) Appl. No.: 11/226,605

(22) Filed: Sep. 14, 2005

(65) Prior Publication Data

US 2006/0088859 A1    Apr. 27, 2006

Related U.S. Application Data

(60) Provisional application No. 60/609,940, filed on Sep. 15, 2004.

(51) Int. Cl.
*C07H 21/04* (2006.01)
*C12N 1/19* (2006.01)
*C12N 15/63* (2006.01)

(52) U.S. Cl. .................. 536/24.1; 435/254.2; 435/320.1
(58) Field of Classification Search ........................ None
See application file for complete search history.

(56) References Cited

U.S. PATENT DOCUMENTS

| 5,527,687 | A | 6/1996 | Kirsch et al. | |
|---|---|---|---|---|
| 6,602,699 | B2 | 8/2003 | Kozian et al. | |
| 2005/0112573 | A1* | 5/2005 | Iwahashi et al. | 435/6 |
| 2007/0031851 | A1* | 2/2007 | Velculescu et al. | 435/6 |

OTHER PUBLICATIONS

GenBank accession No. AX596774.*
GenBank accession No. AY189982.*
New et al. Reporter Gene Assays and their Applications to Bioassays of Natural Products. Phytother. Res. 17: 439-448, 2003.*
Harashima et al. Application of the pho5-gene fusion technology to Molecular Genetics and Biotechnology in Yeast. J. Biosci. & Bioengineer. 91(4): 325-338, 2001.*
Fleischmann et al. Allele-specific supression of a *Saccharomyces cerevisiae* prp20 mutation by overexpression of a nuclear serine/threonine protein kinase. Mol. Gen. Genet. 250: 614-625, 1996.*
Fincham et al. Transformation in Fungi. Micbiol. Review 53(1): 148-170, 1989.*
Comino et al. Ecm11 is located in the cell nucleus throughout mitosis. Pflugers Arch.—Eur J Physiol. 442 [Suppl. 1]: R179-R181, 2001.*
Accession No. U33007.*
Elledge et al. Two genes differentially regulated in the cell cycle and by DNA-damaging agents encode alternative regulatory subunits of ribonucleotide reductase. Genes Dev. 4: 740-751, 1990.*
Accession No. AY692668.*
http://db.yeastgenome.org/cgi-bin/locus.pl?locus=RNR3.*
http://www.yeastgenome.org/cgi-bin/locus.fpl?locus=yil066w.*
http://www.yeastgenome.org/cgi-bin/locus.fpl?locus=yil066w, 2009.*
Accession No. U33007, 2008.*
Accession No. AY692668, 2008.*
http://db.yeastgenome.org/cgi-bin/locus.pl?locus=RNR3, 2008.*
Accession No. AX596774, 2008.*
Accession No. AY189982, 2008.*
Alksne, L.E., Identification and Analysis of Bacterial Protein Secretion Inhibitors Utilizing a SecA-LacZ Reporter Fusion System. Antimicrob. Agents Chemother, 44(6)1418-1427 (2000).
Bianchi, Allison A., Stress Responses as a Tool to Detect and Characterize the Mode of Action of Antibacterial Agents. Applied and Environmental Microbiology, 65(11):5023-5027 (1999).
Billinton, N., et al., Development of a Green Fluorescent Protein Reporter for a Yeast Genotoxicity Biosensor. Biosensors & Bioelectronics, 13:831-838 (1998).
Dixon, Graham, et al., A Reporter Gene Assay for Fungal Sterol Biosynthesis Inhibitors. J. Steroid Biochem. Molec. Biol. 62(2-3):165-171 (1997).
Fischer, Hans Peter, et al., Identification of Antibiotic Stress-Inducible Promoters: A Systemic Approach to Novel Pathway-Specific Reporter Assays for Antibacterial Drug Discovery. Genome Res., 14(1):90-98 (2004).
Greer, Lee F., et al., Imaging of Light Emission from the Expression of Luciferases in Living Cells and Organisms: a Review. Luminescence 17:43-74 (2002).
Leskinen, P., et al., One-Step Measurement of Firefly Luciferase Activity in Yeast. Yeast, 20:1109-1113 (2003).
Lewis, Jennifer C., et al., Applications of Reporter Genes. Analytical Chemistry News & Features. 579-585 (1998).
Marathe, Sudhir V., et al., Vectors with the gus reporter gene for identifying and quantitating promoter regions in *Saccharomyces cerevisiae*. Gene. 154:105-107 (1995).
Shapiro, Elyse, et al., Stress-Based Identification and Classification of Antibacterial Agents: Second-Generation *Escherichia coli* Reporter Strains and Optimization of Detection. Antimicrobial Agents and Chemotherapy, 46(8):2490-2497 (2002).
Srikantha, Thyagarajan, et al., The Sea Pansy *Renilla reniformis* Luciferase Serves as a Sensitive Bioluminescent Reporter for Differential Gene Expression in *Candida albicans*. Journal of Bacteriology, 178(1):121-129 (1996).
Szittner, Rose, et al., Bright Stable Luminescent Yeast Using Bacterial Luciferase as a Sensor. Biochemical and Biophysical Research Communications, 309:66-70 (2003).
Vanoni, Marco, et al., Secretion of *Escherichia coli* β-Galactosidase in *Saccharomyces cerevisiae* Using the Signal Sequence from the Glucoamylase-Encoding STA2 Gene. Biochemical and Biophysical Research Communications, 164(3):1331-1338 (1989).
Voth, Warren P., et al., Yeast Vectors for Integration at the HO Locus. Nucleic Acids Research, 29(12 e59):1-4 (2001).
Sun, Dongyu, et al., A Pathway-specific Cell Based Screening System to Detect Bacterial Cell Wall Inhibitors. Journal of Antibiotics, 55(3):279-287 (2002).
*Saccharomyces* Genome Database record: YLR330W, 2007.
*Saccharomyces* Genome Database record: YHR012W, 2007.
*Saccharomyces* Genome Database record: YKL053W, 2007.
*Saccharomyces* Genome Database record: YKL196C, 2007.

(Continued)

*Primary Examiner*—Michele K Joike

(57) ABSTRACT

The present invention comprises responsive promoters along with screening methods which make use of the promoters in order to identify anti-fungal substances.

9 Claims, No Drawings

OTHER PUBLICATIONS

*Saccharomyces* Genome Database record: YDL103C, 2007.
*Saccharomyces* Genome Database record: YLR427W, 2007.
*Saccharomyces* Genome Database record: YLL020C, 2007.
*Saccharomyces* Genome Database record: YBL065W, 2007.
*Saccharomyces* Genome Database record: YPL033C, 2007.
*Saccharomyces* Genome Database record: YOL058W, 2007.
*Saccharomyces* Genome Database record: YOR255W, 2007.
*Saccharomyces* Genome Database record: YDR250C, 2007.
*Saccharomyces* Genome Database record: YDR446W, 2007.
*Saccharomyces* Genome Database record: YDR536W, 2007.
*Saccharomyces* Genome Database record: YDR243C, 2007.
*Saccharomyces* Genome Database record: YDR256C, 2007.
*Saccharomyces* Genome Database record: YFL020C, 2007.
*Saccharomyces* Genome Database record: YPL205C, 2007.
*Saccharomyces* Genome Database record: YGL205W, 2007.
*Saccharomyces* Genome Database record: YGL117W, 2007.
*Saccharomyces* Genome Database record: YHR029C, 2007.
*Saccharomyces* Genome Database record: YML116C, 2007.
*Saccharomyces* Genome Database record: YJR109C, 2007.
*Saccharomyces* Genome Database record: YCL030C, 2007.
*Saccharomyces* Genome Database record: YLR338W, 2007.
*Saccharomyces* Genome Database record: YIL066W-A, 2007.
*Saccharomyces* Genome Database record: YNL093W, 2007.
*Saccharomyces* Genome Database record: YRL381W, 2007.
*Saccharomyces* Genome Database record: YKL159C, 2007.
*Saccharomyces* Genome Database record: YIL058W, 2007.
*Saccharomyces* Genome Database record: YKR037C, 2007.
*Saccharomyces* Genome Database record: YNL279W, 2007.
*Saccharomyces* Genome Database record: YOR032C, 2007.
*Saccharomyces* Genome Database record: YML058W, 2007.
*Saccharomyces* Genome Database record: YMR303C, 2007.
*Saccharomyces* Genome Database record: YLR092W, 2007.
*Saccharomyces* Genome Database record: YFL052W, 2007.
*Saccharomyces* Genome Database record: YIR017C, 2007.
*Saccharomyces* Genome Database record: YLL062C, 2007.
*Saccharomyces* Genome Database record: YMR323W, 2007.
*Saccharomyces* Genome Database record: YPL171C, 2007.
*Saccharomyces* Genome Database record: YER065C, 2007.
*Saccharomyces* Genome Database record: YDR114C, 2007.
*Saccharomyces* Genome Database record: YJL153C, 2007.
*Saccharomyces* Genome Database record: YFR026C, 2007.
*Saccharomyces* Genome Database record: YMR175W, 2007.
*Saccharomyces* Genome Database record: YOR387C, 2007.

* cited by examiner

SEQUENCE LISTING

<160> NUMBER OF SEQ ID NOS: 88

<210> SEQ ID NO 1
<211> LENGTH: 1006
<212> TYPE: DNA
<213> ORGANISM: Saccharomyces cerevisiae

<400> SEQUENCE: 1

```
gccagggaag cctatatctg attccctgtt tcataatcca atgcagccac tagcttataa      60
ttatttgaac tatttgtcga acatcacagt aataaaatcc ccagaaagtt ccacttgctg     120
catattggca cctgttgatt cactctccat cacttttttg ttagccgccc agcctagaaa     180
gtctttaaat acatctgaaa ttttttttt tttaacagtg cacccgtgca tcatacctca     240
tgcaaggtac cttttttct caaaggtatt gtcttccatt gaagtggcac tatggcatga     300
tgaaccctga gcatttctga attcaacaga accaaattgt ccagaaataa atctgtccga     360
catgaattat gaaacttttt ttcaattaag tgaagagaat tttgcagcgt cttaccatta     420
ttttgaccca ttggtcgcat gtttgcgctt tgacttcgag aaccatgtta aagcttactt     480
gtacgacaac caatgaagta tattacggca gtttttttgg actgggtcaa aaaaagtgtt     540
gcataatcaa atcaggaaca cattaaaatg ttgtaaaatt tgtcttagta tcacctgagt     600
ggttattcat tacgtactac tgtcaaaata ttcggatctt tcctaaacgg gcttttgaat     660
tagtgttgct tctattcctg gaatggaagg taatactttc atgcattctc gcttttcgga     720
cttttaacaa taaattaaaa acaatgatac tttcatcaac tacctataca ccctgcgggt     780
```

-continued

| | |
|---|---|
| caattattttt tttttcgaat aaccgctgag gttggaaata tagaaacata ttccagatct | 840 |
| gtattttcag ttgctagaaa aaggttaata taatcattaa ggttttcagc atataacagg | 900 |
| tataattgat atataagcat cgtaatttc attcaaaatg gagagctact gcttctgata | 960 |
| gattgtacaa tctcaagaaa tcaagaacaa caaccatacc atgagt | 1006 |

<210> SEQ ID NO 2
<211> LENGTH: 1003
<212> TYPE: DNA
<213> ORGANISM: Saccharomyces cerevisiae

<400> SEQUENCE: 2

| | |
|---|---|
| ttgtgtttag acttaagtat gaaaatttta tgtatgagct gtggctatgt atccgctggc | 60 |
| aaataggtct gcttttttcta cactttccac cctcaaccta acagagcccg ctggcacaaa | 120 |
| taatcgatag taggacaaca gagctactcc ttcttatgcc ccgccccttt gagcttgttg | 180 |
| tattgctctt gatagttgtg ttttcactt tcatcagcat cggtagtctt gccgtccttg | 240 |
| tcttgactag ccattttctt aaaagcgtca ctcactacct ttgcatcgcc ctgcaatttt | 300 |
| tcctttgagc tctgaaatat ttcgctcact ttttgttggt ctgtattcat tctggatgtc | 360 |
| ttggttgtag aaatttcttt tattggttca ttaaagtcaa ggtaaatggc gagaactaga | 420 |
| atagagtttt attcttttta ccgttatata gataattcta gccggggggcg gtcgcccctg | 480 |
| agattcccga catcagtaag acatagtact gtacgattac tgtacgatta atctatccac | 540 |
| ttcagatgtt caacaattcc ttttggcatt acgtattaat acttcatagg atcggcaccc | 600 |
| tcccttaagc ctcccctaaa tgctttcggt accccttttaa gacaactatc tcttaacctt | 660 |
| ctgtatttac ttgcatgtta cgttgagtct cattggaggt ttgcatcata tgtttaggtt | 720 |
| ttttttggaaa cgtggacggc tcatagtgat tggtaaatgg gagttacgaa taaacgtatc | 780 |
| ttaaagggag cggtatgtaa aatggataga tgatcatgaa tacagtacga ggtgtaaaga | 840 |
| atgatgggac tgagagggca attatcatcc ctcagaatca acatcacaaa catatataaa | 900 |
| gctcccaatt ctgccccaaa gttttgtccc taggcatttt taatctttgt atctgtgctc | 960 |
| tttactttag tagaaaggta tataaaaaag tatagtcaag atg | 1003 |

<210> SEQ ID NO 3
<211> LENGTH: 1003
<212> TYPE: DNA
<213> ORGANISM: Saccharomyces cerevisiae

<400> SEQUENCE: 3

| | |
|---|---|
| gaggtttcaa catgccaaca atggaagtgg ttaagagacg ttttctggtt tctgggcagc | 60 |
| tgttacatag aatctctgat ttacatgctc aagtattcgc aaagatcggt atgatgggaa | 120 |
| aataggtgaa ttttgggata tgactgaga ttataccgtt gttaatgcta taatattaat | 180 |
| tatacagaat atattagaag ttctcctcga ggatatggga acccacagaa gcgaatcgat | 240 |
| gtttctacat aaaagaaaaa aataatctca ttttatcttc ggttttgaat cttttcatt | 300 |
| tttttttccta ttacattatc aattctggca tttcagtgtt tataaaaaga tcaaattgct | 360 |
| gtttgaaact cattgcgcta attccataat tttgcaccat gtatgctcat gactccatat | 420 |
| aggacaaacat actggtagga atattatcaa gtgaacgata acggttcttc tcccaacaag | 480 |
| aagtaagcct ggtgagtgta ttttgaagct ttttggaggg gcggccacgg aataagatat | 540 |
| gaacacatac tggcaattgg gctgagatct gattacattg tcgacagatt cccatgaagg | 600 |
| tgtttgagag aattttgatt gagtcgttat acaaattgct gtggacacgt acgcataaag | 660 |

```
tagttcgggc agctatgttt gccacgtagt agctacaata ttaagcatag cagactaaat    720
gcaattggct gtgttgaaag aaacttctga actgagattc aagtaacgtg attgtgtgcg    780
ccattttaca caggctgcgc ggcaaatcaa aaccaaagat acttctccgg aggtatacgt    840
gttgcatttt caacagacta tacgagtttt ttctgatcgt tgtatattta agtgcagctt    900
ggacttacaa gctctatact aggataatga tctcattgga ttcaagagaa agaaactcta    960
tactggcgcc aaattagcag tgtcaaattt cgaaaaggtg atg                     1003
```

<210> SEQ ID NO 4
<211> LENGTH: 1003
<212> TYPE: DNA
<213> ORGANISM: Saccharomyces cerevisiae

<400> SEQUENCE: 4

```
ttctttttt tttttttttt ttcttttttgg gaacggggga aaaggtctca ctagtatata     60
aaggaaagag agtacagcac gaatgagcca gctgcaggaa aggggctagg ttaaaaaata    120
aaaacccagc agaaagcaaa caaccaaata taatttagaa atggacagag accatattaa    180
tgaccatgac catcgaatga gctattccat caacaaggac gacttgttgt taatggtttt    240
ggcggttttc attcccccag tggccgtctg gaagcgtaag ggtatgttca acagggatac    300
actattgaac ttacttctct tcctactgtt attcttccca gcaatcattc acgcttgcta    360
cgttgtatat gaaacgagta gtgaacgttc gtacgatctt tcacgcagac atgcgactgc    420
gcccgccgta gaccgtgacc tggaagctca ccctgcagag gaatctcaag cacagcctcc    480
agcatatgat gaagacgatg aggccggtgc cgatgtgccc ttgatggaca caaacaaca    540 gctctcttcc ggccgtactt agtgatcgga acgagctctt tatcaccgta gttctaaata    600
acacatagag taaattattg cctttttctt cgttcctttt gttcttcacg tccttttttat    660 gaaatacgtg ccggtgttcc ggggttggat gcggaatcga aagtgttgaa tgtgaaatat    720
gcggaggcca agtatgcgct tcggcggcta aatgcggcat gtgaaaagta ttgtctattt    780
tatcttcatc cttctttccc agaatattga acttatttaa ttcacatgga gcagagaaag    840
cgcacctctg cgttggcggc aatgttaatt tgagacgtat ataaattgga gctttcgtca    900 ccttttttg gcttgttctg ttgtcgggtt cctaatgtta gttttatcct tgatttattc    960
tgtttcattc ccttttttttt ccagtgaaaa agaagtaaca atg                   1003
```

<210> SEQ ID NO 5
<211> LENGTH: 1003
<212> TYPE: DNA
<213> ORGANISM: Saccharomyces cerevisiae

<400> SEQUENCE: 5

```
gaagttacaa ataataacaa caaagttaat aacagtagta gcaaccctga tatttccacc     60
aactcggtag ttcataacgc aatgcaattt acaaatacaa caacaatac aagtagcact    120 gtggatataa acgatcccaa aaatattgca ccccctccta caacctctgt ttcagcccca    180
agcactccaa ccttgtcctc atcaagtcaa atggcgaata tggcttcgcc tagtaccgat    240
aatggtgaca atgaggagaa aaatggtggt aagaagaaga gatttggcct attcaaaaaa    300
aaaaataaat caaagaaata atatccttcg acagcttaat gaacacgcat gtaaatgttt    360
tgtaaacagt ttgttttttc gttttgtat ctgttaattt tctattattt attttttag     420 ttttttttg cggtagaatt gggttatcac tgaatctatt ttatttttg ggttggtttc    480
```

| tccctgtttt cagtttgttt gaattggtgt ttaacaaaat ctggaattat tcactataat | 540 |
| tatttcctct ttttagtttg accaaataaa ctcaactatc ttgtgttatt tctttgtatt | 600 |
| atagctttac acatatttaa ctatccatac cttttacttt ttgtatatac tgttaatttc | 660 |
| ataaaacacg ttttagtacc agaaaatcgt gtcatagcac cgttttagca gtgattttta | 720 |
| aaattgtcca aggtgccaat aaatactggt gggaacaaca ttttaattag aatagctaaa | 780 |
| accttctaag aaaactatcc cagcgtagaa agaaagaaat ctctatcagc cgcgcaagtg | 840 |
| cagtatctct tattttttgca cggccccgtc gctatattgt cacacgcatt tgaattagtg | 900 |
| actcaataat aatacagatt tgtgacgtat aaagaaacca cagaaaaact gcgtatgtcc | 960 |
| gaagcacagg tccactagta atagagccca aaaatctgac atg | 1003 |

<210> SEQ ID NO 6
<211> LENGTH: 1003
<212> TYPE: DNA
<213> ORGANISM: Saccharomyces cerevisiae

<400> SEQUENCE: 6

| aggttgccac atacatggcc aagaccggta agtcagcctt ggaagcagaa aaggaattgc | 60 |
| ttaacggtca atccgcccaa gggataatca catgcagaga agttcacgag tggctacaaa | 120 |
| catgtgagtt gacccaagaa ttcccattat tcgaggcagt ctaccagata gtctacaaca | 180 |
| acgtccgcat ggaagaccta ccggagatga ttgaagagct agacatcgat gacgaataga | 240 |
| cactctcccc cccctcccc ctctgatctt tcctgttgcc tcttttcccc ccaaccaatt | 300 |
| tatcattata cacaagttct acaactacta ctagtaacat tactacagtt attataattt | 360 |
| tctattctct ttttctttaa gaatctatca ttaacgttaa tttctatata tacataacta | 420 |
| ccattataca cgctattatc gtttacatat cacatcaccg ttaatgaaag atacgacacc | 480 |
| ctgtacacta acacaattaa ataatcgcca taacctttc tgttatctat agcccttaaa | 540 |
| gctgtttctt cgagcttttt cactgcagta attctccaca tgggcccagc cactgagata | 600 |
| agagcgctat gttagtcact actgacggct ctccagtcat ttatgtgatt ttttagtgac | 660 |
| tcatgtcgca tttggcccgt ttttttccgc tgtcgcaacc tatttccatt aacggtgccg | 720 |
| tatggaagag tcatttaaag gcaggagaga gagattactc atcttcattg gatcagattg | 780 |
| atgactgcgt acggcagata gtgtaatctg agcagttgcg agacccagac tggcactgtc | 840 |
| tcaatagtat attaatgggc atacattcgt actcccttgt tcttgcccac agttctctct | 900 |
| ctctttactt cttgtatctt gtctccccat gtgtcagcga taaggaacat tgttctaata | 960 |
| tacacggata caaagaaat acacataatt gcataaaata atg | 1003 |

<210> SEQ ID NO 7
<211> LENGTH: 1003
<212> TYPE: DNA
<213> ORGANISM: Saccharomyces cerevisiae

<400> SEQUENCE: 7

| cttagtatac gattgtgttc ttgcccacca tctactaaca aaatatggca agattaaacc | 60 |
| tagtagcgca acataacaaa ccactaataa tggagatgca cttccatcta ccaaaaatct | 120 |
| tggtagagcg ataccatgtg aagtagattg tgggccatct ggatgaccgt atttcaaata | 180 |
| gttttgccta accaattcgt cagtaaggga ttcgtaagcc ttcgtaatct gaacataagt | 240 |
| ttcttccatc acacttttct catcaggtgt taggcccttt gctaatttat ctggatgaaa | 300 |
| tttaacagat aattttctat aagcagattt gatgtctcta tcggaagcac tagtagagat | 360 |

```
accaaggatt tcataaggat caaataattt tgtagcagcg tctttaatcg cgtcattact    420
attaatcctt tgcagaagaa ttgcaactaa gatccaaccc acaataatta taatatttct    480
cctgctccat attttggact tcttattact attttatca aacttccttc taaattgttt    540
gatttcatca ctggtgtatt cttcattcaa gttcttgaaa acttcctcat taaactcctt    600
actcttccct gaattcccat cttcagcatt ggccccaaaa aaaatttggt atatttgaag    660
cagtgtcata ggcccgacga ccatcaagag ccccgttaaa atgaaggacg ccacgtctc    720 actagcctca tcatactcgt aatttgtagg cattgtgctg taatatgcag tatatttatt    780
ttgttgcgaa ggccttcttt ggtcaattat aactgactat tgttccagtc gcatctttta    840
ttcgttcagt gatcttcgac gtgttcaaga caaattttttc agaaaacgcc tttccgtaac    900
gagtgaccaa ttcgcgttat aagagcgatt gtgtcagtaa tgaagtcaga ttgtgacatt    960
ataaagctaa gacgttaata actcaaaata gaaaagaagc atg                   1003
```

<210> SEQ ID NO 8
<211> LENGTH: 1003
<212> TYPE: DNA
<213> ORGANISM: Saccharomyces cerevisiae

<400> SEQUENCE: 8

```
aaataagagg tttggccaaa acgtggtcat ccaaggttga tggattcttc tcttctaata     60
ttattaataa tggatcgaaa catatttgag gcaaagctag ttcccattct tttgccaaga    120
aagcggaggg agaatgatcg taaagagtca caacgtccct aggaaacagt ttttggaaca    180
atttctgaaa tgtattcaaa ataggaataa tatcacttga atagctgttt tcgtgaacgg    240
atgtcgtttg accgatcgaa acagaaaagg atttggcatt tgcagtcgtg aactgtttgt    300
atgagccatt gtccaaccgt cttatgtcat aatcggtgaa atgctgaaa atatttgaca    360 gcgaaagatc aactgaagcc ttgatgaatg gctccaaata tataaacccg ctactttcaa    420
atagtatctt tgttgtctta ttcatcatag gttttatatc tctcaatacc tgcgggattt    480
cttgcagtga gacgcactc attattatca agtcgaatac caagccacca ttttcattat    540
taaggtctac taaatctagg agcgattgga aatggttttg aatctgaaac cgttccgtcc    600
cataaaatag tgaactaacc tcgtagttgg catttttttga gttgttcaca agataaaatt    660
ctatattttt ggcatgttga aacctggatg tgtacagaat gagatttggg tgatctccgc    720
ataccaaaac ccttaatgca gatgtcatta ttcaatatac ctatcgcgag atatgccggg    780
aataaaatgt aggaaacaaa agaaaaata tatgcacagt agttcaaaca gaatagaaat    840
gacggagagc aaatatttgg gtagaatcac agactttagt gttggttaca agcttttcga    900
atggatgtag tttgtaatca aaggacacta ataatagcga aaaaaaaaag ggcaagtatg    960
ttggcagtcg cctctttttc aatttagcgg taagttttta atg                   1003
```

<210> SEQ ID NO 9
<211> LENGTH: 1003
<212> TYPE: DNA
<213> ORGANISM: Saccharomyces cerevisiae

<400> SEQUENCE: 9

```
cgcaaatgat gagaaatagt catctaaatt agtggaagct gaaacgcaag gattgataat     60
gtaataggat caatgaatat taacataaa aacgatgata ataatattta tagaattgtg    120
tagaattgca gattcccttt tatggattcc taaatcctcg aggagaactt ctagtatatc    180
```

```
tacatacccta atattatagc cttaatcaca atggaatccc aacaattaca tcaaaatcca      240
cattctctac attactagta tattatcata tgcggtttaa gaaaatggta taaagattaa      300
gaaacagtca tgaaaattta gtgaagctga aatgccagta ttgataatac gatagaataa      360
tgaatgacaa agtatataag gaagatgaag taacattatt atggagaact atcgactccc      420
ttttgtgaat ttctatatcc tcaaggagaa ttgcttgtat actatgtata tataatatta      480 taaccttga caacaatgga ataattagtc cttaaacgtt agactggctg ggacagcacg       540
acctctgttg gctaattta cttttcccac aaccgtagat cttgatttca tgactgtttt       600
cgtggtaatg tccgaatgat acatatataa gttatatgct ttcactttat aagtattagc      660
gtttttactc accatccact gctttgagaa gatgtggtca gcaaccacgc aatacatcac      720
atattttggc acgggtgatg taccgatcta atggctaagc ttccttttgg aagctgatag      780
agatccagat ttgcatctct atcgctattg tcgtcatcga cactgctcac ttagtgctgc      840
aggtaaattc cgttttttc caaattaata tttatgaacg ttatgatgtc aagttttttc       900
aagaagtaat tatccgcgaa aaaagaata taaaaaatac aaatgtgcat agatcctcac       960
atagtataca actaaaaagc aaacaaaaga acatcctcaa atg                      1003

<210> SEQ ID NO 10
<211> LENGTH: 1003
<212> TYPE: DNA
<213> ORGANISM: Saccharomyces cerevisiae

<400> SEQUENCE: 10
caatgattct gaaatactcc ttttacaacc tttgcaaaga taatgtcttt cagtctgata       60
ttacgagcga cctagaacca ctaatccata ttcttcattc aacttactcc attttccttg      120
gcaaacaatg ccccacaatc atatacgtca taactataag ggatatgtct ggaatgcggc      180
caagatagaa ttaaagggct gcagaacacc actactgata ctcattgcca aggctaggag     240
gcaccatccg tttcattttc tttgaggtaa gccaatcatg aaatagtata cacatccata      300
acggacgtac ggacgaaata agtgccgttg tcccactatt ccaccgcatt tggcccattt      360
ggctcacttt gactcaactt gcgtcatttt aactgatatg aagggtccga ctttgtcctt      420
tttcggccac cgcataccc acggcgatgc ctccgctacc tgcatttgag tagcatctcc      480
gtttcgcggg gtattcggcg ctacgtcgcc tgttcgagcg gctctgttcg ttgcatgaaa      540
ctaaaataag cggaaagtgt ccagccatcc actacgtcag aaagaaataa tggttgtaca      600
ctgtttctcg gctatatacc gttttggtt ggttaatcct cgccaggtgc agctattgcg       660
cttggctgct tcgcgatagt agtaatctga gaaagtgcag atcccggtaa gggaaacact      720
tttggttcac ctttgatagg gctttcattg gggcattcgt aacaaaaagg aagtagatag      780
agaaattgag aaagcttaag tgagatgttt tagcttcaat tttgtcccct tcaacgctgc      840
ttggccttag agggtcagaa ttgcagttca ggagtagtca cactcatagt atataaacaa      900 gcccttatt gattttgaat aattattttg tatacgtgtt ctagcataca agttagaata      960
aataaaaaat agaaaatag aacatagaaa gttttagacc atg                      1003

<210> SEQ ID NO 11
<211> LENGTH: 1003
<212> TYPE: DNA
<213> ORGANISM: Saccharomyces cerevisiae

<400> SEQUENCE: 11
cttagtatac gattgtgttc ttgcccacca tctactaaca aaatatggca agattaaacc       60
```

```
tagtagcgca acataacaaa ccactaataa tggagatgca cttccatcta ccaaaaatct    120
tggtagagcg ataccatgtg aagtagattg tgggccatct ggatgaccgt atttcaaata    180
gttttgccta accaattcgt cagtaaggga ttcgtaagcc ttcgtaatct gaacataagt    240
ttcttccatc acactttcct catcaggtgt taggcccttt gctaatttat ctggatgaaa    300
tttaacagat aattttctat aagcagattt gatgtctcta tcggaagcac tagtagagat    360
accaaggatt tcataaggat caaataattt tgtagcagcg tctttaatcg cgtcattact    420
attaatcctt tgcagaagaa ttgcaactaa gatccaaccc acaataatta taatatttct    480
cctgctccat attttggact tcttattact atttttatca aacttccttc taaattgttt    540
gatttcatca ctggtgtatt cttcattcaa gttcttgaaa acttcctcat aaactccttt    600
actcttccct gaattcccat cttcagcatt ggccccaaaa aaatttggt atatttgaag     660 cagtgtcata ggcccgacga ccatcaagag ccccgttaaa atgaaggacg gccacgtctc    720
actagcctca tcatactcgt aatttgtagg cattgtgctg taatatgcag tatatttatt    780
ttgttgcgaa ggccttcttt ggtcaattat aactgactat tgttccagtc gcatctttta    840
ttcgttcagt gatcttcgac gtgttcaaga caaattttc agaaaacgcc tttccgtaac     900
gagtgaccaa ttcgcgttat aagagcgatt gtgtcagtaa tgaagtcaga ttgtgacatt    960
ataaagctaa gacgttaata actcaaaata gaaagaagc atg                      1003

<210> SEQ ID NO 12
<211> LENGTH: 1003
<212> TYPE: DNA
<213> ORGANISM: Saccharomyces cerevisiae

<400> SEQUENCE: 12
cataagaaac aaattttgta agtttcttgt gccttttgag tttgaaatca ttgaccagaa     60
caatgagaac tctaaacacg acaaatggat cttaaatcaa ttttcttgaa acatcttcc    120 agtttcgata ttcgcacatt tgccggtaaa atagtgcaat ctgcctatac ctttaaaatg    180
ggatcttgaa cgcgtacctg aaggtttttt taaataaggc cgaacctaaa tgttgccttc    240
aaaattaacc tgtatcaaat tttgaagccg aagttggtat cctcacattg tctaacctca    300
tggtctccta aagtccggcg atcactttcc gttgcgtgac tattgatgat cagactgtca    360
acaatgtcgt tccgggcctc catagcttga agaattttcg ttgacggaac tagaggaatg    420
gcagatggag atgaccttag tttcatgtcg ccttgatagt tatcaaagag tacagaaaca    480
agacgtctct tgctcaataa taaggattgg atcaggtgct tacaaatttt attcgtcata    540
caaacaatta ctaatatttt tttaatatta agcgtacccc tatttgattg gctctcttct    600
aaattcatac gttttaaaat ccgctttcaa ccgtcaacat aaaattagta agcagacctc    660
gttccaagac ccaactaagt tgcactaaat atcctcgaac aaattggggg cagattttg    720 aaccatataa aagtcatgac aatatttcca gatcaaggac agttgcagtt cttcctttca    780
tcggccagct gacgaattga ctgagcggct ttgtatttca ctagaataca cttcctatag    840
ctacaaaata ttattcaata atattagtga attatttaaa cctctacctg aaccacctac    900
cgagttggga cgtctcaggg ttctttctaa aactgccggc ataagagttt caccgctaat    960
tctgggagga gcttcaatcg gcgatgcatg gtcaggcttt atg                     1003

<210> SEQ ID NO 13
<211> LENGTH: 1003
<212> TYPE: DNA
```

<213> ORGANISM: Saccharomyces cerevisiae

<400> SEQUENCE: 13

```
agaacatcca aattcggaac tactaagaag atatgggtat gttgaatggg acggttcgaa      60
gtatgatttt ggagaagtgt tacttgaaaa tattgtcgag gcgttaaaag agacttttga     120
gacgaatact gaattttttgg acaggtgtat tgatatctta cgcaataacg ccaatattca    180
agaattctta gaaggtgaag aaatagtact agattcatat gattgttata ataatggtga    240
attgttgcct caactaatac ttttggtcca aatcttgaca attctttgcc aaattccagg    300
tttatgcaaa ctggacataa aagcaatgga aaggcaagtg gagagaattg taaagaagtg    360
tttacaattg atagaaggtg cccgcgccac tacaaactgt agtgccacat ggaaacgttg    420
tattatgaag cgtctagccg attacccat  aaaaaagtgc gtttctatcg aaaaaccttc    480
gaaaggaaac tcattaacaa gggaagaact aagagatgtt atggctcgga gagttttgaa    540
aagcgaaata gattcgctgc aagtttgtga agaaaccatc gacaagaatt acaaggttat    600
tcctgatgaa aagctgctaa ctaatatttt aagagaaag ttgacagagg aagaaaaaag     660
ctctgtcaaa cgtccttgcg tgaagaagtg agcggttgtt ctaaccacta tttaaagccg    720
caattagtaa tgcaaaaagt tggccggaat tagccgcgca agttggtggg gtcccttaat    780
ccgaaaaagg acggctttaa caaatataaa ctccgaaaat ccccacagtg acagaattgg    840
agaaacaacc agtttgata  tcgccataca tataagaga  tgtagaaagc attcttcact    900
gtaatgtcca aatcgtacat ttgaatttct tgtaggttta tttaaaaggt aagttaaata    960
aatataatag tacttacaaa taaatttgga accctagaag atg                     1003
```

<210> SEQ ID NO 14
<211> LENGTH: 1003
<212> TYPE: DNA
<213> ORGANISM: Saccharomyces cerevisiae

<400> SEQUENCE: 14

```
gttgaacttt attcaaatat catcgaagta agaagatata ctactaaaga ctccctttgc     60
tctatattcg agtcaggctc caccagtcat ttcgaaatta accagttaca ggtcaaaaga    120
ctaaacttac tgcaaaacca atttgcttct gttttcactt cttttccaccc caaagataat   180
acaagggca tacatatcaa ttttttttca cctgtcacta ggataactga ccttcaatat    240
tcctttttt atacgaatca gatactgttc ggtacacgat atctaattaa aatgattcaa    300
aactttgtaa caggtaaagt tttcactaga accaatcaat ccaagtgaat taggggaaac    360
catagttgtt gatttgtaga aacctcacat tgtacattgt tggtttgttg ggcatatcag    420
aacgagagat tttccaacat tcaatataca ctaaacccta tgacgagtcc cacagatggc    480
gtaaggtttt tatgatttca gcagggtacg acgactagta ccatattaac atttttagt     540
gtttctaatt tgggaaaagg tccgtgtttt ttctcctagc aaccgtttag tgccaagggt    600
taggcaattg aacgaggcca agacaatatt ggctttgctt ctattacttg gctaacattg    660
tgtctgcagg tcgaaaggca cctttactgt aaggaacatt cttgcgctct aaacatacga    720
agatatgggg aatatgaagc gtgtttctta tacgaagtgc agcatcgttc aaggaaaata    780
cacccccata gtaataatgg ctaagtggcc aggaattaga atatgtgaga tatgagtgca    840
aaatgagtga ccagtaatag cctgtttggg atgtaattgc tcaaaaaatt tatataaata    900
cagcggtttg atcagctttg tttgagacat ttctctgttc ttttccttcc agttaagctt    960
atatctccac taagcaacaa cccaaaaaac aacaaataca atg                     1003
```

<210> SEQ ID NO 15
<211> LENGTH: 1003
<212> TYPE: DNA
<213> ORGANISM: Saccharomyces cerevisiae

<400> SEQUENCE: 15

```
cagacttgtt gtctgtgctg ttacttgcac ttgctgcatt gctatttgcg ttcaaatcac      60
cttttcgat gaggaggtcc ctttgcttct ccaccatcgc ctttgtgtaa cgcaacattg     120
tccaatcgaa caagtggtcg ttgtgatact ctagtttaat actcagatct ttaaacagcc    180
ttgccaagaa caaataatct ggcttctcat cgaatttcaa attcttacag taagccatat    240
attcttgaaa ctctaatggt aaacctgaac atagagtttc cacgctaacg tttaatttct    300
tttccatgat acgatcatac ttttgtttct tggtggttgc tttcaaaccc tgccatggca    360
aagaacccctt acaaaaatag atcaagacat aacctagtga ttctaagtca tctcttctac   420
tttgctctat tccaagatgc gtattgacac ttgcataacg agctgtacct gtcaaggact    480
tgttctccct gtaaggaata tgacgatgtg tgttgaaatc tcggtatttc tttgatagac    540
cgaaatcaat aacatgaacg gtgctaccac ggcgtcctac ccccattaaa aagttgtctg    600
gtttgatatc tctatgaatg aacgaccttc catgtatata ctgaatacgg caaacatttt   660
gcaaagccag catgataacc gtcttaaagg agaaccttct gtgacagtag ttgaataaat    720
cttccaaaga tgggcctaga agatcgatga ccatagcatt atattcaccc tctctgccaa    780
accatctgat gaacgggatt cccacaccac cgcttaagta tctgtagacg cgggactcat    840
agtccaattg aggatgtctg gacctgatcg attccagctt gatggctact tcttcaccac    900
taattaagtt cgtgccgtgg taaatgtcac caaaggaacc actcccaatc ttcctgccaa    960
tacgaaattt ccttcctact cttaagtcca tctctttta atg                      1003
```

<210> SEQ ID NO 16
<211> LENGTH: 1003
<212> TYPE: DNA
<213> ORGANISM: Saccharomyces cerevisiae

<400> SEQUENCE: 16

```
tcactcaacc acctccaaaa aataacaggt tcatctaaag taaaagactt taacttgctc     60
ttagttttcca aattaaatat ctgcacgata gtaccatttg ctctaacgga ataaccatc    120
tgagatggat gcatgatagc agaatcaccg cccatattct tccttgtcac ttcattgcct    180
ttggccaaat ccacgattgc aacagagttt gtaccgtcct ttgtttctct aacagtgacg    240
aagtggtcac tctcgaaagt agttgatctg aagtcaagga attgagggga aattcctaag    300
gacatcagat cgaccaattc ggtaaattca atgggtaggt cactcattgg ttagaacttt    360
cgtgataatt tatttttata gttgaatatc ttctttctct ctcaactctg atccggattg    420
tcgaggtttc aataagttac tctgaacaac taatcaaaat atctccttat ttctgtagat    480
tccttcagtt ccactttta cttttcttaa ttctctttgt atttattcct agcgacgaaa    540
aatgcgagat ctcgaccaaa aaaggggggt agggtaataa aattaaccct attatttttt    600
aactttaaaa cctataatgt gctaatattt tattataaac ctccttttt tgcgttcaaa    660
ccctgacaca ttttaagccc tatatttacg gtattagttg attaaactcc gaagcgaaag    720
gaattcggtc attagcggct aatagccgtt ggggtaaatc acctacaagc aagtacacaa    780
gagaacgttg gcgttgttaa gtcaaagcac taatacattg gggctttaag agtgttata    840
```

```
aaggtctaac ctgtaaaaat tatttaaaca acttgaacag gccttaaagt tttcctcatt    900
ccgctcatca tcactaatat tgctctccgt ttttgaatac acacttgaca ctaataagta    960
tcacagaaaa aaagaaaata taataaatta gtattgcgat atg                     1003
```

<210> SEQ ID NO 17
<211> LENGTH: 1003
<212> TYPE: DNA
<213> ORGANISM: Saccharomyces cerevisiae

<400> SEQUENCE: 17

```
aaaacggctc ctagttatcg tcagttttga taattagtaa ctagaatata gtatcaccaa     60
gaacaggcca ggtaatatac tagaagttgt gtataactac taatattttt atacatatag    120
atgccaagtc aaggtccaat tagtagattt ttcactctac cttgcattat tacctgaaag    180
atcgtttgtg tttccttaaa ttcgccagag gtgcaaacga atgtaaatat ctacatcaat    240
ttacggtttc acgcccgttt cgtttctaat ggcaactcat gtaaactgtg ataaacccgt    300
tatttcagtt ttattttctg ctagtataaa ggatgatagt agccatttcg ctggaatatg    360
tatcgggttt aaaagatggc atagttcgaa acattttcgc acaagattct aactgtcttc    420
gaacgtcgta gaaaccgcaa cgcaagaaat gacagcgcaa taaaatttat tttactaact    480
gatagaacaa atgtaaaaaa tttcataata tcaagtagaa ttctttattc ctttgtgaa     540 ttcctaaacc catgaaaggg acttgtagta taagctggat acctatttc attggcttcg    600 tttccaaatg acacaaaacc atcacaaaag gaaatagtcc ttccatagtt acccaatcat    660
tctgttgcat attaaatgaa cagctccttg ttgataatgc cagtgtggca tattcaccgc    720
tgcagttatt tcttttcata tataatgagt catttgtttc tgtcatcact tttctatact    780
ttctcttccc cgcgtgtttt ccgtacacca acaatatatg ccataataca cgtaacattt    840
ttttataaaa agaaaaggta agtgatatat ataaaatagc gccatgagta ggaaactttt    900
ctgttactgc agatatgtgc cagactggct caggtggcat aaacacagat taatagtatt    960
ggcgttgctg aaataagaag atctgtaaca atatcttaca atg                     1003
```

<210> SEQ ID NO 18
<211> LENGTH: 1003
<212> TYPE: DNA
<213> ORGANISM: Saccharomyces cerevisiae

<400> SEQUENCE: 18

```
tctaaaaatg ttcaggacta catacatcaa ttaggtttca ttccaaaagt acctttgtc     60 aatttatacc caaatgccaa ttcacaagca ttagacttat tggagcaaat gctcgcgttt    120
gaccctcaaa agagaattac cgtggatgag gccctggagc atccttactt gtctatatgg    180
catgatccag ctgacgaacc tgtgtgtagt gaaaaattcg aatttagttt tgaatcggtt    240
aatgatatgg aggacttaaa acaaatggtt atacaagaag tgcaagattt caggctgttt    300
gtgagacaac cgctattaga agagcaaagg caattacaat tacagcagca gcaacagcag    360
cagcaacagc aacagcaaca gcaacagcag ccttcagatg tggataatgg caacgccgca    420
gcgagtgaag aaaattatcc aaaacagatg gccacgtcta attctgttgc gccacaacaa    480
gaatcatttg gtattcactc ccaaaatttg ccaaggcatg atgcagattt cccacctcga    540
cctcaagaga gtatgatgga gatgagacct gccactggaa ataccgcaga tattccgcct    600
cagaatgata acggcacgct tctagacctt gaaaagagc tggagtttgg attagataga    660
aaatattttt aggacaaaaa actataagta accggggaag tatagaatca ccatagatgt    720
```

```
aagcttacag acaatgtgta tatatgatgt atatgaacgt atacaaatat atatatatat    780
acgtgctctt gttgtagctc gtatatcaaa ttcctcctcc gacgcttatc ttaatcgtac    840
tccgcggaag tttgttatcg cctcttgaat tctttctttt cgttcattta tgattagtca    900
tctatagaca atattcatta tttaagcacc tagaatacta aactaaatgt ctaaatatga    960
cacaaggaag ataagataaa aaaaaccaag cgcttagaat atg                      1003
```

<210> SEQ ID NO 19
<211> LENGTH: 1003
<212> TYPE: DNA
<213> ORGANISM: Saccharomyces cerevisiae

<400> SEQUENCE: 19

```
catcgggatc ttccgactcg tcatcagacg tcgaggtcat tatgcactcc ccgagcgatc     60
ctgaatacgc tttaaaatca caaactctaa gaagctcgag tcagaccgtc attaatagta    120
agagaccagt aaagatagaa gacgaggaag aagccgtagg aatgtcacag ctcaattata    180
ggtcgtcatt aagacaagct cctccaagag ctccctcaac tttgtcatat aatcactcga    240
agaacaacga aacgccaatg caagatattt tcacaaatgg cgaaacagca ataacagaa    300 agaagaagag aggatctttt gcaaggcata gaacgatacc aggatctgac gtcatggccc    360
aataccttgc acaagtgcaa cattcgacat ttatgtatgc agccaatatt ttgggcgcct    420
ctgcggaaga caacacgcat cctgacgagt agtatagctg tgctgagcct gaagtataat    480
gcatatccat cggactattt agacaaagcc caaggaagcc taaggcggcc tgccaaggtg    540
tttctccctt tttttctccg atttctttgt ataaactaaa taatatagtg attactaatg    600
gaatggcggt attatgcacc taacctgttc attctgccac agattacgta agcgatttat    660
tgccggcact tgttgtctta atgaccgagt caccaatgtg gaacgataat tttctctgac    720
tcaaacctgt taattttttt ctacttcgtt tcgttagcga cgacgtcaag ccgcaggatc    780
ctgtctgcct tgacctcttc tctaccttca gaacttacac ttttcaggta agatgacctt    840
tatataaaag ttgacactat tacagttgtt tataaacgtc tgaagaatga gacgttttta    900
taaaatgaat aaaatgcata ttctaagttt aaaacaacat tttcaaagtg tacgattgta    960 aaagagagg caattagaga atctcaaaca ggtaataata atg                      1003
```

<210> SEQ ID NO 20
<211> LENGTH: 1003
<212> TYPE: DNA
<213> ORGANISM: Saccharomyces cerevisiae

<400> SEQUENCE: 20

```
gaaatccaat gagaataccg cataatcttt cccaattacc ttgatattta caaaagacca     60
tagatcctta ccctggtaaa gcttgtaatt ctgtgaatcc gttccctcca attggatttg    120
attagtggaa gtcaacttgg acagtaatgt actacccggg ttttatgca ctccatagat    180 caaaggatat ggaaaccaaa attccgtcga caattgtggt gactcaaaga tcaaatggtg    240
agtagtcaaa tgtaaagtac cttgtgtggc cgtacctctt ctatgcagca ctacattaga    300
tactttggca atcttgatgt actccatctt tgcggaatgg tatactattt cttttccctc    360
tttttagcac tattacaccc cgcccacaaa ataaaaataa taacgacgac ctaatctcac    420
caagtgaccc ttgtaaaacc tccttttctt tataatgttt cttttcttac taatatttgg    480
tacatttagg gtagtgataa aagaatggca acattgttat tattgtgaaa aatgaggaaa    540
```

```
atagaaaatc agaaaccta aaaagtgatt ttacccatc agaaatattc aaatgtccta      600
attaaaaata gtaaatcccc taaacattca gattgtaaac tagggttgag aaaatgactc      660
atccaccact gtcttctttc ctgcggcatt ctatagatta ttgtgaatga ctcttattga      720
tgagatggca ataactttg aatatcagag ataggaacct ccatgtcgta acgattgtgt      780
caccttgagt aagcatcgag aaaatccaat ctttttttt ccgtcataag catttctgcc      840
atgctatttg tatatata attactaata cgtcttctat agtatgcctt atctcttttt      900
tgaagcgcta tttaagttta agcatcgaaa aactaacatc tatagttaaa attagttcta      960
taaaggaaga gcaatacagt acatagacag gaagaaaaga atg                       1003
```

<210> SEQ ID NO 21
<211> LENGTH: 1003
<212> TYPE: DNA
<213> ORGANISM: Saccharomyces cerevisiae

<400> SEQUENCE: 21

```
gaattacgag aagcccaatt gaccatcgaa aagctacaaa ggaaacaact acactacaaa       60
aggctactcg atgaccaaag aatggtcctc gaagaagtgc aaccgacttt tgataggtat      120
gaagccacaa tacaagaaag agagaaagag atagaccatc tcaagcaaca attggagctc      180
gaacgcagac agcaagccaa acaaaagcag ttttttgacg ctgagaatga acagctactt      240
gctgtcgtaa gccaactaca cgaagagatc aaagaaaacg aagagagaaa tctttctcat      300
aatcaaccca ctggtgccaa cgaagatgtc gaactcctga aaaaacagct ggaacaatta      360
cgcaacatag aagaccaatt tgagttacac aagacaaagt gggctaaaga acgcgaacaa      420
ttgaaaatgc ataacgattc gctcagtaaa gaataccaaa atttgagcaa ggaactattt      480
ttgacaaaac cacaagattc ctcatcggaa gaggtggcat ccttaacgaa aaaacttgaa      540
gaggctaatg aaaaaatcaa acagttggaa caggctcaag cacaaacagc cgtggaatcg      600
ttgccaattt tcgaccccc tgcaccagtc gataccacgg caggaagaca acagtggtgt      660
gagcattgcg atacgatggg tcataataca gcagaatgcc cccatcacaa tcctgacaac      720
cagcagttct tctaggcagt cgaactgact ctaatagtga ctccggtaaa ttagttaatt      780
aattgctaaa cccatgcaca gtgactcacg ttttttatc agtcattcga tatagaaggt      840
aagaaaagga tatgactatg aacagtagta tactgtgtat ataatagata tggaacgtta      900
tattcacctc cgatgtgtgt tgtacataca taaaaatatc atagcacaac tgcgctgtgt      960
aatagtaata caatagttta caaaatttt tttctgaata atg                        1003
```

<210> SEQ ID NO 22
<211> LENGTH: 1003
<212> TYPE: DNA
<213> ORGANISM: Saccharomyces cerevisiae

<400> SEQUENCE: 22

```
tgatgcagtt ggagtcggta gcgatgttat aggaggagga ggtgcactag gaggcaaagg       60
aggcgccata gcatccgtat ggggggtgg tgcgttaaaa gcattcgatg atgtttgctt      120
atgtaatttg gattcaattt catccagaaa cgacatacca ttttggctac tctgtttagg      180 cgggttata gatggagaaa taggagaagg tcttacgtta tcatccttag atgaacctat      240
tacatcctct tgtttatctt gggtagtgta tccagtatca ccaccaacca cgaatctatc      300
atctctcttc ttttggatct cagcaagaaa tggtaagggt cccccaggtg ttacggccga      360
ggaagaactg gatgaagata ttttggattg cttactggac gctgagggtt tgtttgtcgt      420
```

```
gagtgttgga ggaggaggag gagccgatgg tactgacgtt gcaaccgaag gaggaggagg        480
aggtggtagt ggtgctaaag gaatagatga tgctgacaag gcagaggatg ttgaaaaagc        540
accaggtggt gggggaggag gaggtggtgg cgcgggcatt gacgatgctt tgttaggagg        600
aactgatgta gtatttggta acggtggtgc taaagttggg ggaaccgggg ttgcttttac        660
gctgttagtc gacgcagagc tcatggctgc tggtagtggt ggtggaggcg gagctggagc        720
tgaagttgct ttttaggtg cagaggtcac atttggtaac gatggtggag gtggtgcagt        780
aggcggtaat ggcggagcat gtgatgtagg aatgggcgga gcagatgatg gaagtggtgg        840
ttgtgaagga gatttatgat tttcggtttg aatctttgtg gaagaaacgc cctcgacggc        900
tcctcgttca gacctcctgg cattaatttc tgccaaaaat ggcaaccgc ctgcaggaac         960 ttcagaagat ggtggtgaga ctgcgttatc tgtaggttta atg                        1003

<210> SEQ ID NO 23
<211> LENGTH: 1003
<212> TYPE: DNA
<213> ORGANISM: Saccharomyces cerevisiae

<400> SEQUENCE: 23
tgaataagcc tgtataactg cgcatgtaag aatagtggct gcaatagatc ccacagcagt         60
cagtgctcca gcctgctctt tcaaatccgt cgtcgtaagt ctatcaacag gtaatcggtc       120
aaatgtgaca ttatttgaga ttcccaacca aaatgtgggg taccaaagta ttacttttgc       180
tatgggcgat ccattttcta gtgttctttt caccgcactc ttccaaacga cgtataaaac       240
aaagcataaa ggtaaaagtc tttgaaatcc cacactgaaa agctcataca cgctagctgg       300
gtcatgtgca tccgttagta atggagggtc tagagataat acaagagtcc aatagcccac       360
tatcgtgttt atccagtacc cgtaaatact gtcatacaaa taaaatattg gcagtccaaa       420
aagcatattc aatgcgacca cagctgctcg aggatcataa cagcccgaca ggataccgcc       480
ttgtatatct ctgaatgaat atgaaccggg aaaaaatgaa ttgaatgcta ctgaaaaccc       540
agtgttatac attcctttt ttgatggaaa agaattttgg gcccttgca tagaaacttt        600 ggtacagcca ccgtaaaatg gtgagataac acctgcatgt actgcagagg cgcatggaaa       660
cgagtcactt ctataagggt aggacacgac catcgggtct tcttcgctaa acagggcacc       720
tccgccaatt tcatacccctg tatatttgac tctcctattc cctacggcaa tggcggagta       780
tgtccatcca cctctatcac acagtgctgg acatctgatc atgtattctt tattatcaag       840
tggaccgcag tttttagcat ttaaaccaca ttcgttattg gtaccctccc agttcaagta       900
ggaattgcaa cttaaagaca atataggaat cttttctgag ccatcatttg gatggaagta       960
tggcggcttg ataagatagg ggtatatgag agaataaaaa atg                       1003

<210> SEQ ID NO 24
<211> LENGTH: 1003
<212> TYPE: DNA
<213> ORGANISM: Saccharomyces cerevisiae

<400> SEQUENCE: 24
ctggctattt atataagatg ttgctctaat tccatgagtg atgtcccatc gcatgatgaa         60
gaagttatga atgaagtgaa caatatcatc gaattacaac aacggcccat gcaaatgacc       120
aagtctaccg tacgtaccag gagaagacca ccaccacctc ccattccttc cactcaaaag       180
ccatcgttga cagaagagca aaccgaaagt ataagaatgt cacgccgtaa taaagatgag       240
```

-continued

```
aacaatgcta aaagagttgc cccaccaccg ttgccgaaca gacagttacc taacttagac    300
gctaatactt actatgtacc atcctcacaa aatgactatg gcatgtatgg tgctttcatg    360
gataaaaaag cagatgaatg aagagaagaa gtaatggact caattcaaaa attgagcaat    420
caagacacca cattgatgtt cttttcggat ccggcattaa gtttggaaga cagtattcgc    480
agaattaggg agaagtattc aaactaaata cactgttatt tatatacatc gggagggagt    540
ttaaaaattg tatacactaa agtgacctta tgaattggaa ccattttcaa cgttttagag    600
tgatgttgca tccttttcat cagatcggga aattaaaaaa acggttatag aagggctaaa    660
tgtaaatatg taaattttat gaagtcaaga gtaaagaaaa tcttcggttg ccgatcaaat    720
acactcttac aaaataccct aaactcagtt tatctttcca ttccaactga ttatcgcgta    780
cgccttggtg accaaccata ccctaaaatg tcaatttccg gggcggaagg ggtccttaaa    840
ctgcaaagcc tcttcccatg taaataaaat aaatccgtag aatttattaa atattgtcat    900
attataagtc gggaaaggcc ttctgaatgc acgtatattg accaaataga gttagattca    960
aattatttat tacatttttt cagcatcgaa gttaagtaga atg                     1003

<210> SEQ ID NO 25
<211> LENGTH: 1003
<212> TYPE: DNA
<213> ORGANISM: Saccharomyces cerevisiae

<400> SEQUENCE: 25
ggcgaaagag ctgtgtatga gaataacgag accggtgtca ttaagaacct ggaattgcaa     60
aaggccacca tccagggtta cgacaatgac atgaggccag tcatccttgt gagacctaga    120
ttacatcatt cttccgacca aactgaacag gagctggaaa aattctccct gttggtcatc    180
gagcaatcaa agcttttctt caaagaaaac taccccgcat ccaccaccat cttgttcgat    240
ctgaacgggt tctccatgtc caatatggac tatgcccccg tcaagtttct aatcacttgt    300
tttgaggctc actacccgga atctttgggc catctactta tccataaggc cccttggatc    360
tttaacccga tttggaacat catcaagaat tggctggatc cggtcgtcgc gtccaagatt    420
gttttcacta agaatatcga cgaattgcac aagtttatcc aaccccaata catccctagg    480
tatctgggcg gagaaaatga caatgatttg gatcattaca ctccaccaga tggctctttg    540
gacgtccatc tgaaagacac cgagactcgc gctatgatcg aaaaggagag agaagaattg    600
gtcgaacaat tcttgactgt cactgcccaa tggattgaac accagccatt gaacgatcca    660
gcatacattc aactgcagga gaaaagagta caactttcca ccgctctttg tgaaaactac    720
tccaagttag atccgtacat cagatcaaga tccgtttatg actacaatgg ttctctaaaa    780
gtttgagcca agccacgcga cgctccatac tgtatagacc tttattataa aaacatctat    840
ttctttatat gtccctctat cttattttc ttttacttt atttgtataa tacgcgaaaa     900
attatagaat catttattat caaaaacaat caactatgaa atgaaaaaca atacgcctgc    960
taatacggtt cgcccttcaa ttttttgtttt ttttacatga atg                    1003

<210> SEQ ID NO 26
<211> LENGTH: 1003
<212> TYPE: DNA
<213> ORGANISM: Saccharomyces cerevisiae

<400> SEQUENCE: 26
agataagaat atgagggtaa caatgaatga gaactcactt tgtaatcacc agttgaagaa     60
tggtaaacaa ggctagtaat acatcctggt atttcggtct catgttcaaa ataatcagtg    120
```

```
gtaatttata ttatgtatat cttttccttg tttctttgtt aagcttttgt gtaaacatac     180
tttagtaatt gtgacgtttt ttggcacttc gcacaggcgt gactagtttc tgtgaacaga     240
gggcgtctat tcatgatctt cacaaatctt gggggagtta atttactctg cttccacatt     300
acattgatgc gcagtgatct actgacgcct gctggtggtg agtacacatt agataaatac     360
ctagggtgtg cagcaataga ccttaaacaa gggtgagctt tgcctattag agaagaacct     420
ctaactgcgc ttttcaataa tagccaccga acaattggca tattatgcaa cctgtgtttt     480
taagtacctt tttatgtcag attttttgaa ctatccttcg attgttattt cttgatataa     540
cgtttacatg atttcttaat ttacaacgcg gacgaattag attgaaatta tttagcatat     600
ctgtctaaga gcacattaga tcgaagtacc gtagcacatc tgccatacta tcaaatgcat     660
catcacgaaa aggcgcagtg ttgatggata gtaaatatga aaaggatctc ttcttaggtg     720
ttccaagcct cgcttcacgt gtaacataca cagtttagaa gtttaccaaa ccgcggcaag     780
gcgctgtaag gttcaagagg ctttgaatta tgctatctta ctatcttgcc gcaagttgct     840
gtcaggtgta gttcctaggc ggctcgttga caagacccct ctgcccaatg acttctatat     900
aaagtatggt tttctttttta aatacagtaa ttccatgaaa aaagagggc caaaaagatc      960 aagcaataaa ccaaccgata tataaaacac agaactgcag atg                      1003

<210> SEQ ID NO 27
<211> LENGTH: 1003
<212> TYPE: DNA
<213> ORGANISM: Saccharomyces cerevisiae

<400> SEQUENCE: 27
acagaagtaa gtaccggggt acctaaatat acgcataaaa gtctctttct ttttttttt      60 tttttttta gcttcctaca tttcgttaat aatattatat agattatatt tatatttaag     120
aaaagtaata tcagcatatt atgaatagac aaaaaagtct aaggtcaaga tttattaaat     180
gttagattat taagattaca attaacaaca tttgttgtta cttcataaaa tttcgttact     240
tcataaaaga actacagtcc cccacttcta aatgagtggt tgtaggggtt catataccct     300
ccatactgtt ggaataaaaa tcaactatca tctactaact agtatttacg ttactagtat     360
attatcatat acgtgttag aagatgacgc aaatgatgag aaatagtcat ctaaattagt     420
ggaagctgaa acgcaaggat tgataatgta ataggatcaa tgaatattaa catataaaat     480
gatgataata atatttatag aattgtgtag aattgcagat tcccttttat ggattcctaa     540
atcctcgagg agaacttcta gtacattcta catacctaat attattgcct tattaaaaat     600
ggaatcccaa caattatctc aaaattcacc aactcttcac atacatacct gcggtagcaa     660
gataggtaca cttttctac gtttcacgaa ggtagcgata ggtacctcac tcattgtagg     720
tgcgggggta gcgatggagg tttctgtacc attaccacca cagccactat actcacgtag     780
tgaagtccct agcgtggaat tgtgtggtat cgttgctatc tgtcgttcgc caccctcggt     840
atatccaacg tgcaggccaa tatcactctc taagaaaatc gtatcaggat tggtacggac     900
aaactcttca tagcctacgt cgaaatcaaa ttctgctaaa gctgtgactg tagttaaacc     960
taaaaccgcg attattgctt gaaaaactgt ggagaaattc atg                      1003

<210> SEQ ID NO 28
<211> LENGTH: 1003
<212> TYPE: DNA
<213> ORGANISM: Saccharomyces cerevisiae
```

```
<400> SEQUENCE: 28
tgtcatcgcc gccagaacgt gctccttact gtgggacgtg ccactggtgg gagtaaacca      60
ctgcattggt cacatcgaaa tggggagaga atcactaaa  gctcaaaatc ctgtggtact     120
gtatgtaagt ggtggaaata cacaagttat tgcatactcg gaaaaaaggt accgtatctt     180
tggtgaaacg cttgatattg ctatcggtaa ttgtcttgat agatttgcaa gaactctgaa     240 gataccaat  gagccctcgc ctggctacaa catcgagcag ttagctaaaa aagcccctca     300
caaagaaaac ttggtagaac ttccctatac agtaaagggg atggatcttt cgatgagtgg     360
tatattggct tccatcgatt tacttgccaa ggatctattt aagggcaata agaaaaataa     420
gatcctattc gacaagacaa cgggcgagca aaaagtcact gtagaggatc tttgctactc     480
tctgcaagag aacctattcg ccatgctagt tgaaataaca gaaagagcta tggctcacgt     540
taactccaat caagttttga tcgtaggcgg tgttggttgt aacgtgcgat tacaagaaat     600
gatggcgcaa atgtgtaaag acagggccaa tgggcaagta catgctacag ataataggtt     660
ttgtatcgat aacggagtta tgattgccca agcaggacta ctagagtata gaatgggtgg     720
gatcgtgaag gacttttctg aaactgttgt tacgcagaaa ttcagaaccg atgaagtata     780
cgcagcctgg cgtgattaac gattttttgtt acagttagcc taatgttcac actacgaata     840
tatatatata tttatatatg ccatacacct tacatttaca gctcagtgta taaccttgtg     900
gaagcgcgaa ataagcaag  agacatttga aaataatcaa taaacaaagc tcaaaaaaat     960
tagatcatca cctaacaaaa taagacgtgg caattacaga atg                      1003

<210> SEQ ID NO 29
<211> LENGTH: 1003
<212> TYPE: DNA
<213> ORGANISM: Saccharomyces cerevisiae

<400> SEQUENCE: 29
ggcaacatag cagtacgtcg ccaaaaagaa cgaaaacaaa atagatatta tgcataaact      60
aacgtgattt tcatacagat attgcaattc aggcaattgt ccatcagtca atttccatct    120
gatagccaaa actaagacca aagttgtaga catggcaatt ccattgatct tatacgaaag    180
cttcgaacca tcccttaact gaacacccctt catgactctg cccggtaaaa tgacgtccaa    240
aactgccagt attccatacc acaggcaata gacagtccat aattcacgat tgcccagata    300
gtagcgcaat ggcttgatac cgttccaaag ctcaactata tcgaaattct ggaaaaatcc    360
cttaataaaa taatcgggcc ttatcatttg attcaagatg atagtgaaaa caggcagccc    420
tatgctgatg cctaaggcac caatcagccc accaaattca aactctgtag ttctgggatt    480
caaagctgat accatccttt tattctctac accgaatttg tctttactcc tatgctgttt    540
acaaggtcta tctgataagc aattgcgcaa gaaaatagta gaatgaaaac tgattattaa    600
aaacaaacgt aaactcaagc ctcacttgat gctcagacgg agtacgtgaa aaacgtccgt    660
tatgcaaaac cctttatatg cacaaccttc acacaatgca aatttccgat gatgcctaca    720
tacaaaagag cgaaaggcga tataaatttt tttcacggga ttttcgttta ggtgaaaata    780
aaatgaacga cagagcatgc agagtccggg taatacatat gtttcaatac tgtttcaata    840
ctgtttcaga agtgcgtcac atattaattt taacttataa ctggcctgtt gctggcaaga    900
ggtatatata tatgacgaat gtgaccaaca taagtcctta agataatccc gaaatatttg    960
gttaggatga ttccctttcg aatttgtgaa cgttgatgat atg                    1003
```

```
<210> SEQ ID NO 30
<211> LENGTH: 1003
<212> TYPE: DNA
<213> ORGANISM: Saccharomyces cerevisiae

<400> SEQUENCE: 30
ctagcggtct acattcgcta tcaactgaac gaatagtgat gcaatctgaa ccttaaactt      60
ttcgctcgct tttactttcc agaaaaaatt ttcttcattg ggattcctct gctgacaaac    120
gggctcacag aactgaggaa acgagaattt tgttaatcaa agcaacatta cgggaaggaa    180
cggaaccgtc tcgttgctgt gggcgcgagt tcgacgcaag aaaaaaatgc tgcagcatcg    240
tcttttgtga acgccaagaa ggagtccggc gaaggtattg ggcgtcacaa cctttttattc   300
tccgcagtgt ctcttgccta caaagcctgc agaagctttt atgccggggt gtacgtatgt    360
taatcagtta cccttttccta ctgtgtgccg caccccctcat ttgctctcga tacgagaagt  420
tccgcgccga ttctggcctt tttgttttct ggctagccta ctttcagggg acgtgccttc   480
ttatgccgct gtaaattaca gcagagattt agatctgagt gaaaacgtgg cgaggaaaaa   540
gggtacaccg ttaaaagcgt agacacaatc ccactttgtt gtgccagtc ttctctgctg    600
tattttaatt ttctgtttga acttttttcc gttcttttcc atcattgttt aattttact    660
ttgagtgggc ttctcaaaag aaaaaaatag ctggtattgt attttttaccg taggcgtttt  720
cttttgtattt ttcccaagag cagcagcacc ttttatatac cttggttaca cattgtaagc 780
ctcaaaaatc gtcctatgta agtgtcttat cgcatcatac ttaaggtcaa acctgtaaag  840
cgcgcttcta gttttatttc tactactcgc cttggctctc gagatcgctt aggtagttta  900
atagttagtc acaccacccc acccattcgc ttagaatata gaatatagag cagttgcagt  960
acacgactca ttttagcaac gataagagta taaattggaa atg                   1003

<210> SEQ ID NO 31
<211> LENGTH: 1003
<212> TYPE: DNA
<213> ORGANISM: Saccharomyces cerevisiae

<400> SEQUENCE: 31
tccttataac ctgtaaaaaa aaaaaaaaaa aaaaaaaga agggtttaaa taaaaatcgg      60
acttactcaa agggttgaaa agcactttaa tataggtttt tagtttcggg taagaagatg   120
tgtcaaaggt ctcgaaaagg aaacattagg gcaaatacgt aaaggttgcc ttcgtatctc   180
gtttccacag caacgagaaa cgagatacga aggcaactga ttcccagcat ataaaaggcc   240
atgaatttt ggcgtttcct attgtctttt cgaaactatt tctttcattc ctttcctttc   300
tgttctttt acttataaga aaataatat acgtatatat ataactacaa accacatcag    360
caataaaaaa aaactatatg accatggacc aaggccttaa cccaaagcaa ttcttccttg  420
acgatgtcgt cctacaagac actttgtgct caatgagcaa ccgtgtcaac aagagtgtca  480
agaccggcta cttattcccc aaggatcacg ttccttctgc aacatcatt gccgtcgaac   540
gtcgcggcgg tctttctgac attggtaaga atacttccaa ctaagagcat gcttctcttt  600
tttttttgtag gccaatgata ggaaagaaca atagattata aatacgtcag aatatagtag 660
atatgttttt atgtttagac ctcgtacata ggaataattg acgtttttt ttggccaaca  720
tttgaaattt tttttttgtta cctcgcgctg agcccaaacg ggctccacta cccgccgcgg 780
tcgccatttt gggaagtcat ccgtcccaaa aaggaaatag ccataacata tcgttactgt  840
tttggaacat cgcccgtttc gcccgattcc gcctcagcgg gtataaaaag agatcttttt  900
```

```
ttttcctggc tgtcccttcc cattttaaa tgtcttatct gctcctttgt gatcttacgg    960
tctcactaac ctctcttcaa ctgctcaata atttcccgct atg                    1003

<210> SEQ ID NO 32
<211> LENGTH: 1003
<212> TYPE: DNA
<213> ORGANISM: Saccharomyces cerevisiae

<400> SEQUENCE: 32
aatggcaaac tgagcacaac aataccagtc cggatcaact ggcaccatct ctcccgtagt     60
ctcatctaat ttttcttccg gatgaggttc cagatatacc gcaacacctt tattatggtt   120
tccctgaggg aataatagaa tgtcccattc gaaatcacca attctaaacc tgggcgaatt   180
gtatttcggg tttgttaact cgttccagtc aggaatgttc cacgtgaagc tatcttccag   240
caaagtctcc acttcttcat caaattgtgg gagaatactc ccaatgctct tatctatggg   300
acttccggga aacacagtac cgatacttcc caattcgtct tcagagctca ttgtttgttt   360
gaagagacta atcaaagaat cgttttctca aaaaaattaa tatcttaact gatagtttga   420
tcaaaggggc aaaacgtagg ggcaaacaaa cggaaaaatc gtttctcaaa ttttctgatg   480
ccaagaactc taaccagtct tatctaaaaa ttgccttatg atccgtctct ccggttacag   540
cctgtgtaac tgattaatcc tgcctttcta atcaccattc taatgtttta attagggat   600 tttgtcttca ttaacggctt cgctcataa aaatgttatg acgttttgcc cgcaggcggg    660
aaaccatcca cttcacgaga ctgatctcct ctgccggaac accgggcatc tccaacttat   720
aagttggaga ataagagaa tttcagattg agagaatgaa aaaaaaaaa aaaaaaaagg    780 cagaggagag catagaaatg gggttcactt tttggtaaag ctatagcatg cctatcacat    840
ataaatagag tgccagtagc gacttttttc acactcgaaa tactcttact actgctctct    900
tgttgttttt atcacttctt gtttcttctt ggtaaataga atatcaagct acaaaaagca    960
tacaatcaac tatcaactat taactatatc gtaatacaca atg                     1003

<210> SEQ ID NO 33
<211> LENGTH: 1003
<212> TYPE: DNA
<213> ORGANISM: Saccharomyces cerevisiae

<400> SEQUENCE: 33
ttcttttttt tttttttttt ttcttttttgg gaacggggga aaaggtctca ctagtatata     60
aaggaaagag agtacagcac gaatgagcca gctgcaggaa agggctagg ttaaaaaata    120 aaacccagc agaaagcaaa caaccaaata taatttagaa atggacagag accatattaa    180
tgaccatgac catcgaatga gctattccat caacaaggac gacttgttgt taatggtttt    240
ggcggttttc attcccccag tggccgtctg gaagcgtaag ggtatgttca acagggatac    300
actattgaac ttacttctct tcctactgtt attcttccca gcaatcattc acgcttgcta    360
cgttgtatat gaaacgagta gtgaacgttc gtacgatctt tcacgcagac atgcgactgc    420
gcccgccgta gaccgtgacc tggaagctca ccctgcagag gaatctcaag cacagcctcc    480
agcatatgat gaagacgatg aggccggtgc cgatgtgccc ttgatggaca acaaacaaca    540
gctctcttcc ggccgtactt agtgatcgga acgagctctt tatcaccgta gttctaaata    600
acacatagag taaattattg cctttttctt cgttcctttt gttcttcacg tccttttat    660 gaaatacgtg ccggtgttcc ggggttggat gcggaatcga aagtgttgaa tgtgaaatat    720
gcggaggcca agtatgcgct tcggcggcta aatgcggcat gtgaaaagta ttgtctattt    780
```

| tatcttcatc cttctttccc agaatattga acttatttaa ttcacatgga gcagagaaag | 840 |
| cgcacctctg cgttggcggc aatgttaatt tgagacgtat ataaattgga gctttcgtca | 900 |
| cctttttttg gcttgttctg ttgtcgggtt cctaatgtta gttttatcct tgatttattc | 960 |
| tgtttcattc cctttttttt ccagtgaaaa agaagtaaca atg | 1003 |

<210> SEQ ID NO 34
<211> LENGTH: 1003
<212> TYPE: DNA
<213> ORGANISM: Saccharomyces cerevisiae

<400> SEQUENCE: 34

| cgctcccacg acatgcgcat ctcttccaaa aacactacca ctttctactg actcactggc | 60 |
| catttgagaa ccacagagac ttggtagatt ccatcgctgt aaacaatggg aaactaaatt | 120 |
| caacgtcttc aaggagcgtc tggctgaagg cggattggaa acactgtttt aacgttaaaa | 180 |
| acccttgggt ccaaacgccg ccatcgttaa tgcgtctgag tgggacagat cttgatacct | 240 |
| tcacaccaga gaggatattc ctgataaatt ctcttggaaa ccactacaaa ttttttaatag | 300 |
| cgaacagtca tctaagctac aatcacaaaa atacccctc cctggcgtg caaattcctg | 360 |
| tcaggaacgc tcttggcgaa gtttctccgg ccaaacaaat tgcccaactt ttcgcaagac | 420 |
| agctgtctca tatttacaag agcctcttca tagaaaaccc cccgctctct cctgagaacg | 480 |
| agctggcatt gactgccgtc ttctatgacg agactgtaga gcgacgcctt agaaggctct | 540 |
| atatgcgagc ttgtgcaagg gcatatacga ctactaatgc cgactccacc acggagcctt | 600 |
| tgatgtttca ttgcacccgg tgggaagttg attagttgtt gttggctgtt atactggagt | 660 |
| aaatgtcacg tgccactgtg gccgtgtcag gtcacgtgaa gagagaaatt cggccacagt | 720 |
| tgtggtccta aacaaggact gaaaaagatc gcagaaacta gcaacgtcgg atagcggtat | 780 |
| ggttgaacca aagtccagtt tttagtcata gccggttgag ggatgatctg ccgttcagtg | 840 |
| ttctgcgttc aataatacgc atatatatat atatcaaggt atcaacacaa tacttgaaca | 900 |
| ggttaggctc gtactaaagc ctggaagttt ttatctttct gtaacatttt tctttcttga | 960 |
| ggtgtgtgtg tgtatagatt agcagggaat tatctaagat atg | 1003 |

<210> SEQ ID NO 35
<211> LENGTH: 1003
<212> TYPE: DNA
<213> ORGANISM: Saccharomyces cerevisiae

<400> SEQUENCE: 35

| cgactaacct ttttcttggc agtatggaga ctgactaggt ctcccaaaca ttcattgtaa | 60 |
| ctgctgttta aagattttgt tctaacctaa attcaagtga gaagctgaac atgtgtctct | 120 |
| acttatgata tcacgacagc aaatactaat cttgccataa atagtctagc gttttgcaac | 180 |
| ttacctctag atatattta tttcttgagg aaccgttttc gtcggtaata acaaaatact | 240 |
| actgaaacgc cacagcattg agagaatacg ttatcgatta cggctttctt ctcgctccag | 300 |
| atgtcgcggg taagatattc acctcaaact tttcttgttg agtgtcgtca caaatctaga | 360 |
| acctacatgc catctcaacg atttttctgg agaaaggcct cactccgttc cgtacgtaat | 420 |
| gcatagataa agtatcagga tcttcacgat gctcgagagt tacttagtag tctgagttta | 480 |
| tgcgaaaaaa actccgccgt tgtaataatc gggaatacac agaagtagta ctgcactatc | 540 |
| actgggatac tcaaaaacct tctttttaac ttttctatcc cacaaataga acataggaaa | 600 |

| | |
|---|---|
| gaacattgac tcctccactt gaagttaaat tacaggaaca aacgcctaac tataatttcg | 660 |
| acattgttgc atcaacgaat cgaccgaaag aaaaatctgg agttgcagtt atcacttgta | 720 |
| tgtgcactaa gatttatatt tttactcctg agatctgcca aatcggtagc ttattgaact | 780 |
| gcgttccttt ttcccctgag ttctcgaggt acctgcggct ttgtctgtgc catctccccc | 840 |
| actttaaagt accccacgtt actaccgcgt ttttccccac cccggcttaa ataaattagc | 900 |
| tatatcttgt tgacttaaat acggagaaaa gaagaaaacc ttcaagaaat gcttcattgt | 960 |
| cttgtcaaaa gagctaaagt aaaagagctc tagttcgaag atg | 1003 |

<210> SEQ ID NO 36
<211> LENGTH: 1003
<212> TYPE: DNA
<213> ORGANISM: Saccharomyces cerevisiae

<400> SEQUENCE: 36

| | |
|---|---|
| ctgtcgagtg ctggtggcgc ttgatagcgg tattgtactt aataggtatc gccttcattg | 60 |
| gtttgaaatt ctcgatcaaa ttctgcagga tagggtcctg agcaggcaca gaggcttgtt | 120 |
| tcagagtaag ggtctccaat ttctgtttaa gggcatgatt ttccgattct ttcgcttgaa | 180 |
| gttcattttg gaggcggttt agtttcgttt cgtagttttt aacgaccctta ctcagtgact | 240 |
| ctatggtttc ctccagcact tgcaacttgt tgttttttgcg ttctctgtag gccctttggg | 300 |
| cgtctctatt ctgccgtttt ttcttctgta gctcctcatc attttcttca gtttcgtaat | 360 |
| cttcgtgaag tcgatgaact cttttcctcc gctgagctgc tctatggggc aaccttggag | 420 |
| gcagtttcca atttttggac acgtggatct tggacaaaag agcgaggtgg cttcctcag | 480 |
| actccttagg ttttatcaga ggtagagcca tgactgtgat aatatgctag ttacactgtt | 540 |
| tatgttgtgt gaacttgttg taatatggtt aacttcactt tcagtgattg atatgatagc | 600 |
| gacatcactg ccgtgcaaaa agaccattcc attactgcac cttttttgtcc ttttccgtgg | 660 |
| aataaaagtt cactcgtcag ttccatgcat tctggaaaaa aatgatctga agatgccac | 720 |
| agttgtgggg cccgcccggc ccaataggta aactaaaata caatagaagg ggtactgagt | 780 |
| gcacgtgact tatttttttt ttttggtttt aggtttcgct ttttttcacct ttttctactt | 840 |
| tctaacacca cagttttggg cgggaagcgg aaacgccata gttgtaggtc actggcgtga | 900 |
| gtcaaggccg ggcagccaat gactaagaac acgaggtaac ttgaatttaa ctatttataa | 960 |
| ccagtggtag ttacgaagac aaattgtttt gttcgtcaat atg | 1003 |

<210> SEQ ID NO 37
<211> LENGTH: 1003
<212> TYPE: DNA
<213> ORGANISM: Saccharomyces cerevisiae

<400> SEQUENCE: 37

| | |
|---|---|
| caattttgaa aattgacata taaaactctg attctgcaaa gcctcttgcc ccaaaaagat | 60 |
| tcaatagcat gcttaaaacg aacgcgattg caacccaggc agcaggattg accgatggtg | 120 |
| cccaataaga gatggtaagc gaacatccta ccagctcgct agggtaagat atgagccaca | 180 |
| tcaataagta gttaattcct atactgaagc cgactgatgg gtctataaat ctactggcgt | 240 |
| gcagcgcata ggagccggaa acagggtact gacatgaaag ttcggcccca cactgaacaa | 300 |
| cacagagcat agatgcgccg accaacaaga aaccaattag caaagaagca ggtccggacg | 360 |
| ctagtgattc ccctaaacca atgaaaagac ccgtccctag agtacctcca atggctatca | 420 |
| tggtcaggtg tctttgatct aggacctttt tatacggctg gttggctaag tcccattgta | 480 |

| | |
|---|---|
| tttttttcttc ctctgaaagc tccgaatacc gcaaaccttc ttggatcgct ggtgaatcat | 540 |
| ttcgcttgaa agagttcttg aatctgtgta ttagattatt tccttcattc gaaggcgtac | 600 |
| ttaacacgct agtggaaaac tgaaccttcg aaagtttggt agattcaaat tcatccattt | 660 |
| cgggtatctt tcatggtatc ctgatggaga actcttgacg gtgattactt aaccacccaa | 720 |
| atctgtaaaa tatatacgca tttatttcct ggcatctctt cgctatcccc gcaaaaagtt | 780 |
| aatgaaaaaa agccattcct gcaggaactg tggaaaagta aaaactgtgg catgaaagta | 840 |
| ctaccaaatt gtggcgaggt attcaatggt aatagcaaaa cagcaacaac gccaatttga | 900 |
| aaatgtacta ctaaggaaga taatttaaac agacaagttg tagaagaaat ctgaatcagc | 960 |
| aactttagt gtgcaacttg aaaaagtaat caaaaaacag atg | 1003 |

<210> SEQ ID NO 38
<211> LENGTH: 1003
<212> TYPE: DNA
<213> ORGANISM: Saccharomyces cerevisiae

<400> SEQUENCE: 38

| | |
|---|---|
| cagttttcct tttgaatgaa ggagaaaagt gttctagaaa tatgttttag ttctaagtat | 60 |
| cgttgtctgg agcaagcaaa gaaaagcaga cctgtatgtg caactttctt gttttccatt | 120 |
| aaaatctcaa gaaccggccc cttgactgtg ctcatatatc aagtatcggt tttaaagtcc | 180 |
| cctaattgtg ataattgcaa gaatgacagt caaaaagata ttttcttt ctttcttttt | 240 |
| acctatcctt catgaaaata cctatgctga tactgaatat cttcatttgc agctatgcaa | 300 |
| tatttcagat actgcatttt acccaagagt ttcttactg gtggttggat tttttttaag | 360 |
| acgagaagat taccagtcct ggatgttcat gaatgtgcct attgcgtcat cagcgactcc | 420 |
| gcgccaagaa aagaaatact cgcatgctcg gatttataga atcgcataat ggaaatagct | 480 |
| tccttaaagg atggagataa ggaaaaaatg acaagaacaa ggaagtactt gggagctttc | 540 |
| tccgacatgt taaatatttg aaactcacgc agctctcctg gaaagttgca tctggaaagg | 600 |
| taaggttgtt ttttgttcag acatcaaaat cggctcttgt agacaatgtc acagatccac | 660 |
| aagttgaaaa aaagtttcg atgaactgga taggggaga ggtcacaaac aaagtgtagg | 720 |
| gggtgagtag tatagtggta acttgttcat ttacctaaat aacattctca ctagaaaaga | 780 |
| gatattgaaa gactcctcgt ttacctaact tggctggttc ttaggtatat aatagaaaca | 840 |
| tggatctggc aggttattac ttacagtttg cattcccacc aggtaacaat ttcattata | 900 |
| tatagttatt ttttaccacc acttcttctt ctttcacttt gtcttgcaat agaaatacca | 960 |
| aaacaaggtg aggaaaaaat cgaatctcaa cgataaaaat atg | 1003 |

<210> SEQ ID NO 39
<211> LENGTH: 1003
<212> TYPE: DNA
<213> ORGANISM: Saccharomyces cerevisiae

<400> SEQUENCE: 39

| | |
|---|---|
| cggttggatc ctcacttgtt ttaacacctc caaataacaa gttttaatg aaggacattt | 60 |
| gttctctata atattccgat gtacgtgtgt gtggctgatg agatttagac tggttagact | 120 |
| atttgacgcg tctattatag cttactgcaa caagaaaatg atcgttgata tataaactct | 180 |
| cagatgtata tatcgttctg gaaacatcga gcataataca atacaattca acaaaaatgc | 240 |
| gagaaggcac tgatgtcttg tcgttaaaga accaaaaacg cggacactac gaccgtctta | 300 |

-continued

```
tttccggtag aaaaagggta catacagttg aaggaacgaa gaaaattaaa attagaaaaa      360
aaagtaaaat aaaacaagga aggtagggta atatggtctc gtttcctttg tcgctccgca      420
aataaaggag cttattcccg cacgctcaca tggtaatttg cgccaaatca cggatgtgga      480
aaactgatca cgtgcttcga tcgccaacta ctgagcgtcg tcccacactg atctggcaca      540
gcttacctcg ccttgaaaat tttaatctgt cctgctcgtt tgttgtatat tgcttcttct      600
cagaatatgc ccgcgataac tgacaaagag ggttcgacgt ttcagagatt ctactcttga      660
ccactgtttc gtgtagccgc tcaaggttta tttctttctt ctttaatgtt cttggcactt      720
aggcggctcc gtcctccgtc tgaaattgcc gatcctatta tttgcggagg gctccttaga      780
agggctcctt agtaagcagt ttgcgttcct gatataactc cgttcagaac aaggataaag      840
tcgcaataac cattactaag cacagtgttg taagtaggac aactcgaacc tatataaggg      900
ttgtgaactg tgcttgattc ttgcccatca tatgcaaaaa agtacgtact tgatatatac      960
aacaactgta gttcagtata gcgaagttta aatttagaag atg                      1003
```

<210> SEQ ID NO 40
<211> LENGTH: 1003
<212> TYPE: DNA
<213> ORGANISM: Saccharomyces cerevisiae

<400> SEQUENCE: 40

```
tggaaatgta aaggataatg agtgagcata taaaatggaa gaaaaaataa taataggatt      60
atgtataaaa tatcgattcc cttttgtaga tttcgagatc ttcgaggaga acttctagca     120
cgttgtttac atatctaatg ttgtaacacg gcctttgtta tcttgtgaat atatccatca     180
cctacgtcgc ttgaggtttc gtatcaaaga aagagagttc aaacataatc atacgtgttt     240
cactccaaat ttgatcacaa atggccaccc attatagctt gttattattt acttcttctt     300
gagttcattt tattgaaaga tgcccgctgg gaacaaaaca taaataaaat tcaagagtac     360
aatatagcgt agcatagttg cgagcaaggg aaggcaacac agttaaaatg acaatgttag     420
aaggaaaaac taaatcaagc tcccatagga aatttcttgt gtcagtaata tgtctcgaga     480
aaataataat aattgaatct atttattgaa aagtaaatat ctcgtaaccc ggatgctttg     540
ggcggtcggg ttttgctact cgtcatccga tgagaaaaac tgttcccttt tgccccaggt     600
ttccattcat ccgagcgatc acttatctga cttcgtcact ttttcatttc atccgaaaca     660
atcaaaactg aagccaatca ccacaaaatt aacactcaac gtcatctttc actacccttt     720
acagaagaaa atatccatag tccggactag catcccagta tgtgactcaa tattggtgca     780
aaagagaaaa gcataagtca gtccaaagtc cgcccttaac caggcacatc ggaattcaca     840
aaacgtttct ttattatata aaggagctgc ttcactggca aaattcttat tatttgtctt     900
ggcttgctaa tttcatctta tccttttttt cttttcacac ccaaataccT aacaattgag     960
agaaaactct tagcataaca taacaaaaag tcaacgaaaa atg                     1003
```

<210> SEQ ID NO 41
<211> LENGTH: 1003
<212> TYPE: DNA
<213> ORGANISM: Saccharomyces cerevisiae

<400> SEQUENCE: 41

```
ttcctaagcc tttgagatat atcaaaattg ctgcctttac caacgacgaa agtaaattgg      60
aagagcttcg tgagaaatac ccaaatcatt tgattggcgg agcagatctt gttgccaaaa     120
ttaaaagcgg tgaaattagc gttgattttg acaaagcatt tgcaactcct gatattgttc     180
```

-continued

```
cagctttaca atcgcaggtg gccaggatac ttggtcctcg tggggtttta ccctctgtca    240
aaaaaggtac ggtgagtgat gatataagct ccttacttca agaaagtcta ggatctatgc    300
ctttcaggca aagggaaac tctatcagca ttggagtcgg caaatgctac ttcactgatc     360
gagaaatttt acaaaacatt atatccgcta gagcggcatt taaaactgct gttgataatc    420
aaaaatctaa gaaccaaat atactgagta aaaccacatt atcaagcaca catggccccg     480
gtattgtaat cgattttgct taatcagcga atcagttttg tcttgttgga cttttttaat    540
tgtatatata tatatactgg tgcattttct ttcttttat ataaaatcat gtacatacaa     600
agtaaccgtc ttttaaagt ggaataaagt aactgctctt ttattttga ataatagtga      660
aagtgtatgt tgcataatca ttagataacct atgtacaaga agtattcaaa tttatctgaa   720
tagtatgtga aatttcaatg agacaaaaac cacctacctt tgagcttcct cctttttcaat   780
atcttagagc cctgtttgct cttggcccta gccaagaaac caaagttct cttccgtttc     840
aatgtactag gttgataggt gttaccccctt gatttccatc ttctttgacc tattaagcca   900
aatcccaacg gtgtgaagga cggagtcttc aatggtgaac tgtttaagag cataccggtt    960
tgtgggcgta acacagatag agcagagaaa gaagatatag atg                     1003
```

<210> SEQ ID NO 42
<211> LENGTH: 1716
<212> TYPE: DNA
<213> ORGANISM: Saccharomyces cerevisiae

<400> SEQUENCE: 42

```
atggattcta gaacagttgg tatattagga gggggacaat tgggacgtat gattgttgag    60
gcagcaaaca ggctcaacat taagacggta atactagatg ctgaaaattc tcctgccaaa    120
caaataagca actccaatga ccacgttaat ggctcctttt ccaatcctct tgatatcgaa    180
aaactagctg aaaaatgtga tgtgctaacg attgagattg agcatgttga tgttcctaca    240
ctaaagaatc ttcaagtaaa acatcccaaa ttaaaaattt acccttctcc agaaacaatc    300
agattgatac aagacaaata tattcaaaaa gagcatttaa tcaaaaatgg tatagcagtt    360
acccaaagtg ttcctgtgga acaagccagt gagacgtccc tattgaatgt tggaagagat    420
ttgggttttc cattcgtctt gaagtcgagg actttggcat acgatggaag aggtaacttc    480
gttgtaaaga ataaggaaat gattccggaa gctttggaag tactgaagga tcgtccttg    540
tacgccgaaa aatgggcacc atttactaaa gaattagcag tcatgattgt gagatctgtt    600
aacggtttag tgttttctta cccaattgta gagactatcc acaaggacaa tatttgtgac    660
ttatgttatg cgcctgctag agttccggac tccgttcaac ttaaggcgaa gttgttggca    720
gaaaatgcaa tcaaatcttt tcccggttgt ggtatatttg gtgtggaaat gttctattta    780
gaaacagggg aattgcttat taacgaaatt gccccaaggc ctcacaactc tggacattat    840
accattgatg cttgcgtcac ttctcaattt gaagctcatt tgagatcaat attggattg    900
ccaatgccaa agaatttcac atctttctcc accattacaa cgaacgccat tatgctaaat    960
gttcttggag acaaacatac aaaagataaa gagctagaaa cttgcgaaag agcattggcg   1020
actccaggtt cctcagtgta cttatatgga aaagagtcta gacctaacag aaaagtaggt   1080
cacataaata ttattgcctc cagtatggcg gaatgtgaac aaaggctgaa ctacattaca   1140
ggtagaactg atattccaat caaaatctct gtcgctcaaa agttggactt ggaagcaatg   1200
gtcaaaccat tggttggaat catcatggga tcagactctg acttgccggt aatgtctgcc   1260
```

-continued

```
gcatgtgcgg ttttaaaaga ttttggcgtt ccatttgaag tgacaatagt ctctgctcat    1320
agaactccac ataggatgtc agcatatgct atttccgcaa gcaagcgtgg aattaaaaca    1380
attatcgctg gagctggtgg ggctgctcac ttgccaggta tggtggctgc aatgacacca    1440
cttcctgtca tcggtgtgcc cgtaaaaggt tcttgtctag atggagtaga ttctttacat    1500
tcaattgtgc aaatgcctag aggtgttcca gtagctaccg tcgctattaa taatagtacg    1560
aacgctgcgc tgttggctgt cagactgctt ggcgcttatg attcaagtta tacaacgaaa    1620
atggaacagt ttttattaaa gcaagaagaa gaagttcttg tcaaagcaca aaagttagaa    1680
actgtcggtt acgaagctta tctagaaaac aagtaa                              1716

<210> SEQ ID NO 43
<211> LENGTH: 4179
<212> TYPE: DNA
<213> ORGANISM: Saccharomyces cerevisiae

<400> SEQUENCE: 43
atgactaacg aaaaggtctg gatagagaag ttggataatc caactctttc agtgttacca      60
catgactttt tacgcccaca acaagaacct tatacgaaac aagctacata ttcgttacag     120
ctacctcagc tcgatgtgcc tcatgatagt ttttctaaca aatacgctgt cgctttgagt     180
gtatgggctg cattgatata tagagtaacc ggtgacgatg atattgttct ttatattgcg     240
aataacaaaa tcttaagatt caatattcaa ccaacgtggt catttaatga gctgtattct     300
acaattaaca atgagttgaa caagctcaat tctattgagg ccaattttc ctttgacgag      360 ctagctgaaa aaattcaaag ttgccaagat ctggaaagga cccctcagtt gttccgtttg     420 gccttttgg aaaaccaaga tttcaaatta gacgagttca agcatcattt agtggacttt      480
gctttgaatt tggataccag taataatgcg catgttttga acttaattta taacagctta     540
ctgtattcga atgaaagagt aaccattgtt gcggaccaat ttactcaata tttgactgct     600
gcgctaagcg atccatccaa ttgcataact aaaatctctc tgatcaccgc atcatccaag     660
gatagtttac ctgatccaac taagaacttg ggctggtgcg atttcgtggg gtgtattcac     720
gacattttcc aggacaatgc tgaagccttc ccagagagaa cctgtgttgt ggagactcca     780
acactaaatt ccgacaagtc ccgttctttc acttatcgcg acatcaaccg cacttctaac     840
atagttgccc attatttgat aaaacaggt atcaaaagag gtgatgtagt gatgatctat      900
tcttctaggg gtgtggattt gatggtatgt gtgatgggtg tcttgaaagc cggcgcaacc     960 tttttcagtta tcgaccctgc atatccccca gccagacaaa ccatttactt aggtgttgct    1020
aaaccacgtg ggttgattgt tattagagct gctggacaat tggatcaact agtgagaagat    1080 tacatcaatg atgaattgga gattgtttca agaatcaatt ccatcgctat tcaagaaaat     1140
ggtaccattg aaggtggcaa attggacaat ggcgaggatg ttttggctcc atatgatcac     1200
tacaaagaca ccgaacaggg tgttgtagtt ggaccagatt ccaacccaac cctatctttc     1260
acatctggtt ccgaaggtat tcctaagggt gttcttggta gacattttc cttggcttat     1320 tatttcaatt ggatgtccaa aaggttcaac ttaacagaaa atgataaatt cacaatgctg     1380
agcggtattg cacatgatcc aattcaaaga gatatgttta caccattatt tttaggtgcc     1440
caattgtatg tccctactca agatgatatt ggtacaccgg gccgtttagc ggaatggatg     1500
agtaagtatg gttgcacagt tacccattta acacctgcca tgggtcaatt acttactgcc     1560
caagctacta caccattccc taagttacat catgcgttct ttgtgggtga cattttaaca     1620
aaacgtgatt gtctgaggtt acaaaccttg gcagaaaatt gccgtattgt taatatgtac     1680
```

```
ggtaccactg aaacacagcg tgcagtttct tatttcgaag ttaaatcaaa aaatgacgat   1740
ccaaactttt tgaaaaaatt gaaagatgtc atgcctgctg gtaaaggtat gttgaacgtt   1800
cagctactag ttgttaacag gaacgatcgt actcaaatat gtggtattgg cgaaataggt   1860
gagatttatg ttcgtgcagg tggtttggcc gaaggttata gaggattacc agaattgaat   1920
aaagaaaaat ttgtgaacaa ctggtttgtt gaaaaagatc actggaatta tttggataag   1980
gataatggtg aaccttggag acaattctgg ttaggtccaa gagatagatt gtacagaacg   2040
ggtgatttag gtcgttatct accaaacggt gactgtgaat gttgcggtag gctgatgat    2100
caagttaaaa ttcgtgggtt cagaatcgaa ttaggagaaa tagatacgca catttcccaa   2160
catccattgg taagagaaaa cattacttta gttcgcaaaa atgccgacaa tgagccaaca   2220
ttgatcacat ttatggtccc aagatttgac aagccagatg acttgtctaa gttccaaagt   2280
gatgttccaa aggaggttga aactgaccct atagttaagg gcttaatcgg ttaccatctt   2340
ttatccaagg acatcaggac tttcttaaag aaaagattgg ctagctatgc tatgccttcc   2400
ttgattgtgg ttatggataa actaccattg aatccaaatg gtaaagttga taagcctaaa   2460
cttcaattcc caactcccaa gcaattaaat ttggtagctg aaaatacagt ttctgaaact   2520
gacgactctc agtttaccaa tgttgagcgc gaggttagag acttatggtt aagtatatta   2580
cctaccaagc cagcatctgt atcaccagat gattcgtttt tcgatttagg tggtcattct   2640
atcttggcta ccaaaatgat ttttacctta aagaaaaagc tgcaagttga tttaccattg   2700
ggcacaattt tcaagtatcc aacgataaag gcctttgccg cggaaattga cagaattaaa   2760
tcatcgggtg gatcatctca aggtgaggtc gtcgaaaatg tcactgcaaa ttatgcggaa   2820
gacgccaaga aattggttga gacgctacca agttcgtacc cctctcgaga atattttgtt   2880
gaacctaata gtgccgaagg aaaaacaaca attaatgtgt tgttaccgg tgtcacagga    2940
tttctgggct cctacatcct tgcagatttg ttaggacgtt ctccaaagaa ctacagtttc   3000
aaagtgtttg cccacgtcag ggccaaggat gaagaagctg catttgcaag attacaaaag   3060
gcaggtatca cctatggtac ttggaacgaa aaatttgcct caaatattaa agttgtatta   3120
ggcgatttat ctaaaagcca atttggtctt tcagatgaga agtggatgga tttggcaaac   3180
acagttgata taattatcca taatggtgcg ttagttcact gggtttatcc atatgccaaa   3240
ttgagggatc caaatgttat ttcaactatc aatgttatga gcttagccgc cgtcggcaag   3300
ccaaagttct ttgactttgt ttcctccact tctactcttg acactgaata ctactttaat   3360
ttgtcagata acttgttag cgaagggaag ccaggcattt tagaatcaga cgatttaatg    3420
aactctgcaa gcgggctcac tggtggatat ggtcagtcca aatgggctgc tgagtacatc   3480
attagacgtg caggtgaaag gggcctacgt gggtgtattg tcagaccagg ttacgtaaca   3540
ggtgcctctg ccaatggttc ttcaaacaca gatgattct tattgagatt tttgaaaggt    3600
tcagtccaat taggtaagat tccagatatc gaaaattccg tgaatatggt tccagtagat   3660
catgttgctc gtgttgttgt tgctacgtct ttgaatcctc ccaaagaaaa tgaattggcc   3720
gttgctcaag taacgggtca cccaagaata ttattcaaag actacttgta tactttacac   3780
gattatggtt acgatgtcga aatcgaaagc tattctaaat ggaagaaatc attggaggcg   3840
tctgttattg acaggaatga agaaaatgcg ttgtatcctt tgctacacat ggtcttagac   3900
aacttacctg aaagtaccaa agctccggaa ctagacgata ggaacgccgt ggcatcttta   3960
aagaaagaca ccgcatggac aggtgttgat tggtctaatg gaataggtgt tactccagaa   4020
```

<210> SEQ ID NO 44
<211> LENGTH: 675
<212> TYPE: DNA
<213> ORGANISM: Saccharomyces cerevisiae

<400> SEQUENCE: 44

| | | | | | |
|---|---|---|---|---|---|
| atgtctgtta | ttaatttcac | aggtagttct | ggtccattgg | tgaaagtttg | cggcttgcag | 60 |
| agcacagagg | ccgcagaatg | tgctctagat | tccgatgctg | acttgctggg | tattatatgt | 120 |
| gtgcccaata | gaaagagaac | aattgacccg | gttattgcaa | ggaaaatttc | aagtcttgta | 180 |
| aaagcatata | aaatagttc | aggcactccg | aaatacttgg | ttggcgtgtt | tcgtaatcaa | 240 |
| cctaaggagg | atgttttggc | tctggtcaat | gattacggca | ttgatatcgt | ccaactgcat | 300 |
| ggagatgagt | cgtggcaaga | ataccaagag | ttcctcggtt | tgccagttat | taaaagactc | 360 |
| gtatttccaa | aagactgcaa | catactactc | agtgcagctt | cacagaaacc | tcattcgttt | 420 |
| attccccttgt | ttgattcaga | agcaggtggg | acaggtgaac | ttttggattg | gaactcgatt | 480 |
| tctgactggg | ttggaaggca | agagagcccc | gaaagcttac | attttatgtt | agctggtgga | 540 |
| ctgacgccag | aaaatgttgg | tgatgcgctt | agattaaatg | gcgttattgg | tgttgatgta | 600 |
| agcggaggtg | tggagacaaa | tggtgtaaaa | gactctaaca | aaatagcaaa | tttcgtcaaa | 660 |
| aatgctaaga | aatag | | | | | 675 |

<210> SEQ ID NO 45
<211> LENGTH: 1095
<212> TYPE: DNA
<213> ORGANISM: Saccharomyces cerevisiae

<400> SEQUENCE: 45

| | | | | | |
|---|---|---|---|---|---|
| atgtctgccc | taagaagat | cgtcgttttg | ccaggtgacc | acgttggtca | agaaatcaca | 60 |
| gccgaagcca | ttaaggttct | taaagctatt | tctgatgttc | gttccaatgt | caagttcgat | 120 |
| ttcgaaaatc | atttaattgg | tggtgctgct | atcgatgcta | caggtgttcc | acttccagat | 180 |
| gaggcgctgg | aagcctccaa | gaaggctgat | gccgttttgt | taggtgctgt | gggtggtcct | 240 |
| aaatggggta | ccggtagtgt | tagacctgaa | caaggtttac | taaaaatccg | taagaaactt | 300 |
| caattgtacg | ccaacttaag | accatgtaac | tttgcatccg | actctctttt | agacttatct | 360 |
| ccaatcaagc | cacaatttgc | taaaggtact | gacttcgttg | ttgtcagaga | attagtggga | 420 |
| ggtatttact | ttggtaagag | aaaggaagac | gatggtgatg | gtgtcgcttg | ggatagtgaa | 480 |
| caatacaccg | ttccagaagt | gcaaagaatc | acaagaatgg | ccgctttcat | ggccctacaa | 540 |
| catgagccac | cattgcctat | ttggtccttg | gataaagcta | atgttttggc | ctcttcaaga | 600 |
| ttatggagaa | aaactgtgga | ggaaaccatc | aagaacgaat | ccctacatt | gaaggttcaa | 660 |
| catcaattga | ttgattctgc | cgccatgatc | ctagttaaga | acccaacccca | cctaaatggt | 720 |
| attataatca | ccagcaacat | gtttggtgat | atcatctccg | atgaagcctc | cgttatccca | 780 |
| ggttccttgg | gtttgttgcc | atctgcgtcc | ttggcctctt | gccagacaa | gaacaccgca | 840 |
| tttggtttgt | acgaaccatg | ccacggttct | gctccagatt | tgccaaagaa | taaggtcaac | 900 |
| cctatcgcca | ctatccttc | tgctgcaatg | atgttgaaat | tgtcattgaa | cttgcctgaa | 960 |
| gaaggtaagg | ccattgaaga | tgcagttaaa | aaggttttgg | atgcaggtat | cagaactggt | 1020 |

```
gatttaggtg gttccaacag taccaccgaa gtcggtgatg ctgtcgccga agaagttaag    1080
aaaatccttg cttaa                                                    1095

<210> SEQ ID NO 46
<211> LENGTH: 804
<212> TYPE: DNA
<213> ORGANISM: Saccharomyces cerevisiae

<400> SEQUENCE: 46
atgtcgaaag ctacatataa ggaacgtgct gctactcatc ctagtcctgt tgctgccaag      60
ctatttaata tcatgcacga aaagcaaaca aacttgtgtg cttcattgga tgttcgtacc     120
accaaggaat tactggagtt agttgaagca ttaggtccca aaatttgttt actaaaaaca     180
catgtggata tcttgactga tttttccatg gagggcacag ttaagccgct aaaggcatta     240
tccgccaagt acaatttttt actcttcgaa gacagaaaat tgctgacat tggtaataca      300 gtcaaattgc agtactctgc gggtgtatac agaatagcag aatgggcaga cattacgaat     360
gcacacggtg tggtgggccc aggtattgtt agcggtttga agcaggcggc ggaagaagta     420 acaaggaac ctagaggcct tttgatgtta gcagaattgt catgcaaggg ctccctagct      480
actggagaat atactaaggg tactgttgac attgcgaaga gcgacaaaga ttttgttatc     540
ggctttattg ctcaaagaga catgggtgga agagatgaag gttacgattg ttgattatg      600 acaccggtg tgggtttaga tgacaaggga gacgcattgg gtcaacagta tagaaccgtg      660
gatgatgtgg tctctacagg atctgacatt attattgttg gaagaggact atttgcaaag     720
ggaagggatg ctaaggtaga gggtgaacgt tacagaaaag caggctggga agcatatttg     780
agaagatgcg gccagcaaaa ctaa                                            804

<210> SEQ ID NO 47
<211> LENGTH: 663
<212> TYPE: DNA
<213> ORGANISM: Saccharomyces cerevisiae

<400> SEQUENCE: 47
atgacagagc agaaagccct agtaaagcgt attacaaatg aaaccaagat tcagattgcg      60
atctctttaa agggtggtcc cctagcgata gagcactcga tcttcccaga aaaagaggca     120
gaagcagtag cagaacaggc cacacaatcg caagtgatta acgtccacac aggtataggg     180
tttctggacc atatgataca tgctctggcc aagcattccg gctggtcgct aatcgttgag     240
tgcattggtg acttacacat agacgaccat cacaccactg aagactgcgg gattgctctc     300
ggtcaagctt ttaaagaggc cctaggggcc gtgcgtggag taaaaaggtt tggatcagga     360
tttgcgcctt tggatgaggc actttccaga gcggtggtag atctttcgaa caggccgtac     420
gcagttgtcg aacttggttt gcaaagggag aaagtaggag atctctcttg cgagatgatc     480
ccgcattttc ttgaaagctt tgcagaggct agcagaatta ccctccacgt tgattgtctg     540
cgaggcaaga atgatcatca ccgtagtgag agtgcgttca aggctcttgc ggttgccata     600
agagaagcca cctcgcccaa tggtaccaac gatgttccct ccaccaaagg tgttcttatg     660
tag                                                                   663

<210> SEQ ID NO 48
<211> LENGTH: 736
<212> TYPE: DNA
<213> ORGANISM: Aequorea victoria
```

<400> SEQUENCE: 48

```
aagctttatt aaaatgtcta aaggtgaaga attattcact ggtgttgtcc caattttggt      60
tgaattagat ggtgatgtta atggtcacaa attttctgtc tccggtgaag gtgaaggtga     120
tgctacttac ggtaaattga ccttaaaatt tatttgtact actggtaaat tgccagttcc     180
atggccaacc ttagtcacta ctttcggtta tggtgttcaa tgttttgcta gatacccaga     240
tcatatgaaa caacatgact ttttcaagtc tgccatgcca gaaggttatg ttcaagaaag     300
aactattttt ttcaaagatg acggtaacta caagaccaga gctgaagtca agtttgaagg     360
tgatacctta gttaatagaa tcgaattaaa aggtattgat tttaaagaag atggtaacat     420
tttaggtcac aaattggaat acaactataa ctctcacaat gtttacatca tggctgacaa     480
acaaaagaat ggtatcaaag ttaacttcaa aattagacac aacattgaag atggttctgt     540
tcaattagct gaccattatc aacaaaatac tccaattggt gatggtccag tcttgttacc     600
agacaaccat tacttatcca ctcaatctgc cttatccaaa gatccaaacg aaaagagaga     660
ccacatggtc ttgttagaat tgttactgc tgctggtatt acccatggta tggatgaatt     720
gtacaaataa ctgcag                                                    736
```

<210> SEQ ID NO 49
<211> LENGTH: 945
<212> TYPE: DNA
<213> ORGANISM: Renilla

<400> SEQUENCE: 49

```
atggcttcga agtttatga tccagaacaa aggaaacgga tgataactgg tccgcagtgg      60
tgggccagat gtaaacaaat gaatgttctt gattcattta ttaattatta tgattcagaa     120
aaacatgcag aaaatgctgt tatttttta catggtaacg cggcctcttc ttatttatgg     180
cgacatgttg tgccacatat tgagccagta gcgcggtgta ttataccaga ccttattggt     240
atgggcaaat caggcaaatc tggtaatggt tcttataggt tacttgatca ttacaaatat     300
cttactgcat ggtttgaact tcttaattta ccaaagaaga tcattttgt cggccatgat     360
tgggtgctt gtttggcatt tcattatagc tatgagcatc aagataagat caaagcaata     420
gttcacgctg aaagtgtagt agatgtgatt gaatcatggg atgaatggcc tgatattgaa     480
gaagatattg cgttgatcaa atctgaagaa ggagaaaaaa tggttttgga gaataacttc     540
ttcgtggaaa ccatgttgcc atcaaaaatc atgagaaagt tagaaccaga gaatttgca     600
gcatatcttg aaccattcaa agagaaaggt gaagttcgtc gtccaacatt atcatggcct     660
cgtgaaatcc cgttagtaaa aggtggtaaa cctgacgttg tacaaattgt taggaattat     720
aatgcttatc tacgtgcaag tgatgattta ccaaaaatgt ttattgaatc ggacccagga     780
ttcttttcca atgctattgt tgaaggtgcc aagaagtttc ctaatactga atttgtcaaa     840
gtaaaaggtc ttcattttc gcaagaagat gcacctgatg aaatgggaaa atatatcaaa     900
tcgttcgttg agcgagttct caaaaatgaa caaagatcta tctag                    945
```

<210> SEQ ID NO 50
<211> LENGTH: 2387
<212> TYPE: DNA
<213> ORGANISM: Photinus pyralis

<400> SEQUENCE: 50

```
ctgcagaaat aactaggtac taagcccgtt tgtgaaaagt ggccaaaccc ataaatttgg      60
caattacaat aaagaagcta aaattgtggt caaactcaca aacatttta ttatatacat     120
```

-continued

```
tttagtagct gatgcttata aaagcaatat ttaaatcgta aacaacaaat aaaataaaat      180
ttaaacgatg tgattaagag ccaaaggtcc tctagaaaaa ggtatttaag caacggaatt      240
cctttgtgtt acattcttga atgtcgctcg cagtgacatt agcattccgg tactgttggt      300
aaaatggaag acgccaaaaa cataaagaaa ggcccggcgc cattctatcc tctagaggat      360
ggaaccgctg gagagcaact gcataaggct atgaagagat acgccctggt tcctggaaca      420
attgcttttg tgagtatttc tgtctgattt ctttcgagtt aacgaaatgt tcttatgttt      480
ctttagacag atgcacatat cgaggtgaac atcacgtacg cggaatactt cgaaatgtcc      540
gttcggttgg cagaagctat gaaacgatat gggctgaata caaatcacag aatcgtcgta      600
tgcagtgaaa actctcttca attctttatg ccggtgttgg gcgcgttatt tatcggagtt      660
gcagttgcgc ccgcgaacga catttataat gaacgtaagc accctcgcca tcagaccaaa      720
gggaatgacg tatttaattt ttaaggtgaa ttgctcaaca gtatgaacat tcgcagcct       780 accgtagtgt ttgtttccaa aaaggggttg caaaaaattt tgaacgtgca aaaaaatta      840 ccaataatcc agaaaattat tatcatggat tctaaaacgg attaccaggg atttcagtcg      900
atgtacacgt tcgtcacatc tcatctacct cccggtttta atgaatacga ttttgtacca      960
gagtcctttg atcgtgacaa aacaattgca ctgataatga attcctctgg atctactggg     1020
ttacctaagg gtgtggccct tccgcataga actgcctgcg tcagattctc gcatgccagg     1080
tatgtcgtat aacaagagat taagtaatgt tgctacacac attgtagaga tcctattttt     1140
ggcaatcaaa tcattccgga tactgcgatt ttaagtgttg ttccattcca tcacggtttt     1200
ggaatgttta ctacactcgg atatttgata tgtggatttc gagtcgtctt aatgtataga     1260
tttgaagaag agctgttttt acgatccctt caggattaca aaattcaaag tgcgttgcta     1320
gtaccaaccc tattttcatt cttcgccaaa agcactctga ttgacaaata cgatttatct     1380
aatttacacg aaattgcttc tgggggcgca cctctttcga aagaagtcgg ggaagcggtt     1440
gcaaaacggt gagttaagcg cattgctagt atttcaaggc tctaaaacgg cgcgtagctt     1500
ccatcttcca gggatacgac aaggatatgg gctcactgag actacatcag ctattctgat     1560
tacacccgag ggggatgata aaccgggcgc ggtcggtaaa gttgttccat tttttgaagc     1620
gaaggttgtg gatctggata ccgggaaaac gctgggcgtt aatcagagag gcgaattatg     1680
tgtcagagga cctatgatta tgtccggtta tgtaaacaat ccggaagcga ccaacgcctt     1740
gattgacaag gatggatggc tacattctgg agacatagct tactgggacg aagacgaaca     1800
cttcttcata gttgaccgct tgaagtcttt aattaaatac aaaggatatc aggtaatgaa     1860
gatttttaca tgcacacacg ctacaatacc tgtaggtggc ccccgctgaa ttggaatcga     1920
tattgttaca acacccccaac atcttcgacg cgggcgtggc aggtcttccc gacgatgacg     1980
ccggtgaact tcccgccgcc gttgttgttt tggagcacgg aaagacgatg acggaaaaag     2040
agatcgtgga ttacgtcgcc agtaaatgaa ttcgttttac gttactcgta ctacaattct     2100
tttcataggt caagtaacaa ccgcgaaaaa ggttgcgcgga ggagttgtgt ttgtggacga     2160
agtaccgaaa ggtcttaccg gaaaactcga cgcaagaaaa atcagagaga tcctcataaa     2220
ggccaagaag ggcggaaagt ccaaattgta aaatgtaact gtattcagcg atgacgaaat     2280
tcttagctat tgtaatatta tatgcaaatt gatgaatggt aattttgtaa ttgtgggtca     2340
ctgtactatt ttaacgaata ataaaatcag gtataggtaa ctaaaaa                  2387
```

<210> SEQ ID NO 51

<211> LENGTH: 3075
<212> TYPE: DNA
<213> ORGANISM: Escherichia coli

<400> SEQUENCE: 51

| | | | | | |
|---|---|---|---|---|---|
| atgaccatga | ttacggattc | actggccgtc | gttttacaac | gtcgtgactg | ggaaaaccct | 60 |
| ggcgttaccc | aacttaatcg | ccttgcagca | catcccccctt | tcgccagctg | gcgtaatagc | 120 |
| gaagaggccc | gcaccgatcg | cccttcccaa | cagttgcgca | gcctgaatgg | cgaatggcgc | 180 |
| tttgcctggt | ttccggcacc | agaagcggtg | ccggaaagct | ggctggagtg | cgatcttcct | 240 |
| gaggccgata | ctgtcgtcgt | cccctcaaac | tggcagatgc | acggttacga | tgcgcccatc | 300 |
| tacaccaacg | tgacctatcc | cattacggtc | aatccgccgt | tgttcccac | ggagaatccg | 360 |
| acgggttgtt | actcgctcac | atttaatgtt | gatgaaagct | ggctacagga | aggccagacg | 420 |
| cgaattattt | ttgatggcgt | taactcggcg | tttcatctgt | ggtgcaacgg | gcgctgggtc | 480 |
| ggttacggcc | aggacagtcg | tttgccgtct | gaatttgacc | tgagcgcatt | tttacgcgcc | 540 |
| ggagaaaacc | gcctcgcggt | gatggtgctg | cgctggagtg | acggcagtta | tctggaagat | 600 |
| caggatatgt | ggcggatgag | cggcattttc | cgtgacgtct | cgttgctgca | taaaccgact | 660 |
| acacaaatca | gcgatttcca | tgttgccact | cgctttaatg | atgatttcag | ccgcgctgta | 720 |
| ctggaggctg | aagttcagat | gtgcggcgag | ttgcgtgact | acctacgggt | aacagtttct | 780 |
| ttatggcagg | gtgaaacgca | ggtcgccagc | ggcaccgcgc | ctttcggcgg | tgaaattatc | 840 |
| gatgagcgtg | tggttatgc | cgatcgcgtc | acactacgtc | tgaacgtcga | aaacccgaaa | 900 |
| ctgtggagcg | ccgaaatccc | gaatctctat | cgtgcggtgg | ttgaactgca | caccgccgac | 960 |
| ggcacgctga | ttgaagcaga | agcctgcgat | gtcggtttcc | gcgaggtgcg | gattgaaaat | 1020 |
| ggtctgctgc | tgctgaacgg | caagccgttg | ctgattcgag | gcgttaaccg | tcacgagcat | 1080 |
| catcctctgc | atggtcaggt | catggatgag | cagacgatgg | tgcaggatat | cctgctgatg | 1140 |
| aagcagaaca | actttaacgc | cgtgcgctgt | tcgcattatc | cgaaccatcc | gctgtggtac | 1200 |
| acgctgtgcg | accgctacgg | cctgtatgtg | gtggatgaag | ccaatattga | aacccacggc | 1260 |
| atggtgccaa | tgaatcgtct | gaccgatgat | ccgcgctggc | taccggcgat | gagcgaacgc | 1320 |
| gtaacgcgaa | tggtgcagcg | cgatcgtaat | cacccgagtg | tgatcatctg | gtcgctgggg | 1380 |
| aatgaatcag | gccacggcgc | taatcacgac | gcgctgtatc | gctggatcaa | atctgtcgat | 1440 |
| ccttcccgcc | cggtgcagta | tgaaggcggc | ggagccgaca | ccacggccac | cgatattatt | 1500 |
| tgcccgatgt | acgcgcgcgt | ggatgaagac | cagcccttcc | cggctgtgcc | gaaatggtcc | 1560 |
| atcaaaaaat | ggcttttcgct | acctggagag | acgcgcccgc | tgatcctttg | cgaatacgcc | 1620 |
| cacgcgatgg | gtaacagtct | ggcggtttc | gctaaatact | ggcaggcgtt | tcgtcagtat | 1680 |
| ccccgtttac | agggcggctt | cgtctgggac | tgggtggatc | agtcgctgat | taaatatgat | 1740 |
| gaaaacggca | acccgtggtc | ggcttacggc | ggtgattttg | gcgatacgcc | gaacgatcgc | 1800 |
| cagttctgta | tgaacggtct | ggtctttgcc | gaccgcacgc | gcatccagc | gctgacggaa | 1860 |
| gcaaaacacc | agcagcagtt | tttccagttc | cgtttatccg | ggcaaaccat | cgaagtgacc | 1920 |
| agcgaatacc | tgttccgtca | tagcgataac | gagctcctgc | actggatggt | ggcgctggat | 1980 |
| ggtaagccgc | tggcaagcgg | tgaagtgcct | ctggatgtcg | ctccacaagg | taaacagttg | 2040 |
| attgaactgc | ctgaactacc | gcagccggag | agcgccgggc | aactctggct | cacagtacgc | 2100 |
| gtagtgcaac | gaacgcgac | cgcatggtca | gaagccgggc | acatcagcgc | ctggcagcag | 2160 |
| tggcgtctgg | cggaaaacct | cagtgtgacg | ctccccgccg | cgtcccacgc | catcccgcat | 2220 |

```
ctgaccacca gcgaaatgga ttttttgcatc gagctgggta ataagcgttg gcaatttaac    2280
cgccagtcag gctttctttc acagatgtgg attggcgata aaaaacaact gctgacgccg    2340
ctgcgcgatc agttcacccg tgcaccgctg gataacgaca ttggcgtaag tgaagcgacc    2400
cgcattgacc ctaacgcctg ggtcgaacgc tggaaggcgg cgggccatta ccaggccgaa    2460
gcagcgttgt tgcagtgcac ggcagataca cttgctgatg cggtgctgat tacgaccgct    2520
cacgcgtggc agcatcaggg gaaaaccta tttatcagcc ggaaaaccta ccggattgat     2580
ggtagtggtc aaatggcgat taccgttgat gttgaagtgg cgagcgatac accgcatccg    2640
gcgcggattg gcctgaactg ccagctggcg caggtagcag agcgggtaaa ctggctcgga    2700
ttagggccgc aagaaaacta tcccgaccgc cttactgccg cctgttttga ccgctgggat    2760
ctgccattgt cagacatgta tacccgtac gtcttcccga gcgaaaacgg tctgcgctgc     2820
gggacgcgcg aattgaatta tggcccacac cagtggcgcg cgacttcca gttcaacatc     2880 agccgctaca gtcaacagca actgatggaa accagccatc gccatctgct gcacgcggaa    2940
gaaggcacat ggctgaatat cgacggtttc catatgggga ttggtggcga cgactcctgg    3000
agcccgtcag tatcggcgga attccagctg agcgccggtc gctaccatta ccagttggtc    3060
tggtgtcaaa aataa                                                     3075

<210> SEQ ID NO 52
<211> LENGTH: 1003
<212> TYPE: DNA
<213> ORGANISM: Saccharomyces cerevisiae

<400> SEQUENCE: 52
tctaaatatc gtcccgttac cctcatcgct actgccgggc gttcccaacc ccttccgagg      60
cagattatat ttatttatct ttttaacaat ttgtccctat ataggcgggc cgaacacagc     120
acgtgaaaga actctcaggc ttccacaaca ggcatatca gtccacact tccctcatta      180 ctagcatttt tacacaagca gtccacgcat tccgcaacag tgttcacctt tctttttcct    240
aacttatctt attatttgtt tgttgatcgc aaacagaccc tttttttttgg tgagcgcatt    300 ttacacagtc tcaagtgtcc tctactataa aaatacaacc tcaaacagta cttactggcg    360
tccgcagaat attactgcac tctcaatctg taaagaatat aacaagtgac ccattccctt    420
gttttattca acttcgaaat ctctctggct atctttgcat gcttatctaa ctttcacgtg    480
acccggatat tgttctctgc tcaaaaaaga actgcaaaga aggaaataga aaaatagcat    540
acaggctcaa agctatagtt ttctgaaaag ggacaccacg aatacagtag tatcaaagag    600
aaaaaagact tctttatact tacagaaggt tcatttctg attctactct tccaatctag     660
tgtcgcaaaa aaacaaaact tactggtatt agctggcaaa aaaaaaaga ataggttata     720 attaaagaca tcttttctct ataaattttt cttagaaga aaaagccaaa aaaaaaaac       780 ctgcttcata cccgccatca aatcttatag gccttataga ctgcatatta ccggattctt    840
tctctccgtt aaccctacta ttctttcact atactttaac ctaaaataaa aaggaaaaa     900 aaaaattaaa aacttccaaa aacttagaaa tttcaaatac aaaacaaaaa gacacgtaaa    960
gttagtgcaa tatttttttc ttacaatttt ttgaaactcg atg                      1003

<210> SEQ ID NO 53
<211> LENGTH: 1003
<212> TYPE: DNA
<213> ORGANISM: Saccharomyces cerevisiae
```

```
<400> SEQUENCE: 53
agaacattat gaagtaaaag gacaatcagc acgccttcca gacttttaag aaacattgat      60
ggagccattg atatcggcac cgtacctaac aacaacaaaa atgtctgctc ctgctacgct     120
tgatgctgcc tgtattttt gcaagattat taaaagtatg tcacattact aataaagagc     180
ttacactcac accaatgatg gcgatagtct ctatgtagta catatacata aagcagaata     240
ctaacaatcg atccgctatg caacaggcga aattccatcc ttcaaattga ttgaaacaaa     300
gtactcgtat gctttcttgg acatccaacc tactgctgaa ggtcatgctt taatcattcc     360
taagtaccat ggtgcgaagt tgcatgacat cccggacgaa ttccttaccg atgctatgcc     420
gattgccaag agactggcca aggcaatgaa gttggacact taatgtgtt gcagaataa      480 tggtaaaatt gcgcatcaag aagtcgacca cgtccacttc catttgattc ctaagagaga     540
tgagaaaagt ggtttgattg tagggtggcc agcccaagaa acggacttcg ataagttggg     600
caagctacac aaggaattgc ttgccaaact agaaggctcc gattagagta atgcatgcta     660
tgatttcttt tagcgttttc ttttcatatt taagtttata catatgggtg tgtttgcttc     720
cattcatatc cactctataa tgctaacaat catgttacta gccatcgttg ctatcgatac     780
cttatgaaca gctctaactc cttccttttt aacctaccgc cttttgcgca ctacccggca     840
acccctcgaa tgtgaattcg gtggcaaaaa aggacatata tcaggccgt gtatttaaga     900 gatccgcagt tgatgtagtc aattaatcta gttctattaa gatttgactc aacgccattg     960
actcgataac tggctcaact acaagacaga tatacaaatc atg                    1003

<210> SEQ ID NO 54
<211> LENGTH: 1003
<212> TYPE: DNA
<213> ORGANISM: Saccharomyces cerevisiae

<400> SEQUENCE: 54
cgaactatag ggagattggt cctcaacaat atatttcttc cttgtcgacc cattaggtgt      60
atgggcgagt tgctgcaggg aagacaacga atccctagaa gcgcacttgt aaagatcttg     120
ctcttgtaag tagcgatgac ggtcatgaag atgaaagggt gcggttgaag tcaagttgaa     180
cgtgatcgga tactgatttc tagaaacagg ggggctggt gttggttctg gcgaagccgc     240
ttgctccgac tgctttgatg tcacagcttt gggtttctcc gctacactgt ctaccttagg     300
attattgatc atgactcaag cttgcgatat gtgttggtgt catgcacaag acgccacaaa     360
tgatagaaca gaaaagaaag tgaactaatc ttccaagacg aagaaaacca aaatccggga     420
tgagttgaaa gtcaaaaaga ctgtatatat aaatttcaac ttttgtagaa gatgcagaaa     480
aagaaaatga tatggtatgc agaaaaagaa ataaaccgct attatcctcg cggtttgtca     540
ttataacagg caattacact agagaaagcc gcacacctcc ctccgtttct tttgccctgc     600 gagttttcc ggaaaagaaa aaaaaaacga aaattaaaac ccgcctgccc cgcggggtgg     660 gggagggggtc accggaacaa atcggataat ccctcgcctg ccttagatat cgttctgaac     720
ggctgaaatt atgaaagaag aagaacatca ctttacacgg atcgcacgcc cataattctt     780
tttttttttt ttttcatatc ttcgacgttt gccactgcct tctcttttc tttcttttt     840 ggcggccggt ggccaaacgc gccaaaaccg aaacgcttat aaaatgtagt tgccttgctc     900
tttcattcga tatacatata agaacgctca ctgttatctt acattagaag ctagaaacta     960
taacagtata acacagcaca agagaaccga gcagcccgcc atg                    1003
```

<210> SEQ ID NO 55
<211> LENGTH: 1003
<212> TYPE: DNA
<213> ORGANISM: Saccharomyces cerevisiae

<400> SEQUENCE: 55

| | | | | | |
|---|---|---|---|---|---|
| agtaaaaaga | atagtaatta | ttacaatgga | gaagataaga | taaagttagc | ggcaacaaat | 60 |
| aaagaactca | tcagagttct | tggcttctct | atgagtgaaa | gtgtttcaaa | ggtgttttt | 120 |
| tatgagacaa | cagtaattcc | cctccttcag | aacagagtgt | agtgattggc | agtgaagcta | 180 |
| tccctctttg | ccacccaatt | tgacggcag | ttctcatagc | atctcaaagc | aatagcagtg | 240 |
| caaaagtaca | taaccgtagg | aaggtacgcg | gtaggtattt | gagttcgttg | gtggttatcc | 300 |
| tccgcaaggc | gcttcggcgg | ttatttgttg | atagtcgaag | aacaccaaaa | aaaatgctgt | 360 |
| tattgctttc | tccgtaaaca | ataaaacccg | gtagcgggat | aacgcggctg | atgcttttat | 420 |
| ttaggaagga | atacttacat | tatcatgaga | acattgtcaa | gggcattctg | atacgggcct | 480 |
| tccatcgcaa | gaaaaaggca | gcaacggact | gagggacgga | gagagttacg | gcataagaag | 540 |
| tagtaggaga | gcagagtgtc | ataaagttat | attattctcg | tcctaaagtc | aattagttct | 600 |
| gttgcgcttg | acaatatatg | tcgtgtaata | ccgtccctta | gcagaagaaa | gaaagacgga | 660 |
| tccatatatg | ttaaaatgct | tcagagatgt | ttctttaatg | tgccgtccaa | caaaggtatc | 720 |
| ttctgtagct | tcctctattt | tcgatcagat | ctcatagta | gaaggcgcaa | ttcagtagtt | 780 |
| aaaagcgggg | aacagtgtga | atccggagac | ggcaagattg | cccggccctt | tttgcggaaa | 840 |
| agataaaaca | agatatattg | cacttttttcc | accaagaaaa | acaggaagtg | gattaaaaaa | 900 |
| tcaacaaagt | ataacgccta | ttgtcccaat | aagcgtcggt | tgttcttctt | tattatttta | 960 |
| ccaagtacgc | tcgagggtac | attctaatgc | attaaaagac | atg | | 1003 |

<210> SEQ ID NO 56
<211> LENGTH: 1003
<212> TYPE: DNA
<213> ORGANISM: Saccharomyces cerevisiae

<400> SEQUENCE: 56

| | | | | | |
|---|---|---|---|---|---|
| ataattgcgt | ttaaacgcct | ttcctttct | tcatccattt | tcctggtatt | tatctcatcg | 60 |
| tctctcttaa | ttcttaattt | actaccttca | tctgggatta | tgaactgtgg | atgttccata | 120 |
| tcacattcat | ccttccctaa | aggacaaaat | ccggtcatgt | atctttgaca | gaaaaccttc | 180 |
| ttaatatgcc | gtctaggaca | agaactcccc | agaggacaga | atcccatttc | gtaattttca | 240 |
| cattttggta | tcttgctagc | gggatctatg | tgtagatatt | gacaatctgg | actttgtgta | 300 |
| cagtacccgt | ttttgctgaa | gaagacacat | tcaggcattt | ttcgaagatt | gtattcatgt | 360 |
| aagtattcac | attggtcatt | ctttttgcac | aaccctcgaa | gccaatgtct | acaaacaatt | 420 |
| ttattctgaa | atattggtaa | cacatgcttt | tttggacata | acggtcccct | cggacatgat | 480 |
| ttagggcctt | ctctagaatt | gtaaaattca | caaataggtc | tgtcaggatc | gagtgaaaac | 540 |
| gaatactctt | gcctgaggaa | aggttcaaat | ttaaaaggat | atttttgctgt | atcggggtga | 600 |
| attaggctca | ttacataaac | ttattgattt | tattcgtcct | agaatacttg | tttaagatac | 660 |
| agtgcagaaa | tctttagctt | ataattcaga | aatgtgatat | tttgaagcga | ttggaacaac | 720 |
| aaagtacagt | gcattctata | taattattaa | aagttatagt | ggactattgt | aataacactt | 780 |
| gttttcccca | tatcataacc | gacggcgcgt | aaatgcatgc | tcaatcaagt | ttccgaataa | 840 |
| gttaagtttg | ccaccattg | aggattaata | tacacaaggc | agcattgaaa | aacctaattg | 900 |

| | |
|---|---:|
| ttaacactac acaaatctct attgttgtag taaactgcgc tttttaccac tgttacaata | 960 |
| gttactaata cacgcaaaaa ttctggataa acacggcaaa atg | 1003 |

<210> SEQ ID NO 57
<211> LENGTH: 1003
<212> TYPE: DNA
<213> ORGANISM: Saccharomyces cerevisiae

<400> SEQUENCE: 57

| | |
|---|---:|
| gcacgtgaat gtgatgtctt gtgatggcgg gtgaattagg accggggtcc gctgagtgtt | 60 |
| gaacttcaca aagcatatat cattgacata atcagaaacg tgcttgatca attgtgctat | 120 |
| ggggaggtcc cggtgcaaga ttccaatcat cctttttgttc gtgtcacctt tgttctgtgc | 180 |
| catcaacgac aaatagtgcg tcacaagcag cttcatcgtg attctctcct tcaggtggaa | 240 |
| gttcaagaac tgcgaaattt gaactttgg gtaacacgat tggatttcct gaagaccttt | 300 |
| tgccaatacc acaatggcgt cctcgtggtc gtccagcagt tctgtgaact tggcctgtat | 360 |
| cttgggagga ttgtgcaact cgtacgggta tgcgattgat agcaacgttt gcaagctttt | 420 |
| caaatacaaa gagttggttc tctcaatatg agggttgatt accgcattat acggtagcct | 480 |
| ctgaatggca ttaagccgtt tacacgtcaa tgaaagcaac aggttgattg tcttgatcgt | 540 |
| cagcatgtac tcctccttct tggtcagcgg cggcctgtat tgcaggaaat actcgtagtt | 600 |
| taggggcgca attggtttac tagcgtagtc ctgtatcagc agctcaatgt tcgacctaat | 660 |
| cttgtaatgc tggtcgaacg acagttgcga cagcagctcg tgtgagggtc gctggcgatg | 720 |
| tgcccagcgc attccccac atttccatga acgcataatc ttccacatac taccgtgaag | 780 |
| gcgtcttgat accacgtctt ccagttatgg tcttgactca ccaatgttct cagtttaatg | 840 |
| ttgtttgctt catactggca gacattttcc cttattaccg tgagaagcga gcggtggatt | 900 |
| aatcgggatg tcaaaaacaa gaaaattgca accttcttca cctataaccct atatgatttg | 960 |
| taggcagagg agtggaataa gcaacaaatc atagtcatca atg | 1003 |

<210> SEQ ID NO 58
<211> LENGTH: 1003
<212> TYPE: DNA
<213> ORGANISM: Saccharomyces cerevisiae

<400> SEQUENCE: 58

| | |
|---|---:|
| aaatctcact tcagaaacga aaatactac atagatatca ccgaattgtt ccatgaggtc | 60 |
| accttccaaa ccgaattggg ccaattgatg gacttaatca ctgcacctga agacaaagtc | 120 |
| gacttgagta agttctccct aaagaagcac tccttcatag ttactttcaa gactgcttac | 180 |
| tattctttct acttgcctgt cgcattggcc atgtacgttg ccggtatcac ggatgaaaag | 240 |
| gatttgaaac aagccagaga tgtcttgatt ccattgggtg aatacttcca aattcaagat | 300 |
| gactacttag actgcttcgg taccccagaa cagatcggta agatcggtac agatatccaa | 360 |
| gataacaaat gttcttgggt aatcaacaag gcattggaac ttgcttccgc agaacaaaga | 420 |
| aagactttag acgaaaatta cggtaagaag gactcagtcg cagaagccaa atgcaaaaag | 480 |
| atttcaatg acttgaaaat tgaacagcta taccacgaat atgaagagtc tattgccaag | 540 |
| gatttgaagg ccaaaatttc tcaggtcgat gagtctcgtg gcttcaaagc tgatgtctta | 600 |
| actgcgttct tgaacaaagt ttacaagaga agcaaataga actaacgcta atcgataaaa | 660 |
| cattagattt caaactagat aaggaccatg tataagaact atatacttcc aatataaatat | 720 |
| agtataagct ttaagatagt atctctcgat ctaccgttcc acgtgactag tccaaggatt | 780 |

```
ttttttaagc caatgaaaat gaagaaatgc gtgatcggaa attacgggta gtacgagaag    840
gaaacttgag ccaccccca aatttattc atataataat aggaaaagca acgacctcat     900
ctctcgaaca ttgtttactt gagcaagtcc gattaagagt aagttgtcgt acgttaaata   960 caataatca acaaaacact acacaaaaac ttctacgata atg                     1003
```

<210> SEQ ID NO 59
<211> LENGTH: 1003
<212> TYPE: DNA
<213> ORGANISM: Saccharomyces cerevisiae

<400> SEQUENCE: 59

```
aaaaaactga aatatagggt ttgttaatcc tggtaaaaat ctgatgtgac atcttctgta    60
cttaggtggt cttaccatga agtcagcatc gatacaattg atgttatatt tcgttggttc   120
caatatgtaa attgcctcga tggaggattg tccttttctt gttggggaat caatcaaatc   180
aacagatgtg acattattta aagttcttg gggtgtgagg aaaagataac tcaatattgt    240
ctccacagtt ttatcgataa taagaaactt caagttattt tcgtctcaa tctgattcaa    300 aaccctatc aaatagttcc tctgtaattc aattaaatca gacatcgttc cgccaaacca    360
agcatgtgca cactcttcta cttttgtcagt ggattctaat tatttttcaag gtcttacaaa  420 gcaatgtctt actagtttca atagggactt aaactgatcg tttaagcaaa agaaaaacac   480
cgtgctgtgt gaccatctac caataattgc gagaacataa gacgacgccg ccattcacct   540
ctctatcact tacaccatgt tatagggata agtgtgtagt cgatcggcta ttcgatgatt   600
tttaaagagt gcctgtaata atagctgtat cgcaagtaag gaatacaaga ttactgatat   660
tttgatccag gaggatggac atgttagata gaaaaactaa gagggctact acatccggtt   720
tagtattctg ttattgggaa tgcttttccc aagacgcaag caagaggtga cacataaaca   780
tagttttctt attgtatcgt tacatattct tattttacgc tgctgtcatt aaatatggca   840
cttatctcag atacatttct tttaatcagc gaaaaaatg gcgaggtgaa aaaaatcgat    900
gagatgaaaa aatttttac tagtaaaggc gtattgatga tatattagca gctaaagtat    960
agcaaggttt gtcaatttga agcagtccgc gtgttttaca atg                    1003
```

<210> SEQ ID NO 60
<211> LENGTH: 1003
<212> TYPE: DNA
<213> ORGANISM: Saccharomyces cerevisiae

<400> SEQUENCE: 60

```
ctaactataa taactggtag ctttgtcact cgtaccagga aaagtgaaga ttaaactgaa    60
ttttaaaatg aacgatcgat tagttacgga agagcaagag ttgtttacaa aattgcgcga   120
gattgtaggt tcaagtattc gcttttggga ggaacaactg ttttatcaag ttcaagatgt   180
aagcaccata gaaaaccacg tcattctcag tttaaaatgt acaattttaa cggatgctca   240
gataagtacg ttcataagca aacccagaga gcttcatacg catgccaaag gatatcctga   300
aatctattac ctttccgagt tatcaacaac tgtcaatttt ttttctaaag agggaaacta   360
tgtcgaaata agccaggtta ttcctcattt taatgaatat ttttcctctt taatagtgtc   420
tcaattggaa tttgaatacc cgatggtctt ctccatgatt tcaaggctcc gattgaagtg   480
gcaacaaagt tcgctcgctc cgatatccta cgccctaacg agcaattcag tacttcttcc   540
aataatgctt aacatgattg cccaagacaa atcttcaaca accgcgtatc aaattctgtg   600
```

```
tcgaagaaga ggtcctccaa ttcagaatttt tcaaattttt tccttaccgg ctgtaacgta    660
caataagtag catgcataaa atataattta atcaaatact tttgggcaat taaaatttta    720
gttaacaata gttatgcaat gcgctttatg ttcatgatg accgtttata agctattgcc    780
atatccttat cttattgctt ccagtagcct cgagtcgacc actaaaaaga tgtcacttaa    840
gacggaaatt atgtagctgc acttcttttt taacaagttc ggtcggccct tcaagttctc    900
ctttctaaag cctcattatt tattgcgtag atgctaaatg ttatcgcggt ttagcttgca    960
tgttacgttt ccgttttaga acctggtcga gtagcgaata atg    1003
```

<210> SEQ ID NO 61
<211> LENGTH: 1003
<212> TYPE: DNA
<213> ORGANISM: Saccharomyces cerevisiae

<400> SEQUENCE: 61

```
ttcgccaacc atcatacccg aatgtttcat tagcgaactg aatgagagca tgccctggta     60
tcagcttaga taagttgtgc ttcccatatt tattattgtg gtaaatattg tacgtgtacc    120
tttcgatctt ggactgtaga agcccaatcc tctgcaccga ccaagcgctg gcaggtcttc    180
cattccaatc ttcgatgatt tggaactctt ttatatccaa gcccggtgct gtgccgtatg    240
tagtcgaatc atacgatatg ctcgaactgg gcttcgcttg tatcgtcatt attttgtctg    300
tttatcctga aatatgctct tctcctctac gtaacccttt aatggtccaa agcatgtgct    360
aaactgccac agactccctc aatgatgttc ttatccttcc ttgccgttac tgcttcctat    420
catatctgcc cttgccaaac tgtggcttcc tctaatcaat ttgccccagt acattgaaaa    480
gcacgtgacg tgacaccaac ttgaaagaca ttagtgtcca acgcgatata atggtcaata    540
aaatacccaa ttttatcaag tgaacatgat attattcaat actatagtac tttaaagaaa    600
acttcaacaa gttgcttcat tgctatatta tacaattatg ggtgatgccg gtcggctaac    660 cttttctttcg cagcgccaca tacaagaaca tatggtaatt actaagaact ttttggaaac    720
tatttccatg aagaaaacaa aatttactgg cttctgtctt cgaagtaaat ttagcgaact    780
tgatactttc gtttggacag tcgtttagat ttgcaactgt ctgttcttat ttcttgctat    840
tattaccaga aataaagcct aaagcgcgtg gttcttacga aaaaaataga ccttgcacat    900
taacagggtt tagacatcac agagactgaa tactggagag aagacaattc ttgttcacga    960
cttcgagtga ttaatatcta taacaaccct cctatcaaga atg    1003
```

<210> SEQ ID NO 62
<211> LENGTH: 1003
<212> TYPE: DNA
<213> ORGANISM: Saccharomyces cerevisiae

<400> SEQUENCE: 62

```
tgaaaggcaa atttacgctc ttcaagacac caatttagga ttggtggcta ccgcggagat     60
acctttggca ggtctagggg caaacaaagt tctagagtta aactcgggag aatgttctaa    120
gaaactagtt ggagtaagta gatgttacag agctgaggca ggtgccaggg gaaaagatac    180
gaaaggtctc tatcgcgttc atgagtttac taaagtagaa ttattttgct ggagcaagcc    240
agaaaccagt gcaaaggtcc ttgaggaaat aaagcaattt cagatttctg tagttgagga    300
attaggaata ccggccaaag tactaaaatat gccatcaaac gatcttggta atcccgcttt    360
caagaaatac gacatcgaag cttggatgcc aggaaggggg aaatttggcg agataagtag    420
tgcctccaat tgtaccgatt tccaaagtag aagattaaat acaaagtaca gggacgataa    480
```

```
cacaggaaag ctagaatatg tgcacacgct gaatggcaca gcaatggcta tcccaagagt      540
gatagtagca ctagtagaaa atttctatga cccaagcacc ggtaagatat ctgttcctga      600
atgtttgagg gagtttatga atggccaacg atacatttaa taagtaagaa aatcttgtaa      660
atatgtaatc ttatgttaac cgtagcatca ttgtgttgga cgaaatcctc tgtgatgttc      720
tgtgtgattg aaattgtatg gtattttcga tcatacgagt attttcccta agatgaaag       780 agaactcgat tcctaaacag ttgtttgtag ggcataacgt tgtatcgtaa atacttacca      840
tacgcttagg tatattcctt tagatttccg taacacctt cagttttact attccgcgtg       900
gcgaggtaaa gatcataaaa atacaagttt gttatagcat ttcctgcaaa taattgctgt      960
aactagtggc gaaaaggtca tagaattatt cgcctaaatt atg                       1003
```

<210> SEQ ID NO 63
<211> LENGTH: 1003
<212> TYPE: DNA
<213> ORGANISM: Saccharomyces cerevisiae

<400> SEQUENCE: 63

```
ccggaagtaa ttttatcaat tatagtttcc aaatcatcat attcttgaac tatatcaatt       60
aaatcatcac tcgtccagtc agggaacaat tctgtaagcg tatctatttt ggactttagc      120
gcaggattta gttttttact actatgacta ttatgattag acttcctaaa ttgtgtagac      180
attatatata tatgatgatg tagattatat tgagaaaacg accaaacaaa aataaatatg      240
taagtacttt atgatggtga ttttttgggg gtaattggta agagttttc ttgtagcttc       300 aaaagatcaa atataaaata cgaatgtttc tgaaattact gtaaaagact taggaaaagg      360
aatgaaacgt ttatatggga gagaacgaaa attttccctt ttcccgccac tacttttgc       420 caccatttcc cgttatttat ttgggcgagt gctcacctcc gacggaatca cgggtgacgg      480
atatcctaaa aaggtaaaga attgaaacag atcattaat atacggatca ctatacatta       540
ttataagtcg atattgcagt attagtattt acatgttgaa taatgcacat tctgtgctaa      600
aatatatact tcatttgtca acttcttta gtttgccgcc attttcaaac ggcgcctcct       660
ccctagcttc gtctagagca ggcttaatac cttgtttgac gagagctgcg ttgacacatg      720
tagtataagc gtaccattgt tttgagcact cgttctcaac ggattttccc ttcaggaatt      780
tttcgctata ccattcatta aaacaactat cgtatttcgt cttcaggtca gtgcattcag      840
gcgcaaaact agctgacatt atattcccca tataaaactg gtattattgt tattgtaatt      900
caagttaaaa cacaaacaga tgttttctaa tgacctctcc cggcatatat ctggcgcact      960
tagaataaat ttctacatgc aaatactctg aatattctga atg                       1003
```

<210> SEQ ID NO 64
<211> LENGTH: 1003
<212> TYPE: DNA
<213> ORGANISM: Saccharomyces cerevisiae

<400> SEQUENCE: 64

```
ttcttcttct ccattattat cttcagtagt tgtcttgtca tcagattgtc cctgttgcga       60 ttttcatca tctgaatgtt ctggatcttt tttttcagaa gatccagcat tgttgtctag       120
tgttttgtca ctagtatttt cttccgagtt ctcagaactt atgttttcat ccttttgatt      180
gttagcggtg gcattgtctt cattggattc ctcatcatct ttggttgata cctttgattc      240
atcagtatct ttatcttcgg aagacttgtt gtcttcttct gctagaacaa ccaattcacc      300
```

```
atcttcagct actttttgaag caccaatttt atcacccccct aattgagggc cagcttcagt      360
ttcatcgttt ttgctgtcgt tgtcatctcc attttcatcg cttttgctgt tgttgtcatc      420
ttcattttct ggtgattgct caccaccact ggaaagctct tcctctgcgg ttttatcgga      480
ttctaccttc cttgaggcga aaagaggctt cctattagga gcaataaaat ataaagcacc      540
agccatagaa agaatcccca ttataaagcc cgctgttttt tcctgattgg agttcctacc      600
gaactgaggg gaggacgcca tgagacgtct tgtttggtgt cggcataacc cccttgccac      660
ttgaattgac ggcctgtttc tgcacgcatt cctgacgact aagttgcgaa gcattttact      720
gataatatac actctttgga tcgagcctac ttccagttgg taattggtgt tccacaattt      780
cagcattata tgtttttaaa ccaaaattcg gctcctttc cctttttttc ttattgggtg      840
gcgtgccgta cagaacgatt ggcttggtgt gaaatcaaga gcaagcacaa tagatatcaa      900
catgaacaat atacaaaagt ctctggcaca gtttgactgc gttagaccag gctagggcat      960
ttctgaagct ttacgtatca ctagagaagt tattttggca atg                      1003

<210> SEQ ID NO 65
<211> LENGTH: 1003
<212> TYPE: DNA
<213> ORGANISM: Saccharomyces cerevisiae

<400> SEQUENCE: 65
gaaagatgac ctctttcaaa cgcagtacgc agtttgttga ccatatgcgg ataggtgacg       60 tatatttttcc agaatggtaa tttggtatct ccggaataac cccagataga ctgtttagat      120
acaacttcaa tcgaatcaat agcgtggtca aatgtttcgt ttaaatagtg cacaaacttg      180
ttgatttgct cctgatcgtt agcgtcggaa gaattgggcg ctgggacgta agatagttc       240 ttgaaccctg taacattaca aagtacagag tgtccttcac tagtgacacc aaaaaacctt      300
accacggtag atgtattttc atctttgata ccattcagta cgctctgttc cgcatcaatt      360
tgttggaaag aaatatcata caaacttggg tcaaaatcgg ttggaagttt cttacgctcg      420
aatgatgaca ggtcatgctc ttcttggtcg gccatatcat gttccatttg cgatacgtct      480
tgttcaaaag tagactctaa ttgcgtaccc attaaatctg tatcctttgc tttgaagcct      540
tgactattat attttcgaaa agaatcactc ggaataatct ctattgttga aacaggttca      600
cttccaacac catgatctat tgattgccgt ttgattttct tttccaactg gggagtatcc      660
tcgtcatcga tcttcacatc aaccatggga agggatcttt tttcactcat tgctgtgcgt      720
atatgtataa agattaatgc ttaatagcaa gtgctcaata tctatttttcc tttatccttg      780 aaaattgcct tagatcagta gtactgagtg tttgttcttc ataagcgaat agcagatgtc      840
ctcattgaac attttataga ataaaaagtt acgcgtaata cgaaaaattg cctattacgt      900
taaggcatac ttttaccaca caaaaccaag atcaaccgtc aagcaagaac gctgcaaaga      960
aacgcagata taaggagaa caccagatcg aactgcaact atg                       1003

<210> SEQ ID NO 66
<211> LENGTH: 1003
<212> TYPE: DNA
<213> ORGANISM: Saccharomyces cerevisiae

<400> SEQUENCE: 66
tcttgaatgt cgacatatgc ccatcatcag tgaggaatac tcgcgtgaag gatctcatct       60
gcgacctgag tgatgatgaa gaagttgcag cactactgaa tttgttgaaa agaaagtata      120
aaaatgaaat ccgattgatt gtgaacaatg ctggagtaag ggccaacttc accggattca      180
```

```
acggcatgga acgggataat cttgataaga ttttaagat aaacacattt gcaccacttc      240
agttcattca agaactggcc cctagtagac actcaactag acagtgttat attgtcaata      300
tcgcaagcat tttgggcata ttgacgccgg ccaaagtagc agcttatgcg gcgagcaaag      360
cagcattgat agcctttcat cagtcgtaca gttttgaatt gcaaaacgaa ggcgtaagaa      420
atatcagaac actattagtg accccagggc aactgaatac ggaaatgttt gcaggattca      480
agcctcctcg ccagttcttt gcccctgtaa tagacattac tactctagct gccaagatag      540
tccgttattg tgagctgggt cagaggggac agctaaatga accctttat tgtagttttg       600 ctcatcttt gatgtgcgta ccttattcgc tacaacgcat tgtaagaagc ttctctcgca       660
tagattgctg cctcccggac gagtagaaag ctatacatag taaatagaat atttatagat      720
gaatccgagt agacagcctt ggtgtttgct tatacattct ttgcaattat gcacgccctc      780
attaccgttg ctcatatttt tgggcattaa ttgtattttg aaaagtgctc gttcaggccc      840
gtgtaaaaaa aggtgatgaa gcaaacatta taataaacac ttctgagaag ccacgtgtag      900
aggggtaagc tatatcgtaa acaccgttgg atgtggacca cggtgcactg ataaaataaa      960
gatatagtag tagaatctgt tactaatctt aacactttg atg                       1003

<210> SEQ ID NO 67
<211> LENGTH: 1003
<212> TYPE: DNA
<213> ORGANISM: Saccharomyces cerevisiae

<400> SEQUENCE: 67
gctgtagata gatatagaga agccgccaaa acagaactaa gaattctaca gactatcctg       60
aataatgacc ctcaaggtca gttccagtgc ctcttgctaa gggagtgctt cgattacaaa      120
aatcacattt gtttggtgac agatctatac ggcaggtcca tttacgattt tatgtgctcc      180
aacggcattg ccaggttccc cggctctcat attcaggcca ttgccagaca gctaatcaga      240
tctgtctgct tcttgcacga tttgggcata atacacacgg atttgaaacc agaaaatatc      300
ctgatttgtg acgaaaccca tattgctcaa aaattgcctt tgaaaaccgt acagtcgcta      360
agcaagagac gccgtgaagc cagtaagggg aagcgcaaaa tcttgaaaaa tccagaaatc      420
aaaatcattg atttcggtag cgcaattttc cattacgaat atcatcctcc tgtaatatcc      480
actcgtcact atagagcccc ggaaattgtc cttggcttgg gctggtcgtt cccctgcgac      540
atttggtcca tcgcgtgtgt cctagtgaaa ctggttattg gcgaatctct ttaccccatt      600
catgaaaatc tagaacatat ggctatgatg caacgaatca atggaacccc tttcccaca       660 gacattattg ataagatgtt ttacaaatct aaacataaat tgggcaactc tccatcagac      720
ctaaattcaa cggtgataaa gcatttcgac agaaaaactt taagcttaca atggcctgaa      780
aaaaataaac gcggagatac cataaccacc gaaaagtcaa tgaaaagggt cttgcagtca      840
tgtgatcgct tagatattta catctcaaag gtcttgaaac aggattacgg cgatagctta      900
agcatcaatt ggaatctacc gccggagaaa aactggtctt tgataaattc gaaattggca      960
tggaaaagac aaacacattc ctcttcttcc tcaactactg atg                      1003

<210> SEQ ID NO 68
<211> LENGTH: 987
<212> TYPE: DNA
<213> ORGANISM: Saccharomyces cerevisiae

<400> SEQUENCE: 68
```

```
cggtccagaa aagcaactga gattgggagt ataattcggt ggcgttattg gaatacataa      60
taggaaaata cggcagatac ctagtcacga aatatggtg taatctattc gcttttcaa       120 tggaaatact aatatcgccc agtacaaact catctacatt tgcatgcggc gaaggcaata     180
atggcatagt cgtggtggtg gctactaccg gcgtcttcgt cctatctgca ttgttatttg    240
ttgctacgtg gcttgttgct gcaaatggtg gttgatttgt tgtcgttgta acggtggtcg    300
acgtagtatg aggggaatat gtttttgaa ttggagagaa ggggccgttc ggagtgttac     360
ctgcagagtt gttcttataa aaagccattt gcaaagcagg aggtaaagat tcttttgaat    420
tattaggcaa tgctgagtca tttagcagcg ggggcagctt atttggctct gttgcaacca    480
agcctttcga atcttgcgct aaagaagatg cgcgcaacgt catgtgagaa gatgcttcat    540
tatttgcttt aaatttattc gtattgctgc cctgatttgc ttgtaagagt tggggttccc    600
tggacaaata agtttgaact gaaaccttag aatctcgttg agccgcggaa gaagttggag    660
aacctgagga aggagaagaa tctgggttag ggataatagt acccggagtt ggagttggat    720
gcagattgag cttattcaaa aggctattgc ccatgggaat ctgttgtaaa agatgaacga    780
aaacgctgtc attggccaga agagtatcga gtttagattt gatttcatcc acatcttgtc    840
tcagtagttg caactgtgag cccttcttag gcctgaattg aggattgatt tcacagtgga    900 gaccaattt ttcgcatctg gagcaaggat gagggaaatt ttgactagca tcgcatttga     960
ttttgtgctg tctacaatgt gtacatg                                        987

<210> SEQ ID NO 69
<211> LENGTH: 30
<212> TYPE: DNA
<213> ORGANISM: Artificial Sequence
<220> FEATURE:
<223> OTHER INFORMATION: Primer

<400> SEQUENCE: 69
tttgcgcgcg ggccgcatca tgtaattagt                                      30

<210> SEQ ID NO 70
<211> LENGTH: 30
<212> TYPE: DNA
<213> ORGANISM: Artificial Sequence
<220> FEATURE:
<223> OTHER INFORMATION: Primer

<400> SEQUENCE: 70
aaaagatctg accgagcgca gcgagtcagt                                      30

<210> SEQ ID NO 71
<211> LENGTH: 83
<212> TYPE: DNA
<213> ORGANISM: Artificial Sequence
<220> FEATURE:
<223> OTHER INFORMATION: Primer

<400> SEQUENCE: 71
cccatgttaa ttaaatctgt tgtttattca attttagccg cttctttggc caatgcaggt    60
gcttccaagg tgtacgaccc cga                                             83

<210> SEQ ID NO 72
<211> LENGTH: 32
<212> TYPE: DNA
<213> ORGANISM: Artificial Sequence
<220> FEATURE:
<223> OTHER INFORMATION: Primer
```

<400> SEQUENCE: 72
aaaggcgcgc cttactgctc gttcttcagc ac                                        32

<210> SEQ ID NO 73
<211> LENGTH: 19
<212> TYPE: PRT
<213> ORGANISM: Artificial Sequence
<220> FEATURE:
<223> OTHER INFORMATION: PHO5 signal sequence

<400> SEQUENCE: 73

Met Leu Ile Lys Ser Val Val Tyr Ser Ile Leu Ala Ala Ser Leu Ala
1               5                   10                  15

Asn Ala Gly

<210> SEQ ID NO 74
<211> LENGTH: 31
<212> TYPE: DNA
<213> ORGANISM: Artificial Sequence
<220> FEATURE:
<223> OTHER INFORMATION: Primer

<400> SEQUENCE: 74
tttggatcca cggattagaa gccgccgagc g                                         31

<210> SEQ ID NO 75
<211> LENGTH: 35
<212> TYPE: DNA
<213> ORGANISM: Artificial Sequence
<220> FEATURE:
<223> OTHER INFORMATION: Primer

<400> SEQUENCE: 75
cccttaatta acatggtttt ttctccttga cgtta                                     35

<210> SEQ ID NO 76
<211> LENGTH: 34
<212> TYPE: DNA
<213> ORGANISM: Artificial Sequence
<220> FEATURE:
<223> OTHER INFORMATION: Primer

<400> SEQUENCE: 76
tttggatcct gtgcacgatg gcttcgtttt agcc                                      34

<210> SEQ ID NO 77
<211> LENGTH: 33
<212> TYPE: DNA
<213> ORGANISM: Artificial Sequence
<220> FEATURE:
<223> OTHER INFORMATION: Primer

<400> SEQUENCE: 77
cttaattaac atcgagtttc aaaaaattgt aag                                       33

<210> SEQ ID NO 78
<211> LENGTH: 32
<212> TYPE: DNA
<213> ORGANISM: Artificial Sequence
<220> FEATURE:
<223> OTHER INFORMATION: Primer

<400> SEQUENCE: 78
cccggatcct ctacgatata tcctgtaaat ag                                        32

<210> SEQ ID NO 79
<211> LENGTH: 34
<212> TYPE: DNA
<213> ORGANISM: Artificial Sequence
<220> FEATURE:
<223> OTHER INFORMATION: Primer

<400> SEQUENCE: 79
cttaattaac attttgagta cgtctaatct gtat                              34

<210> SEQ ID NO 80
<211> LENGTH: 84
<212> TYPE: DNA
<213> ORGANISM: Artificial Sequence
<220> FEATURE:
<223> OTHER INFORMATION: Primer

<400> SEQUENCE: 80
cccatgggat ccaaatctgt tgtttattca attttagccg cttctttggc caatgcaggt    60
gaagacgcca aaacataaa gaaa                                          84

<210> SEQ ID NO 81
<211> LENGTH: 34
<212> TYPE: DNA
<213> ORGANISM: Artificial Sequence
<220> FEATURE:
<223> OTHER INFORMATION: Primer

<400> SEQUENCE: 81
aaaggcgcgc cttactttcc gcccttcttg gcct                              34

<210> SEQ ID NO 82
<211> LENGTH: 19
<212> TYPE: PRT
<213> ORGANISM: Artificial Sequence
<220> FEATURE:
<223> OTHER INFORMATION: PHO5 signal sequence

<400> SEQUENCE: 82

Met Leu Ile Lys Ser Val Val Tyr Ser Ile Leu Ala Ala Ser Leu Ala
1               5                   10                  15

Asn Ala Gly

<210> SEQ ID NO 83
<211> LENGTH: 31
<212> TYPE: DNA
<213> ORGANISM: Artificial Sequence
<220> FEATURE:
<223> OTHER INFORMATION: Primer

<400> SEQUENCE: 83
tttggatcca cggattagaa gccgccgagc g                                 31

<210> SEQ ID NO 84
<211> LENGTH: 33
<212> TYPE: DNA
<213> ORGANISM: Artificial Sequence
<220> FEATURE:
<223> OTHER INFORMATION: Primer

<400> SEQUENCE: 84
tttggatccc atggtttttt ctccttgacg tta                               33

<210> SEQ ID NO 85
<211> LENGTH: 7393
<212> TYPE: DNA
<213> ORGANISM: Artificial Sequence
<220> FEATURE:
<223> OTHER INFORMATION: pSPRT47

<400> SEQUENCE: 85

| | | | | | |
|---|---|---|---|---|---|
| gtacgctgca | ggtcgacgga | tccccgggtt | aattaaatct | gttgtttatt | caattttagc | 60 |
| cgcttctttg | gccaatgcag | gtgcttccaa | ggtgtacgac | cccgagcaac | gcaaacgcat | 120 |
| gatcactggg | cctcagtggt | gggctcgctg | caagcaaatg | aacgtgctgg | actccttcat | 180 |
| caactactat | gattccgaga | agcacgccga | gaacgccgtg | attttctgc | atggtaacgc | 240 |
| tgcctccagc | tacctgtgga | ggcacgtcgt | gcctcacatc | gagcccgtgg | ctagatgcat | 300 |
| catccctgat | ctgatcggaa | tgggtaagtc | cggcaagagc | gggaatggct | catatcgcct | 360 |
| cctggatcac | tacaagtacc | tcaccgcttg | gttcgagctg | ctgaaccttc | caaagaaaat | 420 |
| catctttgtg | ggccacgact | gggggggcttg | tctggccttt | cactactcct | acgagcacca | 480 |
| agacaagatc | aaggccatcg | tccatgctga | gagtgtcgtg | gacgtgatcg | agtcctggga | 540 |
| cgagtggcct | gacatcgagg | aggatatcgc | cctgatcaag | agcgaagagg | gcgagaaaat | 600 |
| ggtgcttgag | aataacttct | tcgtcgagac | catgctccca | agcaagatca | tgcggaaact | 660 |
| ggagcctgag | gagttcgctg | cctacctgga | gccattcaag | gagaagggcg | aggttagacg | 720 |
| gcctaccctc | tcctggcctc | gcgagatccc | tctcgttaag | ggaggcaagc | ccgacgtcgt | 780 |
| ccagattgtc | cgcaactaca | acgcctacct | tcgggccagc | gacgatctgc | ctaagatgtt | 840 |
| catcgagtcc | gaccctgggt | tctttttccaa | cgctattgtc | gagggagcta | gaagttccc | 900 |
| taacaccgag | ttcgtgaagg | tgaagggcct | ccacttcagc | caggaggacg | ctccagatga | 960 |
| aatgggtaag | tacatcaaga | gcttcgtgga | gcgcgtgctg | aagaacgagc | agtaaggcgc | 1020 |
| gcgggccgca | tcatgtaatt | agttatgtca | cgcttacatt | cacgccctcc | ccccacatcc | 1080 |
| gctctaaccg | aaaaggaagg | agttagacaa | cctgaagtct | aggtcccta | ttattttttt | 1140 |
| atagttatgt | tagtattaag | aacgttattt | atatttcaaa | ttttttcttt | ttttctgtac | 1200 |
| agacgcgtgt | acgcatgtaa | cattatactg | aaaaccttgc | ttgagaaggt | tttgggacgc | 1260 |
| tcgaaggctt | taatttgcgg | ccctgcatta | atgaatcggc | caacgcgcgg | ggagaggcgg | 1320 |
| tttgcgtatt | gggcgctctt | ccgcttcctc | gctcactgac | tcgctgcgct | cggtcagatc | 1380 |
| tgtttagctt | gcctcgtccc | cgccgggtca | cccggccagc | gacatggagg | cccagaatac | 1440 |
| cctccttgac | agtcttgacg | tgcgcagctc | aggggcatga | tgtgactgtc | gcccgtacat | 1500 |
| ttagcccata | catccccatg | tataatcatt | tgcatccata | cattttgatg | gccgcacggc | 1560 |
| gcgaagcaaa | aattacggct | cctcgctgca | gacctgcgag | cagggaaacg | ctcccctcac | 1620 |
| agacgcgttg | aattgtcccc | acgccgcgcc | cctgtagaga | aatataaaag | gttaggattt | 1680 |
| gccactgagg | ttcttctttc | atatacttcc | ttttaaaatc | ttgctaggat | acagttctca | 1740 |
| catcacatcc | gaacataaac | aaccatgggt | aaggaaaaga | ctcacgtttc | gaggccgcga | 1800 |
| ttaaattcca | acatggatgc | tgatttatat | gggtataaat | gggctcgcga | taatgtcggg | 1860 |
| caatcaggtg | cgacaatcta | tcgattgtat | gggaagcccg | atgcgccaga | gttgtttctg | 1920 |
| aaacatggca | aaggtagcgt | tgccaatgat | gttacagatg | agatggtcag | actaaactgg | 1980 |
| ctgacggaat | ttatgcctct | tccgaccatc | aagcatttta | tccgtactcc | tgatgatgca | 2040 |
| tggttactca | ccactgcgat | ccccggcaaa | acagcattcc | aggtattaga | agaatatcct | 2100 |

```
gattcaggtg aaaatattgt tgatgcgctg gcagtgttcc tgcgccggtt gcattcgatt   2160
cctgtttgta attgtccttt taacagcgat cgcgtatttc gtctcgctca ggcgcaatca   2220
cgaatgaata acggtttggt tgatgcgagt gattttgatg acgagcgtaa tggctggcct   2280
gttgaacaag tctggaaaga aatgcataag cttttgccat tctcaccgga ttcagtcgtc   2340
actcatggtg atttctcact tgataacctt attttttgacg aggggaaatt aataggttgt   2400
attgatgttg gacgagtcgg aatcgcagac cgataccagg atcttgccat cctatggaac   2460
tgcctcggtg agttttctcc ttcattacag aaacggcttt ttcaaaaata tggtattgat   2520
aatcctgata tgaataaatt gcagtttcat ttgatgctcg atgagttttt ctaatcagta   2580
ctgacaataa aaagattctt gttttcaaga acttgtcatt tgtatagttt ttttatattg   2640
tagttgttct attttaatca aatgttagcg tgatttatat ttttttttcgc ctcgacatca   2700 tctgcccaga tgcgaagtta agtgcgcaga agtaatatc atgcgtcaat cgtatgtgaa   2760
tgctggtcgc tatactgctg tcgattcgat actaacgccg ccatccagtg tcgaaaacga   2820
gctcgaattc ctgggggaac aacttcacag aatgttttgt catattgtcg aagtggtcac   2880
aaaacaagag aagttccgcc aattataaaa agggaacccg tatatttcag cttcacggat   2940
gatttccagg gtgagagtac tgtatatggg cttacgatag aaggccataa aaatttcttg   3000
cttggcaaca aaatagaagt gaaatcatgt cgaggctgct gtgtgggaga acagcttaaa   3060
atatcacaaa aaaagaatct aaaacactgt gttgcttgtc ccagaaaggg aatcaagtat   3120
ttttataaag attggagtgg taaaaatcga gtatgtgcta gatgctatgg aagatacaaa   3180
ttcagcggtc atcactgtat aaattgcaag tatgtaccag aagcacgtga agtgaaaaag   3240
gcaaaagaca aaggcgaaaa attgggcatt acgcccgaag gtttgccagt taaaggacca   3300
gagtgtataa aatgtggcgg aatcttacag tggcctatgc ggccgctcta gaactagtgg   3360
atcgatcccc aattcgccct atagtgagtc gtattacaat tcactggccg tcgttttaca   3420
acgtcgtgac tgggaaaacc ctggcgttac ccaacttaat cgccttgcag cacatccccc   3480
tttcgccagc tggcgtaata gcgaagaggc ccgcaccgat cgcccttccc aacagttgcg   3540
cagcctgaat ggcgaatggc gcctgatgcg gtattttctc cttacgcatc tgtgcggtat   3600
ttcacaccgc atacgtcaaa gcaaccatag tacgcgccct gtagcggcgc attaagcgcg   3660
gcgggtgtgg tggttacgcg cagcgtgacc gctacacttg ccagcgccct agcgcccgct   3720
cctttcgctt tcttcccttc ctttctcgcc acgttcgccg gctttccccg tcaagctcta   3780
aatcggggtg ggccatcgcc ctgatagacg gttttttcgcc ctttgacgtt ggagtccacg   3840
ttctttaata gtggactctt gttccaaact ggaacaacac tcaaccctat ctcgggctat   3900
tcttttgatt tataagggat tttgccgatt tcggcctatt ggttaaaaaa tgagctgatt   3960
taacaaaaat ttaacgcgaa ttttaacaaa atattaacgt ttacaatttt atggtgcact   4020
ctcagtacaa tctgctctga tgccgcatag ttaagccagc cccgacaccc gccaacaccc   4080
gctgacgcgc cctgacgggc ttgtctgctc ccggcatccg cttacagaca agctgtgacc   4140
gtctccggga gctgcatgtg tcagaggttt tcaccgtcat caccgaaacg cgcgagacga   4200
aagggcctcg tgatacgcct atttttatag gttaatgtca tgataataat ggtttcttag   4260
acgtcaggtg gcacttttcg gggaaatgtg cgcggaaccc ctatttgttt attttttctaa   4320 atacattcaa atatgtatcc gctcatgaga cataaccct gataaatgct tcaataatat   4380
tgaaaaagga agagtatgag tattcaacat ttccgtgtcg cccttattcc cttttttgcg   4440
gcattttgcc ttcctgtttt tgctcaccca gaaacgctgg tgaaagtaaa agatgctgaa   4500
```

```
gatcagttgg gtgcacgagt gggttacatc gaactggatc tcaacagcgg taagatcctt    4560
gagagttttc gccccgaaga acgttttcca atgatgagca cttttaaagt tctgctatgt    4620
ggcgcggtat tatcccgtat tgacgccggg caagagcaac tcggtcgccg catacactat    4680
tctcagaatg acttggttga gtactcacca gtcacagaaa agcatcttac ggatggcatg    4740
acagtaagag aattatgcag tgctgccata accatgagtg ataacactgc ggccaactta    4800
cttctgacaa cgatcggagg accgaaggag ctaaccgctt ttttgcacaa catgggggat    4860
catgtaactc gccttgatcg ttgggaaccg gagctgaatg aagccatacc aaacgacgag    4920
cgtgacacca cgatgcctgt agcaatggca acaacgttgc gcaaactatt aactggcgaa    4980
ctacttactc tagcttcccg gcaacaatta atagactgga tggaggcgga taaagttgca    5040
ggaccacttc tgcgctcggc ccttccggct ggctggttta ttgctgataa atctggagcc    5100
ggtgagcgtg ggtctcgcgg tatcattgca gcactggggc cagatggtaa gccctcccgt    5160
atcgtagtta tctacacgac ggggagtcag gcaactatgg atgaacgaaa tagacagatc    5220
gctgagatag gtgcctcact gattaagcat tggtaactgt cagaccaagt ttactcatat    5280
atactttaga ttgatttaaa acttcatttt taatttaaaa ggatctaggt gaagatcctt    5340
tttgataatc tcatgaccaa aatcccttaa cgtgagtttt cgttccactg agcgtcagac    5400
cccgtagaaa agatcaaagg atcttcttga gatcctttt ttctgcgcgt aatctgctgc    5460
ttgcaaacaa aaaaccacc gctaccagcg gtggtttgtt tgccggatca agagctacca    5520
actctttttc cgaaggtaac tggcttcagc agagcgcaga taccaaatac tgtccttcta    5580
gtgtagccgt agttaggcca ccacttcaag aactctgtag caccgcctac atacctcgct    5640
ctgctaatcc tgttaccagt ggctgctgcc agtggcgata gtcgtgtct taccgggttg    5700 gactcaagac gatagttacc ggataaggcg cagcggtcgg gctgaacggg gggttcgtgc    5760
acacagccca gcttggagcg aacgacctac accgaactga gatacctaca gcgtgagcat    5820
tgagaaagcg ccacgcttcc cgaagggaga aaggcggaca ggtatccggt aagcggcagg    5880
gtcggaacag gagagcgcac gagggagctt ccagggggaa acgcctggta tctttatagt    5940
cctgtcgggt ttcgccacct ctgacttgag cgtcgatttt tgtgatgctc gtcaggggg    6000 cggagcctat ggaaaaacgc cagcaacgcg gcctttttac ggttcctggc cttttgctgg    6060
ccttttgctc acatgttctt tcctgcgtta tcccctgatt ctgtggataa ccgtattacc    6120
gcctttgagt gagctgatac cgctcgccgc agccgaacga ccgagcgcag cgagtcagtg    6180
agcgaggaag cggaagagcg cccaatacgc aaaccgcctc tccccgcgcg ttggccgatt    6240
cattaatgca gctggcacga caggtttccc gactggaaag cgggcagtga gcgcaacgca    6300
attaatgtga gttagctcac tcattaggca ccccaggctt tacactttat gcttccgcgg    6360
ctcgtatgtt gtgtggaatt gtgagcggat aacaatttca cacaggaaac agctatgacc    6420
atgattacgc cactagtccg aggcctcgag atccgatatc gccgtggcgg ccgccagctg    6480
aagcttaatt atcctgggca cgagtgaaac aaagctaaaa cctttattta gcatggccat    6540
tgaatgtaac aattatatat atcgcaagca caaaaatca aggagagaga actaccactt    6600
tgttcatgtg tacaatgttc attatctcca taagcaaaaa aaaaaatag aaaacatatg    6660 ctataaggtt gatattctca cgagtaagcg gcacttgcta cttattgaca ttgcagattt    6720
ttggctacag aaatagtata ttagagatta taattgctaa tcaaatcaaa atataaaatt    6780
agtaaaccaa accatttata cccttcctta gtagttatgg attgtttttt aatgatattt    6840
```

```
ctgcaaacca aagaaagatt gttatccaga tagaatttag ttttgatatt cattttttg    6900
ttgaagattg aacgccatat ctgggcctca taattcaaaa gacggtgcca ttatcggtag    6960
cgtttcgcat tgtactggat ttcagaaatt tcacagttga tgaatcgaaa agaatggtct    7020
cattgcaaca cgtaaggtta agatgtccct ttttaccatt ataggcaata aatgaatcat    7080
aaaacgaccg tatactggtg aaatagtagg gagaacgagt acctgtagta aaagtataa     7140
atcatagtta atcgggcaat gtccctcgat caaggagtat tgtgtcatgt tcgagacaaa    7200
cgccaacatt tttgtttctt ttggacaaat gttgtttgca tttatgatcc gttatatttt    7260
gatctaatgt agagttgcac gtagttctta ctggcaaaga aatcgatgca taccaaaaaa    7320
gaataaaggt gatatttgat ctttaccgtt tagttccaac gtaaaattgt gcctttggac    7380
ttaaaatggc gtc                                                       7393

<210> SEQ ID NO 86
<211> LENGTH: 8090
<212> TYPE: DNA
<213> ORGANISM: Artificial Sequence
<220> FEATURE:
<223> OTHER INFORMATION: pSPRT50

<400> SEQUENCE: 86
gtacgctgca ggtcgacgga tccaaatctg ttgtttattc aattttagcc gcttctttgg      60
ccaatgcagg tgaagacgcc aaaaacataa agaaaggccc ggcgccattc tatcctctag     120
aggatggaac cgctggagag caactgcata aggctatgaa gagatacgcc ctggttcctg     180
gaacaattgc ttttacagat gcacatatcg aggtgaacat cacgtacgcg gaatacttcg     240
aaatgtccgt tcggttggca gaagctatga acgatatggg gctgaataca atcacagaa     300
tcgtcgtatg cagtgaaaac tctcttcaat tctttatgcc ggtgttgggc gcgttattta    360
tcggagttgc agttgcgccc gcgaacgaca tttataatga acgtgaattg ctcaacagta    420
tgaacatttc gcagcctacc gtagtgtttg tttccaaaaa ggggttgcaa aaatttga     480
acgtgcaaaa aaaattacca ataatccaga aaattattat catggattct aaaacggatt    540
accagggatt tcagtcgatg tacacgttcg tcacatctca tctacctccc ggttttaatg    600
aatacgattt tgtaccagag tcctttgatc gtgacaaaac aattgcactg ataatgaatt    660
cctctggatc tactgggtta cctaagggtg tggcccttcc gcatagaact gcctgcgtca    720
gattctcgca tgccagagat cctatttttg gcaatcaaat cattccggat actgcgattt    780
taagtgttgt tccattccat cacggttttg gaatgtttac tacactcgga tatttgatat    840
gtggatttcg agtcgtctta atgtatagat ttgaagaaga ctgttttta cgatcccttc    900
aggattacaa aattcaaagt gcgttgctag taccaaccct attttcattc ttcgccaaaa    960
gcactctgat tgacaaatac gatttatcta atttacacga aattgcttct ggggggcgcac   1020
ctctttcgaa agaagtcggg gaagcggttg caaaacgctt ccatcttcca gggatacgac   1080
aaggatatgg gctcactgag actacatcag ctattctgat tacacccgag ggggatgata   1140
aaccgggcgc ggtcggtaaa gttgttccat tttttgaagc gaaggttgtg gatctggata   1200
ccgggaaaac gctgggcgtt aatcagagag gcgaattatg tgtcagagga cctatgatta   1260
tgtccggtta tgtaaacaat ccggaagcga ccaacgcctt gattgacaag gatggatggc   1320
tacattctgg agacatagct tactgggacg aagacgaaca cttcttcata gttgaccgct   1380
tgaagtcttt aattaaatac aaaggatatc aggtggcccc cgctgaattg gaatcgatat   1440
tgttacaaca ccccaacatc ttcgacgcgg gcgtggcagg tcttcccgac gatgacgccg   1500
```

-continued

```
gtgaacttcc cgccgccgtt gttgttttgg agcacggaaa gacgatgacg gaaaaagaga    1560
tcgtggatta cgtcgccagt caagtaacaa ccgcgaaaaa gttgcgcgga ggagttgtgt    1620
ttgtggacga agtaccgaaa ggtcttaccg gaaaactcga cgcaagaaaa atcagagaga    1680
tcctcataaa ggccaagaag ggcggaaagt aaggcgcgcg ggccgcatca tgtaattagt    1740
tatgtcacgc ttacattcac gccctccccc cacatccgct ctaaccgaaa aggaaggagt    1800
tagacaacct gaagtctagg tccctatttta ttttttttata gttatgttag tattaagaac    1860
gttatttata tttcaaattt ttcttttttt tctgtacaga cgcgtgtacg catgtaacat    1920
tatactgaaa accttgcttg agaaggtttt gggacgctcg aaggctttaa tttgcggccc    1980
tgcattaatg aatcggccaa cgcgcgggga gaggcggttt gcgtattggg cgctcttccg    2040
cttcctcgct cactgactcg ctgcgctcgg tcagatctgt ttagcttgcc tcgtccccgc    2100
cgggtcaccc ggccagcgac atggaggccc agaataccct ccttgacagt cttgacgtgc    2160
gcagctcagg ggcatgatgt gactgtcgcc cgtacattta gcccatacat ccccatgtat    2220
aatcatttgc atccatacat tttgatggcc gcacggcgcg aagcaaaaat tacggctcct    2280
cgctgcagac ctgcgagcag ggaaacgctc ccctcacaga cgcgttgaat tgtccccacg    2340
ccgcgcccct gtagagaaat ataaaaggtt aggatttgcc actgaggttc ttctttcata    2400
tacttccttt taaaatcttg ctaggataca gttctcacat cacatccgaa cataaacaac    2460
catgggtaag gaaaagactc acgtttcgag gccgcgatta aattccaaca tggatgctga    2520
tttatatggg tataaatggg ctcgcgataa tgtcgggcaa tcaggtgcga caatctatcg    2580
attgtatggg aagcccgatg cgccagagtt gtttctgaaa catggcaaag gtagcgttgc    2640
caatgatgtt acagatgaga tggtcagact aaactggctg acggaattta tgcctcttcc    2700
gaccatcaag catttttatcc gtactcctga tgatgcatgg ttactcacca ctgcgatccc    2760
cggcaaaaca gcattccagg tattagaaga atatcctgat tcaggtgaaa atattgttga    2820
tgcgctggca gtgttcctgc gccggttgca ttcgattcct gtttgtaatt gtccttttaa    2880
cagcgatcgc gtatttcgtc tcgctcaggc gcaatcacga atgaataacg gtttggttga    2940
tgcgagtgat tttgatgacg agcgtaatgg ctggcctgtt gaacaagtct ggaaagaaat    3000
gcataagctt ttgccattct caccggattc agtcgtcact catggtgatt tctcacttga    3060
taaccttatt tttgacgagg gaaattaat aggttgtatt gatgttggac gagtcggaat    3120
cgcagaccga taccaggatc ttgccatcct atggaactgc ctcggtgagt tttctccttc    3180
attacagaaa cggctttttc aaaaatatgg tattgataat cctgatatga ataaattgca    3240
gtttcatttg atgctcgatg agttttttcta atcagtactg acaataaaaa gattcttgtt    3300
ttcaagaact tgtcatttgt atagtttttt tatattgtag ttgttctatt ttaatcaaat    3360
gttagcgtga tttatatttt ttttcgcctc gacatcatct gcccagatgc gaagttaagt    3420
gcgcagaaag taatatcatg cgtcaatcgt atgtgaatgc tggtcgctat actgctgtcg    3480
attcgatact aacgccgcca tccagtgtcg aaaacgagct cgaattcctg ggggaacaac    3540
ttcacagaat gttttgtcat attgtcgaag tggtcacaaa acaagagaag ttccgccaat    3600
tataaaaagg gaacccgtat atttcagctt cacggatgat ttccagggtg agagtactgt    3660
atatgggctt acgatagaag gccataaaaa tttcttgctt ggcaacaaaa tagaagtgaa    3720
atcatgtcga ggctgctgtg tgggagaaca gcttaaaata tcacaaaaaa agaatctaaa    3780
acactgtgtt gcttgtccca gaaagggaat caagtatttt tataaagatt ggagtggtaa    3840
```

```
aaatcgagta tgtgctagat gctatggaag atacaaattc agcggtcatc actgtataaa    3900
ttgcaagtat gtaccagaag cacgtgaagt gaaaaaggca aaagacaaag gcgaaaaatt    3960
gggcattacg cccgaaggtt tgccagttaa aggaccagag tgtataaaat gtggcggaat    4020
cttacagtgg cctatgcggc cgctctagaa ctagtggatc gatccccaat tcgccctata    4080
gtgagtcgta ttacaattca ctggccgtcg ttttacaacg tcgtgactgg gaaaaccctg    4140
gcgttaccca acttaatcgc cttgcagcac atcccccttt cgccagctgg cgtaatagcg    4200
aagaggcccg caccgatcgc ccttcccaac agttgcgcag cctgaatggc gaatggcgcc    4260
tgatgcggta ttttctcctt acgcatctgt gcggtatttc acaccgcata cgtcaaagca    4320
accatagtac gcgccctgta gcggcgcatt aagcgcggcg ggtgtggtgg ttacgcgcag    4380
cgtgaccgct acacttgcca gcgccctagc gcccgctcct ttcgctttct tcccttcctt    4440
tctcgccacg ttcgccggct ttccccgtca agctctaaat cggggtgggc catcgccctg    4500
atagacggtt tttcgccctt tgacgttgga gtccacgttc tttaatagtg gactcttgtt    4560
ccaaactgga acaacactca accctatctc gggctattct tttgatttat aagggatttt    4620
gccgatttcg gcctattggt taaaaaatga gctgatttaa caaaaattta acgcgaattt    4680
taacaaaata ttaacgttta caattttatg gtgcactctc agtacaatct gctctgatgc    4740
cgcatagtta agccagcccc gacacccgcc aacacccgct gacgcgccct gacgggcttg    4800
tctgctcccg gcatccgctt acagacaagc tgtgaccgtc tccgggagct gcatgtgtca    4860
gaggttttca ccgtcatcac cgaaacgcgc gagacgaaag gcctcgtga tacgcctatt     4920 tttataggtt aatgtcatga taataatggt ttcttagacg tcaggtggca cttttcgggg    4980
aaatgtgcgc ggaaccccta tttgtttatt tttctaaata cattcaaata tgtatccgct    5040
catgagacaa taaccctgat aaatgcttca ataatattga aaaggaaga gtatgagtat    5100 tcaacatttc cgtgtcgccc ttattccctt ttttgcggca ttttgccttc ctgttttgc     5160 tcacccagaa acgctggtga agtaaaaga tgctgaagat cagttgggtg cacgagtggg    5220
ttacatcgaa ctggatctca acagcggtaa gatccttgag agttttcgcc ccgaagaacg    5280
ttttccaatg atgagcactt ttaaagttct gctatgtggc gcggtattat cccgtattga    5340
cgccgggcaa gagcaactcg gtcgccgcat acactattct cagaatgact tggttgagta    5400
ctcaccagtc acagaaaagc atcttacgga tggcatgaca gtaagagaat tatgcagtgc    5460
tgccataacc atgagtgata acactgcggc caacttactt ctgacaacga tcggaggacc    5520
gaaggagcta accgcttttt tgcacaacat ggggatcat gtaactcgcc ttgatcgttg     5580
ggaaccggag ctgaatgaag ccataccaaa cgacgagcgt gacaccacga tgcctgtagc    5640
aatggcaaca acgttgcgca aactattaac tggcgaacta cttactctag cttcccggca    5700
acaattaata gactggatgg aggcggataa agttgcagga ccacttctgc gctcggccct    5760
tccggctggc tggtttattg ctgataaatc tggagccggt gagcgtgggt ctcgcggtat    5820
cattgcagca ctggggccag atggtaagcc ctcccgtatc gtagttatct acacgacggg    5880
gagtcaggca actatggatg aacgaaatag acagatcgct gagataggtg cctcactgat    5940
taagcattgg taactgtcag accaagttta ctcatatata ctttagattg atttaaaact    6000 tcattttaa tttaaaagga tctaggtgaa gatcctttt gataatctca tgaccaaaat     6060
cccttaacgt gagttttcgt tccactgagc gtcagacccc gtagaaaaga tcaaaggatc    6120
ttcttgagat cctttttttc tgcgcgtaat ctgctgcttg caaacaaaaa aaccaccgct    6180
accagcggtg gtttgtttgc cggatcaaga gctaccaact cttttttccga aggtaactgg    6240
```

```
cttcagcaga gcgcagatac caaatactgt ccttctagtg tagccgtagt taggccacca    6300
cttcaagaac tctgtagcac cgcctacata cctcgctctg ctaatcctgt taccagtggc    6360
tgctgccagt ggcgataagt cgtgtcttac cgggttggac tcaagacgat agttaccgga    6420
taaggcgcag cggtcgggct gaacggggggg ttcgtgcaca cagcccagct tggagcgaac    6480
gacctacacc gaactgagat acctacagcg tgagcattga aaagcgcca cgcttcccga      6540 agggagaaag gcggacaggt atccggtaag cggcagggtc ggaacaggag agcgcacgag     6600
ggagcttcca gggggaaacg cctggtatct ttatagtcct gtcgggtttc gccacctctg     6660
acttgagcgt cgatttttgt gatgctcgtc aggggggcgg agcctatgga aaaacgccag    6720
caacgcggcc ttttttacggt tcctggcctt ttgctggcct tttgctcaca tgttctttcc     6780
tgcgttatcc cctgattctg tggataaccg tattaccgcc tttgagtgag ctgataccgc    6840
tcgccgcagc cgaacgaccg agcgcagcga gtcagtgagc gaggaagcgg aagagcgccc    6900
aatacgcaaa ccgcctctcc ccgcgcgttg gccgattcat taatgcagct ggcacgacag    6960
gtttcccgac tggaaagcgg gcagtgagcg caacgcaatt aatgtgagtt agctcactca     7020
ttaggcaccc caggctttac actttatgct tccgcggctc gtatgttgtg tggaattgtg     7080
agcggataac aatttcacac aggaaacagc tatgaccatg attacgccac tagtccgagg    7140
cctcgagatc cgatatcgcc gtggcggccg ccagctgaag cttaattatc ctgggcacga    7200
gtgaaacaaa gctaaaacct ttattagca tggccattga atgtaacaat tatatatatc     7260
gcaagcacaa aaaatcaagg agagagaact accactttgt tcatgtgtac aatgttcatt    7320
atctccataa gcaaaaaaaa aaaatagaaa acatatgcta taaggttgat attctcacga     7380
gtaagcggca cttgctactt attgacattg cagatttttg gctacagaaa tagtatatta     7440
gagattataa ttgctaatca aatcaaaata taaaattagt aaaccaaacc atttataccc     7500
ttccttagta gttatggatt gttttttaat gatatttctg caaaccaaag aaagattgtt     7560
atccagatag aatttagttt tgatattcat tttttttgttg aagattgaac gccatatctg    7620
ggcctcataa ttcaaaagac ggtgccatta tcggtagcgt ttcgcattgt actggatttc    7680
agaaatttca cagttgatga atcgaaaaga atggtctcat tgcaacacgt aaggttaaga    7740
tgtccctttt taccattata ggcaataaat gaatcataaa acgaccgtat actggtgaaa     7800
tagtagggag aacgagtacc tgtagtaaaa agtataaatc atagttaatc gggcaatgtc     7860
cctcgatcaa ggagtattgt gtcatgttcg agacaaacgc caacatttt gtttcttttg     7920 gacaaatgtt gtttgcattt atgatccgtt atattttgat ctaatgtaga gttgcacgta    7980
gttcttactg gcaaagaaat cgatgcatac caaaaaagaa taaggtgat atttgatctt     8040 taccgtttag ttccaacgta aaattgtgcc tttggactta aaatggcgtc                8090
```

<210> SEQ ID NO 87
<211> LENGTH: 7103
<212> TYPE: DNA
<213> ORGANISM: Artificial Sequence
<220> FEATURE:
<223> OTHER INFORMATION: pSPRT190

<400> SEQUENCE: 87

```
tcgaggcggc cgccaaaata gaatttgaag gagatgattt gttttcctcc caagtgcctc     60
cactgacgtt taaatgtttc ctgatcatca gatgaccttc ctcggtcaag atggattccg    120
gatgaaattg cacaccttct acagtgtact tcttgtgtct tacacccatg ataattccat    180
```

```
tttcggtact cgcagtaacc ttcaagcagg atggtaggga cgattctgtc ccggccaatg    240
aatggtatct tgtcacagca ataccttgcg gcacgttctt gaaaattcca cagttgtcgt    300
gagagattgg ggacgtttta ccgtggacaa tctcaccagc gtaggcaact tcaccaccaa    360
atacgtcaaa catgcattgc tggcccatac agattccaaa tacaggaatt ttcccagtaa    420
agtaccggat acagtctctt gaaatgccag aatctgtctt tgggtggcct ggtccaggcg    480
agataagcaa tgtgtcggga ttcaaggcgg caatttctgg aactgtaatt gcatcgttac    540
ggtagacgct cactttggcg ccctcctggc acaagtactc gtaaacgttc caggtaaagg    600
aatcgtagtt gtcaattaga accacatgct tattgattgg gtttgttgca gcgtgcacag    660
acatatttaa atcgaggcgc gccatgttaa ttaaatctgt gtttattca attttagccg    720 cttctttggc caatgcaggt gcttccaagg tgtacgaccc cgagcaacgc aaacgcatga    780
tcactgggcc tcagtggtgg gctcgctgca agcaaatgaa cgtgctggac tccttcatca    840
actactatga ttccgagaag cacgccgaga acgccgtgat ttttctgcat ggtaacgctg    900
cctccagcta cctgtggagg cacgtcgtgc ctcacatcga gcccgtggct agatgcatca    960
tccctgatct gatcggaatg ggtaagtccg gcaagagcgg gaatggctca tatcgcctcc   1020
tggatcacta caagtacctc accgcttggt tcgagctgct gaaccttcca aagaaaatca   1080
tctttgtggg ccacgactgg ggggcttgtc tggcctttca ctactcctac gagcaccaag   1140
acaagatcaa ggccatcgtc catgctgaga gtgtcgtgga cgtgatcgag tcctgggacg   1200
agtggcctga catcgaggag gatatcgccc tgatcaagag cgaagagggc gagaaaatgg   1260
tgcttgagaa taacttcttc gtcgagacca tgctcccaag caagatcatg cggaaactgg   1320
agcctgagga gttcgctgcc tacctggagc cattcaagga aagggcgag gttagacggc   1380 ctaccctctc ctggcctcgc gagatccctc tcgttaaggg aggcaagccc gacgtcgtcc   1440
agattgtccg caactacaac gcctaccttc gggccagcga cgatctgcct aagatgttca   1500
tcgagtccga ccctgggttc tttccaacg ctattgtcga gggagctaag aagttccta   1560 acaccgagtt cgtgaaggtg aagggcctcc acttcagcca ggaggacgct ccagatgaaa   1620
tgggtaagta catcaagagc ttcgtggagc gcgtgctgaa gaacgagcag taaggcgcgc   1680
gggccgcatc atgtaattag ttatgtcacg cttacattca cgccctcccc ccacatccgc   1740
tctaaccgaa aaggaaggag ttagacaacc tgaagtctag gtccctattt atttttttat   1800
agttatgtta gtattaagaa cgttatttat atttcaaatt tttctttttt ttctgtacag   1860
acgcgtgtac gcatgtaaca ttatactgaa aaccttgctt gagaaggttt tgggacgctc   1920
gaaggcttta atttgcggcc ctgcattaat gaatcggcca acgcgcgggg agaggcggtt   1980
tgcgtattgg gcgctcttcc gcttcctcgc tcactgactc gctgcgctcg gtcagatctg   2040
tttagcttgc ctcgtccccg ccgggtcacc cggccagcga catggaggcc cagaataccc   2100
tccttgacag tcttgacgtg cgcagctcag ggcatgatg tgactgtcgc ccgtacattt   2160
agcccataca tccccatgta taatcatttg catccataca ttttgatggc cgcacggcgc   2220
gaagcaaaaa ttacgctcc tcgctgcaga cctgcgagca gggaaacgct cccctcacag   2280
acgcgttgaa ttgtccccac gccgcgcccc tgtagagaaa tataaaaggt taggatttgc   2340
cactgaggtt cttctttcat atacttcctt ttaaaatctt gctaggatac agttctcaca   2400
tcacatccga acataaacaa ccatgggtaa ggaaaagact cacgtttcga ggccgcgatt   2460
aaattccaac atggatgctg atttatatgg gtataaatgg gctcgcgata atgtcgggca   2520
atcaggtgcg acaatctatc gattgtatgg gaagcccgat gcgccagagt tgtttctgaa   2580
```

```
acatggcaaa ggtagcgttg ccaatgatgt tacagatgag atggtcagac taaactggct    2640
gacggaattt atgcctcttc cgaccatcaa gcattttatc cgtactcctg atgatgcatg    2700
gttactcacc actgcgatcc ccggcaaaac agcattccag gtattagaag aatatcctga    2760
ttcaggtgaa aatattgttg atgcgctggc agtgttcctg cgccggttgc attcgattcc    2820
tgtttgtaat tgtcctttta acagcgatcg cgtatttcgt ctcgctcagg cgcaatcacg    2880
aatgaataac ggtttggttg atgcgagtga ttttgatgac gagcgtaatg gctggcctgt    2940
tgaacaagtc tggaaagaaa tgcataagct tttgccattc tcaccggatt cagtcgtcac    3000
tcatggtgat ttctcacttg ataaccttat ttttgacgag gggaaattaa taggttgtat    3060
tgatgttgga cgagtcggaa tcgcagaccg ataccaggat cttgccatcc tatggaactg    3120
cctcggtgag ttttctcctt cattacagaa acggcttttt caaaaatatg gtattgataa    3180
tcctgatata aataaattgc agtttcattt gatgctcgat gagttttttct aatcagtact    3240
gacaataaaa agattcttgt tttcaagaac ttgtcatttg tatagttttt ttatattgta    3300
gttgttctat tttaatcaaa tgttagcgtg atttatattt tttttcgcct cgacatcatc    3360
tgcccagatg cgaagttaag tgcgcagaaa gtaatatcat gcgtcaatcg tatgtgaatg    3420
ctggtcgcta tactgctgtc gattcgatac taacgccgcc atccagtgtc gaaaacgagc    3480
tcgaattcct gggggaacaa cttcacagaa tgttttgtca tattgtcgaa gtggtcacaa    3540
aacaagagaa gttccgccaa ttataaaaag ggaacccgta tatttcagct tcacggatga    3600
tttccagggt gagagtactg tatatgggct tacgatagaa ggccataaaa atttcttgct    3660
tggcaacaaa atagaagtga aatcatgtcg aggctgctgt gtgggagaac agcttaaaat    3720
atcacaaaaa aagaatctaa aacactgtgt tgcttgtccc agaaagggaa tcaagtattt    3780
ttataaagat tggagtggta aaaatcgagt atgtgctaga tgctatggaa gatacaaatt    3840
cagcggtcat cactgtataa attgcaagta tgtaccagaa gcacgtgaag tgaaaaaggc    3900
aaaagacaaa ggcgaaaaat tgggcattac gcccgaaggt ttgccagtta aaggaccaga    3960
gtgtataaaa tgtggcggaa tcttacagtg gcctatgcgg ccgctctaga actagtggat    4020
cgatccccaa ttcgccctat agtgagtcgt attacaattc actggccgtc gttttacaac    4080
gtcgtgactg ggaaaaccct ggcgttaccc aacttaatcg ccttgcagca catccccctt    4140
tcgccagctg gcgtaatagc gaagaggccc gcaccgatcg cccttcccaa cagttgcgca    4200
gcctgaatgg cgaatggcgc ctgatgcggt attttctcct tacgcatctg tgcggtattt    4260
cacaccgcat acgtcaaagc aaccatagta cgcgccctgt agcggcgcat taagcgcggc    4320
gggtgtggtg gttacgcgca gcgtgaccgc tacacttgcc agcgccctag cgcccgctcc    4380
tttcgctttc ttcccttcct ttctcgccac gttcgccggc tttccccgtc aagctctaaa    4440
tcggggtggg ccatcgccct gatagacggt ttttcgccct ttgacgttgg agtccacgtt    4500
ctttaatagt ggactcttgt tccaaactgg aacaacactc aaccctatct cgggctattc    4560
ttttgattta agggattt  tgccgatttc ggcctattgg ttaaaaaatg agctgattta    4620
acaaaaattt aacgcgaatt ttaacaaaat attaacgttt acaattttat ggtgcactct    4680
cagtacaatc tgctctgatg ccgcatagtt aagccagccc cgacacccgc caacacccgc    4740
tgacgcgccc tgacgggctt gtctgctccc ggcatccgct tacagacaag ctgtgaccgt    4800
ctccgggagc tgcatgtgtc agaggttttc accgtcatca ccgaaacgcg cgagacgaaa    4860
gggcctcgtg atacgcctat ttttataggt taatgtcatg ataataatgg tttcttagac    4920
```

```
gtcaggtggc acttttcggg gaaatgtgcg cggaacccct atttgtttat ttttctaaat    4980
acattcaaat atgtatccgc tcatgagaca ataaccctga taaatgcttc aataatattg    5040
aaaaaggaag agtatgagta ttcaacattt ccgtgtcgcc cttattccct tttttgcggc    5100
attttgcctt cctgttttg ctcacccaga acgctggtg aaagtaaaag atgctgaaga     5160
tcagttgggt gcacgagtgg gttacatcga actggatctc aacagcggta agatccttga    5220
gagttttcgc cccgaagaac gttttccaat gatgagcact tttaaagttc tgctatgtgg    5280
cgcggtatta tcccgtattg acgccgggca agagcaactc ggtcgccgca tacactattc    5340
tcagaatgac ttggttgagt actcaccagt cacagaaaag catcttacgg atggcatgac    5400
agtaagagaa ttatgcagtg ctgccataac catgagtgat aacactgcgg ccaacttact    5460
tctgacaacg atcggaggac cgaaggagct aaccgctttt ttgcacaaca tgggggatca    5520
tgtaactcgc cttgatcgtt gggaaccgga gctgaatgaa gccataccaa acgacgagcg    5580
tgacaccacg atgcctgtag caatggcaac aacgttgcgc aaactattaa ctggcgaact    5640
acttactcta gcttcccggc aacaattaat agactggatg gaggcggata agttgcagg     5700
accacttctg cgctcggccc ttccggctgg ctggtttatt gctgataaat ctggagccgg    5760
tgagcgtggg tctcgcggta tcattgcagc actggggcca gatggtaagc cctcccgtat    5820
cgtagttatc tacacgacgg ggagtcaggc aactatggat gaacgaaata gacagatcgc    5880
tgagataggt gcctcactga ttaagcattg gtaactgtca gaccaagttt actcatatat    5940
actttagatt gatttaaaac ttcattttta atttaaaagg atctaggtga agatcctttt    6000
tgataatctc atgaccaaaa tcccttaacg tgagttttcg ttccactgag cgtcagaccc    6060
cgtagaaaag atcaaaggat cttcttgaga tccttttttt ctgcgcgtaa tctgctgctt    6120
gcaaacaaaa aaaccaccgc taccagcggt ggtttgtttg ccggatcaag agctaccaac    6180
tcttttccg aaggtaactg gcttcagcag agcgcagata ccaaatactg tccttctagt    6240
gtagccgtag ttaggccacc acttcaagaa ctctgtagca ccgcctacat acctcgctct    6300
gctaatcctg ttaccagtgg ctgctgccag tggcgataag tcgtgtctta ccgggttgga    6360
ctcaagacga tagttaccgg ataaggcgca gcggtcgggc tgaacggggg gttcgtgcac    6420
acagcccagc ttggagcgaa cgacctacac cgaactgaga tacctacagc gtgagcattg    6480
agaaagcgcc acgcttcccg aagggagaaa ggcggacagg tatccggtaa gcggcagggt    6540
cggaacagga gagcgcacga gggagcttcc agggggaaac gcctggtatc tttatagtcc    6600
tgtcgggttt cgccacctct gacttgagcg tcgatttttg tgatgctcgt caggggggcg    6660
gagcctatgg aaaaacgcca gcaacgcggc cttttacgg ttcctggcct tttgctggcc     6720
ttttgctcac atgttctttc ctgcgttatc ccctgattct gtggataacc gtattaccgc    6780
ctttgagtga gctgataccg ctcgccgcag ccgaacgacc gagcgcagcg agtcagtgag    6840
cgaggaagcg gaagagcgcc caatacgcaa accgcctctc cccgcgcgtt ggccgattca    6900
ttaatgcagc tggcacgaca ggtttcccga ctggaaagcg ggcagtgagc gcaacgcaat    6960
taatgtgagt tagctcactc attaggcacc ccaggcttta cactttatgc ttccgcggct    7020
cgtatgttgt gtggaattgt gagcggataa caatttcaca caggaaacag ctatgaccat    7080
gattacgcca ctagtccgag gcc                                            7103
```

<210> SEQ ID NO 88
<211> LENGTH: 9685
<212> TYPE: DNA
<213> ORGANISM: Artificial Sequence
<220> FEATURE:
<223> OTHER INFORMATION: pSPRT192

<400> SEQUENCE: 88

| | | | | | |
|---|---|---|---|---|---|
| taaatctgtt | gtttattcaa | ttttagccgc | ttctttggcc | aatgcaggtg | cttccaaggt | 60 |
| gtacgacccc | gagcaacgca | aacgcatgat | cactgggcct | cagtggtggg | ctcgctgcaa | 120 |
| gcaaatgaac | gtgctggact | ccttcatcaa | ctactatgat | tccgagaagc | acgccgagaa | 180 |
| cgccgtgatt | tttctgcatg | gtaacgctgc | ctccagctac | ctgtggaggc | acgtcgtgcc | 240 |
| tcacatcgag | cccgtggcta | gatgcatcat | ccctgatctg | atcggaatgg | gtaagtccgg | 300 |
| caagagcggg | aatggctcat | atcgcctcct | ggatcactac | aagtacctca | ccgcttggtt | 360 |
| cgagctgctg | aaccttccaa | agaaaatcat | ctttgtgggc | cacgactggg | gggcttgtct | 420 |
| ggcctttcac | tactcctacg | agcaccaaga | caagatcaag | gccatcgtcc | atgctgagag | 480 |
| tgtcgtggac | gtgatcgagt | cctgggacga | gtggcctgac | atcgaggagg | atatcgccct | 540 |
| gatcaagagc | gaagagggcg | agaaaatggt | gcttgagaat | aacttcttcg | tcgagaccat | 600 |
| gctcccaagc | aagatcatgc | ggaaactgga | gcctgaggag | ttcgctgcct | acctggagcc | 660 |
| attcaaggag | aagggcgagg | ttagacggcc | taccctctcc | tggcctcgcg | agatccctct | 720 |
| cgttaaggga | ggcaagcccg | acgtcgtcca | gattgtccgc | aactacaacg | cctaccttcg | 780 |
| ggccagcgac | gatctgccta | agatgttcat | cgagtccgac | cctgggttct | tttccaacgc | 840 |
| tattgtcgag | ggagctaaga | agttccctaa | caccgagttc | gtgaaggtga | agggcctcca | 900 |
| cttcagccga | gaggacgctc | cagatgaaat | gggtaagtac | atcaagagct | tcgtggagcg | 960 |
| cgtgctgaag | aacagcagt | aaggcgcgcg | ggccgcatca | tgtaattagt | tatgtcacgc | 1020 |
| ttacattcac | gccctccccc | cacatccgct | ctaaccgaaa | aggaaggagt | tagacaacct | 1080 |
| gaagtctagg | tccctattta | ttttttata | gttatgttag | tattaagaac | gttatttata | 1140 |
| tttcaaattt | ttcttttttt | tctgtacaga | cgcgtgtacg | catgtaacat | tatactgaaa | 1200 |
| accttgcttg | agaaggtttt | gggacgctcg | aaggctttaa | tttgcggccc | tgcattaatg | 1260 |
| aatcggccaa | cgcgcgggga | gaggcggttt | gcgtattggg | cgctcttccg | cttcctcgct | 1320 |
| cactgactcg | ctgcgctcgg | tcagatctcg | ctgttccagt | caatcagggt | attgaagctc | 1380 |
| atggtctta | ctccatcaca | gggttccgcc | ttatccggcc | tacagaaccc | aaaatatcaa | 1440 |
| cgcattacgt | aggcctgata | agcgcagcgc | catcaggcgt | cagatcactc | catcatcttc | 1500 |
| tcgatcggca | gtaccagaat | cgagctggcc | ccaagcgctt | tcagtttctc | catggtttcc | 1560 |
| cagaacaacg | tttcgctgct | gaccatgtgc | atcgccacgc | gctgttgctc | gcctgccagc | 1620 |
| ggcagaattg | tcggcctttc | ggcgcctggc | agcagggcga | taacctcttc | caggcgttca | 1680 |
| cttggcgcgt | gcatcatgat | gtatttcgat | tcgcgcgcct | gaatcacgcc | ctgaatacgg | 1740 |
| gtcagcaatt | tatcgatcag | ctcttgcttg | ctctgtgcca | tctcaccgtc | gcgctgaatc | 1800 |
| agacaggctt | tagagcggta | gataacttcg | acttcacgca | ggccgttagc | ttcaagcgtc | 1860 |
| gcgccggtag | agaccaaatc | gcagatagc | tcggccagcc | ccgcgcgcgg | cgcgacttcg | 1920 |
| acagaaccat | ttaacagaca | cgatttaaaa | gagacgcctt | tctggtcgag | gtagcgtttg | 1980 |
| aggaggtgcg | gatatgaggt | agcgatacgt | ttaccgtcca | gcgcggccgg | gccgtcccag | 2040 |
| gcttcgtcaa | ccggtgttgc | cagcgataaa | cggcagccgc | cgaagtcaag | acggcgcagg | 2100 |
| gttaaatagc | gtggatcttc | gccctgtgcg | cggcggttga | gtagctcttc | ttccagcacg | 2160 |
| ttttcgccga | taataccgag | atcgaccacg | ccatccatta | ccagacccgg | aatgtcatca | 2220 |

```
tcacgcacgc gcaggatatc aatcggcatg tttttccgcca tcgcaatcag gcgctgagtg    2280
tgtaaattaa tttttatgcc gcagcgggcc agcaattctc gtgaatcatc gcttaaacgg    2340
cctgatttct gaatagctat gcgtaagcgg gtgttgtcta acattctgcg ttcctcttta    2400
tcctgtctga accggtctgt atcgcgcgcc aaaaaaaaag cccccggaag atgatcttcc    2460
gggggctttc tcatgcgttc atgcaccact ggaagatcca caggacgggt gtggtcgcca    2520
tgatcgcgta gtcgatagtg gctccaagta gcgaagcgag caggactggg cggcggccaa    2580
agcggtcgga cagtgctccg agaacgggtg cgcatagaaa ttgcatcaac gcatatagcg    2640
ctagcagcac gccatagtga ctggcgatgc tgtcggaatg gacgatatcc cgcaagaggc    2700
ccggcagtac cggcataacc aagcctatgc ctacagcatc cagggtgacg gtgccgagga    2760
tgacgatgag cgcattgtta gatttcatac acggtgcctg actgcgttag caatttaact    2820
gtgataaact accgcattaa agcttttttct ttccaatttt ttttttttcg tcattataaa    2880
aatcattacg accgagattc ccgggtaata actgatataa ttaaattgaa gctctaattt    2940
gtgagtttag tatacatgca tttacttata atacagtttt ttagttttgc tggccgcatc    3000
ttctcaaata tgcttcccag cctgcttttc tgtaacgttc accctctacc ttagcatccc    3060
ttccctttgc aaatagtcct cttccaacaa taataatgtc agatcctgta gagaccacat    3120
catccacggt tctatactgt tgacccaatg cgtctccctt gtcatctaaa cccacaccgg    3180
gtgtcataat caaccaatcg taaccttcat ctcttccacc catgtctctt tgagcaataa    3240
agccgataac aaaatctttg tcgctcttcg caatgtcaac agtacccctta gtatattctc    3300 cagtagatag ggagcccttg catgacaatt ctgctaacat caaaaggcct ctaggttcct    3360
ttgttacttc ttctgccgcc tgcttcaaac cgctaacaat acctgggccc accacaccgt    3420
gtgcattcgt aatgtctgcc cattctgcta ttctgtatac acccgcagag tactgcaatt    3480
tgactgtatt accaatgtca gcaaattttc tgtcttcgaa gagtaaaaaa ttgtacttgg    3540
cggataatgc ctttagcggc ttaactgtgc cctccatgga aaaatcagtc aagatatcca    3600
catgtgtttt tagtaaacaa attttgggac ctaatgcttc aactaactcc agtaattcct    3660
tggtggtacg aacatccaat gaagcacaca agtttgtttg cttttcgtgc atgatattaa    3720
atagcttggc agcaacagga ctaggatgag tagcagcacg ttccttatat gtagctttcg    3780
acatgattta tcttcgtttc ctgcaggttt ttgttctgtg cagttgggtt aagaatactg    3840
ggcaatttca tgtttcttca acactacata tgcgtatata taccaatcta agtctgtgct    3900
ccttccttcg ttcttccttc tgttcggaga ttaccgaatc aaaaaaattt caaagaaacc    3960
gaaatcaaaa aaagaataaa aaaaaaaatg atgaattgaa ttgaaaagct tatcgatgat    4020
aagctgtcaa acatgagaat taattcagat ccgctgttcc agtcaatcag ggtattgaag    4080
ctcatggtct ttactccatc acagggttcc gccttatccg gcctacagaa cccaaaatat    4140
caacgcatta cgtaggcctg ataagcgcag cgccatcagg cgtcagatca ctccatcatc    4200
ttctcgatcg gcagtaccag aatcgagctg gcgccaagcg ctttcagttt ctccatggtt    4260
tcccagaaca acgtttcgct gctgaccatg tgcatcgcca cgcgctgttg ctcgcctgcc    4320
agcggcagaa ttgtcggcct ttcggcgcct ggcagcaggg cgataacctc ttccaggcgt    4380
tcacttggcg cgtgcatcat gatgtatttc gattcgcgcg cctgaatcac gccctgaata    4440
cgggtcagca atttatcgat cagctcttgc ttgctctgtg ccatctcacc gtcgcgctga    4500
atcagacagg cttagagcg gtagataact tcgacttcac gcaggccgtt agcttcaagc    4560
gtcgcgccgg tagagaccaa atcgcagata gcgtcggcca gccccgcgcg cggcgcgact    4620
```

```
tcgacagaac catttaacag acacgattta aaagagacgc ctttctggtc gaggtagcgt   4680
ttgaggaggt gcggatatga ggtagcgata cgtttaccgt ccagcgcggc cgggccgtcc   4740
caggcttcgt caaccggtgt tgccagcgat aaacggcagc cgccgaagtc aagacggcgc   4800
agggttaaat agcgtggatc ttcgccctgt gcgcggcggt tgagtagctc ttcttccagc   4860
acgttttcgc cgataatacc gagatcgacc acgccatcca ttaccagacc cggaatgtca   4920
tcatcacgca cgcgcaggat atcaatcggc atgttttccg ccatcgcaat caggcgctga   4980
gtgtgtaaat taattttat gccgcagcgg gccagcaatt ctcgtgaatc atcgcttaaa   5040
cggcctgatt tctgaatagc tatgcgtaag cgggtgttgt ctaacattct gcgttcctct   5100
ttatcctgtc tgaaccggtc tgtatcgcgc gccaaaaaaa aagcccccgg aagatgatct   5160
tccgggggct ttctcatgcg ttcatgcacc actggaagat cagatctgtt tagcttgcct   5220 cgtcccccgcc gggtcacccg gccagcgaca tggggtattt aggtctacgt tgaatgaatg   5280
caggtcccta ttattgacac ctacaacttt agcaccaatt tctagagccc tttgtaattc   5340
ctctttggag ttcacctcaa cgagaggttc catgttcaaa tctttactgt agctgtacag   5400
ttccttcaat aagggttgag atagcatctt gactataaga aggacagtgt cagctccagc   5460
taatcttgct tctagtattt gatacttgct gaaaataaat tcttttctca aaacacaagg   5520
cctctccttg ggaggaaatt tcaaatctag gattttcctc acatttacta aatcctgtaa   5580
cgaaccgtga aaccaatgag gttcggtcaa tacggaaatt gcggatgcac cagcctctgc   5640
gtatttgaga gcctgttcag cagcaacagc ttttaaacaa atgggtccct tcgatggaga   5700
ggcacgcttg acttcagcaa gaacaacggc tcttttatgg gatgatgaca acaccgtgta   5760
gaaatcctgt aacggtgggg caagacctaa atcatagtta gattgtaagt cttgaaaggt   5820
gaaacctggg attttagact gctcattgac gtctatttta cgccgagcat agatacggtc   5880
ggcctatgcg gccgctctag aactagtgga tcgatcccca attcgcccta gtgtgagtcg   5940
tattacaatt cactggccgt cgttttacaa cgtcgtgact gggaaaaccc tggcgttacc   6000
caacttaatc gccttgcagc acatcccccct ttcgccagct ggcgtaatag cgaagaggcc   6060
cgcaccgatc gcccttccca acagttgcgc agcctgaatg gcgaatggcg cctgatgcgg   6120
tattttctcc ttacgcatct gtgcggtatt tcacaccgca tacgtcaaag caaccatagt   6180
acgcgccctg tagcggcgca ttaagcgcgg cgggtgtggt ggttacgcgc agcgtgaccg   6240
ctacacttgc cagcgcccta gcgcccgctc ctttcgcttt cttcccttcc tttctcgcca   6300
cgttcgccgg ctttccccgt caagctctaa atcggggtgg ccatcgccc tgatagacgg   6360 tttttcgccc tttgacgttg gagtccacgt tctttaatag tggactcttg ttccaaactg   6420
gaacaacact caaccctatc tcgggctatt cttttgattt ataagggatt ttgccgattt   6480
cggcctattg gttaaaaaat gagctgattt aacaaaaatt taacgcgaat tttaacaaaa   6540
tattaacgtt tacaatttta tggtgcactc tcagtacaat ctgctctgat gccgcatagt   6600
taagccagcc ccgacacccg ccaacacccg ctgacgcgcc ctgacgggct tgtctgctcc   6660
cggcatccgc ttacagacaa gctgtgaccg tctccgggag ctgcatgtgt cagaggtttt   6720
caccgtcatc accgaaacgc gcgagacgaa agggcctcgt gatacgccta ttttttatagg   6780 ttaatgtcat gataataatg gtttcttaga cgtcaggtgg cacttttcgg ggaaatgtgc   6840
gcggaacccc tatttgttta ttttctaaa tacattcaaa tatgtatccg ctcatgagac   6900
aataaccctg ataaatgctt caataatatt gaaaaaggaa gagtatgagt attcaacatt   6960
```

-continued

```
tccgtgtcgc ccttattccc ttttttgcgg cattttgcct tcctgttttt gctcacccag    7020
aaacgctggt gaaagtaaaa gatgctgaag atcagttggg tgcacgagtg ggttacatcg    7080
aactggatct caacagcggt aagatccttg agagttttcg ccccgaagaa cgttttccaa    7140
tgatgagcac ttttaaagtt ctgctatgtg gcgcggtatt atcccgtatt gacgccgggc    7200
aagagcaact cggtcgccgc atacactatt ctcagaatga cttggttgag tactcaccag    7260
tcacagaaaa gcatcttacg gatggcatga cagtaagaga attatgcagt gctgccataa    7320
ccatgagtga taacactgcg gccaacttac ttctgacaac gatcggagga ccgaaggagc    7380
taaccgcttt tttgcacaac atgggggatc atgtaactcg ccttgatcgt tgggaaccgg    7440
agctgaatga agccatacca aacgacgagc gtgacaccac gatgcctgta gcaatggcaa    7500
caacgttgcg caaactatta actggcgaac tacttactct agcttcccgg caacaattaa    7560
tagactggat ggaggcggat aaagttgcag gaccacttct gcgctcggcc cttccggctg    7620
gctggtttat tgctgataaa tctggagccg gtgagcgtgg gtctcgcggt atcattgcag    7680
cactggggcc agatggtaag ccctcccgta tcgtagttat ctacacgacg gggagtcagg    7740
caactatgga tgaacgaaat agacagatcg ctgagatagg tgcctcactg attaagcatt    7800
ggtaactgtc agaccaagtt tactcatata cttttagat tgatttaaaa cttcattttt    7860
aatttaaaag gatctaggtg aagatccttt ttgataatct catgaccaaa atcccttaac    7920
gtgagttttc gttccactga gcgtcagacc ccgtagaaaa gatcaaagga tcttcttgag    7980
atccttttt tctgcgcgta atctgctgct tgcaaacaaa aaaaccaccg ctaccagcgg    8040
tggtttgttt gccggatcaa gagctaccaa ctctttttcc gaaggtaact ggcttcagca    8100
gagcgcagat accaaatact gtccttctag tgtagccgta gttaggccac cacttcaaga    8160
actctgtagc accgcctaca tacctcgctc tgctaatcct gttaccagtg gctgctgcca    8220
gtggcgataa gtcgtgtctt accgggttgg actcaagacg atagttaccg gataaggcgc    8280
agcggtcggg ctgaacgggg ggttcgtgca cacagcccag cttggagcga acgacctaca    8340
ccgaactgag atacctacag cgtgagcatt gagaaagcgc cacgcttccc gaagggagaa    8400
aggcggacag gtatccggta agcggcaggg tcggaacagg agagcgcacg agggagcttc    8460
caggggggaaa cgcctggtat ctttatagtc ctgtcgggtt cgccacctc tgacttgagc    8520
gtcgattttt gtgatgctcg tcagggggc ggagcctatg gaaaaacgcc agcaacgcgg    8580
ccttttacg gttcctggcc ttttgctggc cttttgctca catgttcttt cctgcgttat    8640
cccctgattc tgtggataac cgtattaccg cctttgagtg agctgatacc gctcgccgca    8700
gccgaacgac cgagcgcagc gagtcagtga gcgaggaagc ggaagagcgc ccaatacgca    8760
aaccgcctct ccccgcgcgt tggccgattc attaatgcag ctggcacgac aggtttcccg    8820
actggaaagc gggcagtgag cgcaacgcaa ttaatgtgag ttagctcact cattaggcac    8880
cccaggcttt acactttatg cttccgcggc tcgtatgttg tgtggaattg tgagcggata    8940
acaatttcac acaggaaaca gctatgacca tgattacgcc actagtccga ggcctcgagg    9000
cggccgccaa aatagaattt gaaggagatg atttgttttc ctcccaagtg cctccactga    9060
cgtttaaaat gttcctgatc atcagatgac cttcctcggt caagatggat tccggatgaa    9120
attgcacacc ttctacagtg tacttcttgt gtcttacacc catgataatt ccattttcgg    9180
tactcgcagt aaccttcaag caggatggta gggacgattc tgtcccggcc aatgaatggt    9240
atcttgtcac agcaatacct tgcggcacgt tcttgaaaat tccacagttg tcgtgagaga    9300
ttggggacgt tttaccgtgg acaatctcac cagcgtaggc aacttcacca ccaaatacgt    9360
```

```
caaacatgca ttgctggccc atacagattc caaatacagg aattttccca gtaaagtacc    9420
ggatacagtc tcttgaaatg ccagaatctg tctttgggtg gcctggtcca ggcgagataa    9480
gcaatgtgtc gggattcaag gcggcaattt ctggaactgt aattgcatcg ttacggtaga    9540
cgctcacttt ggcgccctcc tggcacaagt actcgtaaac gttccaggta aaggaatcgt    9600
agttgtcaat tagaaccaca tgcttattga ttgggtttgt tgcagcgtgc acagacatat    9660
ttaaatcgag gcgcgccatg ttaat                                          9685
```

US 7,872,115 B2

REPORTER ASSAY SCREENS FOR PROTEIN TARGETS IN *SACCHAROMYCES CEREVISIAE*

The present application claims the benefit of U.S. provisional patent application No. 60/609,940; filed Sep. 15, 2004; which is herein incorporated by reference in its entirety.

FIELD OF THE INVENTION

The present invention relates to compositions and methods for screening for compounds which modulate the function of an essential gene, for example, in fungal cells.

BACKGROUND OF THE INVENTION

High throughput assays, for identifying candidate compounds which inhibit one or more target proteins in an organism, are most efficient when they include an easily identifiable signal for identifying compounds with the desired inhibitory activity. One such well known system utilizes a responsive promoter, which is activated by the inactivation of the target by a candidate compound, and which is fused to an easily identifiable reporter. When the target protein is inactivated by a candidate compound, the reporter is expressed and the corresponding compound is identified as inhibitory. Such responsive promoters can be identified simply by identifying promoters which are activated by the genetic activation or inactivation of a target gene of interest (e.g., by construction of a temperature-sensitive mutation in the gene).

Responsive promoter screening assays have been used to identify anti-fungal compounds such as azoles which inhibit the egosterol biosynthesis pathway. U.S. Pat. No. 5,527,687; Dixon et al., J. Steroid Biochem. Mol. Biol. 1997 June;62(2-3):165-71. In addition, screens have been developed to screen for inhibitors of protein secretion, membrane stability, protein synthesis and cell wall integrity. Bianchi et al., Appl Environ. Microbiol. 1999 November;65(11):5023-7; Alksne et al., Antimicrob. Agents Chemother. 2000 June;44(6): 1418-27; Shapiro et al., Antimicrob. Agents Chemother. 2002 August;46(8):2490-7; Sun et al., J. Antibiot. (Tokyo). 2002; 55(3): 279-287. These screens are convenient for high-throughput assay systems requiring short incubation times, sub-lethal compound concentrations and the selective induction of the reporter fusion indicates that the compound is perturbing the pathway of interest. Fischer et al., Genome Res. 2004 January;14(1):90-8.

Although some responsive promoters are known and they have been used to identify anti-microbial substances, there still exists a need in the art for the identification of new responsive promoters which may be used to identify other substances of clinical interest.

SUMMARY OF THE INVENTION

The present invention addresses the need in the art for additional responsive promoters for use in assays to identify novel anti-fungal and anti-cancer substances.

The present invention provides an isolated hybrid polynucleotide comprising a member selected from the group consisting of *S. cerevisiae* YOR387C Promoter, *S. cerevisiae* YMR175W Promoter, *S. cerevisiae* YFR026C Promoter, *S. cerevisiae* YJL153C Promoter, *S. cerevisiae* YPL033C Promoter, *S. cerevisiae* YOL058W Promoter, *S. cerevisiae* YOR255W Promoter, *S. cerevisiae* YDR250C Promoter, *S. cerevisiae* YDR446W Promoter, *S. cerevisiae* YDR536W Promoter, *S. cerevisiae* YOR255W Promoter, *S. cerevisiae* YDL243C Promoter *S. cerevisiae* YDR256C Promoter, *S. cerevisiae* YFL020C Promoter, *S. cerevisiae* YPL205C Promoter, *S. cerevisiae* YGL205W Promoter, *S. cerevisiae* YGL117W Promoter, *S. cerevisiae* YHR029C Promoter, *S. cerevisiae* YML116W Promoter *S. cerevisiae* YJR109C Promoter, *S. cerevisiae* YCL030C Promoter, *S. cerevisiae* YLR338W Promoter, *S. cerevisiae* YIL066W-A Promoter, *S. cerevisiae* YNL093W Promoter, *S. cerevisiae* YLR381W Promoter, *S. cerevisiae* YKL159C Promoter, *S. cerevisiae* YIL058W Promoter, *S. cerevisiae* YKR037C Promoter, *S. cerevisiae* YNL279W Promoter, *S. cerevisiae* YOR032C Promoter, *S. cerevisiae* YML058W Promoter, *S. cerevisiae* YMR303C Promoter, *S. cerevisiae* YJL153C Promoter *S. cerevisiae* YLR092W Promoter, *S. cerevisiae* YFL052W Promoter, *S. cerevisiae* YLR017C Promoter, *S. cerevisiae* YLL062C Promoter, *S. cerevisiae* YMR323W Promoter *S. cerevisiae* YPL171C Promoter, *S. cerevisiae* YER065C Promoter, *S. cerevisiae* YDR114C Promoter, *S. cerevisiae* YHR082C Promoter, *S. cerevisiae* YDL126C Promoter *S. cerevisiae* YBR106W Promoter, *S. cerevisiae* YLL043W Promoter, *S. cerevisiae* YPR108W Promoter, *S. cerevisiae* YIL041W Promoter, *S. cerevisiae* YJL166W Promoter *S. cerevisiae* YDR165W Promoter, *S. cerevisiae* YLR330W Promoter, *S. cerevisiae* YDL058W Promoter, *S. cerevisiae* YHR012W Promoter, *S. cerevisiae* YKL053W Promoter, *S. cerevisiae* YKL196C Promoter, *S. cerevisiae* YDL103C Promoter *S. cerevisiae* YLR427W Promoter, *S. cerevisiae* YLL020C Promoter and *S. cerevisiae* YBL065W Promoter (e.g., SEQ ID NOs: 1-41, 52-68); optionally operably linked to a reporter (e.g., *S. cerevisiae* ADE2, *S. cerevisiae* LYS2, *S. cerevisiae* TRP1, *S. cerevisiae* LEU2, *S. cerevisiae* URA3, *S. cerevisiae* HIS3, *Aequorea victoria* GFP mutant 3, *Renilla* luciferase, *Photinus pyralis* luciferase, *Photinus pyralis* luciferase slk mutant, *Vibrio fischeri* luxA, *Vibrio fischeri* luxB, *Vibrio fischeri* luxC, *Vibrio fischeri* luxD, *Vibrio fischeri* luxE, *Vibrio fischeri* luxAB, *Vibrio fischeri* luxCDABE, *Vibrio harveyi* luxA, *Vibrio harveyi* luxB, *Vibrio harveyi* luxC, *Vibrio harveyi* luxD, *Vibrio harveyi* luxE, *Vibrio harveyi* luxAB, *Vibrio harveyi* luxCDABE, *Photorhabdus luminscens* LuxA, *Photorhabdus luminscens* LuxB, *Photorhabdus luminscens* LuxC, *Photorhabdus luminscens* LuxD, *Photorhabdus luminscens* LuxE, *Photorhabdus luminscens* LuxCDABE, *E. coli* lacZ, the *Aequorea victoria* Aequorin gene, KanMX, pat1, nat1, hph, CAT, Sh Ble, GUS, CYH2 or CAN1 (e.g., SEQ ID NOs: 42-51)). Also within the scope of the invention is an embodiment comprising one of the foregoing promoters, operably linked to a reporter with the proviso that the reporter is not the open reading frame that is naturally located downstream of the promoter in the *S. cerevisiae* genome. An embodiment of the invention comprises a vector comprising a promoter of the present invention or hybrid thereof along with a host cell comprising the vector. In another embodiment of the invention, the vector in the host cell is episomal or integrated into a chromosome of the host cell.

The present invention also provides the isolated plasmids pSPRT47; pSPRT50; pSPRT190 and pSPRT192 (SEQ ID NOs.:85-88).

The present invention also provides a method for identifying a substance that inhibits fungal cell growth comprising (a) introducing a hybrid comprising a promoter selected from the group consisting of *S. cerevisiae* YOR387C Promoter, *S. cerevisiae* YMR175W Promoter, *S. cerevisiae* YFR026C Promoter, *S. cerevisiae* YJL153C Promoter, *S. cerevisiae* YPL033C Promoter, *S. cerevisiae* YOL058W Promoter, *S. cerevisiae* YOR255W Promoter, *S. cerevisiae* YDR250C Promoter, *S. cerevisiae* YDR446W Promoter, *S. cerevisiae* YDR536W Promoter, *S. cerevisiae* YOR255W Promoter, *S.* cerevisiae YDL243C Promoter S. cerevisiae YDR256C Promoter, S. cerevisiae YFL020C Promoter, S. cerevisiae YPL205C Promoter, S. cerevisiae YGL205W Promoter, S. cerevisiae YGL117W Promoter, S. cerevisiae YHR029C Promoter, S. cerevisiae YML116W Promoter S. cerevisiae YJR109C Promoter, S. cerevisiae YCL030C Promoter, S. cerevisiae YLR338W Promoter, S. cerevisiae YEL066W-A Promoter, S. cerevisiae YNL093W Promoter, S. cerevisiae YLR381W Promoter, S. cerevisiae YKL159C Promoter, S. cerevisiae YIL058W Promoter, S. cerevisiae YKR037C Promoter, S. cerevisiae YNL279W Promoter, S. cerevisiae YOR032C Promoter, S. cerevisiae YML058W Promoter, S. cerevisiae YMR303C Promoter, S. cerevisiae YJL153C Promoter S. cerevisiae YLR092W Promoter, S. cerevisiae YFL052W Promoter, S. cerevisiae YIR017C Promoter, S. cerevisiae YLL062C Promoter, S. cerevisiae YMR323W Promoter S. cerevisiae YPL171C Promoter, S. cerevisiae YER065C Promoter, S. cerevisiae YDR114C Promoter and S. cerevisiae YBL065W Promoter (e.g., SEQ ID NOs: 1-41 or 68) operably linked to a reporter (e.g., S. cerevisiae ADE2, S. cerevisiae LYS2, S. cerevisiae TRP1, S. cerevisiae LEU2, S. cerevisiae URA3, S. cerevisiae HIS3, Aequorea victoria GFP mutant 3, Renilla luciferase, Photinus pyralis luciferase, Photinus pyralis luciferase slk mutant, Vibrio fischeri luxA, Vibrio fischeri luxB, Vibrio fischeri luxC, Vibrio fischeri luxD, Vibrio fischeri luxE, Vibrio fischeri luxAB, Vibrio fischeri luxCDABE, Vibrio harveyi luxA, Vibrio harveyi luxB, Vibrio harveyi luxC, Vibrio harveyi luxD, Vibrio harveyi luxE, Vibrio harveyi luxAB, Vibrio harveyi luxCDABE, Photorhabdus luminscens LuxA, Photorhabdus luminscens LuxB, Photorhabdus luminscens LuxC, Photorhabdus luminscens LuxD, Photorhabdus luminscens LuxE, Photorhabdus luminscens LuxCDABE, E. coli lacZ, the Aequorea victoria Aequorin gene, KanMX, pat1, nat1, hph, CAT, Sh Ble, GUS, CYH2 or CAN1 (e.g., SEQ ID NOs: 42-51)) into a suitable fungal cell (e.g., Absidia corymbifera; Absidia spp; Acremonium spp; Ajellomyces capsulatus; Ajellomyces dermatitidis; Alternaria spp; Aphanoascus fulvescens; Apophysomyces spp; Arthroderma benhamiae; Arthroderma fulvum; Arthroderma gypseum; Arthroderma incurvatum; Arthroderma otae; Arthroderma vanbreuseghemii; Aspergillus flavus; Aspergillus fumigatus; Aspergillus glaucus; Aspergillus nidulans; Aspergillus niger; Aspergillus oryzae; Aspergillus spp; Aspergillus sydowi; Aspergillus terreus; Aspergillus ustus; Aspergillus versicolor; Aureobasidium pullulans; Basidiomycetes; Beauveria spp; Bipolaris hawaiiensis; Bipolaris spicifera; Bipolaris spp; Bjerkandera adusta; Blastomyces dermatitidis; Blastoschizomyces capitatus; Candida albicans; Candida beigelii; Candida colluculosa; Candida dubliniensis; Candida dubliniensis; Candida famata; Candida famata; Candida glabrata; Candida guilliermondii; Candida haemulonii; Candida holmii; Candida inconspicua; Candida intermedia; Candida keyfyr; Candida krusei; Candida krusei; Candida lambica; Candida lipolytica; Candida lusitaniae; Candida maris; Candida melibiosica; Candida norvegensis; Candida parapsilosis; Candida parapsilosis; Candida pelliculosa; Candida pelliculosa; Candida pseudotropicalis; Candida pulcherrima; Candida rugosa; Candida sake; Candida sphaerica; Candida spp; Candida stellatoidea; Candida tropicalis; Candida tropicalis; Candida viswanathii; Candida zeylanoides; Chrysosporium spp; Cladophialophora bantiana; Cladophialophora carrionii; Cladosporium spp; Coccidioides immitis; Cokeromyces recurvatus; Coprinus spp; Cryptococcus albidus; Cryptococcus gattii; Cryptococcus laurentii; Cryptococcus neoformans; Cunninghamella bertholletiae; Cunninghamella spp; Curvularia lunata; Curvularia spp; Dekkera bruxellensis; Epidermophyton floccosum; Epidermophyton floccosum; Exophiala dermatitidis; Exophiala jeanselmei; Exophiala moniliae; Exserohilum rostratum; Filobasidiella neoformans; Fonsecaea pedrosoi; Fusarium dimerum; Fusarium moniliforme; Fusarium oxysporum; Fusarium proliferatum; Fusarium solani; Fusarium spp; Geotrichum candidum; Geotrichum spp; Histoplasma capsulatum; Hortaea werneckii; Issatschenkia orientalis; Kluveromyces lactis; Kluyveromyces marxianus; Madurella grisae; Malassezia furfur; Malassezia globosa; Malassezia obtusa; Malassezia pachydermatis; Malassezia restricta; Malassezia slooffiae; Malassezia sympodialis; Metarrhizium anisopliae; Microsporum audouinii; Microsporum canis; Microsporum fulvum; Microsporum gypseum; Microsporum persicolor; Mucor circinelloides; Mucor hiemalis; Mucor racemosus; Mucor rouxii; Mucor spp; Nattrassia mangiferae; Nectria haematococca; Onychocola canadensis; Paecilomyces lilacinus; Paecilomyces spp; Paecilomyces variotii; Paracoccidioides brasiliensis; Penicillium marneffei; Penicillium spp; Phialophora spp; Phialophora verrucosa; Phoma spp; Pichia anomala; Pichia etchellsii; Pichia guilliermondii; Pichia ohmeri; Pithomyces spp; Pneumocystis carinii; Pseudallescheria boydii; Ramichloridium obovoideum; Rhizomucor miehei; Rhizomucor pusillus; Rhizomucor spp; Rhizopus arrhizus; Rhizopus microsporus; Rhizopus oryzae; Rhizopus schipperae; Rhizopus spp; Rhodotorula mucilaginosa; Rhodotorula rubra; Rhodotorula spp; Saccharomyces cerevisiae; Saccharomyces spp; Sagrahamala spp; Saksenaea vasiformis; Scedosporium apiospermum; Scedosporium prolificans; Schizophyllum commune; Schizosaccharomyces pombe; Scopulariopsis brevicaulis; Scytalidium dimidiatum Ulocladium spp; Sporobolomyces spp; Sporothrix schenckii; Trichoderma spp; Trichophyton krajdenii; Trichophyton mentagrophytes; Trichophyton raubitschekii; Trichophyton rubrum; Trichophyton soudanense; Trichophyton spp; Trichophyton terrestre; Trichophyton tonsurans; Trichophyton verrucosum; Trichophyton violaceum; Trichosporon asahii; Trichosporon beigelii; Trichosporon capitatum; Trichosporon cutaneum; Trichosporon inkin; Trichosporon mucoides; Trichosporon spp; Tritirachium spp; Wangiella dermatitidis and Yarrowia lipolytica); (b) contacting the cell with a substance to be tested for the ability to inhibit fungal cell growth; (c) detecting expression driven by the promoter or signal from the reporter in the hybrid; (d) selecting the substance if it modulates expression from the promoter or signal from the reporter. In an embodiment of the invention, the method is carried out along with a negative-control comprising (i) introducing the hybrid into a suitable fungal cell; (ii) contacting the cell with a blank substance which is known to not modulate expression from the promoter or signal from the reporter in the hybrid; and (iii) detecting expression driven by the promoter or signal from the reporter in the hybrid; and (iv) comparing the expression level from the promoter or signal from the reporter in the cell contacted with the blank substance with the expression level from the promoter or the signal from the reporter in the cell contacted with the substance to be tested for the ability to inhibit fungal cell growth. Embodiments of the invention also include methods wherein a positive-control is carried out comprising (i) introducing the hybrid into a suitable fungal cell; (ii) contacting the cell with a positive-control which is known to modulate expression from the promoter or signal from the reporter in the hybrid; (iii) detecting expression driven by the promoter or signal from the reporter in the hybrid; and (iv) comparing the expression level from the promoter or signal from the reporter in the cell contacted with the positive-control substance with the expression level from the promoter or signal from the reporter in the cell contacted with the substance to be tested for the ability to inhibit fungal cell growth.

The present invention further comprises a method for identifying a substance that inhibits fungal cell growth comprising (a) introducing, into a suitable fungal cell (e.g., *Absidia corymbifera; Absidia* spp; *Acremonium* spp; *Ajellomyces capsulatus; Ajellomyces dermatitidis; Alternaria* spp; *Aphanoascus fulvescens; Apophysomyces* spp; *Arthroderma benhamiae; Arthroderma fulvum; Arthroderma gypseum; Arthroderma incurvatum; Arthroderma otae; Arthroderma vanbreuseghemii; Aspergillus flavus; Aspergillus fumigatus; Aspergillus glaucus; Aspergillus nidulans; Aspergillus niger; Aspergillus oryzae; Aspergillus* spp; *Aspergillus sydowi; Aspergillus terreus; Aspergillus ustus; Aspergillus versicolor; Aureobasidium pullulans; Basidiomycetes; Beauveria* spp; *Bipolaris hawaiiensis; Bipolaris spicifera; Bipolaris* spp; *Bjerkandera adusta; Blastomyces dermatitidis; Blastoschizomyces capitatus; Candida albicans; Candida beigelii; Candida colluculosa; Candida dubliniensis; Candida dubliniensis; Candida famata; Candida famata; Candida glabrata; Candida guilliermondii; Candida haemulonii; Candida holmii; Candida inconspicua; Candida intermedia; Candida keyfyr; Candida krusei; Candida krusei; Candida lambica; Candida lipolytica; Candida lusitaniae; Candida maris; Candida melibiosica; Candida norvegensis; Candida parapsilosis; Candida parapsilosis; Candida pelliculosa; Candida pelliculosa; Candida pseudotropicalis; Candida pulcherrima; Candida rugosa; Candida sake; Candida sphaerica; Candida* spp; *Candida stellatoidea; Candida tropicalis; Candida tropicalis; Candida viswanathii; Candida zeylanoides; Chrysosporium* spp; *Cladophialophora bantiana; Cladophialophora carrionii; Cladosporium* spp; *Coccidioides immitis; Cokeromyces recurvatus; Coprinus* spp; *Cryptococcus albidus; Cryptococcus gattii; Cryptococcus laurentii; Cryptococcus neoformans; Cunninghamella bertholletiae; Cunninghamella* spp; *Curvularia lunata; Curvularia* spp; *Dekkera bruxellensis; Epidermophyton floccosum; Epidermophyton floccosum; Exophiala dermatitidis; Exophiala jeanselmei; Exophiala moniliae; Exserohilum rostratum; Filobasidiella neoformans; Fonsecaea pedrosoi; Fusarium dimerum; Fusarium moniliforme; Fusarium oxysporum; Fusarium proliferatum; Fusarium solani; Fusarium* spp; *Geotrichum candidum; Geotrichum* spp; *Histoplasma capsulatum; Hortaea werneckii; Issatschenkia orientalis; Kluveromyces lactis; Kluyveromyces marxianus; Madurella grisae; Malassezia furfur; Malassezia globosa; Malassezia obtusa; Malassezia pachydermatis; Malassezia restricta; Malassezia slooffiae; Malassezia sympodialis; Metarrhizium anisopliae; Microsporum audouinii; Microsporum canis; Microsporum fulvum; Microsporum gypseum; Microsporum persicolor; Mucor circinelloides; Mucor hiemalis; Mucor racemosus; Mucor rouxii; Mucor* spp; *Nattrassia mangiferae; Nectria haematococca; Onychocola canadensis; Paecilomyces lilacinus; Paecilomyces* spp; *Paecilomyces variotii; Paracoccidioides brasiliensis; Penicillium marneffei; Penicillium* spp; *Phialophora* spp; *Phialophora verrucosa; Phoma* spp; *Pichia anomala; Pichia etchellsii; Pichia guilliermondii; Pichia ohmeri; Pithomyces* spp; *Pneumocystis carinii; Pseudallescheria boydii; Ramichloridium obovoideum; Rhizomucor miehei; Rhizomucor pusillus; Rhizomucor* spp; *Rhizopus arrhizus; Rhizopus microsporus; Rhizopus oryzae; Rhizopus schipperae; Rhizopus* spp; *Rhodotorula mucilaginosa; Rhodotorula rubra; Rhodotorula* spp; *Saccharomyces cerevisiae; Saccharomyces* spp; *Sagrahamala* spp; *Saksenaea vasiformis; Scedosporium apiospermum; Scedosporium prolificans; Schizophyllum commune; Schizosaccharomyces pombe; Scopulariopsis brevicaulis; Scytalidium dimidiatum Ulocladium* spp; *Sporobolomyces* spp; *Sporothrix schenckii; Trichoderma* spp; *Trichophyton krajdenii; Trichophyton mentagrophytes; Trichophyton raubitschekii; Trichophyton rubrum; Trichophyton soudanense; Trichophyton* spp; *Trichophyton terrestre; Trichophyton tonsurans; Trichophyton verrucosum; Trichophyton violaceum; Trichosporon asahii; Trichosporon beigelii; Trichosporon capitatum; Trichosporon cutaneum; Trichosporon inkin; Trichosporon mucoides; Trichosporon* spp; *Tritirachium* spp; *Wangiella dermatitidis* or *Yarrowia lipolytica*), a first hybrid comprising a first promoter selected from the group consisting of *S. cerevisiae* YOR387C Promoter, *S. cerevisiae* YMR175W Promoter, *S. cerevisiae* YFR026C Promoter, *S. cerevisiae* YJL153C Promoter, *S. cerevisiae* YPL033C Promoter, *S. cerevisiae* YOL058W Promoter, *S. cerevisiae* YOR255W Promoter, *S. cerevisiae* YDR250C Promoter, *S. cerevisiae* YDR446W Promoter, *S. cerevisiae* YDR536W Promoter, *S. cerevisiae* YOR255W Promoter, *S. cerevisiae* YDL243C Promoter *S. cerevisiae* YDR256C Promoter, *S. cerevisiae* YFL020C Promoter, *S. cerevisiae* YPL205C Promoter, *S. cerevisiae* YGL205W Promoter, *S. cerevisiae* YGL117W Promoter, *S. cerevisiae* YHR029C Promoter, *S. cerevisiae* YML116W Promoter *S. cerevisiae* YJR109C Promoter, *S. cerevisiae* YCL030C Promoter, *S. cerevisiae* YLR338W Promoter, *S. cerevisiae* YIL066W-A Promoter, *S. cerevisiae* YNL093W Promoter, *S. cerevisiae* YLR381W Promoter, *S. cerevisiae* YKL159C Promoter, *S. cerevisiae* YIL058W Promoter, *S. cerevisiae* YKR037C Promoter, *S. cerevisiae* YNL279W Promoter, *S. cerevisiae* YOR032C Promoter, *S. cerevisiae* YML058W Promoter, *S. cerevisiae* YMR303C Promoter, *S. cerevisiae* YJL153C Promoter *S. cerevisiae* YLR092W Promoter, *S. cerevisiae* YFL052W Promoter, *S. cerevisiae* YIR117C Promoter, *S. cerevisiae* YLL062C Promoter, *S. cerevisiae* YMR323W Promoter *S. cerevisiae* YPL171C Promoter, *S. cerevisiae* YER065C Promoter, *S. cerevisiae* YDR114C Promoter and *S. cerevisiae* YBL065W Promoter (e.g., SEQ ID NOs: 1-41 or 68); operably linked to a first reporter (e.g., *S. cerevisiae* ADE2, *S. cerevisiae* LYS2, *S. cerevisiae* TRP1, *S. cerevisiae* LEU2, *S. cerevisiae* URA3, *S. cerevisiae* HIS3, *Aequorea victoria* GFP mutant 3, *Renilla* luciferase, *Photinus pyralis* luciferase, *Photinus pyralis* luciferase slk mutant, *Vibrio fischeri* luxA, *Vibrio fischeri* luxB, *Vibrio fischeri* luxC, *Vibrio fischeri* luxD, *Vibrio fischeri* luxE, *Vibrio fischeri* luxAB, *Vibrio fischeri* luxCDABE, *Vibrio harveyi* luxA, *Vibrio harveyi* luxB, *Vibrio harveyi* luxC, *Vibrio harveyi* luxD, *Vibrio harveyi* luxE, *Vibrio harveyi* luxAB, *Vibrio harveyi* luxCDABE, *Photorhabdus luminscens* LuxA, *Photorhabdus luminscens* LuxB, *Photorhabdus luminscens* LuxC, *Photorhabdus luminscens* LuxD, *Photorhabdus luminscens* LuxE, *Photorhabdus luminscens* LuxCDABE, *E. coli* lacZ, the *Aequorea victoria* Aequorin gene, KanMX, pat1, nat1, hph, CAT, Sh Ble, GUS, CYH2 or CAN1 (e.g., SEQ ID NOs: 42-51 )); and a second hybrid comprising a second promoter selected from the group consisting of: *S. cerevisiae* YHR082C Promoter, *S. cerevisiae* YDL126C Promoter *S. cerevisiae* YBR106W Promoter, *S. cerevisiae* YLL043W Promoter, *S. cerevisiae* YPR108W Promoter, *S. cerevisiae* YIL041W Promoter, *S. cerevisiae* YJL166W Promroter *S. cerevisiae* YDR 165W Promoter, *S. cerevisiae* YLR330W Promoter, *S. cerevisiae* YDL058W Promoter, *S. cerevisiae* YHR012W Promoter, *S. cerevisiae* YKL053W Promoter, *S. cerevisiae* YKL196C Promoter, *S. cerevisiae* YDL103C Promoter *S. cerevisiae* YLR427W Promoter and *S. cerevisiae* YLL020C Promoter (e.g., SEQ ID NOs: 52-67); operably linked to a second reporter (e.g., *S. cerevisiae* ADE2, *S. cerevisiae* LYS2, *S. cerevisiae* TRP1, *S. cerevisiae*

LEU2, *S. cerevisiae* URA3, *S. cerevisiae* HIS3, *Aequorea victoria* GFP mutant 3, *Renilla* luciferase, *Photinus pyralis* luciferase, *Photinus pyralis* luciferase slk mutant, *Vibrio fischeri* luxA, *Vibrio fischeri* luxB, *Vibrio fischeri* luxC, *Vibrio fischeri* luxD, *Vibrio fischeri* luxE, *Vibrio fischeri* luxAB, *Vibrio fischeri* luxCDABE, *Vibrio harveyi* luxA, *Vibrio harveyi* luxB, *Vibrio harveyi* luxC, *Vibrio harveyi* luxD, *Vibrio harveyi* luxE, *Vibrio harveyi* luxAB, *Vibrio harveyi* luxCDABE, *Photorhabdus luminscens* LuxA, *Photorhabdus luminscens* LuxB, *Photorhabdus luminscens* LuxC, *Photorhabdus luminscens* LuxD, *Photorhabdus luminscens* LuxE, *Photorhabdus luminscens* LuxCDABE, *E. coli* lacZ, the *Aequorea victoria* Aequorin gene, KanMX, pat1, nat1, hph, CAT, Sh Ble, GUS, CYH2 and CAN1 (e.g., SEQ ID NOs: 42-51 )); wherein said first and second reporters are different; (b) contacting the cell with a substance to be tested for the ability to inhibit fungal cell growth; (c) detecting expression driven by the first and second promoters or signal from the reporters; and (d) selecting the substance if it causes the first promoter expression level or reporter signal to increase or decrease in relation to the expression level from the second promoter or signal from the second reporter. In an embodiment of the present invention, the method is carried out along with a negative-control comprising (i) introducing said first and second hybrids into a suitable fungal cell; (ii) contacting the cell with a blank substance which is known to not modulate expression from the promoters or signal from the reporters in the hybrids; and (iii) detecting expression driven by the promoters or signal from the reporters in the hybrids; (iv) comparing the expression level from the first promoter or signal from the first reporter in relation to the expression level from the second promoter or signal from the second reporter in the cell contacted with the blank substance with the expression level from the first promoter or signal from the first reporter in relation to the expression level from the second promoter or signal from the second reporter in the cell contacted with the substance to be tested for the ability to inhibit fungal cell growth. In an embodiment of the invention, the method is carried out along with a positive-control comprising: (i) introducing said first and second hybrids into a suitable fungal cell; (ii) contacting the cell with a positive-control substance which is known to modulate expression from the promoters or signal from the reporters in the hybrids; (iii) detecting expression driven by the promoters or signal from the reporters in the hybrids; and (iv) comparing the expression level from the first promoter or signal from the first reporter in relation to the expression level from the second promoter or signal from the second reporter in the cell contacted with the positive-control substance with the expression level from the first promoter or signal from the first reporter in relation to the expression level from the second promoter or signal from the second reporter in the cell contacted with the substance to be tested for the ability to inhibit fungal cell growth.

The present invention also provides a method for determining whether a substance inhibits growth of a fungal cell comprising (a) introducing a hybrid comprising a promoter selected from the group consisting of *S. cerevisiae* YHR082C Promoter, *S. cerevisiae* YDL126C Promoter *S. cerevisiae* YBR106W Promoter, *S. cerevisiae* YLL043W Promoter, *S. cerevisiae* YPR108W Promoter, *S. cerevisiae* YIL041W Promoter, *S. cerevisiae* YJL166W Promoter *S. cerevisiae* YDR165W Promoter, *S. cerevisiae* YLR330W Promoter, *S. cerevisiae* YDL058W Promoter, *S. cerevisiae* YHR012W Promoter, *S. cerevisiae* YKL053W Promoter, *S. cerevisiae* YKL196C Promoter, *S. cerevisiae* YDL103C Promoter *S. cerevisiae* YLR427W Promoter and *S. cerevisiae* YLL020C Promoter (e.g., SEQ ID NOs: 52-67); operably linked to a reporter (e.g., *S. cerevisiae* ADE2, *S. cerevisiae* LYS2, *S. cerevisiae* TRP1, *S. cerevisiae* LEU2, *S. cerevisiae* URA3, *S. cerevisiae* HIS3, *Aequorea victoria* GFP mutant 3, *Renilla* luciferase, *Photinus pyralis* luciferase, *Photinus pyralis* luciferase slk mutant, *Vibrio fischeri* luxA, *Vibrio fischeri* luxB, *Vibrio fischeri* luxC, *Vibrio fischeri* luxD, *Vibrio fischeri* luxE, *Vibrio fischeri* luxAB, *Vibrio fischeri* luxCDABE, *Vibrio harveyi* luxA, *Vibrio harveyi* luxB, *Vibrio harveyi* luxC, *Vibrio harveyi* luxD, *Vibrio harveyi* luxE, *Vibrio harveyi* luxAB, *Vibrio harveyi* luxCDABE, *Photorhabdus luminscens* LuxA, *Photorhabdus luminscens* LuxB, *Photorhabdus luminscens* LuxC, *Photorhabdus luminscens* LuxD, *Photorhabdus luminscens* LuxE, *Photorhabdus luminscens* LuxCDABE, *E. coli* lacZ, the *Aequorea victoria* Aequorin gene, KanMX, pat1, nat1, hph, CAT, Sh Ble, GUS, CYH2 or CAN1 (e.g., SEQ ID NOs: 42-51)) into a suitable fungal cell (e.g., *Absidia corymbifera; Absidia* spp; *Acremonium* spp; *Ajellomyces capsulatus; Ajellomyces dermatitidis; Alternaria* spp; *Aphanoascus fulvescens; Apophysomyces* spp; *Arthroderma benhamiae; Arthroderma fulvum; Arthroderma gypseum; Arthroderma incurvatum; Arthroderma otae; Arthroderma vanbreuseghemii; Aspergillus flavus; Aspergillus fumigatus; Aspergillus glaucus; Aspergillus nidulans; Aspergillus niger; Aspergillus oryzae; Aspergillus* spp; *Aspergillus sydowi; Aspergillus terreus; Aspergillus ustus; Aspergillus versicolor; Aureobasidium pullulans; Basidiomycetes; Beauveria* spp; *Bipolaris hawaiiensis; Bipolaris spicifera; Bipolaris* spp; *Bjerkandera adusta; Blastomyces dermatitidis; Blastoschizomyces capitatus; Candida albicans; Candida beigelii; Candida colluculosa; Candida dubliniensis; Candida dubliniensis; Candida famata; Candida famata; Candida glabrata; Candida guilliermondii; Candida haemulonii; Candida holmii; Candida inconspicua; Candida intermedia; Candida keyfyr; Candida krusei; Candida krusei; Candida lambica; Candida lipolytica; Candida lusitaniae; Candida maris; Candida melibiosica; Candida norvegensis; Candida parapsilosis; Candida parapsilosis; Candida pelliculosa; Candida pelliculosa; Candida pseudotropicalis; Candida pulcherrima; Candida rugosa; Candida sake; Candida sphaerica; Candida* spp; *Candida stellatoidea; Candida tropicalis; Candida tropicalis; Candida viswanathii; Candida zeylanoides; Chrysosporium* spp; *Cladophialophora bantiana; Cladophialophora carrionii; Cladosporium* spp; *Coccidioides immitis; Cokeromyces recurvatus; Coprinus* spp; *Cryptococcus albidus; Cryptococcus gattii; Cryptococcus laurentii; Cryptococcus neoformans; Cunninghamella bertholletiae; Cunninghamella* spp; *Curvularia lunata; Curvularia* spp; *Dekkera bruxellensis; Epidermophyton floccosum; Epidermophyton floccosum; Exophiala dermatitidis; Exophiala jeanselmei; Exophiala moniliae; Exserohilum rostratum; Filobasidiella neoformans; Fonsecaea pedrosoi; Fusarium dimerum; Fusarium moniliforme; Fusarium oxysporum; Fusarium proliferatum; Fusarium solani; Fusarium* spp; *Geotrichum candidum; Geotrichum* spp; *Histoplasma capsulatum; Hortaea werneckii; Issatschenkia orientalis; Kluveromyces lactis; Kluyveromyces marxianus; Madurella grisae; Malassezia furfur; Malassezia globosa; Malassezia obtusa; Malassezia pachydermatis; Malassezia restricta; Malassezia slooffiae; Malassezia sympodialis; Metarrhizium anisopliae; Microsporum audouinii; Microsporum canis; Microsporum fulvum; Microsporum gypseum; Microsporum persicolor; Mucor circinelloides; Mucor hiemalis; Mucor racemosus; Mucor rouxii; Mucor* spp; *Nattrassia mangiferae; Nectria haematococca; Onychocola canadensis; Paecilomyces lilacinus; Paecilomyces* spp; *Paecilomyces variotii; Paracoccidioides brasiliensis; Penicillium marneffei; Penicillium* spp; *Phialophora* spp; *Phialophora verrucosa; Phoma* spp; *Pichia anomala; Pichia etchellsii; Pichia guilliermondii; Pichia ohmeri; Pithomyces* spp; *Pneumocystis carinii; Pseudallescheria boydii; Ramichloridium obovoideum; Rhizomucor miehei; Rhizomucor pusillus; Rhizomucor* spp; *Rhizopus arrhizus; Rhizopus microsporus; Rhizopus oryzae; Rhizopus schipperae; Rhizopus* spp; *Rhodotorula mucilaginosa; Rhodotorula rubra; Rhodotorula* spp; *Saccharomyces cerevisiae; Saccharomyces* spp; *Sagrahamala* spp; *Saksenaea vasiformis; Scedosporium apiospermum; Scedosporium prolificans; Schizophyllum commune; Schizosaccharomyces pombe; Scopulariopsis brevicaulis; Scytalidium dimidiatum Ulocladium* spp; *Sporobolomyces* spp; *Sporothrix schenckii; Trichoderma* spp; *Trichophyton krajdenii; Trichophyton mentagrophytes; Trichophyton raubitschekii; Trichophyton rubrum; Trichophyton soudanense; Trichophyton* spp; *Trichophyton terrestre; Trichophyton tonsurans; Trichophyton verrucosum; Trichophyton violaceum; Trichosporon asahii; Trichosporon beigelii; Trichosporon capitatum; Trichosporon cutaneum; Trichosporon inkin; Trichosporon mucoides; Trichosporon* spp; *Tritirachium* spp; *Wangiella dermatitidis* or *Yarrowia lipolytica*); (b) contacting the cell with a substance to be tested for the ability to inhibit growth of the cell; (c) detecting signal from the reporter; and (d) selecting the substance if it causes a reduction in the signal from the reporter and/or calculating the IC of the substance. In an embodiment of the present invention, the method is carried out along with a negative-control comprising: (i) introducing the hybrid into a suitable fungal cell; (ii) contacting the cell with a blank substance which is known to not inhibit fungal cell growth; (iii) detecting signal from the reporter in the hybrid; and (iv) comparing the signal from the reporter in the cell contacted with the blank substance with the signal from the reporter in the cell contacted with the substance to be tested for the ability to inhibit fungal cell growth. In an embodiment of the invention, the method is carried out along with a positive-control comprising (i) introducing the hybrid into a suitable fungal cell; (ii) contacting the cell with a positive-control substance which is known to inhibit fungal cell growth; (iii) detecting signal from the reporter in the hybrid; and (iv) comparing the signal from the reporter in the cell contacted with the positive-control substance with the signal from the reporter in the cell contacted with the substance to be tested for the ability to inhibit fungal cell growth.

The present invention further provides a method for determining whether a substance inhibits growth of a fungal cell comprising (a) introducing a first hybrid comprising a first promoter selected from the group consisting of *S. cerevisiae* YHR082C Promoter, *S. cerevisiae* YDL126C Promoter *S. cerevisiae* YBR106W Promoter, *S. cerevisiae* YLL043W Promoter, *S. cerevisiae* YPR108W Promoter, *S. cerevisiae* YIL041W Promoter, *S. cerevisiae* YJL166W Promoter *S. cerevisiae* YDR165W Promoter, *S. cerevisiae* YLR330W Promoter, *S. cerevisiae* YDL058W Promoter, *S. cerevisiae* YHR012W Promoter, *S. cerevisiae* YKL053W Promoter, *S. cerevisiae* YKL196C Promoter, *S. cerevisiae* YDL103C Promoter *S. cerevisiae* YLR427W Promoter and *S. cerevisiae* YLL020C Promoter (e.g., SEQ ID NOs: 52-67); operably linked to a first reporter (e.g., *S. cerevisiae* ADE2, *S. cerevisiae* LYS2, *S. cerevisiae* TRP1, *S. cerevisiae* LEU2, *S. cerevisiae* URA3, *S. cerevisiae* HIS3, *Aequorea Victoria* GFP mutant 3, *Renilla* luciferase, *Photinus pyralis* luciferase, *Photinus pyralis* luciferase slk mutant, *Vibrio fischeri* luxA, *Vibrio fischeri* luxB, *Vibrio fischeri* luxC, *Vibrio fischeri* luxD, *Vibrio fischeri* luxE, *Vibrio fischeri* luxAB, *Vibrio fischeri* luxCDABE, *Vibrio harveyi* luxA, *Vibrio harveyi* luxB, *Vibrio harveyi* luxC, *Vibrio harveyi* luxD, *Vibrio harveyi* luxE, *Vibrio harveyi* luxAB, *Vibrio harveyi* luxCDABE, *Photorhabdus luminscens* LuxA, *Photorhabdus luminscens* LuxB, *Photorhabdus luminscens* LuxC, *Photorhabdus luminscens* LuxD, *Photorhabdus luminscens* LuxE, *Photorhabdus luminscens* LuxCDABE, *E. coli* lacZ, the *Aequorea victoria* Aequorin gene, KanMX, pat1, nat1, hph, CAT, Sh Ble, GUS, CYH2 or CAN1 (e.g., SEQ ID NOs: 42-51)) and a second hybrid comprising a second promoter selected from the group consisting of *S. cerevisiae* YHR082C Promoter, *S. cerevisiae* YDL126C Promoter *S. cerevisiae* YBR106W Promoter, *S. cerevisiae* YLL043W Promoter, *S. cerevisiae* YPR108W Promoter, *S. cerevisiae* YIL041W Promoter, *S. cerevisiae* YJL166W Promoter *S. cerevisiae* YDR165W Promoter, *S. cerevisiae* YLR330W Promoter, *S. cerevisiae* YDL058W Promoter, *S. cerevisiae* YHR012W Promoter, *S. cerevisiae* YKL053W Promoter, *S. cerevisiae* YKL196C Promoter, *S. cerevisiae* YDL103C Promoter *S. cerevisiae* YLR427W Promoter and *S. cerevisiae* YLL020C Promoter (e.g., SEQ ID NOs: 52-67); operably linked to a second reporter (e.g., *S. cerevisiae* ADE2, *S. cerevisiae* LYS2, *S. cerevisiae* TRP1, *S. cerevisiae* LEU2, *S. cerevisiae* URA3, *S. cerevisiae* HIS3, *Aequorea victoria* GFP mutant 3, *Renilla* luciferase, *Photinus pyralis* luciferase, *Photinus pyralis* luciferase slk mutant, *Vibrio fischeri* luxA, *Vibrio fischeri* luxB, *Vibrio fischeri* luxC, *Vibrio fischeri* luxD, *Vibrio fischeri* luxE, *Vibrio fischeri* luxAB, *Vibrio fischeri* luxCDABE, *Vibrio harveyi* luxA, *Vibrio harveyi* luxB, *Vibrio harveyi* luxC, *Vibrio harveyi* luxD, *Vibrio harveyi* luxE, *Vibrio harveyi* luxAB, *Vibrio harveyi* luxCDABE, *Photorhabdus luminscens* LuxA, *Photorhabdus luminscens* LuxB, *Photorhabdus luminscens* LuxC, *Photorhabdus luminscens* LuxD, *Photorhabdus luminscens* LuxE, *Photorhabdus luminscens* LuxCDABE, *E. coli* lacZ, the *Aequorea victoria* Aequorin gene, KanMX, pat1, nat1, hph, CAT, Sh Ble, GUS, CYH2 or CAN1 (e.g., SEQ ID NOs: 42-51)) into a suitable fungal cell (e.g., *Absidia corymbifera; Absidia* spp; *Acremonium* spp; *Ajellomyces capsulatus; Ajellomyces dermatitidis; Alternaria* spp; *Aphanoascus fulvescens; Apophysomyces* spp; *Arthroderma benhamiae; Arthroderma fulvum; Arthroderma gypseum; Arthroderma incurvatum; Arthroderma otae; Arthroderma vanbreuseghemii; Aspergillus flavus; Aspergillus fumigatus; Aspergillus glaucus; Aspergillus nidulans; Aspergillus niger; Aspergillus oryzae; Aspergillus* spp; *Aspergillus sydowi; Aspergillus terreus; Aspergillus ustus; Aspergillus versicolor; Aureobasidium pullulans; Basidiomycetes; Beauveria* spp; *Bipolaris hawaiiensis; Bipolaris spicifera; Bipolaris* spp; *Bjerkandera adusta; Blastomyces dermatitidis; Blastoschizomyces capitatus; Candida albicans; Candida beigelii; Candida colluculosa; Candida dubliniensis; Candida dubliniensis; Candida famata; Candida famata; Candida glabrata; Candida guilliermondii; Candida haemulonii; Candida holmii; Candida inconspicua; Candida intermedia; Candida keyfyr; Candida krusei; Candida krusei; Candida lambica; Candida lipolytica; Candida lusitaniae; Candida maris; Candida melibiosica; Candida norvegensis; Candida parapsilosis; Candida parapsilosis; Candida pelliculosa; Candida pelliculosa; Candida pseudotropicalis; Candida pulcherrima; Candida rugosa; Candida sake; Candida sphaerica; Candida* spp; *Candida stellatoidea; Candida tropicalis; Candida tropicalis; Candida viswanathii; Candida zeylanoides; Chrysosporium* spp; *Cladophialophora bantiana; Cladophialophora carrionii; Cladosporium* spp; *Coccidioides immitis; Cokeromyces recurvatus; Coprinus* spp; *Cryptococcus albidus; Cryptococcus gattii; Cryptococcus laurentii; Cryptococcus neoformans; Cunninghamella bertholletiae; Cunninghamella* spp;

*Curvularia lunata; Curvularia* spp; *Dekkera bruxellensis; Epidermophyton floccosum; Epidermophyton floccosum; Exophiala dermatitidis; Exophiala jeanselmei; Exophiala moniliae; Exserohilum rostratum; Filobasidiella neoformans; Fonsecaea pedrosoi; Fusarium dimerum; Fusarium moniliforme; Fusarium oxysporum; Fusarium proliferatum; Fusarium solani; Fusarium* spp; *Geotrichum candidum; Geotrichum* spp; *Histoplasma capsulatum; Hortaea werneckii; Issatschenkia orientalis; Kluveromyces lactis; Kluyveromyces marxianus; Madurella grisae; Malassezia furfur; Malassezia globosa; Malassezia obtusa; Malassezia pachydermatis; Malassezia restricta; Malassezia slooffiae; Malassezia sympodialis; Metarrhizium anisopliae; Microsporum audouinii; Microsporum canis; Microsporum fulvum; Microsporum gypseum; Microsporum persicolor; Mucor circinelloides; Mucor hiemalis; Mucor racemosus; Mucor rouxii; Mucor* spp; *Nattrassia mangiferae; Nectria haematococca; Onychocola canadensis; Paecilomyces lilacinus; Paecilomyces* spp; *Paecilomyces variotii; Paracoccidioides brasiliensis; Penicillium marneffei; Penicillium* spp; *Phialophora* spp; *Phialophora verrucosa; Phoma* spp; *Pichia anomala; Pichia etchellsii; Pichia guilliermondii; Pichia ohmeri; Pithomyces* spp; *Pneumocystis carinii; Pseudallescheria boydii; Ramichloridium obovoideum; Rhizomucor miehei; Rhizomucor pusillus; Rhizomucor* spp; *Rhizopus arrhizus; Rhizopus microsporus; Rhizopus oryzae; Rhizopus schipperae; Rhizopus* spp; *Rhodotorula mucilaginosa; Rhodotorula rubra; Rhodotorula* spp; *Saccharomyces cerevisiae; Saccharomyces* spp; *Sagrahamala* spp; *Saksenaea vasiformis; Scedosporium apiospermum; Scedosporium prolificans; Schizophyllum commune; Schizosaccharomyces pombe; Scopulariopsis brevicaulis; Scytalidium dimidiatum Ulocladium* spp; *Sporobolomyces* spp; *Sporothrix schenckii; Trichoderma* spp; *Trichophyton krajdenii; Trichophyton mentagrophytes; Trichophyton raubitschekii; Trichophyton rubrum; Trichophyton soudanense; Trichophyton* spp; *Trichophyton terrestre; Trichophyton tonsurans; Trichophyton verrucosum; Trichophyton violaceum; Trichosporon asahii; Trichosporon beigelii; Trichosporon capitatum; Trichosporon cutaneum; Trichosporon inkin; Trichosporon mucoides; Trichosporon* spp; *Tritirachium* spp; *Wangiella dermatitidis* or *Yarrowia lipolytica*); wherein said first and second promoter are different and wherein said first and second reporter are different; (b) contacting the cell with a substance to be tested for the ability to inhibit growth of the cell; (c) detecting signal from the reporters; and (d) selecting the substance if it causes a reduction in the signal from both the first and second reporter and/or calculating the IC of the substance. In an embodiment of the present invention, the method is carried out along with a negative-control comprising (i) introducing the first and second hybrids into a suitable fungal cell; (ii) contacting the cell with a blank substance which is known to not inhibit fungal cell growth; (iii) detecting signal from the first and second reporters in the hybrids; and (iv) comparing the signal from the first and second reporters in the cell contacted with the blank substance with the signal from the first and second reporters in the cell contacted with the substance to be tested for the ability to inhibit fungal cell growth. In another embodiment of the invention, the method is carried out along with a positive-control comprising (i) introducing the first and second hybrids into a suitable fungal cell; (ii) contacting the cell with a positive control substance which is known to inhibit fungal cell growth; (iii) detecting signal from the first and second promoters in the hybrids; and (iv) comparing the signal from the first and second reporters in the cell contacted with the positive control substance with the signal from the first and second reporters in the cell contacted with the substance to be tested for the ability to inhibit fungal cell growth.

The present invention also provides a method for determining whether a substance inhibits growth of a malignant cell comprising (a) introducing, into a suitable fungal cell (e.g., *Absidia corymbifera; Absidia* spp; *Acremonium* spp; *Ajellomyces capsulatus; Ajellomyces dermatitidis; Alternaria* spp; *Aphanoascus fulvescens; Apophysomyces* spp; *Arthroderma benhamiae; Arthroderma fulvum; Arthroderma gypseum; Arthroderma incurvatum; Arthroderma otae; Arthroderma vanbreuseghemii; Aspergillus flavus; Aspergillus fumigatus; Aspergillus glaucus; Aspergillus nidulans; Aspergillus niger; Aspergillus oryzae; Aspergillus* spp; *Aspergillus sydowi; Aspergillus terreus; Aspergillus ustus; Aspergillus versicolor; Aureobasidium pullulans; Basidiomycetes; Beauveria* spp; *Bipolaris hawaiiensis; Bipolaris spicifera; Bipolaris* spp; *Bjerkandera adusta; Blastomyces dermatitidis; Blastoschizomyces capitatus; Candida albicans; Candida beigelii; Candida colluculosa; Candida dubliniensis; Candida dubliniensis; Candida famata; Candida famata; Candida glabrata; Candida guilliermondii; Candida haemulonii; Candida holmii; Candida inconspicua; Candida intermedia; Candida keyfyr; Candida krusei; Candida krusei; Candida lambica; Candida lipolytica; Candida lusitaniae; Candida maris; Candida melibiosica; Candida norvegensis; Candida parapsilosis; Candida parapsilosis; Candida pelliculosa; Candida pelliculosa; Candida pseudotropicalis; Candida pulcherrima; Candida rugosa; Candida sake; Candida sphaerica; Candida* spp; *Candida stellatoidea; Candida tropicalis; Candida tropicalis; Candida viswanathii; Candida zeylanoides; Chrysosporium* spp; *Cladophialophora bantiana; Cladophialophora carrionii; Cladosporium* spp; *Coccidioides immitis; Cokeromyces recurvatus; Coprinus* spp; *Cryptococcus albidus; Cryptococcus gattii; Cryptococcus laurentii; Cryptococcus neoformans; Cunninghamella bertholletiae; Cunninghamella* spp; *Curvularia lunata; Curvularia* spp; *Dekkera bruxellensis; Epidermophyton floccosum; Epidermophyton floccosum; Exophiala dermatitidis; Exophiala jeanselmei; Exophiala moniliae; Exserohilum rostratum; Filobasidiella neoformans; Fonsecaea pedrosoi; Fusarium dimerum; Fusarium moniliforme; Fusarium oxysporum; Fusarium proliferatum; Fusarium solani; Fusarium* spp; *Geotrichum candidum; Geotrichum* spp; *Histoplasma capsulatum; Hortaea werneckii; Issatschenkia orientalis; Kluveromyces lactis; Kluyveromyces marxianus; Madurella grisae; Malassezia furfur; Malassezia globosa; Malassezia obtusa; Malassezia pachydermatis; Malassezia restricta; Malassezia slooffiae; Malassezia sympodialis; Metarrhizium anisopliae; Microsporum audouinii; Microsporum canis; Microsporum fulvum; Microsporum gypseum; Microsporum persicolor; Mucor circinelloides; Mucor hiemalis; Mucor racemosus; Mucor rouxii; Mucor* spp; *Nattrassia mangiferae; Nectria haematococca; Onychocola canadensis; Paecilomyces lilacinus; Paecilomyces* spp; *Paecilomyces variotii; Paracoccidioides brasiliensis; Penicillium marneffei; Penicillium* spp; *Phialophora* spp; *Phialophora verrucosa; Phoma* spp; *Pichia anomala; Pichia etchellsii; Pichia guilliermondii; Pichia ohmeri; Pithomyces* spp; *Pneumocystis carinii; Pseudallescheria boydii; Ramichloridium obovoideum; Rhizomucor miehei; Rhizomucor pusillus; Rhizomucor* spp; *Rhizopus arrhizus; Rhizopus microsporus; Rhizopus oryzae; Rhizopus schipperae; Rhizopus* spp; *Rhodotorula mucilaginosa; Rhodotorula rubra; Rhodotorula* spp; *Saccharomyces cerevisiae; Saccharomyces* spp; *Sagrahamala* spp; *Saksenaea vasiformis; Scedosporium apiospermum; Scedosporium prolificans; Schizophyllum commune; Schizosaccharomyces*

*pombe; Scopulariopsis brevicaulis; Scytalidium dimidiatum Ulocladium* spp; *Sporobolomyces* spp; *Sporothrix schenckii; Trichoderma* spp; *Trichophyton krajdenii; Trichophyton mentagrophytes; Trichophyton raubitschekii; Trichophyton rubrum; Trichophyton soudanense; Trichophyton* spp; *Trichophyton terrestre; Trichophyton tonsurans; Trichophyton verrucosum; Trichophyton violaceum; Trichosporon asahii; Trichosporon beigelii; Trichosporon capitatum; Trichosporon cutaneum; Trichosporon inkin; Trichosporon mucoides; Trichosporon* spp; *Tritirachium* spp; *Wangiella dermatitidis* or *Yarrowia lipolytica*), a first hybrid comprising a first promoter selected from the group consisting of: *S. cerevisiae* YLR338W, *S. cerevisiae* YIL066W, *S. cerevisiae* YNL093W, *S. cerevisiae* YDR250C, *S. cerevisiae* YLR381W, *S. cerevisiae* YBL065W, *S. cerevisiae* YMR323W and *S. cerevisiae* YPL171C (e.g., SEQ ID NOs: 8, 22-25, 38, 39 and 68); operably linked to a first reporter (e.g., *S. cerevisiae* ADE2, *S. cerevisiae* LYS2, *S. cerevisiae* TRP1, *S. cerevisiae* LEU2, *S. cerevisiae* URA3, *S. cerevisiae* HIS3, *Aequorea victoria* GFP mutant 3, *Renilla* luciferase, *Photinus pyralis* luciferase, *Photinus pyralis* luciferase slk mutant, *Vibrio fischeri* luxA, *Vibrio fischeri* luxB, *Vibrio fischeri* luxC, *Vibrio fischeri* luxD, *Vibrio fischeri* luxE, *Vibrio fischeri* luxAB, *Vibrio fischeri* luxCDABE, *Vibrio harveyi* luxA, *Vibrio harveyi* luxB, *Vibrio harveyi* luxC, *Vibrio harveyi* luxD, *Vibrio harveyi* luxE, *Vibrio harveyi* luxAB, *Vibrio harveyi* luxCDABE, *Photorhabdus luminscens* LuxA, *Photorhabdus luminscens* LuxB, *Photorhabdus luminscens* LuxC, *Photorhabdus luminscens* LuxD, *Photorhabdus luminscens* LuxE, *Photorhabdus luminscens* LuxCDABE, *E. coli* lacZ, the *Aequorea victoria* Aequorin gene, KanMX, pat1, nat1, hph, CAT, Sh Ble, GUS, CYH2 or CAN1 (e.g., SEQ ID NO: 42-51)); and a second hybrid comprising a second promoter selected from the group consisting of: *S. cerevisiae* YHR082C Promoter, *S. cerevisiae* YDL126C Promoter *S. cerevisiae* YBR106W Promoter, *S. cerevisiae* YLL043W Promoter, *S. cerevisiae* YPR108W Promoter, *S. cerevisiae* YIL041W Promoter, *S. cerevisiae* YJL166W Promoter *S. cerevisiae* YDR165W Promoter, *S. cerevisiae* YLR330W Promoter, *S. cerevisiae* YDL058W Promoter, *S. cerevisiae* YHR012W Promoter, *S. cerevisiae* YKL053W Promoter, *S. cerevisiae* YKL196C Promoter, *S. cerevisiae* YDL103C Promoter *S. cerevisiae* YLR427W Promoter and *S. cerevisiae* YLL020C Promoter (e.g., SEQ ID NOs: 52-67); operably linked to a second reporter (e.g., *S. cerevisiae* ADE2, *S. cerevisiae* LYS2, *S. cerevisiae* TRP1, *S. cerevisiae* LEU2, *S. cerevisiae* URA3, *S. cerevisiae* HIS3, *Aequorea victoria* GFP mutant 3, *Renilla* luciferase, *Photinus pyralis* luciferase, *Photinus pyralis* luciferase slk mutant, *Vibrio fischeri* luxA, *Vibrio fischeri* luxB, *Vibrio fischeri* luxC, *Vibrio fischeri* luxD, *Vibrio fischeri* luxE, *Vibrio fischeri* luxAB, *Vibrio fischeri* luxCDABE, *Vibrio harveyi* luxA, *Vibrio harveyi* luxB, *Vibrio harveyi* luxC, *Vibrio harveyi* luxD, *Vibrio harveyi* luxE, *Vibrio harveyi* luxAB, *Vibrio harveyi* luxCDABE, *Photorhabdus luminscens* LuxA, *Photorhabdus luminscens* LuxB, *Photorhabdus luminscens* LuxC, *Photorhabdus luminscens* LuxD, *Photorhabdus luminscens* LuxE, *Photorhabdus luminscens* LuxCDABE, *E. coli* lacZ, the *Aequorea Victoria* Aequorin gene, KanMX, pat1, nat1, hph, CAT, Sh Ble, GUS, CYH2 or CAN1 (e.g., SEQ ID NO: 42-51)); (b) contacting the cell with a substance to be tested for the ability to inhibit growth of a malignant cell; (c) detecting expression driven by the first and second promoters; and (d) selecting the substance if it causes the expression level from the first promoter to increase or decrease in relation to the expression level from the second promoter. In an embodiment of the invention, the method is carried out along with a negative-control comprising (i) introducing said first and second hybrids into a suitable fungal cell; (ii) contacting the cell with a blank substance which is known to not modulate expression from the promoters in the hybrids; and (iii) detecting expression driven by the promoters in the hybrids; (iv) comparing the expression level from the first promoter in relation to the expression level from the second promoter in the cell contacted with the blank substance with the expression level from the first promoter in relation to the expression level from the second promoter in the cell contacted with the substance to be tested for the ability to inhibit malignant cell growth. In an embodiment of the invention, the method is carried out along with a positive-control comprising (i) introducing said first and second hybrids into a suitable fungal cell; (ii) contacting the cell with a positive-control substance which is known to modulate expression from the promoters in the hybrids; (iii) detecting expression driven by the promoters in the hybrids; and (iv) comparing the expression level from the first promoter in relation to the expression level from the second promoter in the cell contacted with the positive-control substance with the expression level from the first promoter in relation to the expression level from the second promoter in the cell contacted with the substance to be tested for the ability to inhibit malignant cell growth.

DETAILED DESCRIPTION OF THE INVENTION

Each of the following isolated polynucleotides (with the exception SEQ ID NOs: 42-51), optionally fused to a reporter, are part of the present invention along with the various methods of use thereof which are described herein.

TABLE 1

Polynucleic acids of the invention.

| SEQUENCE | SEQUENCE IDENTIFIER |
|---|---|
| S.cerevisiae YOR387C Promoter | SEQ ID NO: 1 |
| S.cerevisiae YMR175W Promoter | SEQ ID NO: 2 |
| S.cerevisiae YFR026C Promoter | SEQ ID NO: 3 |
| S.cerevisiae YJL153C Promoter | SEQ ID NO: 4 |
| S.cerevisiae YPL033C Promoter | SEQ ID NO: 5 |
| S.cerevisiae YOL058W Promoter | SEQ ID NO: 6 |
| S.cerevisiae YOR255W Promoter | SEQ ID NO: 7 |
| S.cerevisiae YDR250C Promoter | SEQ ID NO: 8 |
| S.cerevisiae YDR446W Promoter | SEQ ID NO: 9 |
| S.cerevisiae YDR536W Promoter | SEQ ID NO: 10 |
| S.cerevisiae YOR255W Promoter | SEQ ID NO: 11 |
| S.cerevisiae YDL243C Promoter | SEQ ID NO: 12 |
| S.cerevisiae YDR256C Promoter | SEQ ID NO: 13 |
| S.cerevisiae YFL020C Promoter | SEQ ID NO: 14 |
| S.cerevisiae YPL205C Promoter | SEQ ID NO: 15 |
| S.cerevisiae YGL205W Promoter | SEQ ID NO: 16 |
| S.cerevisiae YGL117W Promoter | SEQ ID NO: 17 |
| S.cerevisiae YHR029C Promoter | SEQ ID NO: 18 |

TABLE 1-continued

Polynucleic acids of the invention.

| SEQUENCE | SEQUENCE IDENTIFIER |
|---|---|
| S.cerevisiae YML116W Promoter | SEQ ID NO: 19 |
| S.cerevisiae YJR109C Promoter | SEQ ID NO: 20 |
| S.cerevisiae YCL030C Promoter | SEQ ID NO: 21 |
| S.cerevisiae YLR338W Promoter | SEQ ID NO: 22 |
| S.cerevisiae YIL066W-A Promoter | SEQ ID NO: 23 |
| S.cerevisiae YNL093W Promoter | SEQ ID NO: 24 |
| S.cerevisiae YLR381W Promoter | SEQ ID NO: 25 |
| S.cerevisiae YKL159C Promoter | SEQ ID NO: 26 |
| S.cerevisiae YIL058W Promoter | SEQ ID NO: 27 |
| S.cerevisiae YKR037C Promoter | SEQ ID NO: 28 |
| S.cerevisiae YNL279W Promoter | SEQ ID NO: 29 |
| S.cerevisiae YOR032C Promoter | SEQ ID NO: 30 |
| S.cerevisiae YML058W Promoter | SEQ ID NO: 31 |
| S.cerevisiae YMR303C Promoter | SEQ ID NO: 32 |
| S.cerevisiae YJL153C Promoter | SEQ ID NO: 33 |
| S.cerevisiae YLR092W Promoter | SEQ ID NO: 34 |
| S.cerevisiae YFL052W Promoter | SEQ ID NO: 35 |
| S.cerevisiae YIR017C Promoter | SEQ ID NO: 36 |
| S.cerevisiae YLL062C Promoter | SEQ ID NO: 37 |
| S.cerevisiae YMR323W Promoter | SEQ ID NO: 38 |
| S.cerevisiae YPL171C Promoter | SEQ ID NO: 39 |
| S.cerevisiae YER065C Promoter | SEQ ID NO: 40 |
| S.cerevisiae YDR114C Promoter | SEQ ID NO: 41 |
| S.cerevisiae ADE2 | SEQ ID NO: 42 |
| S.cerevisiae LYS2 | SEQ ID NO: 43 |
| S.cerevisiae TRP1 | SEQ ID NO: 44 |
| S.cerevisiae LEU2 | SEQ ID NO: 45 |
| S.cerevisiae URA3 | SEQ ID NO: 46 |
| S.cerevisiae HIS3 | SEQ ID NO: 47 |
| Aequorea victoria GFP mutant 3 | SEQ ID NO: 48 |
| Renilla luciferase | SEQ ID NO: 49 |
| Photinus pyralis luciferase | SEQ ID NO: 50 |
| E.coli lacZ | SEQ ID NO: 51 |
| S.cerevisiae YHR082C Promoter | SEQ ID NO: 52 |
| S.cerevisiae YDL126C Promoter | SEQ ID NO: 53 |
| S.cerevisiae YBR106W Promoter | SEQ ID NO: 54 |
| S.cerevisiae YLL043W Promoter | SEQ ID NO: 55 |
| S.cerevisiae YPR108W Promoter | SEQ ID NO: 56 |
| S.cerevisiae YIL041W Promoter | SEQ ID NO: 57 |
| S.cerevisiae YJL166W Promoter | SEQ ID NO: 58 |
| S.cerevisiae YDR165W Promoter | SEQ ID NO: 59 |
| S.cerevisiae YLR330W Promoter | SEQ ID NO: 60 |
| S.cerevisiae YDL058W Promoter | SEQ ID NO: 61 |
| S.cerevisiae YHR012W Promoter | SEQ ID NO: 62 |
| S.cerevisiae YKL053W Promoter | SEQ ID NO: 63 |
| S.cerevisiae YKL196C Promoter | SEQ ID NO: 64 |
| S.cerevisiae YDL103C Promoter | SEQ ID NO: 65 |
| S.cerevisiae YLR427W Promoter | SEQ ID NO: 66 |
| S.cerevisiae YLL020C Promoter | SEQ ID NO: 67 |
| S.cerevisiae YBL065W Promoter | SEQ ID NO: 68 |
| PR131 Primer | SEQ ID NO: 69 |
| PR132 Primer | SEQ ID NO: 70 |
| PR161 Primer | SEQ ID NO: 71 |
| PR162 Primer | SEQ ID NO: 72 |
| PHO 5 signal sequence | SEQ ID NO: 73 |
| PR172 Primer | SEQ ID NO: 74 |
| PR173B Primer | SEQ ID NO: 75 |
| PR207 Primer | SEQ ID NO: 76 |
| PR208 Primer | SEQ ID NO: 77 |
| PR213 Primer | SEQ ID NO: 78 |
| PR214 Primer | SEQ ID NO: 79 |
| PR167 Primer | SEQ ID NO: 80 |
| PR168SLK Primer | SEQ ID NO: 81 |
| PHO5 signal sequence | SEQ ID NO: 82 |
| PR174 Primer | SEQ ID NO: 83 |
| PR175B Primer | SEQ ID NO: 84 |
| pSPRT47 plasmid sequence | SEQ ID NO: 85 |
| pSPRT50 plasmid sequence | SEQ ID NO: 86 |
| pSPRT190 plasmid sequence | SEQ ID NO: 87 |
| pSPRT192 plasmid sequence | SEQ ID NO: 88 |

Since the *Saccharmomyces cerevisiae* genome has been sequenced, the promoter sequences identified in Table 1 can also be found in publicly available databases including the *Saccharomyces* Genome Database; Stanford University, CA.

The term "fungal cell" or "fungal" or "fungus" includes, but is not limited to, any of the following organisms: *Absidia* corymbifera; Absidia spp; Acremonium spp; Ajellomyces capsulatus; Ajellomyces dermatitidis; Alternaria spp; Aphanoascus fulvescens; Apophysomyces spp; Arthroderma benhamiae; Arthroderma fulvum; Arthroderma gypseum; Arthroderma incurvatum; Arthroderma otae; Arthroderma vanbreuseghemii; Aspergillus flavus; Aspergillus fumigatus; Aspergillus glaucus; Aspergillus nidulans; Aspergillus niger; Aspergillus oryzae; Aspergillus spp; Aspergillus sydowi; Aspergillus terreus; Aspergillus ustus; Aspergillus versicolor; Aureobasidium pullulans; Basidiomycetes; Beauveria spp; Bipolaris hawaiiensis; Bipolaris spicifera; Bipolaris spp; Bjerkandera adusta; Blastomyces dermatitidis; Blastoschizomyces capitatus; Candida albicans; Candida beigelii; Candida colluculosa; Candida dubliniensis; Candida dubliniensis; Candida famata; Candida famata; Candida glabrata; Candida guilliermondii; Candida haemulonii; Candida holmui; Candida inconspicua; Candida intermedia; Candida keyfyr; Candida krusei; Candida krusei; Candida lambica; Candida lipolytica; Candida lusitaniae; Candida maris; Candida melibiosica; Candida norvegensis; Candida parapsilosis; Candida parapsilosis; Candida pelliculosa; Candida pelliculosa; Candida pseudotropicalis; Candida pulcherrima; Candida rugosa; Candida sake; Candida sphaerica; Candida spp; Candida stellatoidea; Candida tropicalis; Candida tropicalis; Candida viswanathii; Candida zeylanoides; Chrysosporium spp; Cladophialophora bantiana; Cladophialophora carrionii; Cladosporium spp; Coccidioides immitis; Cokeromyces recurvatus; Coprinus spp; Cryptococcus albidus; Cryptococcus gattii; Cryptococcus laurentii; Cryptococcus neoformans; Cunninghamella bertholletiae; Cunninghamella spp; Curvularia lunata; Curvularia spp; Dekkera bruxellensis; Epidermophyton floccosum; Epidermophyton floccosum; Exophiala dermatitidis; Exophiala jeanselmei; Exophiala moniliae; Exserohilum rostratum; Filobasidiella neoformans; Fonsecaea pedrosoi; Fusarium dimerum; Fusarium moniliforme; Fusarium oxysporum; Fusarium proliferatum; Fusarium solani; Fusarium spp; Geotrichum candidum; Geotrichum spp; Histoplasma capsulatum; Hortaea werneckii; Issatschenkia orientalis; Kluyveromyces lactis; Kluyveromyces marxianus; Madurella grisae; Malassezia furfur; Malassezia globosa; Malassezia obtusa; Malassezia pachydermatis; Malassezia restricta; Malassezia slooffiae; Malassezia sympodialis; Metarrhizium anisopliae; Microsporum audouinii; Microsporum canis; Microsporum fulvum; Microsporum gypseum; Microsporum persicolor; Mucor circinelloides; Mucor hiemalis; Mucor racemosus; Mucor rouxii; Mucor spp; Nattrassia mangiferae; Nectria haematococca; Onychocola canadensis; Paecilomyces lilacinus; Paecilomyces spp; Paecilomyces variotii; Paracoccidioides brasiliensis; Penicillium marneffei; Penicillium spp; Phialophora spp; Phialophora verrucosa; Phoma spp; Pichia anomala; Pichia etchellsii; Pichia guilliermondii; Pichia ohmeri; Pithomyces spp; Pneumocystis carinii; Pseudallescheria boydii; Ramichloridium obovoideum; Rhizomucor miehei; Rhizomucor pusillus; Rhizomucor spp; Rhizopus arrhizus; Rhizopus microsporus; Rhizopus oryzae; Rhizopus schipperae; Rhizopus spp; Rhodotorula mucilaginosa; Rhodotorula rubra; Rhodotorula spp; Saccharomyces cerevisiae; Saccharomyces spp; Sagrahamala spp; Saksenaea vasiformis; Scedosporium apiospermum; Scedosporium prolificans; Schizophyllum commune; Schizosaccharomyces pombe; Scopulariopsis brevicaulis; Scytalidium dimidiatum Ulocladium spp; Sporobolomyces spp; Sporothrix schenckii; Trichoderma spp; Trichophyton krajdenii; Trichophyton mentagrophytes; Trichophyton raubitschekii; Trichophyton rubrum; Trichophyton soudanense; Trichophyton spp; Trichophyton terrestre; Trichophyton tonsurans; Trichophyton verrucosum; Trichophyton violaceum; Trichosporon asahii; Trichosporon beigelii; Trichosporon capitatum; Trichosporon cutaneum; Trichosporon inkin; Trichosporon mucoides; Trichosporon spp; Tritirachium spp; Wangiella dermatitidis or Yarrowia lipolytica.

A substance "inhibits" growth of a cell (e.g., a fungal cell) if it reduces the ability of the cell to grow, to any degree (e.g., 10%, 25%, 50%, 75%, 90%, 99%, 100%), as compared to a similar cell's growth in the absence of the substance.

A promoter's expression level is "modulated" if it is increased or decreased to any degree.

Molecular Biology

In accordance with the present invention there may be employed conventional molecular biology, microbiology, and recombinant DNA techniques within the skill of the art. Such techniques are explained in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A "polynucleotide", "nucleic acid" or "nucleic acid molecule" includes the polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in single stranded form, double-stranded form or otherwise.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA, polypeptide, protein, or enzyme, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

As used herein, the term "oligonucleotide" refers to a nucleic acid, generally of no more than about 100 nucleotides (e.g., 30, 40, 50, 60, 70, 80, or 90), that may be hybridizable to a genomic DNA molecule, a cDNA molecule, or an mRNA molecule encoding a gene, mRNA, cDNA, or other nucleic acid of interest. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, preferably on a nucleic acid synthesizer.

A "protein sequence", "peptide sequence" or "polypeptide sequence" or "amino acid sequence" refers to a series of two or more amino acids in a protein, peptide or polypeptide.

"Protein", "peptide" or "polypeptide" includes a contiguous string of two or more amino acids.

The term "isolated polynucleotide" or "isolated polypeptide" includes a polynucleotide (e.g., RNA or DNA molecule, or a mixed polymer) or a polypeptide, respectively, which is partially or fully separated from other components that are normally found in cells or in recombinant DNA expression systems or any other contaminant. These components include, but are not limited to, cell membranes, cell walls, ribosomes, polymerases, serum components and extraneous genomic sequences.

An isolated polynucleotide or polypeptide will, preferably, be an essentially homogeneous composition of molecules but may contain some heterogeneity.

"Amplification" of DNA as used includes the use of polymerase chain reaction (PCR) to increase the concentration of a particular DNA sequence within a mixture of DNA sequences. For a description of PCR see Saiki, et al., Science (1988) 239:487.

The term "host cell" includes any cell of any organism that is selected, modified, transfected, transformed, grown, or used or manipulated in any way, for the production of a substance by the cell, for example the expression or replication, by the cell, of a gene, a DNA or RNA sequence or a protein. For example, a host cell may be a bacteria such as $E.$ $coli$. The scope of the present invention includes a host cell comprising any of the responsive promoters or baseline promoters described herein along with fusions comprising a responsive promoter or baseline promoter fused to a reporter (e.g., a reporter gene). Preferably, the promoter or the fusion is in a vector or is genetically integrated into a chromosome of the host cell. A host cell can be, for example, a $Saccharomyces$ $cerevisiae$ cell (e.g., strain MS1554 or strain WT1554).

The sequence of a nucleic acid may be sequenced by any method known in the art (e.g., chemical sequencing or enzymatic sequencing). "Chemical sequencing" of DNA may denote methods such as that of Maxam and Gilbert (Proc. Natl. Acad. Sci. USA (1977) 74:560), in which DNA is randomly cleaved using individual base-specific reactions. "Enzymatic sequencing" of DNA may denote methods such as that of Sanger (Sanger, et al., Proc. Natl. Acad. Sci. USA (1977) 74:5463).

Aside from the responsive promoters of the invention, nucleic acids of the invention can be flanked by other natural regulatory (expression control) sequences, which may be associated with heterologous sequences, including internal ribosome entry sites (IRES) and other ribosome binding site sequences, enhancers, response elements, suppressors, signal sequences, polyadenylation sequences, introns, 5'- and 3'-non-coding regions, and the like.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention.

A coding sequence (e.g., of a reporter) is "operably linked to", "under the control of", "functionally associated with" or "operably associated with" a transcriptional and translational control sequence (e.g., a responsive promoter) in a cell when the sequence directs RNA polymerase mediated transcription of the coding sequence into RNA, preferably mRNA, which then may be RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species.

The present invention includes vectors which comprise polynucleotides of the invention (e.g., SEQ ID NOs: 1-41 or 52-68 or a functional variant thereof). The term "vector" includes a vehicle (e.g., a plasmid) by which a DNA or RNA sequence can be introduced into a host cell, so as to transform the host and, optionally, promote expression and/or replication of the introduced sequence. In general, a plasmid is circular, includes an origin (e.g., 2 μm origin) and, preferably includes a selectable marker. In plasmids which can be maintained in yeast, the most commonly used yeast markers include URA3, HIS3, LEU2, TRP1 and LYS2, which complement specific auxotrophic mutations in a yeast host cell, such as ura3-52, his3-D1, leu2-D1, trpl-D1 and lys2-201, respectively. If the plasmid can be maintained in $E. coli$, it will include a bacterial origin (ori) and a selectable market such as the β-lactamase gene (bla or AMP$^r$). Commonly used yeast/$E. coli$ shuttle vectors are the Yip (see Myers et al., Gene 45: 299-310, (1986)), Yep (see Myers et al., Gene 45: 299-310, (1986)), YCp and YRp plasmids. The YIp integrative vectors do not replicate autonomously, but integrate into the genome at low frequencies by homologous recombination. The YEp yeast episomal plasmid vectors replicate autonomously because of the presence of a segment of the yeast 2 μm plasmid that serves as an origin of replication (2 μm ori). The 2 μm or is responsible for the high copy-number and high frequency of transformation of YEp vectors. The YCp yeast centromere plasmid vectors are autonomously replicating vectors containing centromere sequences, CEN, and autonomously replicating sequences, ARS. The YCp vectors are typically present at very low copy numbers, from 1 to 3 per cell. Autonomously replicating plasmids (YRp) which carry a yeast origin of replication (ARS sequence; but not centromere) that allows the transformed plasmids to be propagated several hundred-fold. YIp, YEp, YCp and YRp are commonly known in the art and widely available. Another acceptable yeast vector is a yeast artificial chromosome (YAC). A yeast artificial chromosome is a biological vector. It is an artificially constructed chromosome and contains the telomeric, centromeric, and replication origin sequences needed for replication in yeast cells (see Marchuk et al., Nucleic Acids Res. 16(15):7743 (1988); Rech et al., Nucleic Acids Res. 18(5):1313 (1990)).

Vectors that could be used in this invention include plasmids, viruses, bacteriophage, integratable DNA fragments, and other vehicles that may facilitate introduction of the nucleic acids into the genome of the host. Plasmids are the most commonly used form of vector but all other forms of vectors which serve a similar function and which are, or become, known in the art are suitable for use herein. See, e.g., Pouwels, et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass.

A polynucleotides may be expressed in an expression system. The term "expression system" means a host cell and compatible vector which, under suitable conditions, can express a protein or nucleic acid which is carried by the vector and introduced to the host cell. Common expression systems include *E. coli* host cells and plasmid vectors, insect host cells and Baculovirus vectors, and mammalian host cells and vectors.

The present invention also contemplates any superficial or slight modification to the responsive promoter and baseline promoter nucleotide sequences of the invention. For example, the present invention includes any "functional variant" of any responsive promoter of the present invention (e.g., SEQ ID NOs: 1-41 or 68) or of any baseline promoter of the present invention (e.g., SEQ ID NOs: 52-67). A functional variant of a promoter of the present invention includes any sequence variant that retains the ability to cause the expression of a downstream sequence (e.g., reporter such as SEQ ID NOs: 42-51) at any detectable level. Methods for determining whether a particular promoter sequence variant retains the ability to promoter expression of a down-stream sequence are conventional and well known in the art.

The present invention contemplates sequence conservative variants of the nucleic acids (e.g., SEQ ID NOs: 1-41 or 52-68). "Sequence-conservative variants" of a polynucleotide sequence (e.g., SEQ ID NOs: 1-41 or 52-68) are those in which a change of one or more nucleotides results in no significant alteration in the function of the promoter.

The present invention includes nucleic acids which hybridize to the responsive promoter and baseline promoter polynucleotides of the invention (e.g., SEQ ID NOs: 1-41 or 52-68). Preferably, the nucleic acids hybridize under low stringency conditions, more preferably under moderate stringency conditions and most preferably under high stringency conditions. A nucleic acid molecule is "hybridizable" to another nucleic acid molecule when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical low stringency hybridization conditions may be 55° C., 5×SSC, 0.1% SDS, 0.25% milk, and no formamide; or 30% formamide, 5×SSC, 0.5% SDS. Typical, moderate stringency hybridization conditions are similar to the low stringency conditions except the hybridization is carried out in 40% formamide, with 5× or 6×SSC. High stringency hybridization conditions are similar to low stringency conditions except the hybridization conditions are carried out in 50% formamide, 5× or 6×SSC and, optionally, at a higher temperature (e.g., 57 ° C., 59 ° C., 60° C, 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra, 11.7-11.8).

Also included in the present invention are polynucleotides comprising nucleotide sequences which are at least about 70% identical, preferably at least about 80% identical, more preferably at least about 90% identical and most preferably at least about 95% identical (e.g., 95%, 96%, 97%, 98%, 99%, 100%) to the reference responsive promoter and baseline promoter polynucleotides (e.g., SEQ ID NO: 1-41 and 52-68) when the comparison is performed by a BLAST algorithm wherein the parameters of the algorithm are selected to give the largest match between the respective sequences over the entire length of the respective reference sequences.

The following references regarding the BLAST algorithm are herein incorporated by reference: BLAST ALGORITHMS: Altschul, S. F., et al., J. Mol. Biol. (1990) 215:403-410; Gish, W., et al., Nature Genet. (1993) 3:266-272; Madden, T. L., et al., Meth. Enzymol. (1996) 266:131-141; Altschul, S. F., et al., Nucleic Acids Res. (1997) 25:3389-3402; Zhang, J., et al., Genome Res. (1997) 7:649-656; Wootton, J. C., et al., Comput. Chem. (1993) 17:149-163; Hancock, J. M., et al., Comput. Appl. Biosci. (1994) 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, DC; Schwartz, R. M., et al., "Matrices for detecting distant relationships." in *Atlas of Protein Sequence and Structure*, (1978) vol. 5, suppl. 3."M. O. Dayhoff (ed.), pp. 353-358, Natl. Biomed. Res. Found., Washington, DC; Altschul, S. F., J. Mol. Biol. (1991) 219:555-565; States, D. J., et al., Methods (1991) 3:66-70; Henikoff, S., et al., Proc. Natl. Acad. Sci. USA (1992)89:10915-10919; Altschul, S. F., et al., J. Mol. Evol. (1993) 36:290-300; ALIGNMENT STATISTICS: Karlin, S., et al., Proc. Natl. Acad. Sci. USA (1990) 87:2264-2268; Karlin, S., et al., Proc. Natl. Acad. Sci. USA (1993) 90:5873-5877; Dembo, A., et al., Ann. Prob. (1994) 22:2022-2039; and Altschul, S. F. " Evaluating the statistical significance of multiple distinct local alignments." in *Theoretical and Computational Methods in Genome Research* (S. Suhai, ed.), (1997) pp. 1-14, Plenum, New York.

Promoters and Screening Assays

The present invention provides several "gene responsive promoters", "responsive promoters" or "biomarkers" which have been identified in *S. cerevisiae* (e.g., SEQ ID NOs: 1-41 or 68). The expression from each responsive promoter has been correlated with the function of a particular gene which is essential in *S. cerevisiae*. Below, in table 2, each gene ("gene" column) whose temperature-sensitive allele was inactivated by shift to the restrictive temperature is correlated with a promoter ("RP" column) which was up-regulated in response to the shift along with the function of the gene. The responsive promoters of the present invention can be used to identify substances that modulate (increase or decrease) the function of an essential fungal gene, for example, in the assays described below. A substance which modulates (increases or decreases) the function of any of the essential genes mentioned herein is useful as an anti-fungal compound which can be used, inter alia, to treat or prevent fungal infections. For example, if the substance inhibits the activity of the essential gene's translated product, it will lead to the death, or decreased growth, of the host cell carrying the gene. Since fungi, such as *Saccharomyces cerevisiae*, *Aspergillus fumigatus*, *Aspergillus niger*, *Aspergillus flavus* and *Candida albicans*, are genetically related, a substance which modulates an essential gene in *S. cerevisiae* and kills the cell or inhibits its growth will be lethal to or inhibit the growth of all of the cell types. A substance which modulates the function of any of the essential genes mentioned herein is also useful to the treatment or prevention of cancer (e.g., by inhibition of the growth of a malignant cell).

Substances which inhibit fungal cell growth or malignant cell growth reduce it by any measurable degree. For example, a substance which inhibits fungal cell or malignant cell growth can kill the cell completely or reduce its level of growth by 10%. A substance which inhibits fungal cell growth can be "fungistatic" in that it inhibits growth of the cell to any measurable degree without killing the cell.

One embodiment of the present invention includes a screening assay wherein a biomarker of the present invention (e.g., SEQ ID NO: 1-41 or 68 or a functional variant thereof) is used to identify a substance which inhibits fungal cell growth (a modulator of an essential fungal gene) comprising the following steps:(a) introducing a hybrid comprising a responsive promoter (e.g., SEQ ID NO: 1-41 or 68 or a functional variant thereof) operably linked to a reporter (e.g., reporter gene such as SEQ ID NO: 42-51 or a functional variant thereof) into a suitable cell (e.g., a fugal cell); (b) contacting the cell with a substance to be tested for the ability to inhibit fungal cell growth; (c) detecting expression driven by the promoter in the hybrid; (d) selecting the substance if it modulates expression from the responsive promoter.

If the level of expression driven by the promoter is modulated (increased or decreased) in response to the substance, this indicates that the substance does modulate the activity of the essential gene and inhibits fungal cell growth.

In an embodiment of the invention, a negative-control screening assay is also carried out. In this embodiment, a fungal cell comprising the hybrid is contacted with the substance being tested and another, separate cell comprising the same hybrid is contacted with a blank (i.e., a substance known not to modulate the expression level from the promoter) such as DMSO, water or buffer. If the substance being tested increases or decreases the expression level from the promoter in relation to the expression level from the promoter/reporter in the cell contacted with the blank, this indicates that the substance does modulate the expression level from the responsive promoter, and, that it does modulate the activity of the essential fungal gene (i.e., the substance is an anti-fungal substance). A positive-control screening assay can also be performed. In the positive-control assay, a fungal cell comprising the hybrid is contacted with the substance being tested and another, separate cell comprising the same hybrid is contacted with a positive-control substance known to modulate the expression level from the promoter. If the substance being tested and the positive-control substance both increase or decrease the expression level from the promoter, this indicates that the substance being tested does modulate the expression level from the responsive promoter, and, that it does modulate the activity of the essential fungal gene (i.e., the substance inhibits fungal cell growth).

Another embodiment of the present invention includes a ratiometric screening assay wherein a responsive promoter of the present invention is used to identify a substance which inhibits fungal cell growth (a modulator of an essential fungal gene) comprising the following steps: (a) introducing, into a suitable cell, a first hybrid comprising a first (responsive) promoter selected from the group consisting of: *S. cerevisiae* YOR387C Promoter, *S. cerevisiae* YMR175W Promoter, *S. cerevisiae* YFR026C Promoter, *S. cerevisiae* YJL153C Promoter, *S. cerevisiae* YPL033C Promoter, *S. cerevisiae* YOL058W Promoter, *S. cerevisiae* YOR255W Promoter, *S. cerevisiae* YDR250C Promoter, *S. cerevisiae* YDR446W Promoter, *S. cerevisiae* YDR536W Promoter, *S. cerevisiae* YOR255W Promoter, *S. cerevisiae* YDL243C Promoter *S. cerevisiae* YDR256C Promoter, *S. cerevisiae* YFL020C Promoter, *S. cerevisiae* YPL205C Promoter, *S. cerevisiae* YGL205W Promoter, *S. cerevisiae* YGL117W Promoter, *S. cerevisiae* YHR029C Promoter, *S. cerevisiae* YML116W Promoter *S. cerevisiae* YJR109C Promoter, *S. cerevisiae* YCL030C Promoter, *S. cerevisiae* YLR338W Promoter, *S. cerevisiae* YIL066W-A Promoter, *S. cerevisiae* YNL093W Promoter, *S. cerevisiae* YLR381W Promoter, *S. cerevisiae* YKL159C Promoter, *S. cerevisiae* YIL058W Promoter, *S. cerevisiae* YKR037C Promoter, *S. cerevisiae* YNL279W Promoter, *S. cerevisiae* YOR032C Promoter, *S. cerevisiae* YML058W Promoter, *S. cerevisiae* YMR303C Promoter, *S. cerevisiae* YJL 1 53C Promoter *S. cerevisiae* YLR092W Promoter, *S. cerevisiae* YFL052W Promoter, *S. cerevisiae* YIR017C Promoter, *S. cerevisiae* YLL062C Promoter, *S. cerevisiae* YMR323W Promoter *S. cerevisiae* YPL171 C Promoter, *S. cerevisiae* YER065C Promoter and *S. cerevisiae* YDR114C Promoter (e.g., SEQ ID NO: 1-41 or 68 or a functional variant thereof); operably linked to a first reporter (e.g., SEQ ID NO: 42-51 or a functional variant thereof); and a second hybrid comprising a second (baseline) promoter selected from the group consisting of: *S. cerevisiae* YHR082C Promoter, *S. cerevisiae* YDL126C Promoter *S. cerevisiae* YBR106W Promoter, *S. cerevisiae* YLL043W Promoter, *S. cerevisiae* YPR108W Promoter, *S. cerevisiae* YIL041W Promoter, *S. cerevisiae* YJL166W Promoter *S. cerevisiae* YDR165W Promoter, *S. cerevisiae* YLR330W Promoter, *S. cerevisiae* YDL058W Promoter, *S. cerevisiae* YHR012W Promoter, *S. cerevisiae* YKL053W Promoter, *S. cerevisiae* YKL196C Promoter, *S. cerevisiae* YDL103C Promoter *S. cerevisiae* YLR427W Promoter and *S. cerevisiae* YLL020C Promoter (e.g., SEQ ID NO: 52-67 or a functional variant thereof); operably linked to a second reporter (e.g., SEQ ID NO: 42-51 or a functional variant thereof); (b) contacting the cell with a substance to be tested for the ability to inhibit fungal cell growth; (c) detecting expression driven by the first and second promoters; and (d) selecting the substance if it causes the first (gene responsive) promoter expression level to increase or decrease in relation to the expression level from the second (baseline) promoter.

In the ratiometric assay, a responsive promoter expression level that does not increase or decrease in relation to the expression level from the baseline promoter, in response to contacting the cell with the substance being tested for anti-fungal activity, indicates that the substance does not modulate the expression level from the responsive promoter, and, that it does not modulate the activity of the essential fungal gene. A responsive promoter expression level that increases or decreases in relation to the expression level from the baseline promoter, in response to contacting the cell with the substance being tested for anti-fungal activity, indicates that the substance does modulate the expression level from the responsive promoter, and, that it does modulate the activity of the essential fungal gene (i.e., it inhibits fungal growth).

In an embodiment of the invention, a negative-control ratiometric screening assay is also carried out. In this embodiment, a cell comprising the first and second hybrid is contacted with the substance being tested and another, separate cell comprising the first and second hybrid is contacted with a blank (i.e., a substance known not to modulate the expression level from the first or second promoters) such as DMSO, water or buffer. If the substance being tested increases or decreases the expression level from the first promoter in relation to the expression level from the second promoter and if the blank fails to increase or decrease the expression level from the first promoter in relation to the second promoter expression level, this indicates that the substance does modulate the expression level from the responsive promoter, and, that it does modulate the activity of the essential fungal gene (i.e., the substance is an anti-fungal substance). A positive-control ratiometric screening assay may also be performed. In the positive-control assay, a cell comprising the first and second hybrid is contacted with the substance being tested and another, separate cell comprising the first and second hybrid is contacted with a positive-control substance known to modulate the expression level from the first promoter in relation to the expression level from the second promoter. If the substance being tested and the positive-control substance both modulate the expression level from the first promoter in relation to the expression level from the second promoter, this indicates that the substance being tested does modulate the expression level from the responsive promoter/reporter, and, that it does modulate the activity of the essential fungal gene (i.e., the substance inhibits fungal cell growth).

Up-regulation or down regulation of a given responsive promoter, and identification of a substance which inhibits fungal cell growth, can be assayed using an array. For example, a cell comprising a responsive promoter/reporter hybrid or baseline promoter/reporter hybrid can be contacted with a substance to be tested for the ability inhibit fungal cell growth (to modulate an essential fungal gene). Promoter expression can then be assayed using conventional microarray assay techniques.

In one embodiment of the invention, a substance is determined to inhibit fungal cell growth (modulate the activity of an essential fungal gene) in a method as follows: (1) contacting a suitable fungal cell (e.g., an S. cerevisiae cell) with a substance to be tested for the ability to inhibit fungal cell growth (modulate an essential fungal gene) wherein said cell comprises one or more biomarkers operably linked to one or more reporter (e.g., the open reading frame which is located downstream of each biomarker promoter in a wild-type cell); (2) obtaining mRNA from the cell; (3) preparing labeled polynucleotides from the mRNA (e.g., comprising a radiolabel (e.g., $^{32}P$, $^{35}S$, $^{14}C$, $^{3}H$) or another suitable detectable label); (4) contacting the labeled polynucleotide with an array, which comprises one or more polynucleotides encoding said reporters (or oligonucleotide fragments thereof), under conditions sufficient for labeled mRNA to bind with corresponding polynucleotide probes on the array; (5) optionally removing unbound, labeled mRNA from the array; and (6) detecting bound, labeled mRNA.

The polynucleotide, in the array, can comprise a fragment of the reporter polynucleotide, for example 10, 20, 30 or more nucleotides thereof.

A "nucleic acid array", "array" or "matrix" refers to an array, including a microarray (see infra), containing nucleic acid probes, such as oligonucleotides or larger portions of genes. The nucleic acid on the array is preferably single stranded. Arrays wherein the probes are oligonucleotides are referred to as "oligonucleotide arrays" or "oligonucleotide chips." A "microarray", "biochip" or "biological chip" is an array of regions having a density of discrete regions of at least about $100/cm^2$, and preferably at least about $1000/cm^2$. The regions in a microarray have typical dimensions, e.g., diameters, in the range of between about 10-250 μm, and are separated from other regions in the array by about the same distance.

The scope of the present invention includes an array (e.g., a microarray; discussed above) comprising one or more of said reporters (discussed above) which are operably linked to one or more of said biomarkers (discussed above).

Baseline promoters of the invention (e.g., SEQ ID NOs: 52-67 or a functional variant thereof) can also be used in assays for determining if a substance inhibits fungal cell growth and to calculate the inhibitory concentration (IC; e.g., IC50 or IC90) of a particular substance. Since baseline promoters generally exhibit a constant level of expression, they provide a convenient marker for overall cellular growth or cellular mass. Generally, baseline promoters can be used to determine the IC (e.g., IC50 or IC90) of a given substance in a method including the following steps: (a) introducing a hybrid comprising a baseline promoter selected from the group consisting of: S. cerevisiae YHR082C Promoter, S. cerevisiae YDL126C Promoter S. cerevisiae YBR106W Promoter, S. cerevisiae YLL043W Promoter, S. cerevisiae YPR108W Promoter, S. cerevisiae YIL04 1W Promoter, S. cerevisiae YJL166W Promoter S. cerevisiae YDR 165W Promoter, S. cerevisiae YLR330W Promoter, S. cerevisiae YDL058W Promoter, S. cerevisiae YHR012W Promoter, S. cerevisiae YKL053W Promoter, S. cerevisiae YKL196C Promoter, S. cerevisiae YDL103C Promoter S. cerevisiae YLR427W Promoter and S. cerevisiae YLL020C Promoter (e.g., SEQ ID NO: 52-67 or a functional variant thereof); operably linked to a reporter (e.g., SEQ ID NO: 42-51 or a functional variant thereof) into a suitable fungal cell; (b) contacting the cell with a substance to be tested for the ability to inhibit growth of the cell; (c) detecting signal from the reporter; and (d) selecting the substance if it causes a reduction in the signal from the reporter and/or calculating the IC (e.g., IC50 or IC90).

Optionally, this method can be performed with two or more different baseline promoter/reporter fusions (e.g., in a ratiometric assay discussed below). The IC (e.g., IC50 or IC90) can then be determined two or more times when each separate reporter is measured.

In an embodiment of the invention, a negative-control screening assay is also carried out. In this embodiment, a cell comprising the hybrid is contacted with the substance being tested and another, separate cell comprising the same hybrid is contacted with a blank (i.e., a substance known not to modulate the expression level from the first or second promoters) such as DMSO, water or buffer. If the substance being tested decreases the reporter signal in relation to the signal from the reporter in the cell contacted with the blank, this indicates that the substance is an anti-fungal substance. A positive-control screening assay may also be performed. In the positive-control assay, a cell comprising the hybrid is contacted with the substance being tested and another, separate cell comprising the same hybrid is contacted with a positive-control substance known to modulate the reporter signal (e.g., a known anti-fungal substance such as fluconazole, itraconazole, moconazole or terbinafine). If the substance being tested and the positive-control substance both decrease the reporter signal, this indicates that the substance being tested is an anti-fungal substance.

Baseline promoters of the invention (e.g., SEQ ID NOs: 52-67 or a functional variant thereof) can also be used in ratiometric assays, comprising two or more baseline promoters operably linked to two or more different reporters, for determining if a substance inhibits fungal cell growth and to calculate the inhibitory concentration (IC; e.g., IC50 or IC90) of a particular substance. For example, a ratiometric assay comprising use of a baseline promoter will comprise the steps of: (a) introducing two or more hybrids comprising two or more different baseline promoters selected from the group consisting of: *S. cerevisiae* YHR082C Promoter, *S. cerevisiae* YDL126C Promoter *S. cerevisiae* YBR106W Promoter, *S. cerevisiae* YLL043W Promoter, *S. cerevisiae* YPR108W Promoter, *S. cerevisiae* YIL041W Promoter, *S. cerevisiae* YJL166W Promoter *S. cerevisiae* YDR165W Promoter, *S. cerevisiae* YLR330W Promoter, *S. cerevisiae* YDL058W Promoter, *S. cerevisiae* YHR012W Promoter, *S. cerevisiae* YKL053W Promoter, *S. cerevisiae* YKL196C Promoter, *S. cerevisiae* YDL103C Promoter *S. cerevisiae* YLR427W Promoter and *S. cerevisiae* YLL020C Promoter (e.g., SEQ ID NO: 52-67 or a functional variant thereof); operably linked to two or more different reporters (e.g., SEQ ID NO: 42-51 or a functional variant thereof) into a suitable fungal cell; (b) contacting the cell with a substance to be tested for the ability to inhibit growth of the cell; (c) detecting signal from the reporter; and (d) selecting the substance if it causes a reduction in the signal from the reporter and/or calculating the IC (e.g., IC50 or IC90). A range of several concentrations of a given substance can be assayed using this ratiometric method.

Ideally, the extent to which the reporter signal decreases, in response to any given concentration of a substance which is found to inhibit fungal cell growth, will be proportional (e.g., as compared to the promoter's expression level in the absence of any substance) to the extent to which the other reporter signals decrease in response to the same concentration of substance.

In an embodiment of the invention, a negative-control ratiometric screening assay is also carried out. In this embodiment, a cell comprising the first and second hybrid is contacted with the substance being tested and another, separate cell comprising the first and second hybrid is contacted with a blank (i.e., a substance known not to modulate the expression level from the first or second promoters) such as DMSO, water or buffer. If the substance being tested decreases the signal from the first and second reporters and if the blank fails to decrease the signal from the first and second reporters, this indicates that the substance is an anti-fungal substance. A positive-control ratiometric screening assay may also be performed. In the positive-control assay, a cell comprising the first and second hybrid is contacted with the substance being tested and another, separate cell comprising the first and second hybrid is contacted with a positive-control substance known to inhibit fungal growth (e.g., a known anti-fungal substance such as fluconazole, itraconazole, moconazole or terbinafine). If the substance being tested and the positive-control substance both decrease the signal from the first and second reporters, this indicates that the substance being tested is an anti-fungal substance.

Using two or more baseline promoters is advantageous because it facilitates elimination of false positives. For example, a false positive signal, suggesting that a substance being tested inhibits fungal cell growth, would occur if the substance causes a reduction in expression from the baseline promoter without inhibiting fungal cell growth. It is unlikely that the substance would have the ability to reduce baseline promoter expression, without reducing fungal cell growth (i.e., a false positive signal), with respect to two different baseline promoters.

The term "inhibitory concentration" or "IC" refers to the minimum concentration at which the substance being tested can inhibit the growth of the organism being tested. The term includes all inhibitory concentrations, for example, IC90 which is the inhibitor concentration needed to inhibit growth of 90% of the cells being tested and IC50 which is the inhibitor concentration needed to inhibit growth of 50% of the cells being tested. In an embodiment of the invention, a substance being tested for anti-fungal or anti-malignant cell growth activity is selected if it has a relatively low IC50 or IC90.

The present invention also includes compositions comprising any one of the isolated responsive promoters (e.g., SEQ ID NOs: 1-41 or 68 or a functional variant thereof) or baseline promoters identified herein (e.g., SEQ ID NOs: 52-67 or a functional variant thereof). Also included in the present invention is any of the isolated responsive promoters or baseline promoters identified herein fused to a reporter (e.g., a reporter gene including, but not limited to SEQ ID NOs: 42-51 or a functional variant thereof).

A responsive promoter/reporter gene hybrid and/or baseline promoter/reporter gene hybrid can be sustained in a host cell, in which a screening assay of the invention is performed, by any acceptable method known in the art. For example, the hybrid can be genetically integrated into the chromosome of the host cell or it can be maintained episomally, for example, in a plasmid (discussed above) or yeast artificial chromosome (YAC; discussed above) or other vector. In *S. cerevisiae* cells, for example, a hybrid can easily be integrated into the HO locus. Methods for constructing plasmids and vectors and for integrating a polynucleotide into a host cell chromosome are conventional and very well known in the art.

In another embodiment of the invention, anti-cancer agents can be identified using a responsive promoter of the invention. In particular, anti-cancer agents for treatment or prevention of cancer (e.g., by inhibiting growth of a malignant cell) in a mammal, preferably a human can be identified using a responsive promoter of the invention. For example, the *S. cerevisiae* YLR338W (SEQ ID NO: 22), *S. cerevisiae* YIL066W (SEQ ID NO: 23), *S. cerevisiae* YNL093W (SEQ ID NO: 24), *S. cerevisiae* YDR250C (SEQ ID NO: 8), *S. cerevisiae* YLR381W (SEQ ID NO: 25), *S. cerevisiae* YBL065W (SEQ ID NO: 68), *S. cerevisiae* YMR323W (SEQ ID NO: 38) and *S. cerevisiae* YPL171C (SEQ ID NO: 39) responsive promoters are particularly useful for identification of anti-cancer agents. These promoters have been found to modulate when genes in *S. cerevisiae* biochemical pathways and functions, that are homologous to human biochemical pathways and functions found to modulate the development of cancer (e.g., the mitotic cluster, including nucleocytoplasmic transport RAS, mitotic spindle, telomerase maintenance, DNA damage and G1 cell cycle control, establishment of cell polarity, exocyst complex and acetyltransferases). For example, the scope of the invention includes methods for identifying whether a substance can treat or prevent cancer in a mammal (e.g., by inhibiting growth of a malignant cell) comprising the following steps: (a) introducing a hybrid comprising a responsive promoter selected from the group consisting of *S. cerevisiae* YLR338W (SEQ ID NO: 22), *S. cerevisiae* YIL066W (SEQ ID NO: 23), *S. cerevisiae* YNL093W (SEQ ID NO: 24), *S. cerevisiae* YDR250C (SEQ ID NO: 8), *S. cerevisiae* YLR381W (SEQ ID NO: 25), *S. cerevisiae* YBL065W (SEQ ID NO: 68), *S. cerevisiae*

YMR323W (SEQ ID NO: 38) and *S. cerevisiae* YPL171C (SEQ ID NO: 39) operably linked to a reporter (e.g., reporter gene such as SEQ ID NO: 42-51 or a functional variant thereof) into a suitable cell (e.g., a fugal cell); (b) contacting the cell with a substance to be tested for the ability to inhibit or prevent cancer; (c) detecting expression driven by the responsive promoter in the hybrid; (d) selecting the substance if it modulates expression from the responsive promoter.

The present invention also includes a ratiometric screening assay wherein a responsive promoter of the present invention is used to identify a substance that can treat or prevent cancer in a mammal (e.g., by inhibiting growth of a malignant cell) comprising the following steps: (a) introducing, into a suitable fungal cell, a first hybrid comprising a first (gene responsive) promoter selected from the group consisting of: *S. cerevisiae* YLR338W (SEQ ID NO: 22), *S. cerevisiae* YIL066W (SEQ ID NO: 23), *S. cerevisiae* YNL093W (SEQ ID NO: 24), *S. cerevisiae* YDR250C (SEQ ID NO: 8), *S. cerevisiae* YLR381W (SEQ ID NO: 25), *S. cerevisiae* YBL065W (SEQ ID NO: 68), *S. cerevisiae* YMR323W (SEQ ID NO: 38) and *S. cerevisiae* YPL171C (SEQ ID NO: 39); operably linked to a first reporter (e.g., SEQ ID NO: 42-51 or a functional variant thereof); and a second hybrid comprising a second (baseline promoter) selected from the group consisting of: *S. cerevisiae* YHR082C Promoter, *S. cerevisiae* YDL126C Promoter *S. cerevisiae* YBR106W Promoter, *S. cerevisiae* YLL043W Promoter, *S. cerevisiae* YPR108W Promoter, *S. cerevisiae* YIL041W Promoter, *S. cerevisiae* YJL166W Promoter *S. cerevisiae* YDR165W Promoter, *S. cerevisiae* YLR330W Promoter, *S. cerevisiae* YDL058W Promoter, *S. cerevisiae* YHR012W Promoter, *S. cerevisiae* YKL053W Promoter, *S. cerevisiae* YKL196C Promoter, *S. cerevisiae* YDL103C Promoter *S. cerevisiae* YLR427W Promoter and *S. cerevisiae* YLL020C Promoter (e.g., SEQ ID NO: 52-67 or a functional variant thereof); operably linked to a second reporter (e.g., SEQ ID NO: 42-51 or a functional variant thereof); (b) contacting the cell with a substance to be tested for the ability to treat or prevent cancer; (c) detecting expression driven by the first and second promoters; and (d) selecting the substance if it causes the expression level from the first (gene responsive) promoter to increase or decrease in relation to the expression level from the second (baseline) promoter.

In an embodiment of the invention, a negative-control ratiometric screening assay is also carried out. In this embodiment, a cell comprising the first and second hybrid is contacted with the substance being tested and another, separate cell comprising the first and second hybrid is contacted with a blank (i.e., a substance known not to modulate the expression level from the first or second promoters) such as DMSO, water or buffer. If the substance being tested increases or decreases the expression level from the first promoter/reporter in relation to the second promoter/reporter and if the blank fails to increase or decrease the expression level from the first promoter/reporter in relation to the second promoter/reporter, this indicates that the substance does modulate the expression level from the responsive promoter, and, that it does modulate the activity of the fungal gene (i.e., the substance is an anti-cancer substance). A positive-control ratiometric screening assay may also be performed. In the positive-control assay, a cell comprising the first and second hybrid is contacted with the substance being tested and another, separate cell comprising the first and second hybrid is contacted with a positive-control substance known to modulate the expression level from the first promoter/reporter in relation to the expression level from the second promoter/reporter. If the substance being tested and the positive-control substance both modulate the expression level from the first promoter/reporter in relation to the expression level from the second promoter/reporter, this indicates that the substance being tested does modulates the expression level from the responsive promoter/reporter, and, that it does modulate the activity of the essential fungal gene (i.e., the substance is an anti-cancer substance).

Reporters

One embodiment of the invention includes a responsive promoter of the invention (e.g., SEQ ID NOs: 1-41 or 68 or a functional variant thereof) or baseline promoter of the invention (e.g., SEQ ID NOs: 52-67 or a functional variant thereof) fused to a reporter. Any suitable reporter may be fused to the responsive promoter or baseline promoter. A "reporter" is any polynucleic acid which can be detected when expressed from a promoter. The term includes reporter genes whose activity can be detected as well as polynucleic acids which can be detected directly, for example, by northern blot analysis. Alternatively, the translated protein product of the expressed polynucleic acid can be detected by western blot analysis. For example, the term "reporter" includes the genetic sequence which is down-stream of a given responsive promoter on a wild-type yeast chromosome. Reporters include luminescent and fluorescent reporter genes including, but not limited to, green fluorescent protein (e.g., SEQ ID NO: 48), lacZ (e.g., SEQ ID NO: 51), *Renilla* luciferase (e.g., SEQ ID NO: 49; see also Genbank Accession Nos.: AF416990; AR149562; AF362548 or M63501) firefly (*Photinus pyralis*) luciferase (e.g., SEQ ID NO: 50; see also Genbank Accession Nos.: U03687; M15077 and X84846), *S. cerevisiae* ADE2 (e.g., SEQ ID NO: 42), *S. cerevisiae* LYS2 (e.g., SEQ ID NO: 43), *S. cerevisiae* TRP1 (e.g., SEQ ID NO: 44), *S. cerevisiae* LEU2 (e.g., SEQ ID NO: 45), *S. cerevisiae* URA3 (e.g., SEQ ID NO: 46) and *S. cerevisiae* HIS3 (e.g., SEQ ID NO: 47).

The term "signal", in relation to a reporter, refers to the indicia of expression of the reporter or the presence of the reporter's gene product (e.g., protein or mRNA) in a sample. For example, fluorescence is a signal that indicates the presence of green fluorescent protein (GFP) and a "band" on photographic film generated during a northern blot procedure is a signal indicating the presence of a gene's RNA transcript. In an embodiment of the invention, the expression driven from a given promoter fused to a given reporter is measured by determining the signal from the reporter.

Firefly luciferase may also be altered as described in Leskinen et al. (Yeast. 20(13):1109-1113 (2003)) wherein the carboxy-terminal peroxisomal targeting signal, Ser-Lys-Leu (slk), of the firefly luciferase gene was removed; this allowed luciferase activity to be detected in whole *S. cerevisiae* cells.

Other versions of luciferase which may be fused to a responsive promoter of the invention (e.g., SEQ ID NOs: 1-41, 52-68 or a functional variant thereof) include the *Vibrio harveyi* luxA (Genbank Accession No. M10961) and *Vibrio harveyi* luxB (Genbank Accession No. M 10961. 1) genes, together, unfused or fused (i. e., luxAB or luxBA), *Vibrio harveyi* luxC, *Vibrio harveyi* luxD, *Vibrio harveyi* luxE, *Vibrio harveyi* luxCDABE, the *Photorhabdus luminescens* LuxCDABE operon (Genbank Accession No. M62917), *Photorhabdus luminescens* LuxA, *Photorhabdus luminescens* LuxB, *Photorhabdus luminescens* LuxC, *Photorhabdus luminescens* LuxD, *Photorhabdus luminescens* LuxE, optionally expressed in the presence of the *Vibrio fischeri* flavin oxidoreductase gene (frp; see Gupta et al., FEMS Yeast Res. 4(3):305-13 (2003)); *Vibrio fischeri* luxAB (see, e.g., Yang et al., FEMS Microb. Lett. 176(1): 57-65(1999)), the *Vibrio fischeri* LuxCDABE operon (see e.g., Van Dyk et al., Appl. Environ. Microbiol. 60:1414-1420 (1994); Belkin et al., Appl. Environ. Microbiol. 62:2252-2256 (1996); Belkin et al., Water Res. 31:3009-3016 (1997); Genbank Accession No. AF170104); *Vibrio fischeri* luxA, *Vibrio fischeri* luxB, *Vibrio fischeri* luxC, *Vibrio fischeri* luxD or *Vibrio fischeri* luxE. Furthermore, a responsive promoter or baseline promoter of the invention (e.g., SEQ ID NOs: 1-41 or 68 or a functional variant thereof) can be fused to a green fluorescent protein (GFP)-luxAB hybrid gene.

The $Ca^{2+}$ dependent photoprotein Aequorin from *Aequorea victoria* (Campbell, K., *Chemilluminescence*; Ellis Horwood: Chichester, England (1988); Ramanathan et al., Anal. Chim. Acta 369: 181-188 (1998); Witkowski et al., Anal. Chem. 66: 1837-1840 (1994); Galvan et al., Anal. Chem. 68:3545-3550 (1996)) can also be fused to a responsive promoter or baseline promoter of the invention (e.g., SEQ ID NOs: 1-41, 52-68 or a functional variant thereof).

The KanMX selectable marker (e.g., from Tn9O3) can also be fused to a responsive promoter or baseline promoter of the invention (e.g., SEQ ID NOs: 1-41, 52-68 or a functional variant thereof). Expression of the KanMX marker, in a cell, confers resistance to G418 (geniticin; Wach et al., Yeast 10:1793-1808 (1994)).

The pat1 (phosphinothricin N-acetyl-transferase) selectable marker can also be fused to a responsive promoter or baseline promoter of the invention (e.g., SEQ ID NOs: 1-41, 52-68 or a functional variant thereof; Goldstein & McCusker, Yeast 15:1541-1553 (1999)). Expression of the pat1 marker, in a cell, confers resistance to bialaphos.

The nat1 (nourseothricin N-acetyl-transferase) selectable marker can also be fused to a responsive promoter or baseline promoter of the invention (e.g., SEQ ID NOs: 1-41, 52-68 or a functional variant thereof, Goldstein & McCusker, Yeast 15:1541-1553 (1999)). Expression of the nat1 marker, in a cell, confers resistance to nourseothricin.

The hph (hygromycin B phosphotransferase) selectable marker can also be fused to a responsive promoter or baseline promoter of the invention (e.g., SEQ ID NOs: 1-41, 52-68 or a functional variant thereof; Goldstein & McCusker, Yeast 15:1541-1553 (1999)). Expression of the nat1 marker, in a cell, confers resistance to hygromycin B.

The Sh ble selectable marker can also be fused to a responsive promoter or baseline promoter of the invention (e.g., SEQ ID NOs: 1-41, 52-68 or a functional variant thereof). Expression of the Sh ble marker, in a cell, confers resistance to Zeocin™ (Phleomycin D1; Johansson & Hahn-Hagerdal, Yeast 19: 225-231 (2002)).

Other reporter genes which may be fused to a responsive promoter or baseline promoter of the invention (e.g., SEQ ID NOs: 1-41, 52-68 or a functional variant thereof) include β-lactamase, for example, as described in Cartwright et al. (Yeast 10(4):497-508 (1994)) wherein mature β-lactamase was fused to two segments of the K1 preprotoxin.

Furthermore, the *E. coli* β-glucuronidase gene (GUS) can be fused to a responsive promoter or baseline promoter of the invention (e.g., SEQ ID NOs: 1-41, 52-68 or a functional variant thereof) and used as a reporter gene, for example, in *S. cerevisiae* (Marathe et al., Gene. 154(1):105-107 (1995)).

Chloramphenicol acetyltransferase (CAT) can be fused to a responsive promoter or baseline promoter of the invention (e.g., SEQ ID NOs: 1-41, 52-68 or a functional variant thereof). CAT radioassays are described, for example, by Sleigh (Anal. Biochem. 156(1):251-256 (1986)) and a non-radioactive CAT assay is described by Young et al. (Anal. Biochem. 197(2):401-407 (1991)).

Construction of responsive promoter/reporter fusions and baseline promoter/reporter fusions can be accomplished using conventional molecular biological techniques which are commonly known in the art. For example, Myers et al. (Gene. 1986;45(3):299-3 10) disclose methods for fusing various promoters for driving the expression of the *E. coli* lacZ gene.

Expression of reporters, such as green fluorescent protein, luciferase or β-galactosidase (lacZ) or any other reporter mentioned herein, can be easily determined using any of the numerous assays which are conventional and very well known in the art. For example, Billinton et al. (Biosens. Bioelectron. 13(7-8): 831-8) describe the development of a green fluorescent protein reporter in yeast. Dixon et al. (J. Steroid Biochem. Mol. Biol. 62(2-3): 165-71) describe an assay for determination of lacZ expression in yeast. El Barkani et al. (Gene 246(1-2): 151-155 (2000)) describe *Candida glabrata* shuttle vectors suitable for translational fusions to lacZ and use of β-galactosidase as a reporter of gene expression." Greer et al. (Luminescence 17(1): 43-74 (2002)) reviews the use of luciferase in expression assays. Leskinen et al. (Yeast 20(13): 1109-13 (2003)) describes a one-step measurement of firefly luciferase activity in yeast. Marathe et al. (Gene 154(1): 105-7 (1995)) and Gallagher et al. ("Quantiation of GUS activity by fluorometry" In: *GUS Protocols: Using GUS gene as a reporter of gene expression*. Academic Press, San Diego, Calif. (1992), pp.47-59) discloses methods for assaying GUS reporter gene expression. Pignatelli et al. (Biotechnol. Appl. Biochem. 27(Pt 2): 81-88 (1998)) describe the expression and secretion of β-galactosidase in *Saccharomyces cerevisiae* using the signal sequences of GgpI. Srikantha et al. (J Bacteriol 178(1): 121-9 (1996)) describes the use of *Renilla reniformis* luciferase as a reporter gene in *Candida albicans*. Vanoni et al. (Biochem Biophys Res Commun 164(3): 1331-8 (1989)) describes the use of *E. coli* β-galactosidase in *Saccharomyces cerevisiae* using the signal sequence from the glucoamylase-encoding STA2 gene.

Alternatively, there are several auxotrophic reporters which may be fused to a responsive promoter or baseline promoter of the invention (e.g., SEQ ID NOs: 1-41, 52-68 or a functional variant thereof). For example, ADE2, URA3, HIS3, LYS2, TRP1 or LEU2 can be fused to the responsive promoter and introduced into a cell lacking an endogenous copy of the gene (e.g., comprising a ura3-52, his3-D1, leu2-D1, trpl-D1 or lys2-201 mutation). In general activation of auxotrophic reporter genes can be determined, in a cell lacking an endogenous copy of the auxotrophic marker, by growing the cell on media lacking the nutrient whose cellular synthesis is dependent on the auxotrophic reporter gene. In this case, lack of expression of the auxotrophic marker (e.g., because of lack of activation of the responsive promoter-auxotrophic marker hybrid) will result in no growth; expression of the auxotrophic marker (e.g., because of activation of the responsive promoter-auxotrophic marker hybrid) will result in growth. For example, activation of the markers ADE2, URA3, HIS3, LYS2, TRP1 or LEU2 can be assayed on media lacking adenine, uracil, histidine, lysine, tryptophan or leucine, respectively. In another embodiment, expression of ADE2 can be conveniently determined by observing the color of *S. cerevisiae* colonies containing the responsive promoter-ADE2 hybrid. Specifically, ade2⁻ *S. cerevisiae* cells and colonies exhibit a red color phenotype. Expression of ADE2 (e.g., because of activation of the responsive promoter-ADE2 hybrid), in such a cell, will result in the expression of a white color phenotype.

In an embodiment of the present invention, substances which lead to a decrease in the expression level from a responsive promoter of the invention can be negatively selected for.

For example, cell grown in the present of substance that decreases the expression from a responsive promoter/URA3 hybrid can be selected for by growth in the presence of 5-fluoroorotic acid (5-FOA). In other embodiments of the invention, cells in which responsive promoter/HIS3 hybrid expression is decreased, in response to a substance, can be selected for by growing the cells in the presence of 3-azatriazole. In yet another embodiment of the invention, cells in which responsive promoter/LYS2 hybrid expression is decreased, in response to a substance, can be selected for by growing the cells in the presence of DL-alpha-aminoadipic acid. In a further embodiment of the invention, cells in which responsive promoter/CYH2 hybrid expression is decreased, in response to a substance, can be selected for by growing the cells in the presence of cycloheximide. In another embodiment of the invention, cells in which responsive promoter/CAN1 hybrid expression is decreased, in response to a substance, can be selected for by growing the cells in the presence of canavinine.

Transformation and Growth of Fungal Cells

Heterologous nucleic acids can be introduced into host yeast cells by any of a number of known methods. These methods include, but are not limited to, spheroplast transformation (Beggs, Nature 275:104 (1975); Cregg et al., Mol. Cell. Biol. 5:3376 (1985)), lithium transformation (Hiep et al., Yeast 9:1189-1197 (1993); Bogdanova et al., Yeast 11:343 (1995)), polyethylene glycol transformation (Kleve et al., Gene 25:333-341 (1983); Dohmen et al., Yeast 7:691-692 (1991); Dohmen et al., Yeast 7:691-692 (1991)), or electroporation.

Yeast can be grown on rich media or synthetic dropout media. Drop-out media is synthetic media containing all essential nutrients except for one or more. Drop-out media is commonly used for selection of plasmids that contain genes for synthesis of these components. For example, drop-out media lacking histidine can be used to select for his3⁻ host cells containing a plasmid carrying a complementing HIS3 gene. A similar method can be employed for selecting for fungal cells carrying a plasmid containing the ADE2, URA3, LYS2, TRP1 or LEU2 gene, or any combination thereof. For example, one liter of synthetic complete media (with no nutrients dropped out) includes 20 g dextrose, 6.7 g yeast nitrogen base without amino acids and 0.79 g Complete Supplement Mixture CSM (Adenine 10 mg/liter; Arginine 50 mg/liter; Aspartic Acid 80 mg/liter; Histidine 20 mg/liter; Isoleucine 50 mg/liter; Leucine 100 mg/liter; Lysine 50 mg/liter; Methionine 20 mg/liter; Phenylalanine 50 mg/liter; Threonine 100 mg/liter; Tryptophan 50 mg/liter; Tyrosine 50 mg/liter; Uracil 20 mg/liter; Valine 140 mg/liter; Qbiogene; Carlsbad, Calif.). A commonly used "rich media" is YPD (Yeast-Peptone-Dextrose) or 1% yeast extract, 2% peptone, 2% dextrose. For solid media, 2% agar is included.

EXAMPLES

The following examples are provided to more clearly describe the present invention and should not be construed to limit the scope of the invention in any way. Any and all reagents (e.g., plasmids, primers, cells) described herein form part of the present invention along with any methods described herein.

Example 1

Identification of Biomarkers

In this example, genes identified by "Affymetrix Microarray" (Affymetrix, Inc.; Santa Clara, Calif.) technology are used as biomarkers to identify compounds that affect a target protein. By fusing a biomarker promoter to a reporter gene, assays can be developed to screen for antifungal compounds. In addition, several "baseline promoters" have been identified which exhibit a constant level of expression when temperature is shifted.

Yeast temperature-sensitive shift. *Saccharomyces cerevisiae* strains were grown at 30° C. in YPD (1% yeast extract, 2% peptone, 2% glucose). *S. cerevisiae* wild type WT1554 and ts-mutant strains were streaked out from permanent stock and grown on YPD plates (including 2% agar) at 30° C. until colonies formed. Several colonies were picked to start 10 ml cultures, grown up overnight at 30° C. and used to inoculate 25 mls of 30° C. YPD to an OD of 0.15. Cultures were incubated at 30° C. for 2 hrs and then heat shifted to 37° C. by the addition of 25 mls of 46° C. YPD. Strains were grown for 2 hr, 4 hr, 6 hrs and cells were collected for determination of Affymetrix Microarray expression profiles. Cells were harvested by centrifugation for 3 minutes at 3500 rpm, resuspend in 6 ml of ice cold ddH$_2$O centrifuged for 3 minutes at 3500 rpm, the supernatant discarded and the cell pellet flash frozen in a dry ice ethanol bath. Pellets were stored at −80° C. until total RNA preparation.

Isolation of *Saccliaromyces cerevisiae* total RNA. Total RNA was isolated with slight modifications by the method of Schmitt et al. (Nucleic Acids Res. 18(10):3091-3092 (1990)). Cell pellets were removed from the −80° C. freezer and 1.6 ml of pre-warmed 65° C. acid phenol-chloroform-isoamylalcohol (50:50: 1, pH4.7; (Sigma P-1944) and 1.6 ml of TES (10 mM Tris pH 7.5, 10 mM EDTA, 0.5% SDS) were added and the pellet was resuspended by vortexing. Tubes were incubated at 65° C. in a waterbath for 1 hour with vortexing for 20 seconds every 10 minutes. The mixture was transferred to Phaselock tubes (Eppendorf) and centrifuged for 20 minutes at room temperature. Mixtures were re-extracted with 750 µl of acid phenol-chloroform-isoamylalcohol per tube, recentrifuged then extracted with 750 µl 24:1 chloroform:Isoamyl alcohol (Sigma C-0549) and centrifuged for 10 minutes room temperature. The aqueous phase was transferred to an eppendorf tube and total RNA was precipitated by the addition of 50 µl of 3M Sodium acetate (NaOAc) pH 5.2 and 1 ml of 100% EtOH followed by incubation at −20° C. for ½ hr. Total RNA pellets were washed with 500 µl of 80% ETOH and the pellet was resuspended in 50 µl of 65° C. RNAsecure (Ambion; Austin, Tex.) and incubated for 10 min at 65° C. to inactivate RNAses. Total RNA quality and quantity was determined by measurement of the OD$_{260}$/OD$_{280}$ absorbance ratio followed by analysis of RNA utilizing Agilent RNA chips. RNA was stored at −80° C. prior to Affymetrix labeling and hybridization.

Affymetrix total RNA labeling and Affymetrix Yeast Genome YG_S98 microarray probing. Polynucleotide Expression Profiling. Total *S. cerevisiae* RNA from each RNA sample (see supra) was used to prepare biotinylated target RNA according to the Affymetrix Genechip® Expression Analysis Technical Manual, 2003. (www.affymetrix.com/support/technical/manual/ expression_manual.affx).

Briefly, 5 µg of total RNA was used to generate first-strand cDNA by using a T7-linked oligo(dT) primer. After second-strand synthesis probes were generated by in vitro transcription with biotinylated UTP and CTP (Enzo Diagnostics). Biotinylated probes were hybridized to Affymetrix Yeast YG_S98 DNA Microarrays (Affymetrix Inc., Santa Clara, Calif.). Target cDNA generated from each sample were then processed according to the manufacturer's recommended procedures using an Affymetrix GeneChip Instrument System (www.affymetrix.com/support/technical/manual /expression_manual.affx). Briefly, spike controls were added to 5 µg fragmented cRNA before overnight hybridization to Affymetrix Yeast Genome YG_S98 microarrays. Microarrays were then washed and stained with streptavidin-phycoerythrin, before being scanned on an Affymetrix GeneChip scanner. The GeneChip® Yeast Genome YG_S98 Array contains probe sets for approximately 6,400 *S. cerevisiae* (S288C strain) genes identified in the *Saccharomyces* Genome Database. This array also contains approximately 600 additional probe sets representing putative open reading frames (ORFs) identified by SAGE analysis, mitochondrial proteins, TY proteins, plasmids, and a small number of ORFs for strains other than S288C (Affymetrix Santa Clara, Calif.). Scanned image files were inspected for artifacts and analyzed with GeneChip® Expression Analysis software (Affymetrix, Santa Clara, Calif.). Each chip was scaled to 150 (see, Affymetrix, Genechip® Expression Analysis Technical Manual, 2003) to account for minor differences in microarray hybridization intensity, so that overall expression levels for each yeast strain could be compared.

Identification of up-regulated gene biomarkers in heat shifted *S. cerevisiae* ts-alleles by analysis of Affymetrix microarrays by GeneSpring analysis software (Silicon Genetics). Affymetrix Yeast Genome YG_S98 microarray data were loaded onto the GeneSpring analysis software program 6.0 (Silicon Genetics, Redwood City, Calif.). Microarray data from temperature shifted *S. cerevisiae* ts-alleles from the 2, 4, and 6 hr time-points (see supra) were normalized to *S. cerevisiae* wild type strain MS1554 from 2, 4, and 6 hr time-points. Up-regulated gene biomarkers were identified in *S. cerevisiae* ts-alleles that showed a fold increase in expression at a single time-point as compared to wild-type *S. cerevisiae* strain MS 1554. Data were further analyzed to identify up-regulated gene biomarkers that showed up-regulation in expression at 2, 4, and 6 hr time-points by graphical analysis of identified genes. In addition genes that showed up-regulation in expression were analyzed in all ts-alleles to identify genes that were uniquely up-regulated in expression in a single ts-allele or up-regulated in a group of ts-alleles.

Plasmids and Constructs.

(a) Generation PHO5 Signal Sequence Tagged *Renilla* Luciferase

PSPRT17 (Cyc1A term to HO-poly-HO vector). The cyc1 A terminator (REF) was PCR amplified as a 371 bp fragment from pYES2 (Invitrogen) using PCR primers PR131 (5' tttgcgcgcGGGCCGCATCATGTAATTAGT 3') (SEQ ID NO: 69) and PR132 (5' aaaagatctGACCGA GCGCAGCGAGT-CAGT 3') (SEQ ID NO: 70) designed to BssHII and BglII. and cloned into the TOPO-TA to yield pSPRT19. The 371 bp fragment from pSPRT19 was ligated to BssHII and BglII. digested HO-poly-HO (Voth et al., Nuc. Acid Res. 29(12): e59 (2001)) to yield pSPRT17.

pSPRT47 (SEQ ID NO: 85) (*Renilla* cloned into PSPRT17). The *renilla* luciferase gene was amplified by PCR as a 1004 bp fragment amplified from phRG-B (Promega) using primers PR161 (5' CCCATGTTAATTAAATCTGT-TGTTTATTCAATTTTAGCCGCTTCTTTGGCCAAT GCAGGTGCTTCCAAGGTGTACGACCCCGA 3') (SEQ ID NO: 71) and PR162 (5' AAAGGCGCGCCTTACT-GCTCGTCTTCAGCAC 3') (SEQ ID NO: 72), designed to contain the PHO5 signal sequence (MLIKSVVYSI-LAASLANAG) (SEQ ID NO: 73) and PacI/AscI ends. cloned into the TOPO-TA to yield pSPRT27. The PacI/AscI fragment from pSPRT27 was ligated to PacI/BssHII digested pSPRT17 to yield pSPRT47. The PacI site was designed to create an ATG start codon fusion with PacI adapted promoters. This added LI to the signal sequence. The PHO5 tagged luciferase was designated PHO5.hRluc.

pSPRT168 (Ga11 promoter PHO5.hRluc). The GAL1 promoter region was PCR amplified as a BamHI/PacI 474 bp fragment using PCR primers PR172 (5' TTTGGATCCACG-GATTAGAAGCCGCCGAGCG 3') (SEQ ID NO: 74) and PR 173B (5' CCCTTAATTAACATGGTTTTTTCTCCT-TGACGTTA 3') (SEQ ID NO: 75) cloned into the TOPO-TA to yield pSPRT33B. The BamHI/PacI fragment was ligated to BamHI/PacI digested pSPRT47 to yield pSPRT167. pSPRT167 was introduced into *S. cerevisiae* to yield strain Y167.

pSPRT207 (YHR082C promoter PHO5.hRluc). The YHR082C promoter was PCR amplified as a 1.1 kb BamHI/PacI fragment using PCR primers PR207 (5' TTTGGATC-CTGTGCACGATGGCTTCGTTTTAGCC 3') (SEQ ID NO: 76) and PR208 (5' CTTAATTAACATC-GAGTTTCAAAAAATTGTAAG 3') (SEQ ID NO: 77) and cloned into the TOPO-TA to yield pTOPO207. The 1.1 kb BamHI/PacI fragment from pSPRT207TOPO was ligated to BamHI/PacI digested pSPRT47 to yield pSPRT207. pSPRT207 was introduced into *S. cerevisiae* to yield strain Y207.

pSPRT211 (ERG10 promoter PHO5.hRluc). The ERG10 promoter was PCR amplified as a 397bp BamHI/PacI fragment using PCR primers PR213 (5' CCCGGATCCTCTAC-GATATATCCTGTAAATAG 3') (SEQ ID NO: 78) and PR214 (5' CTTAATTAACATTTTGAGTACGTCTAATCTGTAT 3') (SEQ ID NO: 79) and cloned into the TOPO-TA to yield pTOPO211. The 397 bp BamHI/PacI fragment from pSPRT213TOPO was ligated to BamHI/PacI digested pSPRT47 to yield pSPRT211. pSPRT211 was introduced into *S. cerevisiae* to yield strain Y2 11.

(b) Generation PHO5 Signal Sequence Tagged FireFly Luciferase pSPRT50 (SEQ ID NO: 86) (Firefly luciferase cloned into pSPRT17). The firefly luciferase gene was PCR as a 1710 bp bp fragment amplified from pGL2-Basic (Promega; Madison, Wis.) using primers PR167 (5' CCCATGGGATC-CAAATCTGTTGTTTATTCAATTTTA GCCGCT-TCTTTGGCCAATGCAGGTGAAGACGCCAAAAACAT AAAGAAA 3') (SEQ ID NO: 80) and PR168SLK (5' AAAG-GCGCGCCTTACTTTCCGCCCTTCTTGGCCT 3') (SEQ ID NO: 81), designed to contain the PHO5 signal sequence ( MLIKSVVYSILAASLANAG) (SEQ ID NO: 82) and BamHI/AscI ends and remove the C-terminal SLK peroxisomal targeting sequence (Leskinen et al., Yeast 20(13):1109-1113 (2003)). This fragment was cloned into the TOPO-TA to yield pSPRT50. The BamHI/AscI fragment from pSPRT50 was ligated to BamHI/BssHII digested pSPRT17 to yield pSPRT50. The BamHI site was designed to create an ATG start codon fusion with BamHI adapted promoters. The PHO5 tagged firefly luciferase was designated PHO5.firefly.

pSPRT170 (Gall promoter PHO5.firefly). The Galp1 promoter region was PCR amplified as a BamHI 472 bp fragment using PCR primers PR174 (5' TTTGGATCCACGGATTAGAAGCCGCCGAGCG 3') (SEQ ID NO: 83) and PR 175B (5' TTTGGATCCCATGGTTTTTTCTCCTTGACGTTA 3') (SEQ ID NO: 84) cloned into the TOPO-TA to yield pTOPO 174. The BamHI fragment was ligated to BamHI digested pSPRT50 to yield pSPRT170. pSPRT170 was introduced into *S. cerevisiae* to yield strain Y170.

TABLE 2

Biomarkers identified.

| Essential Gene | Function | Affy ID | Fold 2, 4, or 6 hr | RP | Synonym | Function |
|---|---|---|---|---|---|---|
| YCR052W | Chromatin remodeling complex | 8141_AT | 15 | YOR387C | | |
| YBR156C | Mitotic spindle protein | 8141_AT | 5 | YOR387C | | |
| YDR166C | Exocyst complex | 9445_AT | 13 | YMR175W | SIP18 | Salt induced protein |
| YDR166C | Exocyst complex | 5323_AT | | YFR026C | | |
| YDR166C | Exocyst complex | 11185_AT | 17 | YJL153C | INO1 | L-myo-inositol-1-phosphate synthase |
| YKR025W | RNA polymerase III subunit | 7810_AT | 9.2 | YPL033C | | |
| YKR025W | RNA polymerase III subunit | 8593_AT | 7.0 | YOL058W | ARG1 | Arginosuccinate synthetase |
| YDL105W | | 8276_AT | 25 | YOR255W | | |
| YDL105W | | 6215_AT | 14 | YDR250C | | |
| YDL105W | | 6007_AT | 9 | YDR446W | ECM11 | ExtraCellular Mutant |
| YDL105W | | 5915_AT | 8 | YDR536W | STL1 | sugar transporter-like protein |
| YDR016C | spindle integrit, kinetochore | 8276_AT | 16 | YOR255W | | |
| YDR016C | spindle integrit, kinetochore | 6710_AT | 9 | YDL243C | AAD4 | Putative aryl-alcohol dehydrogenase |
| YDR016C | spindle integrit, kinetochore | 6221_AT | 9 | YDR256C | CTA1 | Catalase A |
| YDR016C | spindle integrit, kinetochore | 6215_AT | 9 | YDR250C | | |
| YDR016C | spindle integrit, kinetochore | 6007_AT | 11 | YDR446W | ECM11 | posible chromatin structure maint |
| YDR016C | spindle integrit, kinetochore | 5915_AT | 10 | YDR536W | STL1 | sugar transporter-like protein |
| YNL131W | Translocase Mitochondrial membrane | 5410_F_AT | 5.115 | YFL020C | PAU5 | member of the seripauperin proteinVgene family (see Gene class PAU) |
| YDR464W | Control expression of spliceosome | 7953_AT | 5.8 | YPL205C | | |
| YPL128C | TTAGGG repeat binding factor | 5220_AT | 13.5 | YGL205W | POX1 | fatty-acyl coenzyme A oxidase |
| YLR291C | Translational initiation factor | 5125_AT | 8.9 | YGL117W | | |
| YLR291C | Translational initiation factor | 4503_AT | 8.4 | YHR029C | | |
| YLR291C | Translational initiation factor | 9771_AT | 5.8 | YML116W | ATR1 | predicted protein is very hydrophobic, has many membrane-spanning regions, several potential glycosylation sites, potential ATP-binding site |
| YLR291C | Translational initiation factor | 10902_AT | 5.4 | YJR109C | CPA2 | carbamyl phosphate synthetase |
| YLR291C | Translational initiation factor | 6902_AT | 5.3 | YCL030C | HIS4 | histidinol dehydrogenase |
| YLR293C | Nuclear organization | 10008_AT | 71.13 | YLR338W | | |
| YLR293C | Nuclear organization | 4039_AT | 38.90 | YIL066W-A | RNR3 | Ribonucleotide reductase |
| YLR293C | Nuclear organization | 8939_AT | 32.54 | YNL093W | YPT53 | rab5-like GTPase |
| YLR293C | Nuclear organization | 6215_AT | 25.45 | YDR250C | | |
| YLR293C | Nuclear organization | 9962_AT | 12.40 | YLR381W | | Kinetochore protein |
| YLR293C | Nuclear organization | 10714_AT | 10.96 | YKL159C | | Regulator of calcineurnin |
| YLR293C | Nuclear organization | 4159_AT | 10.96 | YIL058W | | |
| YLR293C | Nuclear organization | 10554_AT | 9.85 | YKR037C | | Spindle pole component |
| YDR499W | Telomere Checkpoint | 10008_AT | 125.0 | YLR338W | | |
| YDR499W | Telomere Checkpoint | 6215_AT | 43.4 | YDR250C | | |
| YDR499W | Telomere Checkpoint | 4039_AT | 42.8 | YIL066W-A | RNR3 | Ribonucleotide reductase |
| YDR499W | Telomere Checkpoint | 9160_AT | 28.9 | YNL279W | | Pheromone-regulated multispanning |
| YDR499W | Telomere Checkpoint | 8939_AT | 22.2 | YNL093W | YPT53 | rab5-like GTPase sorting and endocytosis |
| YDR499W | Telomere Checkpoint | 9962_AT | 15.3 | YLR381W | | Kinetochore protein |
| YDR499W | Telomere Checkpoint | 10554_AT | 9.7 | YKR037C | | Spindle pole component |
| YDR499W | Telomere Checkpoint | 8505_AT | 9.6 | YOR032C | HMS1 | myc-family transcription factor homolog |
| YBR102C | exocyst complex | 10008_AT | 109.7 | YLR338W | | |
| YBR102C | exocyst complex | 9160_AT | 58.7 | YNL279W | | Pheromone-regulated multispanning |
| YBR102C | exocyst complex | 6215_AT | 53.7 | YDR250C | | |
| YBR102C | exocyst complex | 4039_AT | 37.5 | YIL066W-A | RNR3 | Ribonucleotide reductase |
| YBR102C | exocyst complex | 8939_AT | 27.6 | YNL093W | YPT53 | rab5-like GTPase |

TABLE 2-continued

Biomarkers identified.

| Essential Gene | Function | Affy ID | Fold 2, 4, or 6 hr | RP | Synonym | Function |
|---|---|---|---|---|---|---|
| YGL225W | May regulate Golgi function | 9293_AT | 6.3 | YML058W | SML1 | Suppressor of mec lethality |
| YGR065C | Vitamin H transporter | 9309_AT | 5.49 | YMR303C | ADH2 | alcohol dehydrogenase II |
| YML091C | Mitochondrial RNase P | 11185_AT | 23.0 | YJL153C | INO1 | L-myo-inositol-1-phosphate synthase |
| YML091C | Mitochondrial RNase P | 10256_AT | 16.2 | YLR092W | SUL2 | high affinity sulfate permease |
| YML091C | Mitochondrial RNase P | 5428_AT | 15.8 | YFL052W | | |
| YML091C | Mitochondrial RNase P | 4098_AT | 5.2 | YIR017C | MET28 | Transcriptional activator of sulfur amino acid metabolism |
| YML091C | Mitochondrial RNase P | 10414_AT | 4.2 | YLL062C | | |
| YDR081C | Regulates trans of PDC1, PDC5 | 10008_AT | 112 | YLR338W | | |
| YDR081C | Regulates trans of PDC1, PDC5 | 6215_AT | 42 | YDR250C | | |
| YDR081C | Regulates trans of PDC1, PDC5 | 4039_AT | 35 | YIL066W | RNR3 | Ribonucleotide reductase subunit |
| YDR081C | Regulates trans of PDC1, PDC5 | 8939_AT | 21 | YNL093W | YPT53 | rab5-like GTPase |
| YMR033W | Transcriptional regulation | 10008_AT | 57 | YLR338W | | |
| YMR033W | Transcriptional regulation | 6215_AT | 34 | YDR250C | | |
| YMR033W | Transcriptional regulation | 4039_AT | 22 | YIL066W-A | RNR3 | Ribonucleotide reductase subunit |
| YMR033W | Transcriptional regulation | 9288_S_AT | 19.6 | YMR323W | | |
| YMR033W | Transcriptional regulation | 7944_AT | 12 | YPL171C | OYE3 | DAD(P)H dehydrogenase |
| YMR033W | Transcriptional regulation | 5636_AT | 9 | YER065C | ICL1 | Isocitrate lyase |
| YMR033W | Transcriptional regulation | 6349_AT | 9 | YDR114C | | |

Responsive promoters identified in the experiments set forth above are as follows:

```
>YOR387C Chr 15      reverse complement   (SEQ ID NO: 1)
GCCAGGGAAGCCTATATCTGATTCCCTGTTTCATAATCCAATGCAGCCACTAGCTTATAA
TTATTTGAACTATTTGTCGAACATCACAGTAATAAAATCCCCAGAAAGTTCCACTTGCTG
CATATTGGCACCTGTTGATTCACTCTCCATCACTTTTTTGTTAGCCGCCCAGCCTAGAAA
GTCTTTAAATACATCTGAAATTTTTTTTTTTTAACAGTGCACCCGTGCATCATACCTCA
TGCAAGGTACCTTTTTTTCTCAAAGGTATTGTCTTCCATTGAAGTGGCACTATGGCATGA
TGAACCCTGAGCATTTCTGAATTCAACAGAACCAAATTGTCCAGAAATAAATCTGTCCGA
CATGAATTATGAAACTTTTTTTCAATTAAGTGAAGAGAATTTTGCAGCGTCTTACCATTA
TTTTGACCCATTGGTCGCATGTTTGCGCTTTGACTTGAGAACCATGTTAAAGCTTACTT
GTACGACAACCAATGAAGTATATTACGGCAGTTTTTTTGGACTGGGTCAAAAAAAGTGTT
GCATAATCAAATCAGGAACACATTAAAATGTTGTAAAATTTGTCTTAGTATCACCTGAGT
GGTTATTCATTACGTACTACTGTCAAAATATTCGGATCTTTCCTAAACGGGCTTTTGAAT
TAGTGTTGCTTCTATTCCTGGAATGGAAGGTAATACTTTCATGCATTCTCGCTTTTCGGA
CTTTTAACAATAAATTAAAAACAATGATACTTTCATCAACTACCTATACACCCTGCGGGT
CAATTATTTTTTTTCGAATAACCGCTGAGGTTGGAAATATAGAAACATATTTCCAGATCT
GTATTTTCAGTTGCTAGAAAAAGGTTAATATAATCATTAAGGTTTTCAGCATATAACAGG
TATAATTGATATATAAGCATCGTAATTTTCATTCAAAATGGAGAGCTACTGCTTCTGATA
GATTGTACAATCTCAAGAAATCAAGAACAACAACCATACCATGAGT >YMR175W Chr 13                           (SEQ ID NO: 2)
TTGTGTTTAGACTTAAGTATGAAAATTTTATGTATGAGCTGTGGCTATGTATCCGCTGGC
AAATAGGTCTGCTTTTTCTACACTTTCCACCCTCAACCTAACAGAGCCCGCTGGCACAAA
TAATCGATAGTAGGACAACAGAGCTACTCCTTCTTATGCCCCGCCCCTTTGAGCTTGTTG
TATTGCTCTTGATAGTTGTGTTTTTCACTTTCATCAGCATCGGTAGTCTTGCCGTCCTTG
TCTTGACTAGCCATTTTCTTAAAAGCGTCACTCACTACCTTTGCATCGCCCTGCAATTTT
TCCTTTGAGCTCTGAAATATTTCGCTCACTTTTTGTTGGTCTGTATTCATTCTGGATGTC
TTGGTTGTAGAAATTTCTTTTATTGGTTCATTAAAGTCAAGGTAAATGGCGAGAACTAGA
ATAGAGTTTTATTCTTTTTACCGTTATATAGATAATTCTAGCCGGGGCGGTCGCCCCTG
AGATTCCCGACATCAGTAAGACATAGTACTGTACGATTACTGTACGATTAATCTATCCAC
TTCAGATGTTCAACAATTCCTTTTGGCATTACGTATTAATACTTCATAGGATCGGCACCC
TCCCTTAAGCCTCCCCTAAATGCTTTCGGTACCCCTTTAAGACAACTATCTCTTAACCTT
CTGTATTTACTTGCATGTTACGTTGAGTCTCATTGGAGGTTTGCATCATATGTTTAGGTT
TTTTTGAAACGTGGACGGCTCATAGTGATTGGTAAATGGGAGTTACGAATAAACGTATC
TTAAAGGGAGCGGTATGTAAATGGATAGATGATCATGAATACAGTACGAGGTGTAAAGA
```

-continued
ATGATGGGACTGAGAGGGCAATTATCATCCCTCAGAATCAACATCACAAACATATATAAA
GCTCCCAATTCTGCCCCAAAGTTTTGTCCCTAGGCATTTTTAATCTTTGTATCTGTGCTC
TTTACTTTAGTAGAAAGGTATATAAAAAAGTATAGTCAAGATG >YFR026C Chr 6         reverse complement    (SEQ ID NO: 3)
GAGGTTTCAACATGCCAACAATGGAAGTGGTTAAGAGACGTTTTCTGGTTTCTGGGCAGC
TGTTACATAGAATCTCTGATTTACATGCTCAAGTATTCGCAAAGATCGGTATGATGGGAA
AATAGGTGAATTTTGGGATAATGACTGAGATTATACCGTTGTTAATGCTATAATATTAAT
TATACAGAATATATTAGAAGTTCTCCTCGAGGATATGGGAACCCACAGAAGCGAATCGAT
GTTTCTACATAAAAGAAAAAAATAATCTCATTTTATCTTCGGTTTTGAATCTTTTCATTT
TTTTTTCCTATTACATTATCAATTCTGGCATTTCAGTGTTATAAAAAGATCAAATTGCT
GTTTGAAACTCATTGCGCTAATTCCATAATTTTGCACCATGTATGCTCATGACTCCATAT
AGGACAACATACTGGTAGGAATATTATCAAGTGAACGATAACGGTTCTTCTCCCAACAAG
AAGTAAGCCTGGTGAGTGTATTTTGAAGCTTTTTGGAGGGGCGGCCACGGAATAAGATAT
GAACACATACTGGCAATTGGGCTGAGATCTGATTACATTGTCGACAGATTCCCATGAAGG
TGTTTGAGAGAATTTTGATTGAGTCGTTATACAAATTGCTGTGGACACGTACGCATAAAG
TAGTTCGGGCAGCTATGTTTGCCACGTAGTAGCTACAATATTAAGCATAGCAGACTAAAT
GCAATTGGCTGTGTTGAAAGAAACTTCTGAACTGAGATTCAAGTAACGTGATTGTGTGCG
CCATTTTACACAGGCTGCGCGGCAAATCAAAACCAAAGATACTTCTCCGGAGGTATACGT
GTTGCATTTTCAACAGACTATACGAGTTTTTTCTGATCGTTGTATATTTAAGTGCAGCTT
GGACTTACAAGCTCTATACTAGGATAATGATCTCATTGGATTCAAGAGAAAGAAACTCTA
TACTGGCGCCAAATTAGCAGTGTCAAATTTCGAAAAGGTGATG >YJL153C Chr 10        reverse complement    (SEQ ID NO: 4)
TTCTTTTTTTTTTTTTTTTCTTTTTGGGAACGGGGGAAAAGGTCTCACTAGTATATA
AAGGAAAGAGAGTACAGCACGAATGAGCCAGCTGCAGGAAAGGGGCTAGGTTAAAAAATA
AAAACCCAGCAGAAAGCAAACAACCAAATATAATTTAGAAATGGACAGAGACCCATATTAA
TGACCATGACCATCGAATGAGCTATTCCATCAACAAGGACGACTTGTTGTTAATGGTTTT
GGCGGTTTTCATTCCCCCAGTGGCCGTCTGGAAGCGTAAGGGTATGTTCAACAGGGATAC
ACTATTGAACTTACTTCTCTTCCTACTGTTATTCTTCCCAGCAATCATTCACGCTTGCTA
CGTTGTATATGAAACGAGTAGTGAACGTTCGTACGATCTTTCACGCAGACATGCGACTGC
GCCCGCCGTAGACCGTGACCTGGAAGCTCACCCTGCAGAGGAATCTCAAGCACAGCCTCC
AGCATATGATGAAGACGATGAGGCCGGTGCCGATGTGCCCTTGATGGACAACAAACAACA
GCTCTCTTCCGGCCGTACTTAGTGATCGGAACGAGCTCTTTATCACCGTAGTTCTAAATA
ACACATAGAGTAAATTATTGCCTTTTTCTTCGTTCCTTTTGTTCTTCACGTCCTTTTTAT
GAAATACGTGCCGGTGTTCCGGGGTTGGATGCGGAATCGAAAGTGTTGAATGTGAAATAT
GCGGAGGCCAAGTATGCGCTTCGGCGGCTAAATCGGCATGTGAAAAGTATTGTCTATTT
TATCTTCATCCTTCTTTCCCAGAATATTGAACTTATTTAATTCACATGGAGCAGAGAAAG
CGCACCTCTGCGTTGGCGGCAATGTTAATTTGAGACGTATATAAATTGGAGCTTTCGTCA
CCTTTTTTTGGCTTGTTCTGTTGTCGGGTTCCTAATGTTAGTTTTATCCTTGATTTATTC
TGTTTCATTCCCTTTTTTTTCCAGTGAAAAAGAAGTAACAATG >YPL033C Chr 16        reverse complement    (SEQ ID NO: 5)
GAAGTTACAAATAATAACAACAAAGTTAATAACAGTAGTAGCAACCCTGATATTTCCACC
AACTCGGTAGTTCATAACGCAATGCAATTTACAAATACAAACAACAATACAAGTAGCACT
GTGGATATAAACGATCCCAAAAATATTGCACCCCCCTCCTACAACCTCTGTTTCAGCCCCA
AGCACTCCAACCTTGTCCTCATCAAGTCAAATGGCGAATATGGCTTCGCCTAGTACCGAT
AATGGTGACAATGAGGAGAAAATGGTGGTAAGAAGAAGAGATTTGGCCTATTCAAAAAA
AAAAATAAATCAAAGAAATAATATCCTTCGACAGCTTAATGAACACGCATGTAAATGTTT
TGTAAACAGTTTGTTTTTTCGTTTTTGTATCTGTTAATTTTCTATTATTTATTTTTTTAG
TTTTTTTTTGCGGTAGAATTGGGTTATCACTGAATCTATTTTATTTTTTGGGTTGGTTTC
TCCCTGTTTTCAGTTTGTTTGAATTGGTGTTTAACAAAATCTGGAATTATTCACTATAAT
TATTTCCTCTTTTTAGTTTGACCAAATAAACTCAACTATCTTGTGTTATTTCTTTGTATT
ATAGCTTTACACATATTTAACTATCCATACCTTTTACTTTTTGTATATACTGTTAATTTC
ATAAAACGTTTTAGTACCAGAAAATCGTGTCATAGCACCGTTTTAGCAGTGATTTTTA
AAATTGTCCAAGGTGCCAATAAATACTGGTGGGAACAACATTTTAATTAGAATAGCTAAA
ACCTTCTAAGAAAACTATCCCAGCGTAGAAAGAAAGAAATCTCTATCAGCCGCGCAAGTG
CAGTATCTCTTATTTTTGCACGGCCCCGTCGCTATATTGTCACACGCATTTGAATTAGTG
ACTCAATAATAATACAGATTTGTGACGTATAAAGAAACCACAGAAAAACTGCGTATGTCC
GAAGCACAGGTCCACTAGTAATAGAGCCCAAAAATCTGACATG >YOL058W Chr 15                              (SEQ ID NO: 6)
AGGTTGCCACATACATGGCCAAGACCGGTAAGTCAGCCTTGGAGCAGAAAAGGAATTGC
TTAACGGTCAATCCGCCCAAGGGATAATCACATGCAGAGAAGTTCACGAGTGGCTACAAA
CATGTGAGTTGACCCAAGAATTCCCATTATTCGAGGCAGTCTACCAGATAGTCTACAACA
ACGTCCGCATGGAAGACCTACCGGAGATGATTGAAGAGCTAGACATCGATGACGAATAGA
CACTCTCCCCCCCCTCCCCCTCTGATCTTTCCTGTTGCCTCTTTTTCCCCCAACCATT
TATCATTATACACAAGTTCTACAACTACTACTAGTAACATTACTACAGTTATTATAATTT
TCTATTCTCTTTTTCTTTAAGAATCTATCATTAACGTTAATTTCTATATATACATAACTA
CCATTATACACGCTATTATCGTTTACATATCACATCACCGTTAATGAAAGATACGACACC
CTGTACACTAACACAATTAAATAATCGCCATAACCTTTTCTGTTATCTATAGCCCTTAAA
GCTGTTTCTTCGAGCTTTTTCACTGCAGTAATTCTCCACATGGGCCCAGCCACTGAGATA
AGAGCGCTATGTTAGTCACTACTGACGGCTCTCCAGTCATTTATGTGATTTTTTAGTGAC
TCATGTCGCATTTGGCCCGTTTTTTCCGCTGTCGCAACCTATTTCCATTAACGGTGCCG
TATGGAAGAGTCATTTAAAGGCAGGAGAGAGAGATTACTCATCTTCATTGGATCAGATTG
ATGACTGCGTACGGCAGATAGTGTAATCTGAGCAGTTGCGAGACCCAGACTGGCACTGTC
TCAATAGTATATTAATGGGCATACATTCGTACTCCCTTGTTCTTGCCCACAGTTCTCTCT
CTCTTTACTTCTTGTATCTTGTCTCCCCATTGTGCAGCGATAAGGAACATTGTTCTAATA
TACACGGATACAAAAGAAATACACATAATTGCATAAAATAATG >YOR255W Chr 15                          (SEQ ID NO: 7)
CTTAGTATACGATTGTGTTCTTGCCCACCATCTACTAACAAAATATGGCAAGATTAAACC
TAGTAGCGCAACATAACAAACCACTAATAATGGAGATGCACTTCCATCTACCAAAAATCT
TGGTAGAGCGATACCATGTGAAGTAGATTGTGGGCCATCTGGATGACCGTATTTCAAATA
GTTTTGCCTAACCAATTCGTCAGTAAGGGATTCGTAAGCCTTCGTAATCTGAACATAAGT
TTCTTCCATCACACTTTTCTCATCAGGTGTTAGGCCCTTTGCTAATTTATCTGGATGAAA
TTTAACAGATAATTTTCTATAAGCAGATTTGATGTCTCTATCGGAAGCACTAGTAGAGAT
ACCAAGGATTTCATAAGGATCAAATAATTTTGTAGCAGCGTCTTTAATCGCGTCATTACT
ATTAATCCTTTGCAGAAGAATTGCAACTAAGATCCAACCCACAATAATTATAATATTTCT
CCTGCTCCATATTTTGGACTTCTTATTACTATTTTTATCAAACTTCCTTCTAAATTGTTT
GATTTCATCACTGGTGTATTCTTCATTCAAGTTCTTGAAAACTTCCTCATTAAACTCCTT
ACTCTTCCCTGAATTCCCATCTTCAGCATTGGCCCCAAAAAAATTTGGTATATTTGAAG
CAGTGTCATAGGCCCGACGACCATCAAGAGCCCCGTTAAAATGAAGGACGGCCACGTCTC
ACTAGCCTCATCATACTCGTAATTTGTAGGCATTGTGCTGTAATATGCAGTATATTTATT
TTGTTGCGAAGGCCTTCTTTGGTCAATTATAACTGACTATTGTTCCAGTCGCATCTTTTA
TTCGTTCAGTGATCTTCGACGTGTTCAAGACAAATTTTTCAGAAAACGCCTTTCCGTAAC
GAGTGACCAATTCGCGTTATAAGAGCGATTGTGTCAGTAATGAAGTCAGATTGTGACATT
ATAAGCTAAGACGTTAATAACTCAAAATAGAAAAGAAGCATG >YDR250C Chr 4          reverse complement  (SEQ ID NO: 8)
AAATAAGAGGTTTGGCCAAACGTGGTCATCCAAGGTTGATGGATTCTTCTCTTCTAATA
TTATTAATAATGGATCGAAACATATTTGAGGCAAAGCTAGTTCCCATTCTTTTGCCAAGA
AAGCGGAGGGAGAATGATCGTAAAGAGTCACAACGTCCCTAGGAAACAGTTTTTGGAACA
ATTTCTGAAATGTATTCAAAATAGGAATAATATCACTTGAATAGCTGTTTTCGTGAACGG
ATGTCGTTTGACCGATCGAAACAGAAAAGGATTTGGCATTTGCAGTCGTGAACTGTTTGT
ATGAGCCATTGTCCAACCGTCTTATGTCATAATCGGTGAAAATGCTGAAAATATTTGACA
GCGAAAGATCAACTGAAGCCTTGATGAATGGCTCCAAATATATAAACCCGCTACTTTCAA
ATAGTATCTTTGTTGTCTTATTCATCATAGGTTTTATATCTCTCAATACCTGCGGGATTT
CTTGCAGTGAAGACGCACTCATTATTATCAAGTCGAATACCAAGCCACCATTTTCATTAT
TAAGGTCTACTAAATCTAGGAGCGATTGGAAATGGTTTTGAATCTGAAACCGTTCCGTCC
CATAAAATAGTGAACTAACCTCGTAGTTGGCATTTTTTGAGTTGTTCACAAGATAAAATT
CTATATTTTTGGCATGTTGAAACCTGGATGTGTACAGAATGAGATTTGGGTGATCTCCGC
ATACCAAAACCCTTAATGCAGATGTCATTATTCAATATACCTATCGCGAGATATGCCGGG
AATAAAATGTAGGAAACAAAAAGAAAAATATATGCACAGTAGTTCAAACAGAATAGAAAT
GACGGAGAGCAAATATTTGGGTAGAATCACAGACTTTAGTGTTGGTTACAAGCTTTTCGA
ATGGATGTAGTTTGTAATCAAAGGACACTAATAATAGCGAAAAAAAAAAGGGCAAGTATG
TTGGCAGTCGCCTCTTTTTCAATTTAGCGGTAAGTTTTTAATG >YDR44GW Chr 4                           (SEQ ID NO: 9)
CGCAAATGATGAGAAATAGTCATCTAAATTAGTGGAAGCTGAAACGCAAGGATTGATAAT
GTAATAGGATCAATGAATATTAACATATAAAACGATGATAATAATATTTATAGAATTGTG
TAGAATTGCAGATTCCCTTTTATGGATTCCTAAATCCTCGAGGAGAACTTCTAGTATATC
TACATACCTAATATTATAGCCTTAATCACAATGGAATCCCAACAATTACATCAAAATCCA
CATTCTCTACATTACTAGTATATTATCATATGCGGTTTAAGAAAATGGTATAAAGATTAA
GAAACAGTCATGAAAATTTAGTGAAGCTGAAATGCCAGTATTGATAATACGATAGAATAA
TGAATGACAAAGTATATAAGGAAGATGAAGTAACATTATTATGGAGAACTATCGACTCCC
TTTTGTGAATTTCTATATCCTCAAGGAGAATTGCTTGTATACTATGTATATATAATATTA
TAACCCTTGACAACAATGGAATAATTAGTCCTTAAACGTTAGACTGGCTGGGACAGCACG
ACCTCTGTTGGCTAATTTTACTTTTCCCACAACCGTAGATCTTGATTTCATGACTGTTTT
CGTGGTAATGTCCGAATGATACATATATAAGTTATATGCTTTCACTTTATAAGTATTAGC
GTTTTTACTCACCATCCACTGCTTTGAGAAGATGTGGTCAGCAACCACGCAATACATCAC
ATATTTTGGCACGGGTGATGTACCGATCTAATGGCTAAGCTTCCTTTTGGAAGCTGATAG
AGATCCAGATTTGCATCTCTATCGCTATTGTCGTCATCGACACTGCTCACTTAGTGCTGC
AGGTAAATTCCGTTTTTTTCCAAATTAATATTTATGAACGTTATGATGTCAAGTTTTTTC
AAGAAGTAATTATCCGCGAAAAAAAGAATATAAAAAATACAAATGTGCATAGATCCTCAC
ATAGTATACAACTAAAAAGCAAACAAAAGAACATCCTCAAATG >YDR536W Chr 4                           (SEQ ID NO: 10)
CAATGATTCTGAAATACTCCTTTTACAACCTTTGCAAAGATAATGTCTTTCAGTCTGATA
TTACGAGCGACCTAGAACCACTAATCCATATTCTTCATTCAACTTACTCCATTTTCCTTG
GCAAACAATGCCCCACAATCATATACGTCATAACTATAAGGGATATGTCTGGAATGCGGC
CAAGATAGAATTAAAGGGCTGCAGAACACCACTACTGATACTCATTGCCAAGGCTAGGAG
GCACCATCCGTTTCATTTTCTTTGAGGTAAGCCAATCATGAAATAGTATACACATCCATA
ACGGACGTACGGACGAAATAAGTGCCGTTGTCCCACTATTCCACCGCATTTGGCCCATTT
GGCTCACTTTGACTCAACTTGCGTCATTTTAACTGATATGAAGGGTCCGACTTTGTCCTT
TTTCGGCCACCGCATACCCCACGGCGATGCCTCCGCTACCTGCATTTGAGTAGCATCTCC
GTTTCGCGGGGTATTCGGCGCTACGTCGCCTGTTCGAGCGGCTCTGTTCGTTGCATGAAA
CTAAAATAAGCGGAAAGTGTCCAGCCATCCACTACGTCAGAAAGAAATAATGGTTGTACA
CTGTTTCTCGGCTATATACCGTTTTTGGTTGGTTAATCCTCGCCAGGTGCAGCTATTGCG
CTTGGCTGCTTCGCGATAGTAGTAATCTGAGAAAGTGCAGATCCCGGTAAGGGAAACACT
TTTGGTTCACCTTTGATAGGGCTTTCATTGGGGCATTCGTAACAAAAAGGAAGTAGATAG
AGAAATTGAGAAAGCTTAAGTGAGATGTTTTAGCTTCAATTTTGTCCCCTTCAACGCTGC
TTGGCCTTAGAGGGTCAGAATTGCAGTTCAGGAGTAGTCACACTCATAGTATATAAACAA
GCCCTTTATTGATTTTGAATAATTATTTTGTATACGTGTTCTAGCATACAAGTTAGAATA
AATAAAAAATAGAAAAATAGAACATAGAAAGTTTTAGACCATG >YOR255W Chr 15                          (SEQ ID NO: 11)
CTTAGTATACGATTGTGTTCTTGCCCACCATCTACTAACAAAATATGGCAAGATTAAACC
TAGTAGCGCAACATAACAAACCACTAATAATGGAGATGCACTTCCATCTACCAAAAATCT
TGGTAGAGCGATACCATGTGAAGTAGATTGTGGGCCATCTGGATGACCGTATTTCAAATA -continued GTTTTGCCTAACCAATTCGTCAGTAAGGGATTCGTAAGCCTTCGTAATCTGAACATAAGT
TTCTTCCATCACACTTTTCTCATCAGGTGTTAGGCCCTTTGCTAATTTATCTGGATGAAA
TTTAACAGATAATTTTCTATAAGCAGATTTGATGTCTCTATCGGAAGCACTAGTAGAGAT
ACCAAGGATTTCATAAGGATCAAATAATTTTGTAGCAGCGTCTTTAATCGCGTCATTACT
ATTAATCCTTTGCAGAAGAATTGCAACTAAGATCCAACCCACAATAATTATAATATTTCT
CCTGCTCCATATTTTGGACTTCTTATTACTATTTTTATCAAACTTCCTTCTAAATTGTTT
GATTTCATCACTGGTGTATTCTTCATTCAAGTTCTTGAAAACTTCCTCATTAAACTCCTT
ACTCTTCCCTGAATTCCCATCTTCAGCATTGGCCCCAAAAAAATTTGGTATATTTGAAG
CAGTGTCATAGGCCCGACGACCATCAAGAGCCCCGTTAAAATGAAGGACGGCCACGTCTC
ACTAGCCTCATCATACTCGTAATTTGTAGGCATTGTGCTGTAATATGCAGTATATTTATT
TTGTTGCGAAGGCCTTCTTTGGTCAATTATAACTGACTATTGTTCCAGTCGCATCTTTTA
TTCGTTCAGTGATCTTCGACGTGTTCAAGACAAATTTTTCAGAAAACGCCTTTCCGTAAC
GAGTGACCAATTCGCGTTATAAGAGCGATTGTGTCAGTAATGAAGTCAGATTGTGACATT
ATAAAGCTAAGACGTTAATAACTCAAAATAGAAAAGAAGCATG >YDL243C Chr 4        reverse complement    (SEQ ID NO: 12)
CATAAGAAACAAATTTTGTAAGTTTCTTGTGCCTTTTGAGTTTGAAATCATTGACCAGAA
CAATGAGAACTCTAAACACGACAAATGGATCTTAAATCAATTTTCTTGAAAACATCTTCC
AGTTTCGATATTCGCACATTTGCCGGTPAAATAGTGCAATCTGCCTATACCTTTAAAATG
GGATCTTGAACGCGTACCTGAAGGTTTTTTAAATAAGGCCGAACCTAAATGTTGCCTTC
AAAATTAACCTGTATCAAATTTTGAAGCCGAAGTTGGTATCCTCACATTGTCTAACCTCA
TGGTCTCCTAAAGTCCGGCGATCACTTTCCGTTGCGTGACTATTGATGATCAGACTGTCA
ACAATGTCGTTCCGGGCCTCCATAGCTTGAAGAATTTTCGTTGACGGAACTAGAGGAATG
GCAGATGGAGATGACCTTAGTTTCATGTCGCCTTGATAGTTATCAAAGAGTACAGAAACA
AGACGTCTCTTGCTCAATAATAAGGATTGGATCAGGTGCTTACAAATTTTATTCGTCATA
CAAACAATTACTAATATTTTTTTAATATTAAGCGTACCCCTATTTGATTGGCTCTCTTCT
AAATTCATACGTTTTAAAATCCGCTTTCAACCGTCAACATAAAATTAGTAAGCAGACCTC
GTTCCAAGACCCAACTAAGTTGCACTAAATATCCTCGAACAAATTGGGGGCAGATTTTTG
AACCATATAAAAGTCATGACAATATTTCCAGATCAAGGACAGTTGCAGTTCTTCCTTTCA
TCGGCCAGCTGACGAATTGACTGAGCGGCTTTGTATTTCACTAGAATACACTTCCTATAG
CTACAAAATATTATTCAATAATATTAGTGAATTATTTAAACCTCTACCTGAACCACCTAC
CGAGTTGGGACGTCTCAGGGTTCTTTCTAAAACTGCCGGCATAAGAGTTTCACCGCTAAT
TCTGGGAGGAGCTTCAATCGGCGATGCATGGTCAGGCTTTATG >YDR256C Chr 4        reverse complement    (SEQ ID NO: 13)
AGAACATCCAAATTCGGAACTACTAAGAAGATATGGGTATGTTGAATGGGACGGTTCGAA
GTATGATTTGGAGAAGTGTTACTTGAAAATATTGTCGAGGCGTTAAAAGAGACTTTTGA
GACGAATACTGAATTTTTGGACAGGTGTATTGATATCTTACGCAATAACGCCAATATTCA
AGAATTCTTAGAAGGTGAAGAAATAGTACTAGATTCATATGATTGTTATAATAATGGTGA
ATTGTTGCCTCAACTAATACTTTTGGTCCAAATCTTGACAATTCTTTGCCAAATTCCAGG
TTTATGCAAACTGGACATAAAAGCAATGGAAAGGCAAGTGGAGAGAATTGTAAAGAAGTG
TTTACAATTGATAGAAGGTGCCCGCGCCACTACAAACTGTAGTGCCACATGGAAACGTTG
TATTATGAAGCGTCTAGCCGATTACCCCATAAAAAGTGCGTTTCTATCGAAAAACCTTC
GAAAGGAAACTCATTAACAAGGGAAGAACTAAGAGATGTTATGGCTCGGAGAGTTTTGAA
AAGCGAAATAGATTCGCTGCAAGTTTGTGAAGAAACCATCGACAAGAATTACAAGGTTAT
TCCTGATGAAAAGCTGCTAACTAATATTTTAAAGAGAAAGTTGACAGAGGAAGAAAAAAG
CTCTGTCAAACGTCCTTGCGTGAAGAAGTGAGCGGTTGTTCTAACCACTATTTAAAGCCG
CAATTAGTAATGCAAAAAGTTGGCCGGAATTAGCCGCGCAAGTTGGTGGGGTCCCTTAAT
CCGAAAAAGGACGGCTTTAACAAATATAAACTCCGAAAATCCCCACAGTGACAGAATTGG
AGAAACAACCAGTTTTGATATCGCCATACATATAAAGAGATGTAGAAAGCATTCTTCACT
GTAATGTCCAAATCGTACATTTGAATTTCTTGTAGGTTTATTTAAAAGGTAAGTTAAATA
AATATAATAGTACTTACAAATAAATTTGGAACCCTAGAAGATG >YFL020C Chr 6        reverse complement    (SEQ ID NO: 14)
GTTGAACTTTATTCAAATATCATCGAAGTAAGAAGATATACTACTAAAGACTCCCTTTGC
TCTATATTCGAGTCAGGCTCCACCAGTCATTTCGAAATTAACCAGTTACAGGTCAAAAGA
CTAAACTTACTGCAAAACCAATTTGCTTCTGTTTTCACTTCTTTCCACCCCAAAGATAAT
ACAAAGGGCATACATATCAATTTTTTTCACCTGTCACTAGGATAACTGACCTTCAATAT
TCCTTTTTTTATACGAATCAGATACTGTTCGGTACACGATATCTAATTAAAATGATTCAA
AACTTTGTAACAGGTAAAGTTTTCACTAGAACCAATCAATCCAAGTGAATTAGGGGAAAC
CATAGTTGTTGATTGTAGAAACCTCACATTGTACATTGTTGGTTTGTTGGGCATATCAG
AACGAGAGATTTTCCAACATTCAATATACACTAAACCCTATGACGAGTCCCACAGATGGC
GTAAGGTTTTATGATTTCAGCAGGGTACGACGACTAGTACCATATTAACATTTTTTAGT
GTTTCTAATTTGGGAAAAGGTCCGTGTTTTTTCTCCTAGCAACCGTTAGTGCCAAGGGT
TAGGCAATTGAACGAGGCCAAGACAATATTGGCTTTGCTTCTATTACTTGGCTAACATTG
TGTCTGCAGGTCGAAAGGCACCTTTACTGTAAGGAACATTCTTGCGCTCTAAACATACGA
AGATATGGGAATATGAAGCGTGTTTCTTATACGAAGTGCAGCATCGTTCAAGGAAAATA
CACCCCCATAGTAATAATGGCTAAGTGGCCAGGAATTAGAATATGTGAGATATGAGTGCA
AAATGAGTGACCAGTAATAGCCTGTTTGGGATGTAATTGCTCAAAAAATTTATATAAATA
CAGCGGTTTGATCAGCTTTGTTTGAGACATTTCTCTGTTCTTTTCCTTCCAGTTAAGCTT
ATATCTCCACTAAGCAACAACCCAAAAAACAACAAATACAATG >YPL205C Chr 16       reverse complement    (SEQ ID NO: 15)
CAGACTTGTTGTCTGTGCTGTTACTTGCACTTGCTGCATTGCTATTTGCGTTCAAATCAC
CTTTTTCGATGAGGAGGTCCCTTTGCTTCTCCACCATCGCCTTTGTGTAACGCAACATTG
TCCAATCGAACAAGTGGTCGTTGTGATACTCTAGTTTAATACTCAGATCTTTAAACAGCC
TTGCCAAGAACAAATAATCTGGCTTCTCATCGAATTTCAAATTCTTACAGTAAGCCATAT
ATTCTTGAAACTCTAATGGTAAACCTGAACATAGAGTTTCCACGCTAACGTTTAATTTCT
TTTCCATGATACGATCATACTTTTGTTTCTTGGTGGTTGCTTTCAAACCCTGCCATGGCA
AAGAACCCTTACAAAAATAGATCAAGACATAACCTAGTGATTCTAAGTCATCTCTTCTAC -continued
TTTGCTCTATTCCAAGATGCGTATTGACACTTGCATAACGAGCTGTACCTGTCAAGGACT
TGTTCTCCCTGTAAGGAATATGACGATGTGTGTTGAAATCTCGGTATTTCTTTGATAGAC
CGAAATCAATAACATGAACGGTGCTACCACGGCGTCCTACCCCCATTAAAAAGTTGTCTG
GTTTGATATCTCTATGAATGAACGACCTTCCATGTATATACTGAATACGGCAAAACATTT
GCAAAGCCAGCATGATAACCGTCTTAAAGGAGAACCTTCTGTGACAGTAGTTGAATAAAT
CTTCCAAAGATGGGCCTAGAAGATCGATGACCATAGCATTATATTCACCCTCTCTGCCAA
ACCATCTGATGAACGGGATTCCCACACCACCGCTTAAGTATCTGTAGACGCGGGACTCAT
AGTCCAATTGAGGATGTCTGGACCTGATCGATTCCAGCTTGATGGCTACTTCTTCACCAC
TAATTAAGTTCGTGCCGTGGTAAATGTCACCAAAGGAACCACTCCCAATCTTCCTGCCAA
TACGAAATTTCCTTCCTACTCTTAAGTCCATCTCTTTTTAATG >YGL205W Chr 7                                   (SEQ ID NO: 16)
TCACTCAACCACCTCCAAAAAATAACAGGTTCATCTAAAGTAAAAGACTTTAACTTGCTC
TTAGTTTCCAAATTAAATATCTGCACGATAGTACCATTTGCTCTAACGGAAATAACCATC
TGAGATGGATGCATGATAGCAGAATCACCGCCCATATTCTTCCTTGTCACTTCATTGCCT
TTGGCCAAATCCACGATTGCAACAGAGTTTGTACCGTCCTTTGTTTCTAACAGTGACG
AAGTGGTCACTCTCGAAAGTAGTTGATCTGAAGTCAAGGAATTGAGGGGAAATTCCTAAG
GACATCAGATCGACCAATTCGGTAAATTCAATGGGTAGGTCACTCATTGGTTAGAACTTT
CGTGATAATTTATTTTTATAGTTGAATATCTTCTTTCTCTCAACTCTGATCCGGATTG
TCGAGGTTTCAATAAGTTACTCTGAACAACTAATCAAAATATCTCCTTATTTCTGTAGAT
TCCTTCAGTTCCACTTTTTACTTTTCTTAATTCTCTTTGTATTTATTCCTAGCGACGAAA
AATGCGAGATCTCGACCAAAAAAAGGGGGTAGGGTAATAAAATTAACCCTATTATTTTTT
AACTTTAAAACCTATAATGTGCTAATATTTTATTATAAACCTCCTTTTTTTGCGTTCAAA
CCCTGACACATTTTAAGCCCTATATTTACGGTATTAGTTGATTAAACTCCGAAGCGAAAG
GAATTCGGTCATTAGCGGCTAATAGCCGTTGGGGTAAATCACCTACAAGCAAGTACACAA
GAGAACGTTGGCGTTGTTAAGTCAAAGCACTAATACATTGGGGCTTTAAGAGTGTTTATA
AAGGTCTAACCTGTAAAAATTATTTAAACAACTTGAACAGGCCTTAAAGTTTTCCTCATT
CCGCTCATCATCACTAATATTGCTCTCCGTTTTTGAATACACACTTGACACTAATAAGTA
TCACAGAAAAAAGAAAATATAATAAATTAGTATTGCGATATG >YGL117W Chr 7                                   (SEQ ID NO: 17)
AAAACGGCTCCTAGTTATCGTCAGTTTTGATAATTAGTAACTAGAATATAGTATCACCAA
GAACAGGCCAGGTAATATACTAGAAGTTGTGTATAACTACTAATATTTTTATACATATAG
ATGCCAAGTCAAGGTCCAATTAGTAGATTTTTCACTCTACCTTGCATTATTACCTGAAAG
ATCGTTTGTGTTTCCTTAAATTCGCCAGAGGTGCAAACGAATGTAAATATCTACATCAAT
TTACGGTTTCACGCCCGTTTCGTTTCTAATGGCAACTCATGTAAACTGTGATAAACCCGT
TATTTCAGTTTTATTTTCTGCTAGTATAAAGGATGATAGTAGCCATTTCGCTGGAATATG
TATCGGGTTTAAAAGATGGCATAGTTCGAAACATTTTCGCACAAGATTCTAACTGTCTTC
GAACGTCGTAGAAACCGCAACGCAAGAAATGACAGCGCAATAAAATTTATTTTACTAACT
GATAGAACAAATGTAAAAATTTCATAATATCAAGTAGAATTCTTTATTCTCTTTGTGAA
TTCCTAAACCCATGAAAGGGACTTGTAGTATAAGCTGGATACCTATTTTCATTGGCTTCG
TTTCCAAATGACACAAAACCATCACAkAAGGAAATAGTCCTTCCATAGTTACCCAATCAT
TCTGTTGCATATTAAATGAACAGCTCCTTGTTGATAATGCCAGTGTGGCATATTCACCGC
TGCAGTTATTTCTTTTCATATATAATGAGTCATTTGTTTCTGTCATCACTTTTCTATACT
TTCTCTTCCCCGCGTGTTTTCCGTACACCAACAATATATGCCATAATACACGTAACATTT
TTTTATAAAAAGAAAGGTAAGTGATATATATAAAATAGCGCCATGAGTAGGAAACTTTT
CTGTTACTGCAGATATGTGCCAGACTGGCTCAGGTGGCATAAACACAGATTAATAGTATT
GGCGTTGCTGAAATAAGAAGATCGTAACAATATCTTACAATG >YHR029C Chr 8          reverse complement     (SEQ ID NO: 18)
TCTAAAAATGTTCAGGACTACATACATCAATTAGGTTTCATTCCAAAAGTACCTTTTGTC
AATTTATACCCAAATGCCAATTCACAAGCATTAGACTTATTGGAGCAAATGCTCGCGTTT
GACCCTCAAAAGAGAATTACCGTGGATGAGGCCCTGGAGCATCCTTACTTGTCTATATGG
CATGATCCAGCTGACGAACCTGTGTGTAGTGAAAAATTCGAATTTAGTTTTGAATCGGTT
AATGATATGGAGGACTTAAAACAAATGGTTATACAAGAAGTGCAAGATTTCAGGCTGTTT
GTGAGACAACCGCTATTAGAAGAGCAAAGGCAATTACAATTACAGCAGCAGCAACAGCAG
CAGCAACAGCAACAGCAACAGCAACAGCAGCCTTCAGATGTGGATAATGGCAACGCCGCA
GCGAGTGAAGAAAATTATCCAAACAGATGGCCACGTCTAATTCTGTTGCGCCACAACAA
GAATCATTTGGTATTCACTCCCAAAATTTGCCAAGGCATGATGCAGATTTCCCACCTCGA
CCTCAAGAGAGTATGATGGAGATGAGACCTGCCACTGGAAATACCGCAGATATTCCGCCT
CAGAATGATAACGGCACGCTTCTAGACCTTGAAAAAGAGCTGGAGTTTGGATTAGATAGA
AAATATTTTTAGGCAAAAAACTATAAGTAACCGGGGAAGTATAGAATCACCATAGATGT
AAGCTTACAGACAATGTGTATATATGATGTATATGAACGTATACAAATATATATATAT
ACGTGCTCTTGTTGTAGCTCGTATATCAAATTCCTCCTCCGACGCTTATCTTAATCGTAC
TCCGCGGAAGTTTGTTATCGCCTCTTGAATTCTTTCTTTTCGTTCATTTATGATTAGTCA
TCTATAGACAATATTCATTATTTAAGCACCTAGAATACTAAACTAAATGTCTAAATATGA
CACAAGGAAGATAAGATAAAAAAAACCAAGCGCTTAGAATATG >YML116W Chr 13                                  (SEQ ID NO: 19)
CATCGGGATCTTCCGACTCGTCATCAGACGTCGAGGTCATTATGCACTCCCCGAGCGATC
CTGAATACGCTTTAAAATCACAAACTCTAAGAAGCTCGAGTCAGACCGTCATTAATAGTA
AGAGACCAGTAAAGATAGAAGACGAGGAAGAAGCCGTAGGAATGTCACAGCTCAATTATA
GGTCGTCATTAAGACAAGCTCCTCCAAGAGCTCCCTCAACTTTGTCATATAATCACTCGA
AGAACAACGAAACGCCAATGCAAGATATTTTCACAAATGGCGAAACAGCAAATAACAGAA
AGAAGAAGAGAGGATCTTTTGCAAGGCATAGAACGATACCAGGATCTGACGTCATGGCCC
AATACCTTGCACAAGTGCAACATTCGACATTTATGTATGCAGCCAATATTTTGGGCGCCT
CTGCGGAAGACAACACGCATCCTGACGAGTAGTATAGCTGTGCTGAGCCTGAAGTATAAT
GCATATCCATCGGACTATTTAGACAAAGCCCAAGGAAGCCTAAGGCGGCCTGCCAAGGTG
TTTCTCCCTTTTTTTCTCCGATTTCTTTGTATAAACTAAATAATATAGTGATTACTAATG
GAATGGCGGTATTATGCACCTAACCTGTTCATTCTGCCACAGATTACGTAAGCGATTTAT -continued TGCCGGCACTTGTTGTCTTAATGACCGAGTCACCAATGTGGAACGATAATTTTCTCTGAC
TCAAACCTGTTAATTTTTTCTACTTCGTTTCGTTAGCGACGACGTCAAGCCGCAGGATC
CTGTCTGCCTTGACCTCTTCTCTACCTTCAGAACTTACACTTTTCAGGTAAGATGACCTT
TATATAAAGTTGACACTATTACAGTTGTTTATAAACGTCTGAAGAATGAGACGTTTTTA
TAAAATGAATAAAATGCATATTCTAAGTTTAAAACAACATTTTCAAAGTGTACGATTGTA
AAAAGAGAGGCAATTAGAGAATCTCAAACAGGTAATAATAATG >YJR109C Chr 10     reverse complement     (SEQ ID NO: 20)
GAAATCCAATGAGAATACCGCATAATCTTTCCCAATTACCTTGATATTTACAAAAGACCA
TAGATCCTTACCCTGGTAAAGCTTGTAATTCTGTGAATCCGTTCCCTCCAATTGGATTTG
ATTAGTGGAAGTCAACTTGGACAGTAATGTACTACCCGGGTTTTTATGCACTCCATAGAT
CAAAGGATATGGAAACCAAAATTCCGTCGACAATTGTGGTGACTCAAAGATCAAATGGTG
AGTAGTCAAATGTAAAGTACCTTGTGTGGCCGTACCTCTTCTATGCAGCACTACATTAGA
TACTTTGGCAATCTTGATGTACTCCATCTTTGCGGAATGGTATACTATTTCTTTTCCCTC
TTTTTAGCACTATTACACCCCGCCCACAAAATAAAAATAATAACGACGACCTAATCTCAC
CAAGTGACCCTTGTAAAACCTCCTTTTCTTTATAATGTTTCTTTTCTTACTAATATTTGG
TACATTTAGGGTAGTGATAAAAGAATGGCAACATTGTTATTATTGTGAAAAATGAGGAAA
ATAGAAAATCAGAAACCCTAAAAAGTGATTTTACCCTATCAGAAATATTCAAATGTCCTA
ATTAAAAATAGTAAATCCCCTAAACATTCAGATTGTAAACTAGGGTTGAGAAAATGACTC
ATCCACCACTGTCTTCTTTCCTGCGGCATTCTATAGATTATTGTGAATGACTCTTATTGA
TGAGATGGCAATAACTTTTGAATATCAGAGATAGGAACCTCCATGTCGTAACGATTGTGT
CACCTTGAGTAAGCATCGAGAAAATCCAATCTTTTTTTTTCCGTCATAAGCATTTCTGCC
ATGCTATTTGTATATATATAATTACTAATACGTCTTCTATAGTATGCCTTATCTCTTTTT
TGAAGCGCTATTTAAGTTTAAGCATCGAAAAACTAACATCTATAGTTAAAATTAGTTCTA
TAAAGGAAGAGCAATACAGTACATAGACAGGAAGAAAAGAATG >YCL030C Chr 3     reverse complement     (SEQ ID NO: 21)
GAATTACGAGAAGCCCAATTGACCATCGAAAAGCTACAAAGGAAACAACTACACTACAAA
AGGCTACTCGATGACCAAAGAATGGTCCTCGAAGAAGTGCAACCGACTTTTGATAGGTAT
GAAGCCACAATACAAGAAAGAGAGAAAGAGATAGACCATCTCAAGCAACAATTGGAGCTC
GAACGCAGACAGCAAGCCAAACAAAAGCAGTTTTTTGACGCTGAGAATGAACAGCTACTT
GCTGTCGTAAGCCAACTACACGAAGAGATCAAAGAAAACGAAGAGAGAAATCTTTCTCAT
AATCAACCCACTGGTGCCAACGAAGATGTCGAACTCCTGAAAAAACAGCTGGAACAATTA
CGCAACATAGAAGACCAATTTGAGTTACACAAGACAAAGTGGGCTAAAGAACGCGAACAA
TTGAAAATGCATAACGATTCGCTCAGTAAAGAATACCAAAATTTGAGCAAGGAACTATTT
TTGACAAAACCACAAGATTCCTCATCGGAAGAGGTGGCATCCTTAACGAAAAACTTGAA
GAGGCTAATGAAAAAATCAAACAGTTGGAACAGGCTCAAGCACAAACAGCCGTGGAATCG
TTGCCAATTTTCGACCCCCCTGCACCAGTCGATACCACGGCAGGAAGACAACAGTGGTGT
GAGCATTGCGATACGATGGGTCATAATACAGCAGAATGCCCCCATCACAATCCTGACAAC
CAGCAGTTCTTCTAGGCAGTCGAACTGACTCTAATAGTGACTCCGGTAAATTAGTTAATT
AATTGCTAAACCCATGCACAGTGACTCACGTTTTTTTATCAGTCATTCGATATAGAAGGT
AAGAAAAGGATATGACTATGAACAGTAGTATACTGTGTATATAATAGATATGGAACGTTA
TATTCACCTCCGATGTGTGTTGTACATACATAAAAATATCATAGCACAACTGCGCTGTGT
AATAGTAATACAATAGTTTACAAAATTTTTTTCTGAATAATG >YLR338W Chr 12     (SEQ ID NO: 22)
TGATGCAGTTGGAGTCGGTAGCGATGTTATAGGAGGAGGAGGTGCACTAGGAGGCAAAGG
AGGCGCCATAGCATCCGTATGGGGGGTGGTGCGTTAAAAGCATTCGATGATGTTTGCTT
ATGTAATTTGGATTCAATTTCATCCAGAAACGACATACCATTTTGGCTACTCTGTTTAGG
CGGGTTTATAGATGGAGAAATAGGAGAAGGTCTTACGTTATCATCCTTAGATGAACCTAT
TACATCCTCTTGTTTATCTTGGGTAGTGTATCCAGTATCACCACCAACCACGAATCTATC
ATCTCTCTTCTTTTGGATCTCAGCAAGAAATGGTAAGGGTCCCCCAGGTGTTACGGCCGA
GGAAGAACTGGATGAAGATATTTTGGATTGCTTACTGGACGCTGAGGGTTTGTTTGTCGT
GAGTGTTGGAGGAGGAGGAGCCGATGGTACTGACGTTGCAACCGAAGGAGGAGGAGG
AGGTGGTAGTGGTGCTAAAGGAATAGATGATGCTGACAAGGCAGAAGATGTTGAAAAAGC
ACCAGGTGGTGGGGGAGGAGGAGGTGGTGGCGCGGGCATTGACGATGCTTTGTTAGGAGG
AACTGATGTAGTATTTGGTAACGTGGTGCTAAAGTTGGGGAACCGGGGTTGCTTTTAC
GCTGTTAGTCGACGCAGAGCTCATGGCTGCTGGTAGTGGTGGTGGAGGCGGAGCTGGAGC
TGAAGTTGCTTTTTTAGGTGCAGAGGTCACATTTGGTAACGATGGTTGGAGGTGGTGCAGT
AGGCGGTAATGGCGGAGCATGTGATGTAGGAATGGGCGGAGCAGATGATGGAAGTGGTGG
TTGTGAAGGAGATTTATGATTTTCGGTTTGAATCTTTGTGGAAGAAACGCCCTCGACGGC
TCCTCGTTCAGACCTCCTGGCATTAATTTCTGCCAAAAATGGCAACCCGCCTGCAGGAAC
TTCAGAAGATGGTGGTGAGACTGCGTTATCTGTAGGTTTAATG >YIL066W-A Chr 9     (SEQ ID NO: 23)
TGAATAAGCCTGTATAACTGCGCATGTAAGAATAGTGGCTGCAATAGATCCCACAGCAGT
CAGTGCTCCAGCCTGCTCTTTCAAATCCGTCGTCGTAAGTCTATCAACAGGTAATCGGTC
AAATGTGACATTATTTGAGATTCCCAACCAAAATGTGGGGTACCAAAGTATTACTTTTGC
TATGGGCGATCCATTTTCTAGTGTTCTTTTCACCGCACTCTTCCAAACGACGTATAAAAC
AAAGCATAAAGGTAAAGTCTTTGAAATCCCACACTGAAAAGCTCATACACGCTAGCTGG
GTCATGTGCATCCGTTAGTAATGGAGGGTCTAGAGATAATACAAGAGTCCAATAGCCCAC
TATCGTGTTTATCCAGTACCCGTAAATACTGTCATACAAATAAAATATTGGCAGTCCAAA
AAGCATATTCAATGCGACCACAGCTGCTCGAGGATCATAACAGCCCGACAGGATACCGCC
TTGTATATCTCTGAATGAATATGAACCGGGAAAAAATGAATTGAATGCTACTGAAACCC
AGTGTTATACATTCCTTTTTTTGATGGAAAAGAATTTTGGGCCCCTTGCATAGAAATTT
GGTACAGCCACCGTAAAATGGTGAGATAACACCTGCATGTATGCAGAGGCGCATGGAAA
CGAGTCACTTCTATAAGGGTAGGACACGACCATCGGGTCTTCTTCGCTAAACAGGGCACC
TCCGCCAATTTCATACCCTGTATATTTGACTCTCCTATTCCCTACGGCAATGCGGAGTA
TGTCCATCCACCTCTATCACACAGTGCTGGACATCTGATCATGTATTCTTTATTATCAAG
TGGACCGCAGTTTTTAGCATTTAAACCACATTCGTTATTGGTACCCTCCCAGTTCAAGTA -continued
GGAATTGCAACTTAAAGACAATATAGGAATCTTTTCTGAGCCATCATTTGGATGGAAGTA
TGGCGGCTTGATAAGATAGGGGTATATGAGAGAATAAAAAATG >YNL093W Chr 14                                    (SEQ ID NO: 24)
CTGGCTATTTATATAAGATGTTGCTCTAATTCCATGAGTGATGTCCCATCGCATGATGAA
GAAGTTATGAATGAAGTGAACAATATCATCGAATTACAACAACGGCCCATGCAAATGACC
AAGTCTACCGTACGTACCAGGAGAAGACCACCACCACCTCCCATTCCTTCCACTCAAAAG
CCATCGTTGACAGAAGAGCAAACCGAAAGTATAAGAATGTCACGCCGTAATAAAGATGAG
AACAATGCTAAAAGAGTTGCCCCACCACCGTTGCCGAACAGACAGTTACCTAACTTAGAC
GCTAATACTTACTATGTACCATCCTCACAAAATGACTATGGCATGTATGGTGCTTTCATG
GATAAAAAAGCAGATGAATGGAAGAGAAGAGTAATGGACTCAATTCAAAAATTGAGCAAT
CAAGACACCACATTGATGTTCTTTTCGGATCCGGCATTAAGTTTGGAAGACAGTATTCGC
AGAATTAGGGAGAAGTATTCAAACTAAATACACTGTTATTTATATACATCGGGAGGGAGT
TTAAAAATTGTATACACTAAAGTGACCTTATGAATTGGAGCCATTTTCAACGTTTTAGAG
TGATGTTGCATCCTTTTCATCAGATCGGGAATTAAAAAAACGGTTATAGAAGGGCTAAA
TGTAAATATGTAAATTTATGAAGTCAAGAGTAAAGAAAATCTTCGGTTGCCGATCAAAT
ACACTCTTACAAAATACCCTAAACTCAGTTTATCTTTCCATTCCAACTGATTATCGCGTA
CGCCTTGGTGACCAACCATACCCTAAAATGTCAATTTCCGGGGCGGAAGGGGTCCTTAAA
CTGCAAAGCCTCTTCCCATGTAAATAAAATAAATCCGTAGAATTTATTAAATATTGTCAT
ATTATAAGTCGGGAAAGGCCTTCTGAATGCACGTATATTGACCAAATAGAGTTAGATTCA
AATTATTTATTACATTTTTTCAGCATCGAAGTTAAGTAGAATG >YLR381W Chr 12                                    (SEQ ID NO: 25)
GGCGAAAGAGCTGTGTATGAGAATAACGAGACCGGTGTCATTPAGAACCTGGAATTGCAA
AAGGCCACCATCCAGGGTTACGACAATGACATGAGGCCAGTCATCCTTGTGAGACCTAGA
TTACATCATTCTTCCGACCAAACTGAACAGGAGCTGGAAAAATTCTCCCTGTTGGTCATC
GAGCAATCAAAGCTTTTCTTCAAAGAAAACTACCCCGCATCCACCACCATCTTGTTCGAT
CTGAACGGGTTCTCCATGTCCAATATGGACTATGCCCCCGTCAAGTTTCTAATCACTTGT
TTTGAGGCTCACTACCCGGAATCTTTGGGCCATCTACTTATCCATAAGGCCCCTTGGATC
TTTAACCCGATTTGGAACATCATCAAGAATTGGCTGGATCCGGTCGTCGCGTCCAAGATT
GTTTTCACTAAGAATATCGACGAATTGCACAAGTTTATCCAACCCCAATACATCCCTAGG
TATCTGGGCGGAGAAAATGACAATGATTTGGATCATTACACTCCACCAGATGGCTCTTTG
GACGTCCATCTGAAAGACACCGAGACTCGCGCTATGATCGAAAAGGAGAGAGAAGAATTG
GTCGAACAATTCTTGACTGTCACTGCCCAATGGATTGAACACCAGCCATTGAACGATCCA
GCATACATTCAACTGCAGGAGAAAAGAGTACAACTTTCCACCGCTCTTTGTGAAAACTAC
TCCAAGTTAGATCCGTACATCAGATCAAGATCCGTTTATGACTACAATGGTTCTCTAAAA
GTTTGAGCCAAGCCACGCGACGCTCCATACTGTATAGACCTTTATTATAAAAACATCTAT
TTCTTTATATGTCCCTCTATCTTATTTTTCTTTTACTTTTATTTGTATAATACGCGAAAA
ATTATAGAATCATTTATTATCAAAAACAATCAACTATGAAATGAAAAACAATACGCCTGC
TAATACGGTTCGCCCTTCAATTTTTGTTTTTTTTACATGAATG >YKL159C Chr 11         reverse complement         (SEQ ID NO: 26)
AGATAAGAATATGAGGGTAACAATGAATGAGAACTCACTTTGTAATCACCAGTTGAAGAA
TGGTAAACAAGGCTAGTAATACATCCTGGTATTTCGGTCTCATGTTCAAAATAATCAGTG
GTAATTTATATTATGTATATCTTTTCCTTGTTTCTTTGTTAAGCTTTTGTGTAAACATAC
TTTAGTAATTGTGACGTTTTTGGCACTTCGCACAGGCGTGACTAGTTTCTGTGAACAGA
GGGCGTCTATTCATGATCTTCACAAATCTTGGGGGAGTTAATTTACTCTGCTTCCACATT
ACATTGATGCGCAGTGATCTACTGACGCCTGCTGGTGGTGAGTACACATTAGATAAATAC
CTAGGGTGTGCAGCAATAGACCTTAAACAAGGGTGAGCTTTGCCTATTAGAGAAGAACCT
CTAACTGCGCTTTTCAATAATAGCCACCGAACAATTGGCATATTATGCAACCTGTGTTTT
TAAGTACCTTTTTATGTCAGATTTTTTGAACTATCCTTCGATTGTTATTTCTTGATATAA
CGTTTACATGATTTCTTAATTTACAACGCGGACGAATTAGATTGAAATTATTTAGCATAT
CTGTCTAAGAGCACATTAGATCGAAGTACCGTAGCACATCTGCCATACTATCAAATGCAT
CATCACGAAAAGGCGCAGTGTTGATGGATAGTAAATATGAAAGGATCTCTTCTTAGGTG
TTCCAAGCCTCGCTTCACGTGTAACATACACAGTTTAGAAGTTTACCAAACCGCGGCAAG
GCGCTGTAAGGTTCAAGAGGCTTTGAATTATGCTATCTTACTATCTTGCCGCAAGTTGCT
GTCAGGTGTAGTTCCTAGGCGGCTCGTTGACAAGACCCTTCTGCCCAATGACTTCTATAT
AAAGTATGGTTTTCTTTTTAAATACAGTAATTCCATGAAAAAAAGAGGGCCAAAAAGATC
AAGCAATAAACCAACCGATATATAAAACACAGAACTGCAGATG >YIL058W Chr 9                                     (SEQ ID NO: 27)
ACAGAAGTAAGTACCGGGGTACCTAAATATACGCATAAAAGTCTCTTTCTTTTTTTTTTT
TTTTTTTTTAGCTTCCTACATTTCGTTAATAATATTTATATAGATTATATTTATATTTAAG
AAAAGTAATATCAGCATATTATGAATAGACAAAAAAGTCTAAGGTCAAGATTTATTAAAT
GTTAGATTATTAAGATTACAATTAACAACATTTGTTGTTACTTCATAAAATTTCGTTACT
TCATAAAAGAACTACAGTCCCCCACTTCTAAATGAGTGGTTGTAGGGGTTCATATACCTC
CCATACTGTTGGAATAAAAATCAACTATCATCTACTAACTAGTATTTACGTTACTAGTAT
ATTATCATATACGGTGTTAGAAGATGACGCAAATGATGAGAAATAGTCATCTAAATTAGT
GGAAGCTGAAACGCAAGGATTGATAATGTAATAGGATCAATGAATATTAACATATAAAT
GATGATAATAATATTTATAGAATTGTGTAGAATTGCAGATTCCCTTTTATGGATTCCTAA
ATCCTCGAGGAGAACTTCTAGTACATTCTACATACCTAATATTATTGCCTTATTAAAAAT
GGAATCCCAACAATTATCTCAAAATTCACCAACTCTTCACATACATACCTGCGGTAGCAA
GATAGGTACACTTTTTCTACGTTTCACGAAGGTAGCGATAGGTACCTCACTCATTGTAGG
TGCGGGGGTAGCGATGGAGGTTTCTGTACCATTACCACCACAGCCACTATACTCACGTAG
TGAAGTCCCTAGCGTGGAATTGTGTGGTATCGTTGCTATCTGTCGTTCGCCACCCTCGGT
ATATCCAACGTGCAGGCCAATATCACTCTCTAAGAAAATCGTATCAGGATTGGTACGGAC
AAACTCTTCATAGCCTACGTCGAAATCAAATTCTGCTAAAGCTGTGACTGTAGTTAAACC
TAAAACCGCGATTATTGCTTGAAAAACTGTGGAGAAATTCATG -continued >YKR037C Chr 11        reverse complement    (SEQ ID NO: 28)
TGTCATCGCCGCCAGAACGTGCTCCTTACTGTGGGACGTGCCACTGGTGGGAGTAAACCA
CTGCATTGGTCACATCGAAATGGGAGAGAAATCACTAAAGCTCAAAATCCTGTGGTACT
GTATGTAAGTGGTGGAAATACACAAGTTATTGCATACTCGGAAAAAAGGTACCGTATCTT
TGGTGAAACGCTTGATATTGCTATCGGTAATTGTCTTGATAGATTTGCAAGAACTCTGAA
GATACCTAATGAGCCCTCGCCTGGCTACAACATCGAGCAGTTAGCTAAAAAAGCCCCTCA
CAAAGAAAACTTGGTAGAACTTCCCTATACAGTAAAGGGGATGGATCTTTCGATGAGTGG
TATATTGGCTTCCATCGATTTACTTGCCAAGGATCTATTTAAGGGCAATAAGAAAAATAA
GATCCTATTCGACAAGACAACGGGCGAGCAAAAAGTCACTGTAGAGGATCTTTGCTACTC
TCTGCAAGAGAACCTATTCGCCATGCTAGTTGAAATAACAGAAAGAGCTATGGCTCACGT
TAACTCCAATCAAGTTTTGATCGTAGGCGGTGTTGGTTGThACGTGCGATTACAAGAAAT
GATGGCGCAAATGTGTAAAGACAGGGCCAATGGGCAAGTACATGCTACAGATAATAGGTT
TTGTATCGATAACGGAGTTATGATTGCCCAAGCAGGACTACTAGAGTATAGAATGGGTGG
GATCGTGAAGGACTTTTCTGAAACTGTTGTTACGCAGAAATTCAGAACCGATGAAGTATA
CGCAGCCTGGCGTGATTAACGATTTTTGTTACAGTTAGCCTAATGTTCACACTACGAATA
TATATATATATTTATATATGCCATACACCTTACATTTACAGCTCAGTGTATAACCTTGTG
GAAGCGCGAAAATAAGCAAGAGACATTTGAAAATAATCAATAAACAAAGCTCAAAAAAAT
TAGATCATCACCTAACAAAATAAGACGTGGCAATTACAGAATG >YNL279W Chr 14                              (SEQ ID NO: 29)
GGCAACATAGCAGTACGTCGCCAAAAAGAACGAAAACAAAATAGATATTATGCATAAACT
AACGTGATTTTCATACAGATATTGCAATTCAGGCAATTGTCCATCAGTCAATTTCCATCT
GATAGCCAAAACTAAGACCAAAGTTGTAGACATGGCAATTCCATTGATCTTATACGAAAG
CTTCGAACCATCCCTTAACTGAACACCCTTCATGACTCTGCCCGGTAAAATGACGTCCAA
AACTGCCAGTATTCCATACCACAGGCAATAGACAGTCCATAATTCACGATTGCCCAGATA
GTAGCGCAATGGCTTGATACCGTTCCAAAGCTCAACTATATCGAAATTCTGGAAAAATCC
CTTAATAAAATAATCGGGCCTTATCATTTGATTCAAGATGATAGTGAAAACAGGCAGCCC
TATGCTGATGCCTAAGGCACCAATCAGCCCACCAAATTCAAACTCTGTAGTTCTGGGATT
CAAAGCTGATACCATCCTTTTATTCTCTACACCGAATTTGTCTTTACTCCTATGCTGTTT
ACAAGGTCTATCTGATAAGCAATTGCGCAAGAAAATACTAGAATGAAAACTGATTATTAA
AAACAAACGTAAACTCAAGCCTCACTTGATGCTCAGACGGAGTACGTGAAAAACGTCCGT
TATGCAAAACCCTTTATATGCACAACCTTCACACAATGCAAATTTCCGATGATGCCTACA
TACAAAAGAGCGAAAGGCGATATAAATTTTTTTCACGGGATTTTCGTTTAGGTGAAAATA
AAATGAACGACAGAGCATGCAGAGTCCGGGTAATACATATGTTTCAATACTGTTTCAATA
CTGTTTCAGAAGTGCGTCACATATTATTTTAACTTAATAACTGGCCTGTTGCTGGCAAGA
GGTATATATATATGACGAATGTGACCAACATAAGTCCTTAAGATAATCCCGAAATATTTG
GTTAGGATGATTCCCTTTCGAATTTGTGAACGTTGATGATATG >YOR032C Chr 15        reverse complement    (SEQ ID NO: 30)
CTAGCGGTCTACATTCGCTATCAACTGAACGAATAGTGATGCAATCTGAACCTTAAACTT
TTCGCTCGCTTTTACTTTCCAGAAAAAATTTTCTTCATTGGGATTCCTCTGCTGACAAAC
GGGCTCACAGAACTGAGGAAACGAGAATTTTGTTAATCAIAGCAACATTACGGGAAGGAA
CGGAACCGTCTCGTTGCTGTGGGCGCGAGTTCGACGCAAGAAAAAAATGCTGCAGCATCG
TCTTTTGTGAACGCCAAGAAGGAGTCCGGCGAAGGTATTGGGCGTCACAACCTTTTATTC
TCCGCAGTGTCTCTTGCCTACAAAGCCTGCAGAAGCTTTTATGCCGGGGTGTACGTATGT
TAATCAGTTACCCTTTCCTACTGTGTGCCGCACCCCTCATTTGCTCTCGATACGAGAAGT
TCCGCGCCGATTCTGGCCTTTTTGTTTTCTGGCTAGCCTACTTTCAGGGGACGTGCCTTC
TTATGCCGCTGTAAATTACAGCAGAGATTTAGATCTGAGTGAAAACGTGGCGAGGAAAAA
GGGTACACCGTTAAAAGCGTAGACACAATCCCACTTTGTTGTGCCTAGTCTTCTCTGCTG
TATTTTAATTTTCTGTTTGAACTTTTTTCCGTTCTTTTCCATCATTGTTTAATTTTTACT
TTGAGTGGGCTTCTCAAAAGAAAAAAATAGCTGGTATTGTATTTTACCGTAGGCGTTTT
CTTTGTATTTTTCCCAAGAGCAGCAGCACCTTTTATATACCTTGGTTACACATTGTAAGC
CTCAAAAATCGTCCTATGTAAGTGTCTTATCGCATCATACTTAAGGTCAAACCTGTAAAG
CGCGCTTCTAGTTTTATTTCTACTACTCGCCTTGGCTCTCAGATCGCTTAGGTAGTTTA
ATAGTTAGTCACACCCACCCACCCATTCGCTTAGAATATAGAATATAGAGCAGTTGCAGT
ACACGACTCATTTTAGCAACGATAAGAGTATAAATTGGAAATG >YML058W Chr 13                              (SEQ ID NO: 31)
TCCTTATAACCTGTAAAAAAAAAAAAAAAAAAAAAAGAAGGGTTTAAATAAAAATCGG
ACTTACTCAAAGGGTTGAAAAGCACTTTAATATAGGTTTTTAGTTTCGGGTAAGAAGATG
TGTCAAAGGTCTCGAAAAGGAAACATTAGGGCAAATACGTAAAGGTTGCCTTCGTATCTC
GTTTCCACAGCAACGAGAAACGAGATACGAAGGCAACTGATTCCAGCATATAAAAGGCC
ATGAATTTTTGGCGTTTCCTATTGTCTTTTCGAAACTATTTCTTTCATTCCTTTCCTTTC
TTGTTCTTTTACTTATAAGAAAATAATATACGTATATATATAACTACAAACCACATCAG
CAATAAAAAAAAACTATATGACCATGGACCAAGGCCTTAACCCAAAGCAATTCTTCCTTG
ACGATGTCGTCCTACAAGACACTTTGTGCTCAATGAGCAACCTGTCAACAAGAGTGTCA
AGACCGGCTACTTATTCCCCAAGGATCACGTTCCTTCTGCCAACATCATTGCCGTCGAAC
GTCGCGGCGGTCTTTCTGACATTGGTAAGAATACTTCCAACTAAGAGCATGCTTCTCTTTT
TTTTTTGTAGGCCAATGATAGGAAAGAACAATAGATTATAAATACGTCAGAATATAGTAG
ATATGTTTTATGTTTAGACCTCGTACATAGGAATAATTGACGTTTTTTTTTGGCCAACA
TTTGAAATTTTTTTTGTTACCTCGCGCTGAGCCCAAACGGGCTCCACTACCCGCCGCGG
TCGCCATTTTGGGAAGTCATCCGTCCCAAAAAGGAAATAGCCATAACATATCGTTACTGT
TTTGGAACATCGCCCGTTTCGCCCGATTCCGCCTCAGCGGGTATAAAAAGAGATCTTTTT
TTTTCCTGGCTGTCCCTTCCCATTTTTAAATGTCTTATCTGCTCCTTTGTGATCTTACGG
TCTCACTAACCTCTCTTCAACTGCTCAATAATTTCCCGCTATG >YMR303C Chr 13        reverse complement    (SEQ ID NO: 32)
AATGGCAAACTGAGCACAACAATACCAGTCCGGATCAACTGGCACCATCTCTCCCGTAGT
CTCATCTAATTTTTCTTCCGGATGAGGTTCCAGATATACCGCAACACCTTTATTATGGTT -continued TCCCTGAGGGAATAATAGAATGTCCCATTCGAAATCACCAATTCTAAACCTGGGCGAATT
GTATTTCGGGTTTGTTAACTCGTTCCAGTCAGGAATGTTCCACGTGAAGCTATCTTCCAG
CAAAGTCTCCACTTCTTCATCAAATTGTGGGAGAATACTCCCAATGCTCTTATCTATGGG
ACTTCCGGGAAACACAGTACCGATACTTCCCAATTCGTCTTCAGAGCTCATTGTTTGTTT
GAAGAGACTAATCAAAGAATCGTTTTCTCAAAAAAATTAATATCTTAACTGATAGTTTGA
TCAAAGGGGCAAAACGTAGGGGCAAACAAACGGAAAAATCGTTTCTCAAATTTTCTGATG
CCAAGAACTCTAACCAGTCTTATCTAAAAATTGCCTTATGATCCGTCTCTCCGGTTACAG
CCTGTGTAACTGATTAATCCTGCCTTTCTAATCACCATTCTAATGTTTTAATTAAGGGAT
TTTGTCTTCATTAACGGCTTTCGCTCATAAAAATGTTATGACGTTTGCCCGCAGGCGGG
AAACCATCCACTTCACGAGACTGATCTCCTCTGCCGGAACACCGGGCATCTCCAACTTAT
AAGTTGGAGAAATAAGAGAATTTCAGATTGAGAGAATGAAAAAAAAAAAAAAAAAAAAGG
CAGAGGAGAGCATAGAAATGGGGTTCACTTTTTGGTAAAGCTATAGCATGCCTATCACAT
ATAAATAGAGTGCCAGTAGCGACTTTTTTCACACTCGAAATACTCTTACTACTGCTCTCT
TGTTGTTTTTATCACTTCTTGTTTCTTCTTGGTAAATAGAATATCAAGCTACAAAAAGCA
TACAATCAACTATCAACTATTAACTATATCGTAATACACAATG >YJL153C Chr 10      reverse complement    (SEQ ID NO: 33)
TTCTTTTTTTTTTTTTTTTTCTTTTTGGGAACGGGGGAAAAGGTCTCACTAGTATATA
AAGGAAAGAGAGTACAGCACGAATGAGCCAGCTGCAGGAAAGGGGCTAGGTTAAAAAATA
AAAACCCAGCAGAAAGCAAACAACCAAATATAATTTAGAAATGGACAGAGACCATATTAA
TGACCATGACCATCGAATGAGCTATTCCATCAACAAGGACGACTTGTTGTTAATGGTTTT
GGCGGTTTTCATTCCCCCAGTGGCCGTCTGGAAGCGTAAGGGTATGTTCAACAGGGGATAC
ACTATTGAACTTACTTCTCTTCCTACTGTTATTCTTCCCAGCAATCATTCACGCTTGCTA
CGTTGTATATGAAACGAGTAGTGAACGTTCGTACGATCTTTCACGCAGACATGCGACTGC
GCCCGCCGTAGACCGTGACCTGGAAGCTCACCCTGCAGAGGAATCTCAAGCACAGCCTCC
AGCATATGATGAAGACGATGAGGCCGGTGCCGATGTGCCCTTGATGGACAACAAACAACA
GCTCTCTTCCGGCCGTACTTAGTGATCGGAACGAGCTCTTTATCACCGTAGTTCTAAATA
ACACATAGAGTAAATTATTGCCTTTTTCTTCGTTCCTTTTGTTCTTCACGTCCTTTTTAT
GAAATACGTGCCGGTGTTCCGGGGTTGGATGCGGAATCGAAAGTGTTGAATGTGAAATAT
GCGGAGGCCAAGTATGCGCTTCGGCGGCTAAATGCGGCATGTGAAAAGTATTGTCTATTT
TATCTTCATCCTTCTTTCCCAGAATATTGAACTTATTTAATTCACATGGAGCAGAGAAAG
CGCACCTCTGCGTTGGCGGCAATGTTAATTTGAGACGTATATAAATTGGAGCTTTCGTCA
CCTTTTTTTGGCTTGTTCTGTTGTCGGGTTCCTAATGTTAGTTTTATCCTTGATTTATTC
TGTTTCATTCCCTTTTTTTTCCAGTGAAAAAGAAGTAACAATG >YLR092W Chr 12                             (SEQ ID NO: 34)
CGCTCCCACGACATGCGCATCTCTTCCAAAAACACTACCACTTTCTACTGACTCACTGGC
CATTTGAGAACCACAGAGACTTGGTAGATTCCATCGCTGTAAACAATGGGAAACTAAATT
CAACGTCTTCAAGGAGCGTCTGGCTGAAGGCGGATTGGATAACACTGTTTAACGTTAAAA
ACCCTTGGGTCCAAACGCCGCCATCGTTAATGCGTCTGAGTGGGACAGATCTTGATACCT
TCACACCAGAGAGGATATTCCTGATAAATTCTCTTGGAAACCACTACAAATTTTTAATAG
CGAACAGTCATCTAAGCTACAATCACAAAAAATACCCCTCCCCTGGCGTGCAAATTCCTG
TCAGGAACGCTCTTGGCGAAGTTTCTCCGGCCAAACAAATTGCCCAACTTTTCGCAAGAC
AGCTGTCTCATATTTACAAGAGCCTCTTCATAGAAAAACCCCCGCTCTCTCCTGAGAACG
AGCTGGCATTGACTGCCGTCTTCTATGACGAGACTGTAGAGCGACGCCTTAGAAGGCTCT
ATATGCGAGCTTGTGCAAGGGCATATACGACTACTAATGCCGACTCCACCACGGAGCCTT
TGATGTTTCATTGCACCCGGTGGGAAGTTGATTAGTTGTTGTTGGCTGTTATACTGGAGT
AAATGTCACGTGCCACTGTGGCCGTGTCAGGTCACGTGAAGAGAGAAATTCGGCCACAGT
TGTGGTCCTAAACAAGGACTGAAAAAGATCGCAGAAACTAGCAACGTCGGATAGCGGTAT
GGTTGAACCAAAGTCCAGTTTTTAGTCATAGCCGGTTGAGGGATGATCTGCCGTTCAGTG
TTCTGCGTTCAATAATACGCATATATATATATATCAAGGTATCAACACAATACTTGAACA
GGTTAGGCTCGTACTAAAGCCTGGAAGTTTTTATCTTTCTGTAACATTTTTCTTTCTTGA
GGTGTGTGTGTATAGATTAGCAGGGAATTATCTAAGATATG >YFL052W Chr 6                              (SEQ ID NO: 35)
CGACTAACCTTTTTCTTGGCAGTATGGAGACTGACTAGGTCTCCCAAACATTCATTGTAA
CTGCTGTTTAAAGATTTTGTTCTAACCTAAATTCAAGTGAGAAGCTGAACATGTGTCTCT
ACTTATGATATCACGACAGCAAATACTAATCTTGCCATAAATAGTCTAGCGTTTTGCAAC
TTACCTCTAGATATATTTTATTTCTTGAGGAACCGTTTTCGTCGGTAATAACAAAATACT
ACTGAAACGCCACAGCATTGAGAGAATACGTTATCGATTACGGCTTTCTTCTCGCTCCAG
ATGTCGCGGGTAAGATATTCACCTCAAACTTTTCTTGTTGAGTGTCGTCACAAATCTAGA
ACCTACATGCCATCTCAACGATTTTCTGGAGAAAGGCCTCACTCCGTTCCGTACGTAAT
GCATAGATAAAGTATCAGGATCTTCACGATGCTCGAGAGTTACTTAGTAGTCTGAGTTTA
TGCGAAAAAAACTCCGCCGTTGTAATAATCGGGAATACACAGAAGTAGTACTGCACTATC
ACTGGGATACTCAAAAACCTTCTTTTTAACTTTTCTATCCCACAAATAGAACATAGGAAA
GAACATTGACTCCTCCACTTGAAGTTAAATTACAGGAACAAACGCCTAACTATAATTTCG
ACATTGTTGCATCAACGAATCGACCGAAAGAAAAATCTGAGTTGCAGTTATCACTTGTA
TGTGCACTAAGATTTATATTTTACTCCTGAGATCTGCCAAATCGGTAGCTTATTGAACT
GCGTTCCTTTTTCCCCTGAGTTCTCGAGGTACCTGCGGCTTTGTCTGTGCCATCTCCCCC
ACTTTAAAGTACCCCACGTTACTACCGCGTTTTTCCCCACCCCCGGCTTAATAAATTAGC
TATATCTTGTTGACTTAAATACGGAGAAAAGAAGAAAACCTTCAAGAAATGCTTCATTGT
CTTGTCAAAAGAGCTAAAGTAAAAGAGCTCTAGTTCGAAGATG >YIR017C Chr 9       reverse complement    (SEQ ID NO: 36)
CTGTCGAGTGCTGGTGGCGCTTGATAGCGGTATTGTACTTAATAGGTATCGCCTTCATTG
GTTTGAAATTCTCGATCAAATTCTGCAGGATAGGGTCCTGAGCAGGCACAGAGGCTTGTT
TCAGAGTAAGGGTCTCCAATTTCTGTTTAAGGGCATGATTTTCCGATTCTTTCGCTTGAA
GTTCATTTTGGAGGCGGTTTAGTTTCGTTTCGTAGTTTTTAACGACCTTACTCAGTGACT
CTATGGTTTCCTCCAGCACTTGCAACTTGTTGTTTTTGCGTTCTCTGTAGGCCCTTTGGG
CGTCTCTATTCTGCCGTTTTTCTTCTGTAGCTCCTCATCATTTTCTTCAGTTTCGTAAT -continued
CTTCGTGAAGTCGATGAACTCTTTTCCTCCGCTGAGCTGCTCTATGGGGCAACCTTGGAG
GCAGTTTCCAATTTTTGGACACGTGGATCTTGGACAAAAGAGCGAGGTGGCTTTCCTCAG
ACTCCTTAGGTTTTATCAGAGGTAGAGCCATGACTGTGATAATATGCTAGTTACACTGTT
TATGTTGTGTGAACTTGTTGTAATATGGTTAACTTCACTTTCAGTGATTGATATGATAGC
GACATCACTGCCGTGCAAAAAGACCATTCCATTACTGCACCTTTTTGTCCTTTTCCGTGG
AATAAAAGTTCACTCGTCAGTTCCATGCATTCTGGAAAAAAATGATCTGAAAGATGCCAC
AGTTGTGGGGCCCGCCCGGCCCAATAGGTAAACTAAAATACAATAGAAGGGGTACTGAGT
GCACGTGACTTATTTTTTTTTTTGGTTTTAGGTTTCGCTTTTTTCACCTTTTTCTACTT
TCTAACACCACAGTTTTGGGCGGGAAGCGGAAACGCCATAGTTGTAGGTCACTGGCGTGA
GTCAAGGCCGGGCAGCCAATGACTAAGAACACGAGGTAACTTGAATTTAACTATTTATAA
CCAGTGGTAGTTACGAAGACAAATTGTTTTGTTCGTCAATATG >YLL062C Chr 12      reverse complement    (SEQ ID NO: 37)
CAATTTTGAAAATTGACATATAAAACTCTGATTCTGCAAAGCCTCTTGCCCCAAAAAGAT
TCAATAGCATGCTTAAAACGAACGCGATTGCAACCCAGGCAGCAGGATTGACCGATGGTG
CCCAATAAGAGATGGTAAGCGAACATCCTACCAGCTCGCTAGGGTAAGATATGAGCCACA
TCAATAAGTAGTTAATTCCTATACTGAAGCCGACTGATGGGTCTATAAATCTACTGGCGT
GCAGCGCATAGGAGCCGGAAACAGGGTACTGACATGAAAGTTCGGCCCCACACTGAACAA
CACGAGCATAGATGCGCCGACCAACAAGAAACCAATTAGCAAAGAAGCAGGTCCGGACG
CTAGTGATTCCCCTAAACCAATGAAAAGACCCGTCCCTAGAGTACCTCCAATGGCTATCA
TGGTCAGGTGTCTTTGATCTAGGACCTTTTTATACGGCTGGTTGGCTAAGTCCCATTGTA
TTTTTTCTTCCTCTGAAAGCTCCGAATACAGCAAACCTTCTTGGATCGCTGGTGAATCAT
TTCGCTTGAAAGAGTTCTTGAATCTGTGTATTAGATTATTTCCTTCATTCGAAGGCGTAC
TTAACACGCTAGTGGAAAACTGAACCTTCGAAAGTTTGGTAGATTCAAATTCATCCATTT
CGGGTATCTTTCATGGTATCCTGATGGAGAACTCTTGACGGTGATTACTTAACCACCCAA
ATCTGTAAAATATATACGCATTTATTTCCTGGCATCTCTTCGCTATCCCCGCAAAAGTT
AATGAAAAAAAGCCATTCCTGCAGGAACTGTGGAAAAGTAAAAACTGTGGCATGAAAGTA
CTACCAAATTGTGGCGAGGTATTCAATGGTAATAGCAAPACAGCAACAACGCCAATTTGA
AAATGTACTACTAAGGAAGATAATTTAAACAGACAAGTTGTAGAAGAAATCTGAATCAGC
AACTTTTAGTGTGCAACTTGAAAAAGTAATCAAAAAACAGATG >YMR323W Chr 13                           (SEQ ID NO: 38)
CAGTTTTCTTTTTGAATGAAGGAGAAAAGTGTTCTAGAAATATGTTTTAGTTCTAAGTAT
CGTTGTCTGGAGCAAGCAAAGAAAAGCAGACCTGTATGTGCAACTTTCTTGTTTTCCATT
AAAATCTCAAGAACCGGCCCCTTGACTGTGCTCATATATCAAGTATCGGTTTTAAAGTCC
CCTAATTGTGATAATTGCAAGAATGACAGTCAAAAAGATATTTTTCTTTTCTTTCTTTTT
ACCTATCCTTCATGAAAATACCTATGCTGATACTGAATATCTTCATTTGCAGCTATGCAA
TATTTCAGATACTGCATTTTACCCAAGAGTTTCTTTACTGGTGGTTGGATTTTTTTTAAG
ACGAGAAGATTACCAGTCCTGGATGTTCATGAATGTGCCTATTGCGTCATCAGCGACTCC
GCGCCAAGAAAAGAAATACTCGCATGCTCGGATTTATAGAATCGCATAATGGAAATAGCT
TCCTTAAAGGATGGAGATAAGGAAAAAATGACAAGAACAAGGAAGTACTTGGGAGCTTTC
TCCGACATGTTAAATATTTGAAACTCACGCAGCTCTCCTGGAAAGTTGCATCTGGAAAGG
TAAGGTTGTTTTTTGTTCAGACATCAAAATCGGCTCTTGTAGACAATGTCACAGATCCAC
AAGTTGAAAAAAAGTTTCGATGAACTGGATAAGGGGAGAGGTCACAAACAAGTGTAGG
GGGTGAGTAGTATAGTGGTAACTTGTTCATTTACCTAAATAACATTCTCACTAGAAAAGA
GATATTGAAAGACTCCTCGTTTACCTAACTTGGCTGGTTCTTAGGTATATAATAGAAACA
TGGATCTGGCAGGTTATTACTTACAGTTTGCATTCCCACCAGGTAACPATTTTCATTATA
TATAGTTATTTTTTACCACCACTTCTTCTTCTTTCACTTTGTCTTGCAATAGAAATACCA
AAACAAGGTGAGGAAAAAATCGAATCTCAACGATAAAAATATG >YPL171C Chr 16      reverse complement    (SEQ ID NO: 39)
CGGTTGGATCCTCACTTGTTTTAACACCTCCAAATAACAAGTTTTTAATGAAGGACATTT
GTTCTCTATAATATTCCGATGTACGTGTGTGGCTGATGAGATTTAGACTGGTTAGACT
ATTTGACGCGTCTATTATAGCTTACTGCAACAAGAAAATGATCGTTGATATATAAACTCT
CAGATGTATATATCGTTCTGGAAACATCGAGCATAATACAATACAATTCAACAAAAATGC
GAGAAGGCACTGATGTCTTGTCGTTAAAGAACCAAAAACGCGGACACTACGACCGTCTTA
TTTCCGGTAGAAAAAGGGTACATACAGTTGAAGGAACGAAGAAAATTAAAATTAGAAAAA
AAAGTAAAATAAAACAAGGAAGGTAGGGTAATATGGTCTCGTTTCCTTTGTCGCTCCGCA
AATAAAGGAGCTTATTCCCGCACGCTCACATGGTAATTTGCGCCAAATCACGGATGTGGA
AAACTGATCACGTGCTTCGATCGCCAACTACTGAGCGTCGTCCCACACTGATCTGGCACA
GCTTACCTCGCCTTGAAAATTTTAATCTGTCCTGCTCGTTTGTTGTATATTGCTTCTTCT
CAGAATATGCCCGCGATAACTGACAAAGAGGGTTCGACGTTTCAGAGATTCTACTCTTGA
CCACTGTTTCGTGTAGCCGCTCAAGGTTTATTTCTTTCTTCTTTAATGTTCTTGGCACTT
AGGCGGCTCCGTCCTCCGTCTGAAATTGCCGATCCTATTATTTGCGGAGGGCTCCTTAGA
AGGGCTCCTTAGTAAGCAGTTTGCGTTCCTGATATAACTCCGTTCAGAACAAGGATAAAG
TCGCAATAACCATTACTAAGCACAGTGTTGTAAGTAGGACAACTCGAACCTATATAAGGG
TTGTGAACTGTGCTTGATTCTTGCCCATCATATGCAAAAAAGTACGTACTTGATATATAC
AACAACTGTAGTTCAGTATAGCGAAGTTTAAATTTAGAAGATG >YER065C Chr 5       reverse complement    (SEQ ID NO: 40)
TGGAAATGTAAAGGATAATGAGTGAGCATATAAAATGGAAGAAAAAATAATAATAGGATT
ATGTATAAAATATCGATTCCCTTTTGTAGATTTCGAGATCTTCGAGGAGAACTTCTAGCA
CGTTGTTTACATATCTAATGTTGTAACACGGCCTTTGTTATCTTGTGAATATATCCATCA
CCTACGTCGCTTGAGGTTTCGTATCAAAGAAAGAGAGTTCAAACATAATCATACGTGTTT
CACTCCAAATTTGATCACAAATGGCCACCCATTATAGCTTGTTATTATTTACTTCTTCTT
GAGTTCATTTTATTGAAAGATGCCCGCTGGGAACAAAACATAAATAAAATTCAAGAGTAC
AATATAGCGTAGCATAGTTGCGAGCAAGGGAAGGCAACACAGTTAAAATGACAATGTTAG
AAGGAAAACTAAATCAAGCTCCCATAGGAAATTCTTGTGTCAGTAATATGTCTCGAGA
AATAATAATAATTGAATCTATTTATTGAAAAGTAAATATCTCGTAACCCGGATGCTTTG
GGCGGTCGGGTTTTGCTACTCGTCATCCGATGAGAAAAACTGTTCCCTTTTGCCCCAGGT -continued
TTCCATTCATCCGAGCGATCACTTATCTGACTTCGTCACTTTTTCATTTCATCCGAAACA
ATCAAAACTGAAGCCAATCACCACAAAATTAACACTCAACGTCATCTTTCACTACCCTTT
ACAGAAGAAAATATCCATAGTCCGGACTAGCATCCCAGTATGTGACTCAATATTGGTGCA
AAAGAGAAAAGCATAAGTCAGTCCAAAGTCCGCCCTTAACCAGGCACATCGGAATTCACA
AAACGTTTCTTTATTATATAAAGGAGCTGCTTCACTGGCAAATTCTTATTATTTGTCTT
GGCTTGCTAATTTCATCTTATCCTTTTTTTCTTTTCACACCCAAATACCTAACAATTGAG
AGAAAACTCTTAGCATAACATAACAAAAAGTCAACGAAAAATG >YDR114C Chr 4         reverse complement    (SEQ ID NO: 41)
TTCCTAAGCCTTTGAGATATATCAAAATTGCTGCCTTTACCAACGACGAAAGTAAATTGG
AAGAGCTTCGTGAGAAATACCCAAATCATTTGATTGGCGGAGCAGATCTTGTTGCCAAAA
TTAAAAGCGGTGAAATTAGCGTTGATTTTGACAAAGCATTTGCAACTCCTGATATTGTTC
CAGCTTTACAATCGCAGGTGGCCAGGATACTTGGTCCTCGTGGGGTTTTACCCTCTGTCA
AAAAAGGTACGGTGAGTGATGATATAAGCTCCTTACTTCAAGAAAGTCTAGGATCTATGC
CTTTCAGGCAAAGGGGAAACTCTATCAGCATTGGAGTCGGCAAATGCTACTTCACTGATC
GAGAAATTTTACAAAACATTATATCCGCTAGAGCGGCATTTAAAACTGCTGTTGATAATC
AAAAATCTAAGAAACCAAATATACTGAGTAAAACCACATTATCAAGCACACATGGCCCCG
GTATTGTAATCGATTTTGCTTAATCAGCGAATCAGTTTTGTCTTGTTGGACTTTTTTAAT
TGTATATATATATATACTGGTGCATTTTCTTTCTTTTTATATAAAATCATGTACATACAA
AGTAACCGTCTTTTTAAAGTGGAATAAAGTAACTGCTCTTTTATTTTTGAATAATAGTGA
AAGTGTATGTTGCATAATCATTAGATACCTATGTACAAGAAGTATTCAAATTTATCTGAA
TAGTATGTGAAATTTCAATGAGACAAAAACCACCTACCTTTGAGCTTCCTCCTTTTCAAT
ATCTTAGAGCCCTGTTTGCTCTTGGCCCTAGCCAAGAAACCAAAAGTTCTCTTCCGTTTC
AATGTACTAGGTTGATAGGTGTTACCCCTTGATTTCCATCTTCTTTGACCTATTAAGCCA
AATCCCAACGGTGTGAAGGACGGAGTCTTCAATGGTGAACTGTTTAAGAGCATACCGGTT
TGTGGGCGTAACACAGATAGAGCAGAGAAAGAAGATATAGATG YBL065W Chr 2                                 (SEQ ID NO: 68)
CGGTCCAGAAAAGCAACTGAGATTGGGAGTATAATTCGGTGGCGTTATTGGAATACATAA
TAGGAAAATACGGCAGATACCTAGTCACGAAAATATGGTGTAATCTATTCGCTTTTTCAA
TGGAAATACTAATATCGCCCAGTACAAACTCATCTACATTTGCATGCGGCGAAGGCAATA
ATGGCATAGTCGTGGTGGTGGCTACTACCGGCGTCTTCGTCCTATCTGCATTGTTATTTG
TTGCTACGTGGCTTGTTGCTGCAAATGGTGGTTGATTTGTTGTCGTTGTAACGGTGGTCG
ACGTAGTATGAGGGGAATATGTTTTTGAATTGGAGAGAAGGGGCCGTTCGGAGTGTTAC
CTGCAGAGTTGTTCTTATAAAAAGCCATTTGCAAAGCAGGAGGTAAAGATTCTTTTGAAT
TATTAGGCAATGCTGAGTCATTTAGCAGCGGGGGCAGCTTATTTGGCTCTGTTGCAACCA
AGCCTTTCGAATCTTGCGCTAAAGAAGATGCGCGCAACGTCATGTGAGAAGATGCTTCAT
TATTTGCTTTAAATTTATTCGTATTGCTGCCCTGATTTGCTTGTAAGAGTTGGGGTTCCC
TGGACAAATAAGTTTGAACTGAAACCTTAGAATCTCGTTGAGCCGCGGAAGAAGTTGGAG
AACCTGAGGAAGGAGAATCTGGGTTAGGGATAATAGTACCCGGAGTTGGAGTTGGAT
GCAGATTGAGCTTATTCAAAAGGCTATTGCCCATGGGAATCTGTTGTAAAAGATGAACGA
AAACGCTGTCATTGGCCAGAAGAGTATCGAGTTTAGATTTGATTTCATCCACATCTTGTC
TCAGTAGTTGCAACTGTGAGCCCTTCTTAGGCCTGAATTGAGGATTGATTTCACAGTGGA
GACCAATTTTTTCGCATCTGGAGCAAGGATGAGGGAAATTTTGACTAGCATCGCATTTGA
TTTTGTGCTGTCTACAATGTGTACATG

TABLE 3

Baseline promoters identified

| Affymetrix Probe ID | S. cerevisiae Gene | Synonym | Proposed function |
|---|---|---|---|
| 4464_AT | YHR082C | KSP1 | Serine/threonine protein kinases |
| 6604_AT | YDL126C | CDC48 | Microsomal protein of CDC48VPAS1VSEC18 family |
| 7242_AT | YBR106W | PHO88 | membrane protein involved in inorganic phosphate transport |
| 10388_AT | YLL043W | FPS1 | Suppressor of tps1Vfdp1 |
| 7639_AT | YPR108W | RPN7 | Regulatory particle of the proteasome |
| 4130_AT | YIL041W | | |
| 11172_AT | YJL166W | QCR8 | Ubiquinol cytochrome-c reductase |

TABLE 3-continued

Baseline promoters identified

| Affymetrix Probe ID | S. cerevisiae Gene | Synonym | Proposed function |
|---|---|---|---|
| 6311_AT | YDR165W | | |
| 9999_AT | YLR330W | | |
| 6540_AT | YDL058W | USO1 | Integrin analogue gene |
| 4531_AT | YHR012W | VPS29 | |
| 10644_AT | YKL053W | | |
| 10766_AT | YKL196C | YKT6 | v-SNARE |
| 6583_AT | YDL103C | QRI1 | |
| 9874_AT | YLR427W | | |
| 10368_S_AT | YLL020C | | |

Baseline promoters identified in the experiments set forth above are as follows:

>YHR082C Chr 8         reverse complement    (SEQ ID NO: 52)
TCTAAATATCGTCCCGTTACCCTCATCGCTACTGCCGGGCGTTCCCAACCCCTTCCGAGG
CAGATTATATTTATTTATCTTTTTAACAATTTGTCCCTATATAGGCGGGCCGAACACAGC
ACGTGAAAGAACTCTCAGGCTTCCACAACAGGCCATATCAAGTCCACACTTCCCTCATTA
CTAGCATTTTTACACAAGCAGTCCACGCATTCCGCAACAGTGTTCACCTTTCTTTTCCCT
AACTTATCTTATTATTTGTTTGTTGATCGCAAACAGACCCTTTTTTTGGTGAGCGCATT
TTACACAGTCTCAAGTGTCCTCTACTATAAAAATACAACCTCAAACAGTACTTACTGGCG -continued
TCCGCAGAATATTACTGCACTCTCAATCTGTAAAGAATATAACAAGTGACCCATTCCCTT
GTTTTATTCAACTTCGAAATCTCTCTGGCTATCTTTGCATGCTTATCTAACTTTCACGTG
ACCCGGATATTGTTCTCTGCTCAAAAAAGAACTGCAAGAAGGAAATAGAAAAATAGCAT
ACAGGCTCAAAGCTATAGTTTTCTGAAAAGGGACACCACGAATACAGTAGTATCAAAGAG
AAAAAAGACTTTCTTTATACTTACAGAAGGTTCATTTTCTGATTCTACTCTTCCAATCTAG
TGTCGCAAAAAAACAAAACTTACTGGTATTAGCTGGCAAAAAAAAAAAGAATAGGTTATA
ATTAAAGACATCTTTTCTCTATAAATTTTTTCTTAGAAGAAAAAGCCAAAAAAAAAAAAC
CTGCTTCATACCCGCCATCAAATCTTATAGGCCTTATAGACTGCATATTACCGGATTCTT
TCTCTCCGTTAACCCTACTATTCTTTCACTATACTTTAACCTAAAATAAAAAGGAAAAA
AAAAATTAAAAACTTCCAAAAACTTAGAAATTTCAAATACAAAACAAAAAGACACGTAAA
GTTAGTGCAATATTTTTTCTTACAATTTTTTGAAACTCGATG >YDL12GC Chr 4      reverse complement   (SEQ ID NO: 53)
AGAACATTATGAAGTAAAAGGACAATCAGCACGCCTTCCAGACTTTTAAGAAACATTGAT
GGGAGCCATTGATATCGGCACCGTACCTAACAACAACAAAAATGTCTGCTCCTGCTACGCT
TGATGCTGCCTGTATTTTTTGCAAGATTATTAAAAGTATGTCACATTACTAATAAAGAGC
TTACACTCACACCAATGATGGCGATAGTCTCTATGTAGTACATATACATAAAGCAGAATA
CTAACAATCGATCCGCTATGCAACAGGCGAAATTCCATCCTTCAAATTGATTGAAACAAA
GTACTCGTATGCTTCTTGGACATCCAACCTACTGCTGAAGGTCATGCTTTAATCATTCC
TAAGTACCATGGTGCGAAGTTGCATGACATCCCGGACGAATTCCTTACCGATGCTATGCC
GATTGCCAAGAGACTGGCCAAGGCAATGAAGTTGGACACTTATAATGTGTTGCAGAATAA
TGGTAAAATTGCGCATCAAGAAGTCGACCACGTCCACTTCCATTTGATTCCTAAGAGAGA
TGAGAAAAGTGGTTTGATTGTAGGGTGGCCAGCCCAAGAAACGGACTTCGATAAGTTGGG
CAAGCTACACAAGGAATTGCTTGCCAAACTAGAAGGCTCCGATTAGAGTAATGCATGCTA
TGATTTCTTTTAGCGTTTTCTTTTCATATTTAAGTTTATACATATGGGTGTGTTTGCTTC
CATTCATATCCACTCTATAATGCTAACAATCATGTTACTAGCCATCGTTGCTATCGATAC
CTTATGAACAGCTCTAACTCCTTCCTTTTTAACCTACCGCCTTTTGCGCACTACCCGGCA
ACCCCTCGAATGTGAATTCGGTGGCAAAAAAGGACATATATCAGGGCCGTGTATTTAAGA
GATCCGCAGTTGATGTAGTCAATTAATCTAGTTCTATTAAGATTTGACTCAACGCCATTG
ACTCGATAACTGGCTCAACTACAAGACAGATATACAAATCATG >YBR106W Chr 2                            (SEQ ID NO: 54)
CGAACTATAGGGAGATTGGTCCTCAACAATATATTTCTTCCTTGTCGACCCATTAGGTGT
ATGGGCGAGTTGCTGCAGGGAAGACAACGAATCCCTAGAAGCGCACTTGTAAAGATCTTG
CTCTTGTAAGTAGCGATGACGGTCATGAAGATGAAAGGGTGCGGTTGAAGTCAAGTTGAA
CGTGATCGGATACTGATTTCTAGAAACAGGGGGGGCTGGTGTTGGTTCTGGCGAAGCCGC
TTGCTCCGACTGCTTTGATGTCACAGCTTTGGGTTTCTCCGCTACACTGTCTACCTTAGG
ATTATTGATCATGACTCAAGCTTGCGATATGTGTTGGTGTCATGCACAAGACGCCACAAA
TGATAGAACAGAAAAGAAAGTGAACTAATCTTCCAAGACGAAGAAAACCAAAATCCGGGA
TGAGTTGAAAGTCAAAAAGACTGTATATATAAATTTCAACTTTTGTAGAAGATGCAGAAA
AAGAAAATGATATGGTATGCAGAAAAAGAAATAAACCGCTATTATCCTCGCGGTTTGTCA
TTATAACAGGCAATTACACTAGAGAAAGCCGCACACCTCCCTCCGTTTCTTTTGCCCTGC
GAGTTTTTCCGGAAAAGAAAAAAAAAACGAAAATTAAAACCCGCCTGCCCCGCGGGGTGG
GGGAGGGGTCACCGGAACAAATCGGATAATCCCTCGCCTGCCTTAGATATCGTTCTGAAC
GGCTGAAATTATGAAAGAAGAAGAACATCACTTTACACGGATCGCACGCCCATAATTCTT
TTTTTTTTTTTTTCATATCTTCGACGTTTGCCACTGCCTTCTCTTTTTTTCTTCTTTTT
GGCGGCCGGTGGCAAACGCGCCAAAACCGAAACGCTTATAAAATGTAGTTGCCTTGCTC
TTTCATTCGATATACATATAAGAACGCTCACTGTTATCTTACATTAGAAGCTAGAAACTA
TAACAGTATAACACAGCACAAGAGAACCGAGCAGCCCGCCATG >YLL043W Chr 12                           (SEQ ID NO: 55)
AGTAAAAAGAATAGTAATTATTACAATGGAGAAGATAAGATAAAGTTAGCGGCAACAAAT
AAAGAACTCATCAGAGTTCTTGGCTTCTCTATGAGTGAAAGTGTTTCAAAGGTGTTTTTT
TATGAGACAACAGTAATTCCCCTCCTTCAGAACAGAGTGTAGTGATTGGCAGTGAAGCTA
TCCCTCTTTGCCACCCAATTTTGACGGCAGTTCTCATAGCATCTCAAAGCAATAGCAGTG
CAAAAGTACATAACCGTAGGAAGGTACGCGGTAGGTATTTGAGTTCGTTGGTGGTTATCC
TCCGCAAGGCGCTTCGGCGGTTATTTGTTGATAGTCGAAGAACACCAAAAAAAATGCTGT
TATTGCTTTCTCCGTAAACAATAAAACCCGGTAGCGGGATAACGCGGCTGATGCTTTTAT
TTAGGAAGGAATACTTACATTATCATGAGAACATTGTCAAGGGCATTCTTGATACGGGCCT
TCCATCGCAAGAAAAGGCAGCAACGGACTGAGGGACGGAGAGAGTTACGGCATAAGAAG
TAGTAGGAGAGCAGAGTGTCATAAAGTTATATTATTCTCGTCCTAAAGTCAATTAGTTCT
GTTGCGCTTGACAATATATGTCGTGTAATACCGTCCCTTAGCAGAAGAAAGAAAGACGGA
TCCATATATGTTAAAATGCTTCAGAGATGTTTCTTTAATGTGCGTCCAACAAAGGTATC
TTCTGTAGCTTCCTCTATTTTCGATCAGATCTCATAGTGAGAAGGCGCAATTCAGTAGTT
AAAAGCGGGGAACAGTGTGAATCCGGAGACGGCAAGATTGCCCGGCCCTTTTTGCGGAAA
AGATAAAACAAGATATATTGCACTTTTTCCACCAAGAAAAACAGGAAGTGGATTAAAAAA
TCAACAAAGTATAACGCCTATTGTCCCAATAAGCGTCGGTTGTTCTTCTTTATTATTTTA
CCAAGTACGCTCGAGGGTACATTCTAATGCATTAAAAGACATG >YPR108W Chr 16                           (SEQ ID NO: 56)
ATAATTGCGTTTAAACGCCTTTCCTTTTCTTCATCCATTTTCCTGGTATTTATCTCATCG
TCTCTCTTAATTCTTAATTTACTACCTTCATCTGGGATTATGAACTGTGGATGTTCCATA
TCACATTCATCCTTCCCTAAAGGACAAAATCCGGTCATGTATCTTTGACAGAAACCTTC
TTAATATGCCGTCTAGGACAAGAACTCCCCAGAGGACAGAATCCCATTTCGTAATTTTCA
CATTTTGGTATCTTGCTAGCGGGATCTATGTGTAGATATTGACAATCTGGACTTTGTGTA
CAGTACCCGTTTTTGCTGAAGAAGACACATTCAGGCATTTTTCGAAGATTGTATTCATGT
AAGTATTCACATTGGTCATTCTTTTTGCACAACCCTCGAAGCCAATGTCTACAAACAATT
TTATTCTGAAATATTGGTAACACATGCTTTTTTGGACATAACGGTCCCCTCGGACATGAT
TTAGGGCCTTCTCTAGAATTGTAAAATTCACAAATAGGTCTGTCAGGATCGAGTGAAAAC
GAATACTCTTGCCTGAGGAAAGGTTCAAATTTAAAAGGATATTTTGCTGTATCGGGGTGA -continued
ATTAGGCTCATTACATAAACTTATTGATTTTATTCGTCCTAGAATACTTGTTTAAGATAC
AGTGCAGAAATCTTTAGCTTATAATTCAGAAATGTGATATTTTGAAGCGATTGGAACAAC
AAAGTACAGTGCATTCTATATAATTATTAAAAGTTATAGTGGACTATTGTAATAACACTT
GTTTTCCCCATATCATAACCGACGGCGCGTAAATGCATGCTCAATCAAGTTTCCGAATAA
GTTAAGTTTGCCACCCATTGAGGATTAATATACACAAGGCAGCATTGAAAAACCTAATTG
TTAACACTACACAAATCTCTATTGTTGTAGTAAACTGCGCTTTTTACCACTGTTACAATA
GTTACTAATACACGCAAAAATTCTGGATAAACACGGCAAAATG >YIL041W Chr 9                             (SEQ ID NO: 57)
GCACGTGAATGTGATGTCTTGTGATGGCGGGTGAATTAGGACCGGGGTCCGCTGAGTGTT
GAACTTCACAAAGCATATATCATTGACATAATCAGAAACGTGCTTGATCAATTGTGCTAT
GGGGAGGTCCCGGTGCAAGATTCCAATCATCCTTTTGTTCGTGTCACCTTTGTTCTGTGC
CATCAACGACAAATAGTGCGTCACAAGCAGCTTCATCGTGATTCTCTCCTTCAGGTGGAA
GTTCAAGAACTGCGAAATTTGAAACTTTGGGTAACACGATTGGATTTCCTGAAGACCTTT
TGCCAATACCACAATGGCGTCCTCGTGGTCGTCCAGCAGTTCTGTGAACTTGGCCTGTAT
CTTGGGAGGATTGTGCAACTCGTACGGGTATGCGATTGATAGCAACGTTTGCAAGCTTTT
CAAATACAAAGAGTTGGTTCTCTCAATATGAGGGTTGATTACCGCATTATACGGTAGCCT
CTGAATGGCATTAAGCCGTTTACACGTCAATGAAAGCAACAGGTTGATTGTCTTGATCGT
CAGCATGTACTCCTCCTTCTTGGTCAGCGGCGGCCTGTATTGCAGGAAATACTCGTAGTT
TAGGGGCGCAATTGGTTTACTAGCGTAGTCCTGTATCAGCAGCTCAATGTTCGACCTAAT
CTTGTAATGCTGGTCGAACGACAGTTGCGACAGCAGCTCGTGTGAGGGTCGCTGGCGATG
TGCCCAGCGCATTCCCCCACATTTCCATGAACGCATAATCTTCCACATACTACCGTGAAG
GCGTCTTGATACCACGTCTTCCAGTTATGGTCTTGACTCACCAATGTTCTCAGTTTAATG
TTGTTTGCTTCATACTGGCAGACATTTTCCCTTATTACCGTGAGAAGCGAGCGGTGGATT
AATCGGGATGTCAAAAACAAGAAAATTGCAACCTTCTTCACCTATAACCTATATGATTTG
TAGGCAGAGGAGTGGAATAAGCAACAAATCATAGTCATCAATG >YJL166W Chr 10                            (SEQ ID NO: 58)
AAATCTCACTTCAGAAACGAAAAATACTACATAGATATCACCGAATTGTTCCATGAGGTC
ACCTTCCAAACCGAATTGGGCCAATTGATGGACTTAATCACTGCACCTGAAGACAAAGTC
GACTTGAGTAAGTTCTCCCTAAAGAAGCACTCCTTCATAGTTACTTTCAAGACTGCTTAC
TATTCTTTCTACTTGCCTGTCGCATTGGCCATGTACGTTGCCGGTATCACGGATGAAAAG
GATTTGAAACAAGCCAGAGATGTCTTGATTCCATTGGGTGAATACTTCCAAATTCAAGAT
GACTACTTAGACTGCTTCGGTACCCCAGAACAGATCGGTAAGATCGGTACAGATATCCAA
GATAACAAATGTTCTTGGGTAATCAACAAGGCATTGGAACTTGCTTCCGCAGAACAAAGA
AAGACTTTAGACGAAAATTACGGTAAGAAGGACTCAGTCGCAGAAGCCAATGCAAAAAG
ATTTTCAATGACTTGAAAATTGAACAGCTATACCACGAATATGAAGAGTCTATTGCCAAG
GATTTGAAGGCCAAAATTTCTCAGGTCGATGAGTCTCGTGGCTTCAAGGCTGATGTCTTA
ACTGCGTTCTTGAACAAAGTTTACAAGAGAAGCAAATAGAACTAACGCTAATCGATAAAA
CATTAGATTTCAAACTAGATAAGGACCATGTATAAGAACTATATACTTCCAATATAATAT
AGTATAAGCTTTAAGATAGTATCTCTCGATCTACCGTTCCACGTGACTAGTCCAAGGATT
TTTTTTAAGCCAATGAAAATGAAGAAATGCGTGATCGGAAATTACGGGTAGTACGAGAAG
GAAACTTGAGCCACCCCCCAAATTTTATTCATATAATAATAGGAAAAGCAACGACCTCAT
CTCTCGAACATTGTTTACTTGAGCAAGTCCGATTAAGAGTAAGTTGTCGTACGTTAAATA
CAAATAATCAACAAAACACTACACAAAAACTTCTACGATAATG >YDR165W Chr 4                             (SEQ ID NO: 59)
AAAAAACTGAAATATAGGGTTTGTTAATCCTGGTAAAAATCTGATGTGACATCTTCTGTA
CTTAGGTGGTCTTACCATGAAGTCAGCATCGATACAATTGATGTTATATTTCGTTGGTTC
CAATATGTAAATTGCCTCGATGGAGGATTGTCCTTTTCTTGTTGGGGAATCAATCAAATC
AACAGATGTGACATTATTTAAAAGTTCTTGGGGTGTGAGGAAAAGATAACTCAATATTGT
CTCCACAGTTTTATCGATAATAAGAAACTTCAAGTTATTTTTCGTCTCPATCTGATTCAA
AACCCCTATCAAATAGTTCCTCTGTAATTCAATTAAATCAGACATCGTTCCGCCAAACCA
AGCATGTGCACACTCTTCTACTTTGTCAGTGGATTCTAATTATTTTCAAGGTCTTACAAA
GCAATGTCTTACTAGTTTCAATAGGGACTTAAACTGATCGTTTAAGCAAAAGAAAAACAC
CGTGCTGTGTGACCATCTACCAATAATTGCGAGAACATAAGACGACGCCGCCATTCACCT
CTCTATCACTTACACCATGTTATAGGGATAAGTGTGTAGTCGATCGGCTATTCGATGATT
TTTAAAGAGTGCCTGTAATAATAGCTGTATCGCAAGTAAGGAATACAAGATTACTGATAT
TTTGATCCAGGAGGATGGACATGTTAGATAGAAAAACTAAGAGGGCTACTACATCCGGTT
TAGTATTCTGTTATTGGGAATGCTTTTCCCAAGACGCAAGCAAGAGGTGACACATAAACA
TAGTTTTCTTATTGTATCGTTACATATTCTTATTTTACGCTGCTGTCATTAAATATGGCA
CTTATCTCAGATACATTTCTTTTAATCAGCGAAAAAATGGCGAGGTGAAAAAAATCGAT
GAGATGAAAAAATTTTTTACTAGTAAAGGCGTATTGATGATATATTAGCAGCTAAAGTAT
AGCAAGGTTTGTCAATTTGAAGCAGTCCGCGTGTTTTACAATG >YLR330W Chr 12                            (SEQ ID NO: 60)
CTAACTATAATAACTGGTAGCTTTGTCACTCGTACCAGGAAAAGTGAAGATTAAACTGAA
TTTTAAAATGAACGATCGATTAGTTACGGAAGAGCAAGAGTTGTTTACAAAATTGCGCGA
GATTGTAGGTTCAAGTATTCGCTTTTGGGAGGAACAACTGTTTTATCAAGTTCAAGATGT
AAGCACCATAGAAACCACGTCATTCTCAGTTTAAAATGTACAATTTTAACGGATGCTCA
GATAAGTACGTTCATAAGCAAACCCAGAGAGCTTCATACGCATGCCAAAGGATATCCTGA
AATCTATTACCTTTCCGAGTTATCAACAACTGTCAATTTTTTTCTAAAGAGGGAAACTA
TGTCGAAATAAGCCAGGTTATTCCTCATTTTAATGAATATTTTCCTCTTTAATAGTGTC
TCAATTGGAATTTGAATACCCGATGGTCTTCTCCATGATTTCAAGGCTCCGATTGAAGTG
GCAACAAAGTTCGCTCGCTCCGATATCCTACGCCCTAACGAGCAATTCAGTACTTCTTCC
AATAATGCTTAACATGATTGCCCAAGACAAATCTTCAACAACCGCGTATCAAATTCTGTG
TCGAAGAAGAGGTCCTCCAATTCAGAATTTTCAAATTTTTCCTTACCGGCTGTAACGTA
CAATAAGTAGCATGCATAAAATATAATTTAATCAAATACTTTTGGGCAATTAAAATTTTA
GTTAACAATAGTTATGCAATGCGCTTTATGTTCATATGATACCGTTTATAAGCTATTGCC
ATATCCTTATCTTATTGCTTCCAGTAGCCTCGAGTCGACCACTAAAAAGATGTCACTTAA -continued
GACGGAAATTATGTAGCTGCACTTCTTTTTTAACAAGTTCGGTCGGCCCTTCAAGTTCTC
CTTTCTAAAGCCTCATTATTTATTGCGTAGATGCTAAATGTTATCGCGGTTTAGCTTGCA
TGTTACGTTTCCGTTTTAGAACCTGGTCGAGTAGCGAATAATG >YDL058W Chr 4                                    (SEQ ID NO: 61)
TTCGCCAACCATCATACCCGAATGTTTCATTAGCGAACTGAATGAGAGCATGCCCTGGTA
TCAGCTTAGATAAGTTGTGCTTCCCATATTTATTATTGTGGTAAATATTGTACGTGTACC
TTTCGATCTTGGACTGTAGAAGCCCAATCCTCTGCACCGACCAAGCGCTGGCAGGTCTTC
CATTCCAATCTTCGATGATTTGGAACTCTTTTATATCCAAGCCCGGTGCTGTGCCGTATG
TAGTCGAATCATACGATATGCTCGAACTGGGCTTCGCTTGTATCGTCATTATTTTGTCTG
TTTATCCTGAAATATGCTCTTCTCCTCTACGTAACCCTTTAATGGTCCAAAGCATGTGCT
AAACTGCCACAGACTCCCTCAATGATGTTCTTATCCTTCCTTGCCGTTACTGCTTCCTAT
CATATCTGCCCTTGCCAAACTGTGGCTTCCTCTAATCAATTTGCCCCAGTACATTGAAAA
GCACGTGACGTGACACCAACTTGAAAGACATTAGTGTCCAACGCGATATAATGGTCAATA
AAATACCCAATTTTATCAAGTGAACATGATATTATTCAATACTATAGTACTTTAAAGAAA
ACTTCAACAAGTTGCTTCATTGCTATATTATACAATTATGGGTGATGCCGGTCGGCTAAC
CTTTCTTTCGCAGCGCCACATACAAGAACATATGGTAATTACTAAGAACTTTTTGGAAAC
TATTTCCATGAAGAAAACAAAATTTACTGGCTTCTGTCTTCGAAGTAAATTTAGCGAACT
TGATACTTTCGTTTGGACAGTCGTTTAGATTTGCAACTGTCTGTTCTTATTTCTTGCTAT
TATTACCAGAAATAAAGCCTAAAGCGCGTGGTTCTTACGAAAAAAATAGACCTTGCACAT
TAACAGGGTTTAGACATCACAGAGACTGAATACTGGAGAGAAGACAATTCTTGTTCACGA
CTTCGAGTGATTAATATCTATAACAACCCTCCTATCAAGAATG >YHR012W Chr 8                                    (SEQ ID NO: 62)
TGAAAGGCAAATTTACGCTCTTCAAGACACCAATTTAGGATTGGTGGCTACCGCGGAGAT
ACCTTTGGCAGGTCTAGGGGCAAACAAAGTTCTAGAGTTAAACTCGGGAGAATGTTCTAA
GAAACTAGTTGGAGTAAGTAGATGTTACAGAGCTGAGGCAGGTGCCAGGGGAAAAGATAC
GAAAGGTCTCTATCGCGTTCATGAGTTTACTAAAGTAGAATTATTTTGCTGGAGCAAGCC
AGAAACCAGTGCAAAGGTCCTTGAGGAAATAAAGCAATTTCAGATTTCTGTAGTTGAGGA
ATTAGGAATACCGGCCAAAGTACTAAAATATGCCATCAAACGATCTTGGTAATCCCGCTTT
CAAGAAATACGACATCGAAGCTTGGATGCCAGGAAGGGGGAAATTTGGCGAGATAAGTAG
TGCCTCCAATTGTACCGATTTCCAAAGTAGAAGATTAAATACAAAGTACAGGGACGATAA
CACAGGAAAGCTAGAATATGTGCACACGCTGAATGGCACAGCAATGGCTATCCCAAGAGT
GATAGTAGCACTAGTAGAAAATTTCTATGACCCAAGCACCGGTAAGATATCTGTTCCTGA
ATGTTTGAGGGAGTTTATGAATGGCCAACGATACATTTAATAAGTAAGAAAATCTTGTAA
ATATGTAATCTTATGTTAACCGTAGCATCATTGTGTTGGACGAAATCCTCTGTGATGTTC
TGTGTGATTGAAATTGTATGGTATTTTCGATCATACGAGTATTTTCCTAAAGATGAAAG
AGAACTCGATTCCTAAACAGTTGTTTGTAGGGCATAACGTTGTATCGTAAATACTTACCA
TACGCTTAGGTATATTCCTTTAGATTTCCGTAACACCTTTCAGTTTTACTATTCCGCGTG
GCGAGGTAAAGATCATAAAAATACAAGTTTGTTATAGCATTTCCTGCAAATAATTGCTGT
AACTAGTGGCGAAAAGGTCATAGAATTATTCGCCTAAATTATG >YKL053W Chr 11                                   (SEQ ID NO: 63)
CCGGAAGTAATTTTATCAATTATAGTTTCCAAATCATCATATTCTTGAACTATATCAATT
AAATCATCACTCGTCCAGTCAGGGAACAATTCTGTAAGCGTATCTATTTTGGACTTTAGC
GCAGGATTTAGTTTTTTACTACTATGACTATTATGATTAGACTTTCCTAAATTGTGTAGAC
ATTATATATATATGATGATGTAGATTATATTGAGAAAACGACCAAACAAAAATAAATATG
TAAGTACTTTATGATGGTGATTTTTTTGGGGTAATTGGTAAGAGTTTTTCTTGTAGCTTC
AAAAGATCAAATATAAAATACGAATGTTTCTGAAATTACTGTAAAAGACTTAGGAAAAGG
AATGAAACGTTTATATGGGAGAGAACGAAAATTTTTCCTTTTCCCGCCACTACTTTTTGC
CACCATTTCCCGTTATTTATTTGGGCGAGTGCTCACCTCCGACGGAATCACGGGTGACGG
ATATCCTAAAAAGGTAAAGAATTGAAACAGATCTATTAATATACGGATCACTATACATTA
TTATAAGTCGATATTGCAGTATTAGTATTTACATGTTGAATAATGCACATTCTGTGCTAA
AATATATACTTCATTTGTCAACTTCTTTTAGTTTGCCGCCATTTTCAAACGGCGCCTCCT
CCCTAGCTTCGTCTAGAGCAGGCTTAATACCTTGTTTGACGAGAGCTGCGTTGACACATG
TAGTATAAGCGTACCATTGTTTTGAGCACTCGTTCTCAACGGATTTTCCCTTCAGGAATT
TTTCGCTATACCATTCATTAAAACAACTATCGTATTTCGTCTTCAGGTCAGTGCATTCAG
GCGCAAAACTAGCTGACATTATATTCCCCATATAAAACTGGTATTATTGTTATTGTAATT
CAAGTTAAAACACAAACAGATGTTTTCTAATGACCTCTCCCGGCATATATCTGGCGCACT
TAGAATAAATTTCTACATGCAAATACTCTGAATATTCTGAATG >YKL196C Chr 11        reverse complement         (SEQ ID NO: 64)
TTCTTCTTCTCCATTATTATCTTCAGTAGTTGTCTTGTCATCAGATTGTCCCTGTTGCGA
TTTTTCATCATCTGAATGTTCTGGATCTTTTTTTTCAGAAGATCCAGCATTGTTGTCTAG
TGTTTTGTCACTAGTATTTTCTTCCGAGTTCTCAGAACTTATGTTTTCATCCTTTTGATT
GTTAGCGGTGGCATTGTCTTCATTGGATTGCTCATCATCTTTGGTTGATACCTTTGATTC
ATCAGTATCTTTATCTTCGGAAGACTTGTTGTCTTCTTCTGCTAGAACAACCAATTCACC
ATCTTCAGCTACTTTTGAAGCACCAATTTATCACCCCCTAATTGAGGGCCAGCTTCAGT
TTCATCGTTTTTGCTGTCGTTGTCATCTCCATTTTCATCGCTTTTGCTGTTGTTGTCATC
TTCATTTTCTGGTGATTGCTCACCACCACTGGAAAGCTCTTCCTCTGCGGTTTTATCGGA
TTCTACCTTCCTTGAGGCGAAAAGAGGCTTCCTATTAGGAGCAATAAAATATAAAGCACC
AGCCATAGAAAGAATCCCCATTATAAAGCCCGCTGTTTTTTcCTGATTGGAGTTCCTACC
GAACTGAGGGGAGGACGCCATGAGACGTCTTGTTTGGTGTCGGCATAACCCCCTTGCCAC
TTGAATTGACGGCCTGTTTCTGCACGCATTCCTGACGACTAAGTTGCGAAGCATTTTACT
GATAATATACACTCTTTGGATCGAGCCTACTTCCAGTTGGTAATTGGTGTTCCACAATTT
CAGCATTATATGTTTTTAAACCAAAATTCGGCTCCTTTTCCCTTTTTTTCTTATTGGGTG
GCGTGCCGTACAGAACGATTGGCTTGGTGTGAAATCAAGAGCAAGCACAATAGATATCAA
CATGAACAATATACAAAAGTCTCTGGCACAGTTTGACTGCGTTAGACCAGGCTAGGGCAT
TTCTGAAGCTTTACGTATCACTAGAGAAGTTATTTTGGCAATG -continued >YDL103C Chr 4     reverse complement    (SEQ ID NO: 65)
GAAAGATGACCTCTTTCAAACGCAGTACGCAGTTTGTTGACCATATGCGGATAGGTGACG
TATATTTTCCAGAATGGTAATTTGGTATCTCCGGAATAACCCCAGATAGACTGTTTAGAT
ACAACTTCAATCGAATCAATAGCGTGGTCAAATGTTTCGTTTAAATAGTGCACAAACTTG
TTGATTTGCTCCTGATCGTTAGCGTCGGAAGAATTGGGCGCTGGGACGTAAAGATAGTTC
TTGAACCCTGTAACATTACAAAGTACAGAGTGTCCTTCACTAGTGACACCAAAAAACCTT
ACCACGGTAGATGTATTTTCATCTTTGATACCATTCAGTACGCTCTGTTCCGCATCAATT
TGTTGGAAAGAAATATCATACAAACTTGGGTCAAAATCGGTTGGAAGTTTCTTACGCTCG
AATGATGACAGGTCATGCTCTTCTTGGTCGGCCATATCATGTTCCATTTGCGATACGTCT
TGTTCAAAAGTAGACTCTAATTGCGTACCCATTAAATCTGTATCCTTTGCTTTGAAGCCT
TGACTATTATATTTTCGAAAAGAATCACTCGGAATAATCTCTATTGTTGAAACAGGTTCA
CTTCCAACACCATGATCTATTGATTGCCGTTTGATTTTCTTTTCCAACTGGGGAGTATCC
TCGTCATCGATCTTCACATCAACCATGGGAAGGGATCTTTTTTCACTCATTGCTGTGCGT
ATATGTATAAAGATTAATGCTTAATAGCAAGTGCTCAATATCTATTTTCCTTTATCCTTG
AAAATTGCCTTAGATCAGTAGTACTGAGTGTTTGTTCTTCATAAGCGAATAGACAGATGTC
CTCATTGAACATTTTATAGAATAAAAAGTTACGCGTAATACGAAAAATTGCCTATTACGT
TAAGGCATACTTTTACCACACAAAACCAAGATCAACCGTCAAGCAAGAACGCTGCAAAGA
AACGCAGATATAAAGGAGAACACCAGATCGAACTGCAACTATG >YLR427W Chr 12                          (SEQ ID NO: 66)
TCTTGAATGTCGACATATGCCCATCATCAGTGAGGAATACTCGCGTGAAGGATCTCATCT
GCGACCTGAGTGATGATGAAGAAGTTGCAGCACTACTGAATTTGTTGAAAAGAAAGTATA
AAAATGAAATCCGATTGATTGTGAACAATGCTGGAGTAAGGGCCAACTTCACCGGATTCA
ACGGCATGGAACGGGATAATCTTGATAAGATTTTTAAGATAAACACATTTGCACCACTTC
AGTTCATTCAAGAACTGGCCCCTAGTAGACACTCAACTAGACAGTGTTATATTGTCAATA
TCGCAAGCATTTTGGGCATATTGACGCCGGCCAAAGTAGCAGCTTATGCGGCGAGCAAAG
CAGCATTGATAGCCTTTCATCAGTCGTACAGTTTTGAATTGCAAAACGAAGGCGTAAGAA
ATATCAGAACACTATTAGTGACCCCAGGGCAACTGAATACGGAAATGTTTGCAGGATTCA
AGCCTCCTCGCCAGTTCTTTGCCCCTGTAATAGACATTACTACTCTAGCTGCCAAGATAG
TCCGTTATTGTGAGCTGGGTCAGAGGGGACAGCTAAATGAACCCTTTTATTGTAGTTTTG
CTCATCTTTTGATGTGCGTACCTTATTCGCTACAACGCATTGTAAGAAGCTTCTCTCGCA
TAGATTGCTGCCTCCCGGACGAGTAGAAAGCTATACATAGTAAATAGAATATTTATAGAT
GAATCCGAGTAGACAGCCTTGGTGTTTGCTTATACATTCTTTGCAATTATGCACGCCCTC
ATTACCGTTGCTCATATTTTTGGGCATTAATTGTATTTTGAAAAGTGCTCGTTCAGGCCC
GTGTAAAAAAGGTGATGAAGCAAACATTATAATAAACACTTCTGAGAAGCCACGTGTAG
AGGGGTAAGCTATATCGTAAACACCGTTGGATGTGGACCACGGTGCACTGATAAAATAAA
GATATAGTAGTAGAATCTGTTACTAATCTTAACACTTTTGATG >YLL020C Chr 12    reverse complement    (SEQ ID NO: 67)
GCTGTAGATAGATATAGAGAAGCCGCCAAAACAGAACTAAGAATTCTACAGACTATCCTG
AATAATGACCCTCAAGGTCAGTTCCAGTGCCTCTTGCTAAGGGAGTGCTTCGATTACAAA
AATCACATTTGTTTGGTGACAGATCTATACGGCAGGTCCATTTACGATTTTATGTGCTCC
AACGGCATTGCCAGGTTCCCCGGCTCTCATATTCAGGCCATTGCCAGACAGCTAATCAGA
TCTGTCTGCTTCTTGCACGATTTGGGCATAATACACACGGATTTGAAACCAGAAAATATC
CTGATTTGTGACGAAACCCATATTGCTCAAAAATTGCCTTTGAAAACCGTACAGTCGCTA
AGCAAGAGACGCCGTGAAGCCAGTAAGGGGAAGCGCAAAATCTTGAAAAATCCAGAAATC
AAAATCATTGATTTCGGTAGCGCAATTTTCCATTACGAATATCATCCTCCTGTAATATCC
ACTCGTCACTATAGAGCCCCGGAAATTGTCCTTGGCTTGGGCTGGTCGTTCCCCTGCGAC
ATTTGGTCCATCGCGTGTGTCCTAGTAGAACTGGTTATTGGCGAATCTCTTTACCCCATT
CATGAAAATCTAGAACATATGGCTATGATGCAACGAATCAATGGAACCCTTTCCCCACA
GACATTATTGATAAGATGTTTTACAAATCTAAACATAAATTGGGCAACTCTCCATCAGAC
CTAAATTCAACGGTGATAAAGCATTTCGACAGAAAAACTTTAAGCTTACAATGGCCTGAA
AAAAATAAACGCGGAGATACCATAACCACCGAAAAGTCAATGAAAAGGGTCTTGCAGTCA
TGTGATCGCTTAGATATTTACATCTCAAAGGTCTTGAAACAGGATTACGGCGATAGCTTA
AGCATCAATTGGAATCTACCGCCGGAGAAAAACTGGTCTTTGATAAATTCGAAATTGGCA
TGGAAAAGACAAACACATTCCTCTTCTTCCTCAACTACTGATG

Example 2

Ratiometric Screening Assay (Luciferase and β-galactosidase)

In this example, the ability of a substance to modulate the chromatin modeling function of the YCR052W gene is determined using a ratiometric assay.

*S. cerevisiae* strain W3031a cells are transformed with a plasmid comprising a hybrid which includes the responsive promoter YOR387C (SEQ ID NO: 1) operably linked to the *E. coli* lacZ gene along with a plasmid comprising a hybrid which includes the baseline promoter of YHR082C (SEQ ID NOs: 52) operably linked to the *Photinus pyralis* luciferase gene lacking the peroxisomal targeting sequence (see Leskinen et al., Yeast 20:1109-1113 (2003)). The cells are grown, in microtiter dish wells containing 100 μl culture, while shaking at 30° C., to exponential phase and the culture is split in two. One culture is contacted with a substance to be tested for the ability to modulate chromatin modeling and the other culture is not. The cells in each culture are further incubated for another 2 hours.

100 μl of 1 mM D-luciferin in 0.1M M Na-citrate (pH 5.0) are pipetted into each well. The plate is shaken briefly and then the luminescence is measured wuing a Victor mulitlabel counter in luminescence mode (Perkin-Elmer Wallac; Turku, Finland) using a one second counting time. After the measurement of the luminescence, CPRG (chlorophenol red β-D-galactopyranoside) β-galactosidase test buffer (for example, 50 or 150 mg/ml of CPRG in HBSS (Hank's balanced salt solution)) is added. Then, the expression of the lacZ reporter gene is measured by measuring the chlorophenol red reaction product, optical absorption at 540 to 580 nm, after another 2 minutes to 24 hours of incubation.

The levels of expression, in each culture tested, of the lacZ gene is normalized to the level of expression of the luciferase gene. The normalized level of lacZ expression in the presence of the substance being tested is then compared to the normalized level of expression of the lacZ gene in the absence of the substance. If the ratio is above or below 1, this indicates that the test substance is modulating the chromatin modeling activity of the cell.

Example 3

IC90/MIC Calculation

In this example, a baseline promoter of the invention (SEQ ID NO: 53) was used to determine the IC90 of various known anti-fungal compounds. The IC90 value determined was then compared to a visually determined MIC value.

Setting up the Plates:
1. Picked a single colony of yeast Y229-1 ($P_{CDC48}$ (SEQ ID NO: 53)-PH05-*Renlla* Luciferase) and inoculated 10 mL YPD (1% yeast extract, 2% peptone, 2% dextrose) containing 100 μg/mL G418 (Geneticin, GIBCO, Invitrogen Corp.).
2. Incubated the cells overnight at 30° C. with shaking (250 rpm).
3. Measured optical density of the culture at 600 nm ($OD_{600}$) and diluted an aliquot to $OD_{600}$=0.1 in YPD. Made an additional 1:100 dilution of the 0.1 $OD_{600}$ culture in YPD.
4. Transferred 12.5 μL of serially diluted compound or no drug control in 2% DMSO to one well of a black/clear bottom sterile 384 well plate. Covered with a sterile lid.
5. Added a 12.5 μL aliquot of diluted Y229-1 cells to each well of the 384 well plate. Final DMSO concentration was 1%.
6. Covered the 384 well plate with a sterile lid, placed in a plastic bag to limit evaporation, and incubated for 24 hours at 30° C.

Preparing the Luciferase Assay:

A Promega *Renilla* Luciferase Kit was used in these steps (E2820, Promega Corp., Madison, Wis.).
1. Add 12.5 μL 1× Lysis buffer per well.
2. Add 25 μL Assay Reagent per well of 384 well plate. Read light output immediately on an appropriate device (e.g., LeadSeeker, Amersham Biosciences, Piscataway, N.J.).

TABLE 4

Correlation of IC90 calculated from luciferase light output and MIC determined visually

|  | 5FC | AMB | CSP | FLU | TRB | VOR |
|---|---|---|---|---|---|---|
| IC90 (μg/mL) | 1.9 | 0.3 | 0.02 | 0.3 | 1.4 | 0.008 |
| MIC (μg/mL) | 2.5 | 0.3 | 0.015 | 0.2 | 1.56 | 0.015 |

IC90, inhibitor concentration at which there is a 90% drop in signal relative to the uninhibited control; MIC, minimum inhibitor concentration at which there is an approximately 90% drop in cell number relative to the uninhibited control; 5FC, 5-fluorocytosine; AMB, amphotericin B; CSP, caspofungin; FLU, fluconazole; TRB, terbinafine; VOR, voriconazole.

Example 4

High Throughput Screen

In this example, a baseline promoter of the invention (SEQ ID NO: 53) is used in a high throughput screen to discover compounds with antifuingal activity.

Compound Preparation
1. Prepare compounds in 5% DMSO.
2. A control inhibitor, amphotericin B is prepared at 25 μg/mL (in 5% DMSO) to produce 5 μg/mL (final concentration).

Culture Inoculum Preparation
1. Inoculate 10 mL YPDU (1% yeast extract, 2% peptone, 2% dextrose, 80 μg/mL uridine) supplemented with 0.1 mg/mL G418 (from 50 mg/mL stock) with yeast strain Y229-1 ($P_{CDC48}$ (SEQ ID NO: 53)-PHO5-*Renilla* Luciferase).
2. Grow Y229-1 overnight at 30° C. with shaking (250 rpm).
3. Measure the optical density of the yeast culture at 600 nm ($OD_{600}$) and determine volume of yeast culture needed for $OD_{600}$=0.1 in 5 ml YPDU.
4. Further dilute this 5 mL culture 1:20 in YPDU (this volume is sufficient for approximately 5000 assay points).

High Throughput Assay Set Up
1. Add 5 μL compound or 5% DMSO to a sterile 384 well plate (e.g., Matrix Technologies, Hudson, N.H. catalog #4331).
2. Add 20 μL of dilute inoculum to each well containing compound, amphotericin B or DMSO.
3. Cover plate (e.g., Matrix Technologies catalog #4320) and incubate 24 hr at 30° C.
4. Prepare 1× Lysis Reagent from Promega *Renilla* luciferase kit (catalog #E2820) by diluting 5× stock in deionized $H_2O$.
5. Add 12.5 μl 1× Lysis Reagent to each well. Incubate at room temperature for 1 hour.
6. Prepare Assay Reagent as described by manufacturer.
7. Dispense 25 μL Assay Reagent into each well.
8. Read immediately on an appropriate luminescence detection device.

Example 5

Ratiometric Dual Luciferase Assay

In this example, a *Renilla* luciferase and a firefly luciferase reporter is linked to a gene responsive and a baseline promoter, respectively, and used in a ratiometric assay to determine whether a substance inhibits fungal cell growth.

Strain construction. A double recombinant strain comprising a chromsomally integrated YOR387C promoter/Pho5-*Renilla* luciferase hybrid and a chromsomally integrated YHR082C promoter/Pho5-Firefly luciferase (-SLK) hybrid is constructed. The yeast strain, Y229-1, is transformed with plasmid pSPRT190 (SEQ ID NO: 87), comprising gene responsive *S. cerevisiae* YOR387C promoter (SEQ ID NO: 1) operably linked to Pho5-*Renilla* luciferase. The YOR387C promoter/Pho5-*Renilla* luciferase hybrid integates into the Y229-1 cell's chromosomal TRP3 locus. The pSPRT190 plasmid comrpises the KanMX gene for selection. The recombinant strain is, in turn, transformed with plasmid pSPRT50 (SEQ ID NO: 86) comprising baseline *S. cerevisiae* YHR082C promoter (SEQ ID NO:52) operably linked to Pho5-Firefly luciferase (-SLK). The YHR082C promoter/Pho5-Firefly luciferase (-SLK) hybrid is allowed to integrate into the Y229-1 cell's chromosomal HO locus. The pSPRT190 plasmid comrpises the KanMX gene for selection Assay. Test and control double recombinant yeast cells are mixed in growth medium and diluted to $OD_{600}$ of 0.2. Two experiments are set up: (i) double recombinant strain contacted with the substance being tested for the ability to inhibit fungal cell growth and (ii) double recombinant strain contacted only with a blank. Then, 25 μl of the diluted yeast strains are added to microtiter wells containing a compound to be tested for the ability to inhibit fungal cell growth or a blank (10 μl compound [dissolved in 100% DMSO] per well). Yeast and compound are incubated for 3 h at RT, followed by the addition of 25 μl of firefly luciferase reagent (Promega, Madison,Wis.) to each well, and incubated for 1 hour. Luminescence (firefly luciferase reporter) is determined using a Viewlux plate reader (Perkin Elmer,Wellesley,Mass.).

After reading the firefly luciferase counts, using a Victor2 plate reader (Perkin Elmer,Wellesley, Mass.) equipped with an injection system and interfaced in a Thermo-CRS stacker-based robotic system (Thermo-CRS Ltd.,Burlington,Ontario, Canada), 25 μl *Renilla* luciferase reagent (Stop &Glow, Promega,Madison,Wis.) are added to each well individually, and luminescence is determined immediately (within seconds,due to the short half-life of the *Renilla* luminescence).

The relative levels of expression from the YOR387C and YHR082C promoters, in the presence and absence of the substance being tested for the ability to inhibit fungal cell growth, are compared.

In this assay, the compound being tested for the ability to inhibit fungal cell growth is selected if the responsive promoter (YOR387C) expression level (*Renilla* luciferase) decreases or increases in relation to the expression level from the baseline promoter (YHR082C) (fire fly luciferase) when the relative expression levels in the presence of the substance being tested are compared to the relative expression levels in the absence of the substance being tested.

Alternatively, the plasmid pSPRT47 or pSPRT192 can be used to construct the assay strain. Plasmid pSPRT47 comprises a Pho5-*Renilla* luciferase construct to which a promoter can be operably linked, an HO targeting sequence, and the KanMAX gene for selection. Plasmid pSPRT192 comprise a Pho5-*Renilla* luciferase construct to which a promoter can be operably linked, a TRP3 targeting sequence, and a hisG:URA3:hisG consruct for selection and counterselection (e.g., using 5-FOA).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, Genbank Accession Numbers and protocols are cited throughout this application, the disclosures of which are incorporated herein by reference in their entireties for all purposes.

We claim:

1. An isolated hybrid polynucleotide comprising a S.cerevisiae YIL066W-A Promoter operably linked to a reporter; with the proviso that the reporter operably linked to the S.cerevisiae YIL066W-A Promoter, is not the YIL066W-A open reading frame.

2. An isolated polynucleotide of claim 1 wherein said promoter comprises the nucleotide sequence set forth in SEQ ID NO: 23; and/or the reporter comprises a nucleotide sequence selected from the group consisting of SEQ ID NOs: 42-51.

3. An isolated vector comprising the hybrid polynucleotide of claim 1.

4. An isolated host cell comprising the vector of claim 3.

5. The hybrid polynucleotide of claim 1 wherein said reporter is a member selected from the group consisting of S.cerevisiae ADE2, S.cerevisiae LYS2, S.cerevisiae TRP1, S.cerevisiae LEU2, S.cerevisiae URA3, S.cerevisiae HIS3, Aequorea victoria GFP mutant 3, Renilla luciferase, Photinus pyralis luciferase, and E.coli lacZ.

6. The hybrid polynucleotide of claim 5 wherein said reporter comprises the nucleotide sequence set forth in a member selected from the group consisting of SEQ ID NOs: 42-51.

7. The hybrid polynucleotide of claim 1 wherein the reporter is a Pho5 conjugated Renilla luciferase.

8. The host cell of claim 4 wherein said hybrid polynucleotide is chromosomally integrated.

9. The host cell of claim 4 further comprising a baseline promoter operably linked to a reporter.

* * * * *